(12) United States Patent
Ririe et al.

(10) Patent No.: US 11,691,152 B2
(45) Date of Patent: Jul. 4, 2023

(54) ASSAY DEVICES AND METHODS OF USE THEREOF

(71) Applicants: BioFire Defense, LLC, Salt Lake City, UT (US); BioFire Diagnostics, LLC., Salt Lake City, UT (US); bioMérieux, S.A., Marcy (FR)

(72) Inventors: Kirk M. Ririe, Salt Lake City, UT (US); Aaron D Wernerehl, Salt Lake City, UT (US); Christopher P. Pasko, Salt Lake City, UT (US); Ali Laayoun, La Frette (FR); Carole Vachon, Saint Etienne de Crossey (FR); Agnès Dupont-Filliard, Les Adrets (FR); Laurent Mesta, Genas (FR); Andrew C. Hatch, West Jordan, UT (US); Erik W. Huynh, West Jordan, UT (US); David E. Jones, Layton, UT (US)

(73) Assignees: BioFire Defense, LLC, Salt Lake City, UT (US); BioFire Diagnostics, LLC, Salt Lake City, UT (US); bioMérieux, S.A.

( * ) Notice: Subject to any disclaimer, the term of this patent is extended or adjusted under 35 U.S.C. 154(b) by 173 days.

(21) Appl. No.: 16/642,797

(22) PCT Filed: May 23, 2018

(86) PCT No.: PCT/US2018/034208
§ 371 (c)(1),
(2) Date: Feb. 27, 2020

(87) PCT Pub. No.: WO2019/045807
PCT Pub. Date: Mar. 7, 2019

(65) Prior Publication Data
US 2020/0261914 A1  Aug. 20, 2020

Related U.S. Application Data

(60) Provisional application No. 62/552,588, filed on Aug. 31, 2017.

(51) Int. Cl.
*B01L 3/00* (2006.01)
*B01L 7/00* (2006.01)
(Continued)

(52) U.S. Cl.
CPC ......... *B01L 7/525* (2013.01); *B01L 3/502761* (2013.01); *B01L 2200/0668* (2013.01);
(Continued)

(58) Field of Classification Search
CPC ............ C12Q 1/6844; C12Q 2563/143; C12Q 2563/149; C12Q 2565/629;
(Continued)

(56) References Cited

U.S. PATENT DOCUMENTS

2006/0110725 A1  5/2006  Lee et al.
2006/0115385 A1*  6/2006  Jon Meyer ......... A61B 10/0096
422/547
(Continued)

FOREIGN PATENT DOCUMENTS

AU  2012200153 A1  2/2012
CN  103849548 A  6/2014
(Continued)

OTHER PUBLICATIONS

The International Search Report and the Written Opinion of the International Searching Authority, PCT Application Serial No. PCT/US18/34208 (dated Oct. 9, 2018), 22 pages.
(Continued)

*Primary Examiner* — Lydia Edwards
(74) *Attorney, Agent, or Firm* — Kenneth E. Horton; Barnes & Thornburg LLP

(57) ABSTRACT

Systems, methods, and apparatuses are provided for self-contained nucleic acid preparation, amplification, and analysis.

11 Claims, 60 Drawing Sheets

(51) Int. Cl.
    *B01L 99/00*     (2010.01)
    *C12Q 1/6844*     (2018.01)

(52) U.S. Cl.
    CPC ........... *B01L 2200/0689* (2013.01); *B01L 2300/0636* (2013.01); *B01L 2300/0816* (2013.01); *B01L 2300/1811* (2013.01); *B01L 2300/1816* (2013.01); *B01L 2300/1822* (2013.01); *B01L 2300/1827* (2013.01); *B01L 2300/1844* (2013.01); *B01L 2400/043* (2013.01); *C12Q 1/6844* (2013.01)

(58) Field of Classification Search
    CPC ........... B01L 3/502761; B01L 7/525; B01L 2200/0668; B01L 2200/10; B01L 2200/16; B01L 2300/0636; B01L 2300/0816; B01L 2300/087; B01L 2300/1811; B01L 2300/1816; B01L 2300/1822; B01L 2300/1827; B01L 2300/1844; B01L 2400/043; B01L 2400/0481; B01L 2200/0689; C12N 15/10

See application file for complete search history.

(56) References Cited

U.S. PATENT DOCUMENTS

| | | |
|---|---|---|
| 2006/0205006 A1 | 9/2006 | Godfrey et al. |
| 2010/0056383 A1 | 3/2010 | Ririe et al. |
| 2011/0318784 A1 | 12/2011 | Himmelreich et al. |
| 2014/0170667 A1 | 6/2014 | Dykes et al. |
| 2014/0194305 A1* | 7/2014 | Kayyem ............ B01L 3/523 506/18 |
| 2015/0299777 A1 | 10/2015 | Patel et al. |
| 2016/0017274 A1 | 1/2016 | Pflanz et al. |
| 2016/0116381 A1 | 4/2016 | Haupt et al. |

FOREIGN PATENT DOCUMENTS

| | | |
|---|---|---|
| CN | 105799153 A | 7/2016 |
| EP | 1876231 B1 | 8/2016 |
| JP | 2010509918 A | 4/2010 |
| JP | 2011508589 A | 3/2011 |
| JP | 2012529268 A | 11/2012 |
| WO | 2008140568 A2 | 11/2008 |
| WO | 2010057318 A1 | 5/2010 |
| WO | 2015177933 A1 | 11/2015 |
| WO | 2016196827 A1 | 12/2016 |
| WO | 2017019598 A1 | 2/2017 |

OTHER PUBLICATIONS

Japanese Office Action dated Mar. 23, 2022 for corresponding JP Application No. 2020-512427.
JP2010509918, Biofire Diagnostics LLC, Machine Translation, Apr. 2, 2010, 22 pages.
JP2011508589, Gen Probe Inc, Machine Translation, Mar. 17, 2011, 77 pages.
JP2012529268, Integenx Inc, Machine Translation, Nov. 22, 2012, 51 pages.
WO2015177933, Shimadzu Corporation, Machine Translation, Nov. 26, 2015, 10 pages.
Liu Y. et al., Efficiency Comparative Analysis of Three Different Nucleic Acid Analysis System, Acta Agriculturae Boreali-Sinica, 2012, 27(6): 58-61.

* cited by examiner

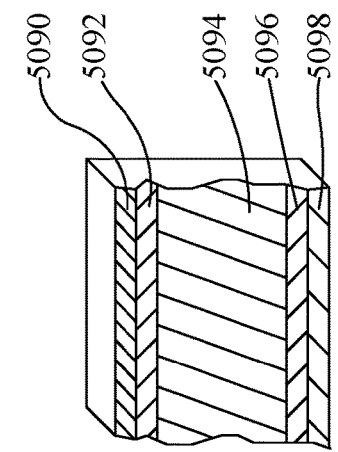
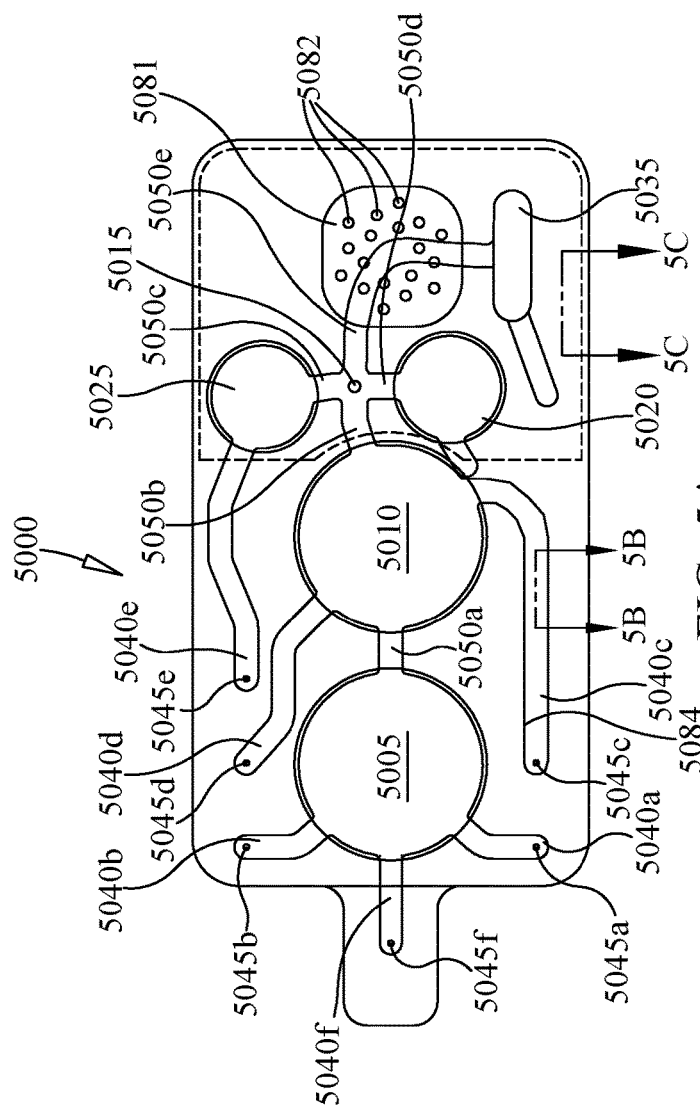
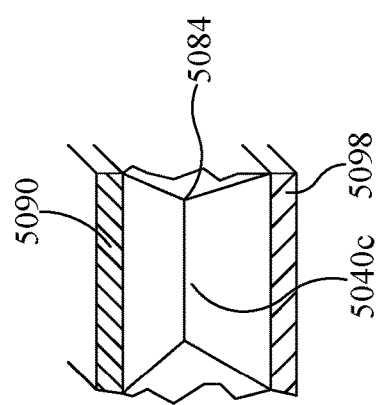

 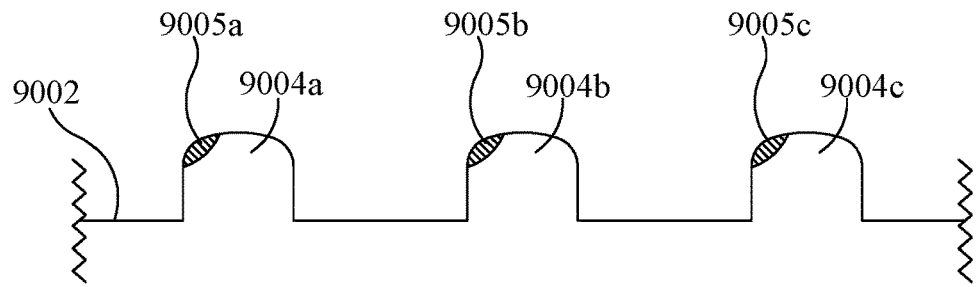
 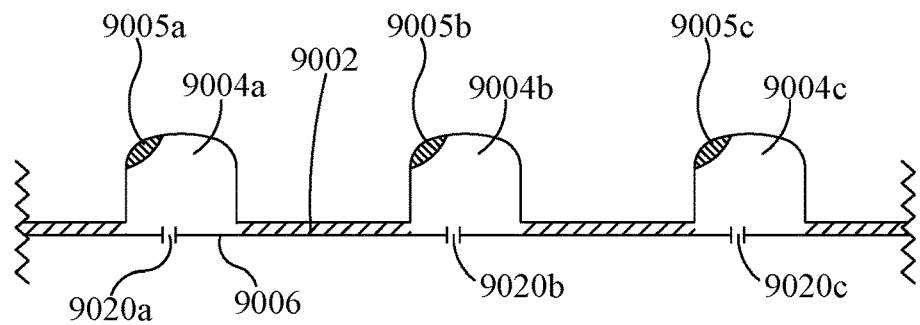
 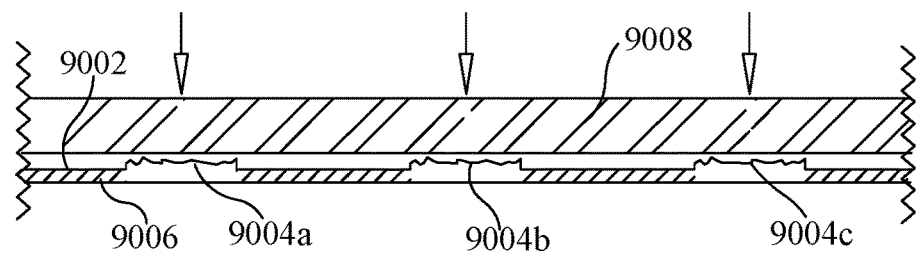
 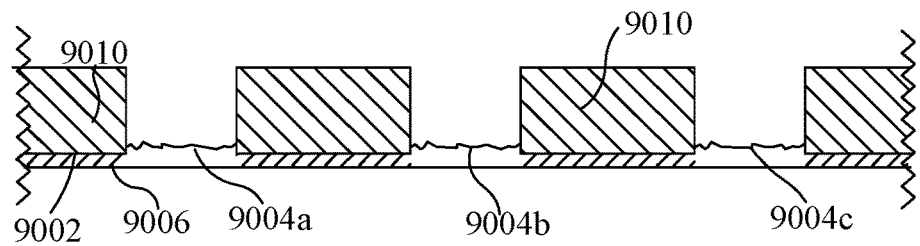
 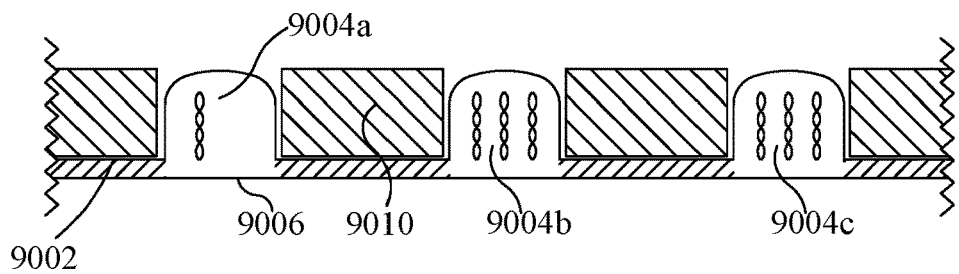
FIG. 9

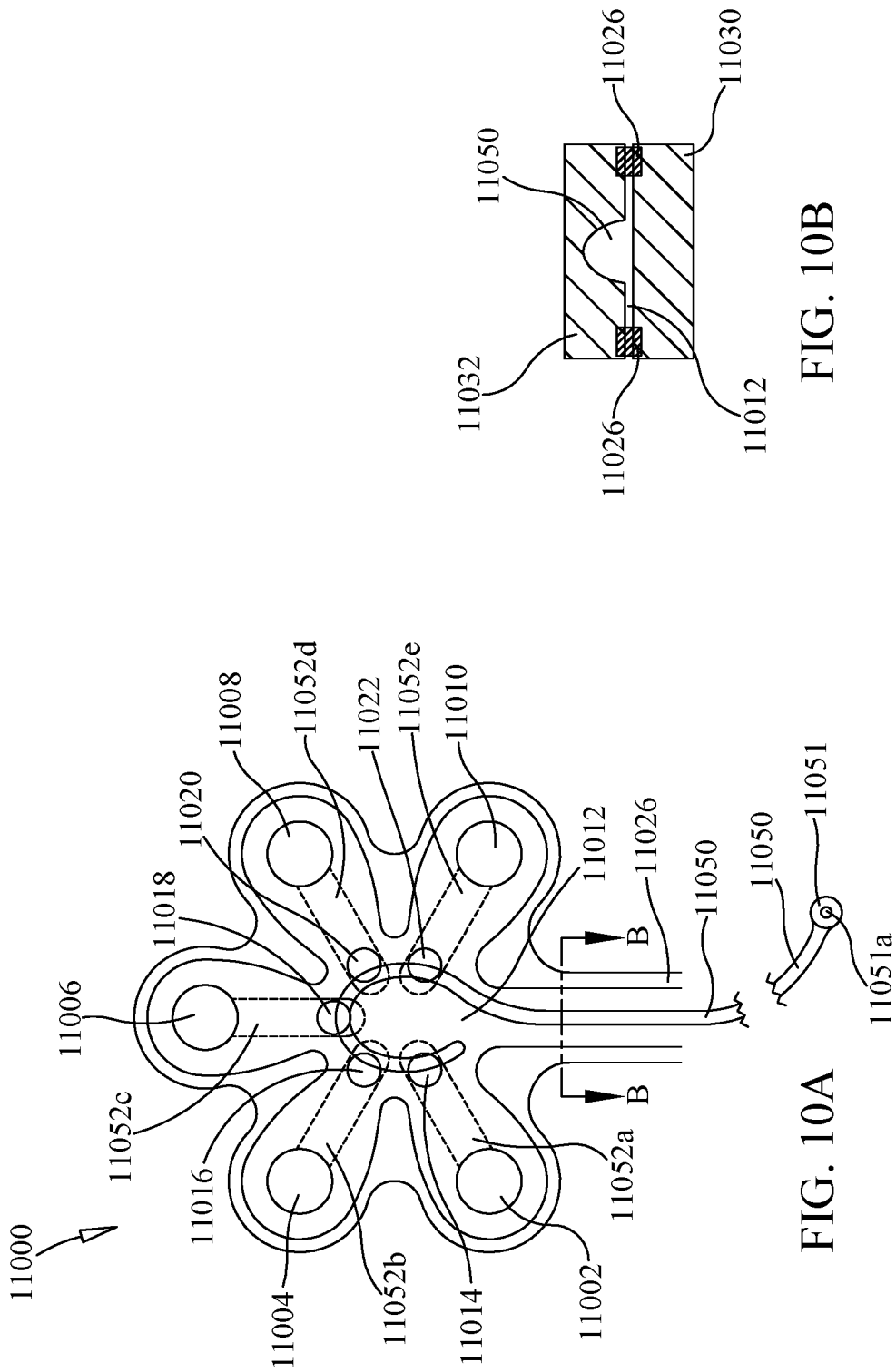

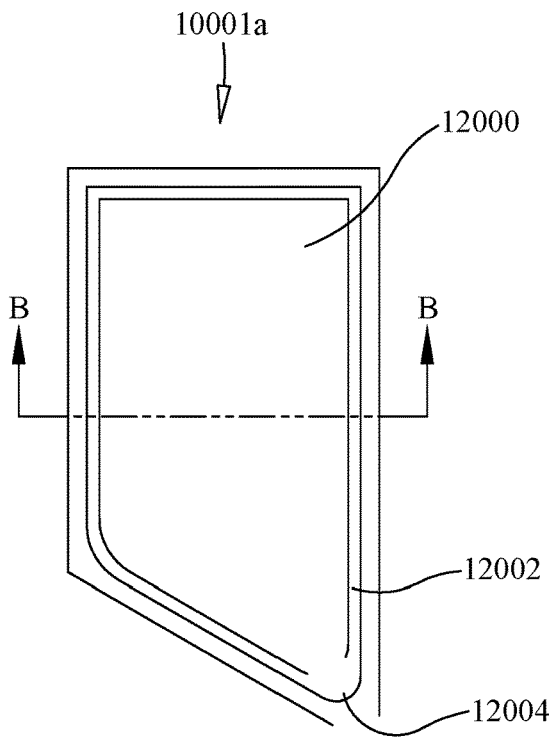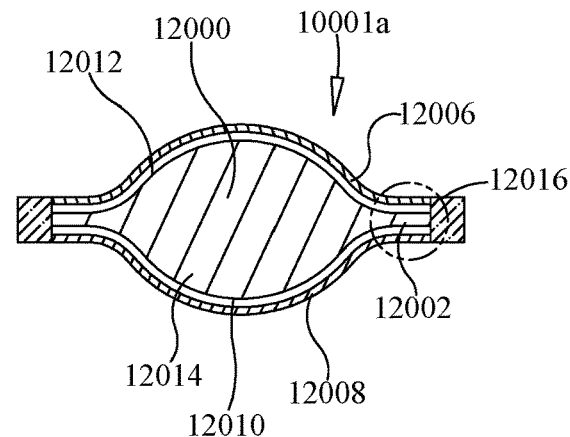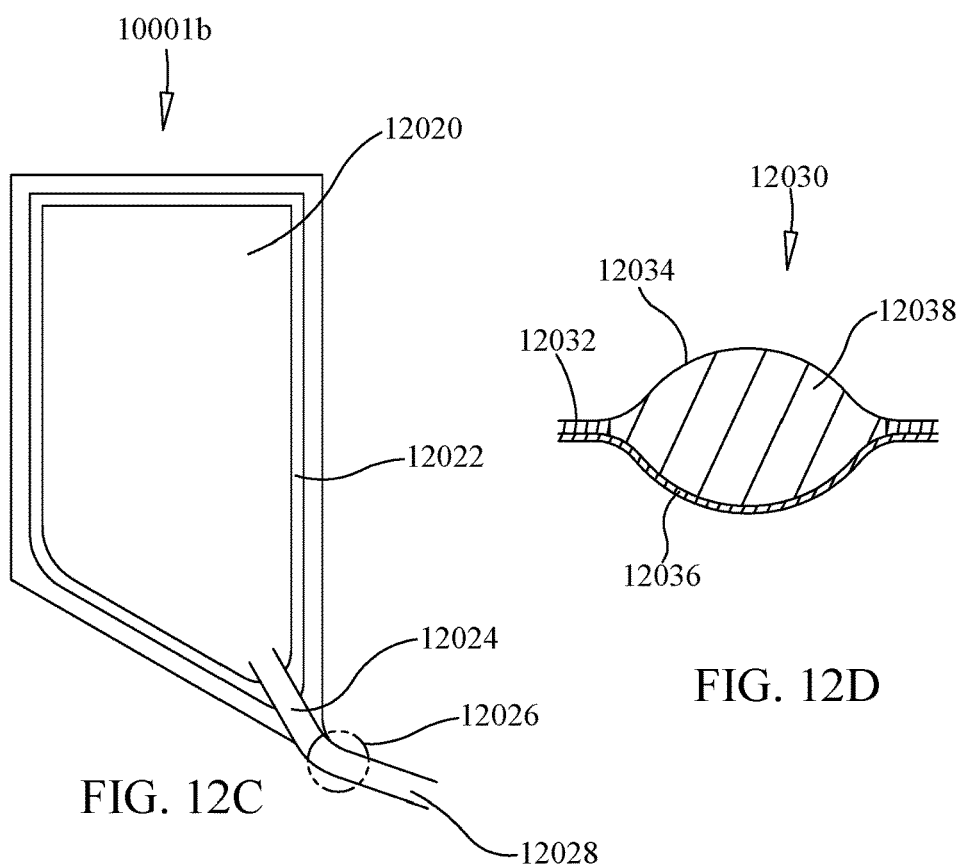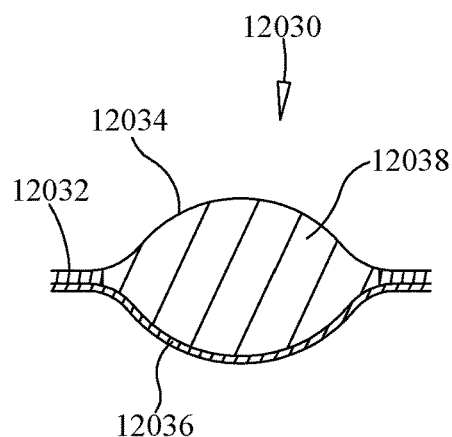
FIG. 12A
FIG. 12B
FIG. 12C
FIG. 12D

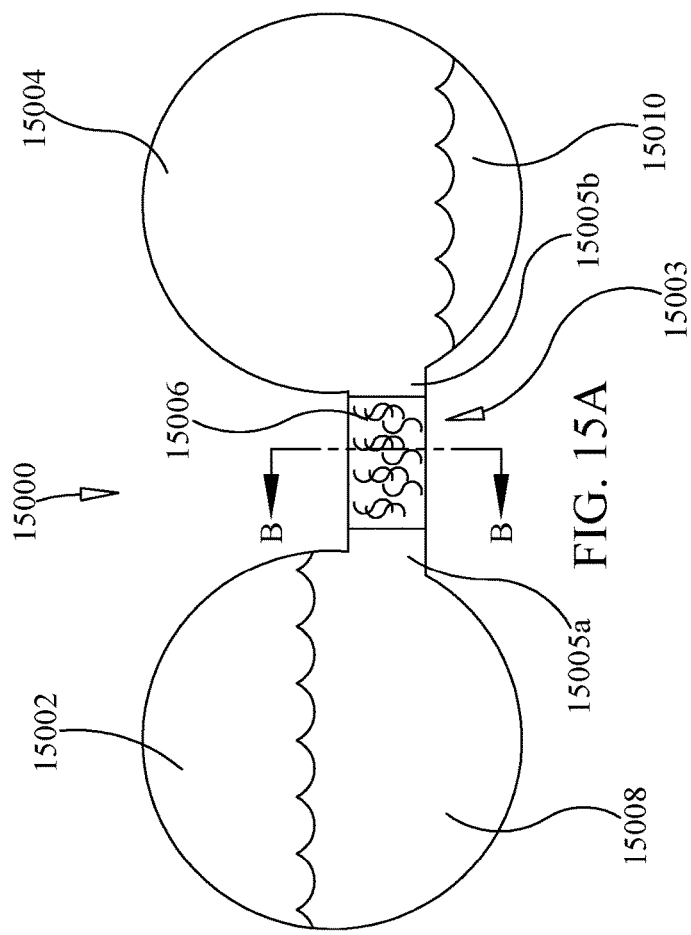
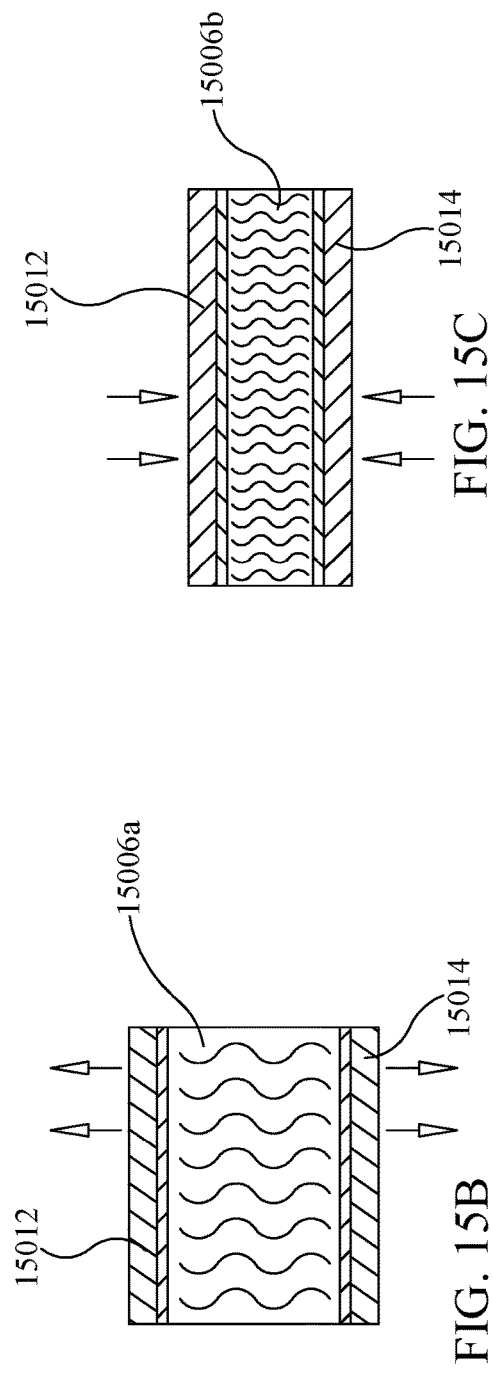

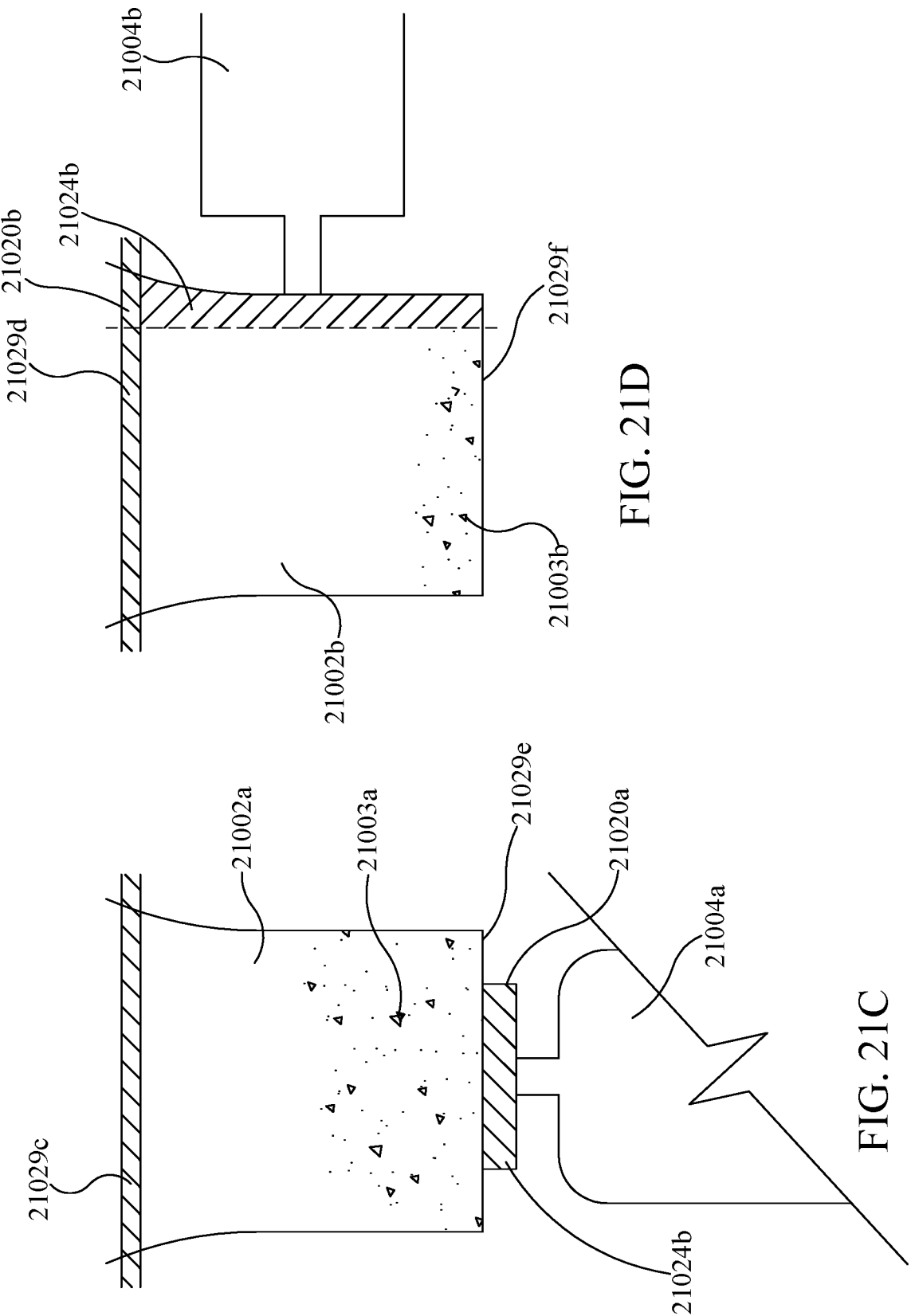

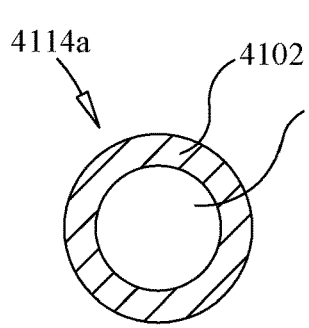
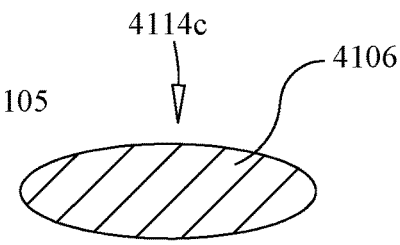
FIG. 43A   FIG. 43B   FIG. 43C
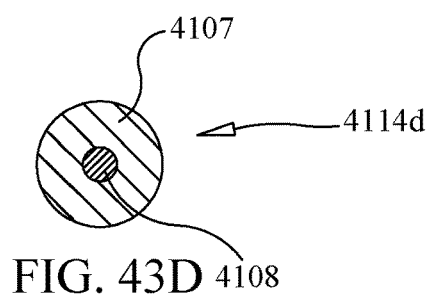
FIG. 43D
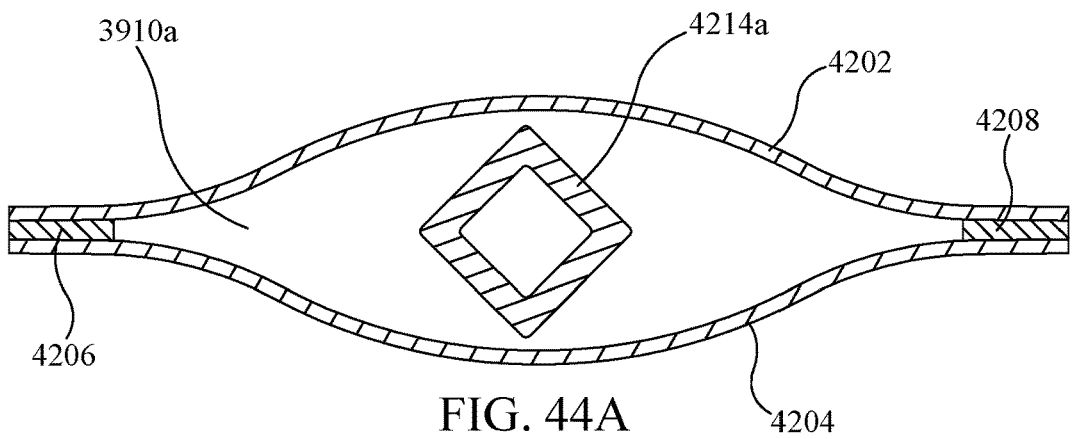
FIG. 44A
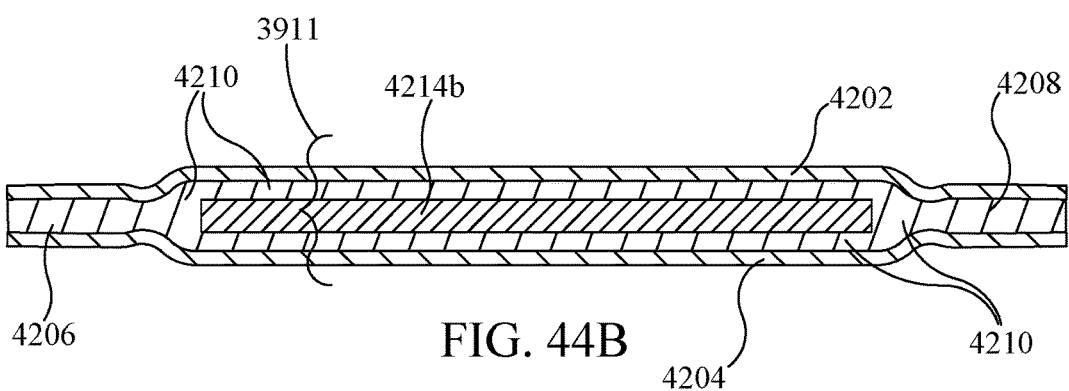
FIG. 44B

ASSAY DEVICES AND METHODS OF USE THEREOF

RELATED APPLICATIONS

This Application claims the benefit of and priority to U.S. Prov. App. Ser. No. 62/552,588 filed on 31 Aug. 2017, the entirety of which is incorporated by reference herein.

BACKGROUND

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. However, a challenge to using PCR as a primary means of diagnosis is the variety of possible causative organisms or viruses and the low levels of organism or virus present in some pathological specimens. It is often impractical to run large panels of PCR assays, one for each possible causative organism or viruses, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. Closed systems such as the FilmArray® (BioFire Diagnostics, LLC, Salt Lake City, Utah) reduce handling, thereby diminishing contamination risk.

The present invention addresses various improvements relating to automated or semi-automated manufacturing of test devices, cost of test devices, and more rapid sample-to-answer.

BRIEF SUMMARY

Described herein are self-contained reaction vessels (referred to herein as 'pouches' or 'cards'), instruments, systems, and methods for rapid amplification of nucleic acids. In an illustrative embodiment, a sample container may include a first-stage chamber fluidly connected to a second-stage reaction zone, the second-stage reaction zone comprising a plurality of second-stage reaction wells. Some sample container embodiments described herein may include an integrated sample preparation (ISP) zone (also referred to herein as a sample lysis zone) upstream of the first-stage chamber that is configured to receive a variety of sample types and prepare the sample for analysis in the pouch with little or no input from the user. Similarly, the pouches or cards described herein may include all of the reagents and components for sample preparation, nucleic acid amplification, and analysis so that, after placing a sample to be analyzed in the pouch, the pouch can be run in an instrument with no additional input from the user. Certain self-contained reaction vessels may be adapted to fabrication by highly automated methods and for simple packaging. Certain self-contained reaction vessels (i.e., pouches or cards) may have flexible portions, rigid portions, or a combination of flexible and rigid portions.

In an embodiment, a self-contained reaction vessel is described. The self-contained reaction vessel includes at least a first reaction zone fluidly connected to a second reaction zone comprising a plurality of second-stage reaction wells. In one embodiment, the second reaction zone may be fabricated from a first film layer, a card layer wherein the plurality of second-stage reaction wells are formed, and a second film layer. In one embodiment, the first film layer may be disposed over a first side of the plurality of second-stage reaction wells and the second film layer may be disposed over a second, opposite side of the plurality of second-stage reaction wells. In another embodiment, the second stage reaction zone may include a third film layer bonded to the second film layer. The self-contained reaction vessel further includes a fill channel fluidly connecting the first reaction zone to the plurality of second-stage reaction wells of the second reaction zone. In one embodiment, the fill channel is formed at least in part as a space between the second layer and the card layer, and the fill channel further forms a convoluted flow path into each of the plurality of second-stage reaction wells so as to suppress fluid communication between wells in the second stage reaction zone. In another embodiment, the fill channel may be formed in part as an open space between the second and third film layers and the fill channel further forms a convoluted flow path into each of the plurality of second-stage reaction wells so as to suppress fluid communication between wells in the second stage reaction zone.

In one embodiment, the convoluted flow path for each second-stage reaction well may include an opening in the second film layer adjacent to but not aligned with a second-stage reaction well and in fluid communication with a cutout in the card layer adjacent to but not aligned with a second-stage reaction well. In another embodiment, the convoluted flow path for each second-stage reaction well may include an opening in the second film layer adjacent to but not aligned with a second-stage reaction well, the opening being in fluid communication with a substantially vertical cutout in the card layer extending adjacent to a second-stage reaction well from the second film layer to a substantially horizontal cutout in the card layer adjacent to the first film layer and creating a fluid conduit from the opening to the substantially vertical cutout and into the second-stage reaction well.

In another embodiment, a self-contained reaction vessel is described. The self-contained reaction vessel includes at least a first reaction zone fluidly connected to a second reaction zone comprising a plurality of second-stage reaction wells, a fill channel fluidly connecting the first reaction zone to the plurality of second-stage reaction wells of the second reaction zone, and a dilution zone comprising a dilution well in the fill channel between the first and second reaction zones, wherein the dilution well is configured to receive a volumetric portion of a reaction product from the first reaction zone, combine the volumetric portion with a dilution medium, and fill the plurality of second-stage reaction wells of the second reaction zone. In one embodiment, the dilution zone may further include at least one dilution blister in fluid communication with the dilution well, wherein the at least one dilution blister is configured to receive the dilution medium, combine the volumetric portion with the dilution medium, and fill the plurality of second-stage reaction wells of the second reaction zone. In one embodiment, the dilution medium may be added to the self-contained reaction vessel at the time of manufacture. Likewise, other dry and liquid reagents and components for use in the self-contained reaction vessel may be added to the pouch at the time of manufacture.

In yet another embodiment, a method for analyzing a sample is described. The method includes steps of (1) providing a self-contained reaction vessel that includes a first reaction zone fluidly connected to a second reaction zone by a fill channel, wherein the second reaction zone comprises a first plurality of second-stage reaction wells and at least a second plurality of second-stage reaction wells, (2) performing a first thermal cycling reaction in the first reaction zone for a selected number of cycles, (3) withdrawing a first sample from the first reaction zone, combining the first sample with a diluent, and filling the first plurality of second-stage reaction wells of the second reaction zone, (4) performing the first thermal cycling reaction in the first reaction zone for an additional number of cycles, (5) withdrawing a second sample from the first reaction zone, combining the second sample with a diluent, and filling the second plurality of second-stage reaction wells of the second reaction zone, (6) performing a second thermal cycling reaction in the second reaction zone. In one embodiment, the first plurality of second-stage reaction wells and the second plurality of second-stage reaction wells may be configured to test parallel analytes. In another embodiment, the first plurality of second-stage reaction wells and the second plurality of second-stage reaction wells may be configured to test different analytes.

In yet another embodiment, a self-contained reaction vessel fabricated from a first film layer bonded to at least a second film layer is described. The self-contained reaction vessel includes an integrated sample preparation zone configured for lysing cells or spores located in a sample, a liquid sample preparation reagent pack disposed in the film layers at the time of manufacture and fluidly connected to the integrated sample preparation zone, a nucleic acid preparation zone fluidly connected to the integrated sample preparation zone, the nucleic acid preparation zone configured for recovering nucleic acids from a lysed sample, a first-stage reaction zone fluidly connected to the nucleic acid preparation zone, the first-stage reaction zone comprising a first-stage reaction blister configured for first-stage amplification of the sample, and a second-stage reaction zone fluidly connected to the first-stage reaction zone, the second-stage reaction zone comprising a plurality of second-stage reaction wells, each second-stage reaction well comprising a pair of primers configured for further amplification of the sample, the second-stage reaction zone configured for contemporaneous thermal cycling of all of the plurality of second-stage reaction chambers. In one embodiment, the liquid sample preparation reagent pack may contain one or more of a sample lysis buffer, sample lysis particles, or silica-coated magnetic beads.

In one embodiment, the self-contained reaction vessel may further include one or more additional liquid reagents disposed in the film layers at the time of manufacture and fluidly connected to one or more of the nucleic acid preparation zone, the first-stage reaction zone, or the second-stage reaction zone. In one embodiment, the one or more additional liquid reagents may be fluidly connected to one or more blisters containing dehydrated or dried reagents, the dehydrated or dried reagents corresponding to one or more of the nucleic acid preparation zone, the first-stage reaction zone, or the second-stage reaction zone. In one embodiment, the one or more liquid reagents may include liquid reagents for performing a reaction in one or more of the nucleic acid preparation zone, the first-stage reaction zone, or the second-stage reaction zone. In one embodiment, liquid reagents and/or components may be added to the self-contained reaction vessel between the film layers at the time of manufacture. In one embodiment, the liquid reagents and/or components may be added to the self-contained reaction vessel as one or more self-contained reagent packets (e.g., foil packets) disposed between the film layers at the time of manufacture.

In yet another embodiment, a method of amplifying nucleic acids in a sample is described. The method includes (1) providing a container fabricated from a first film layer bonded to at least a second film layer having (i) an integrated sample preparation zone configured for lysing cells, viruses, or spores located in the sample, (ii) a liquid sample preparation reagent disposed in the film layers at the time of manufacture and fluidly connected to the integrated sample preparation zone, (iii) a first-stage reaction zone fluidly connected to the integrated sample preparation zone, the first-stage reaction zone comprising a first-stage reaction blister configured for first-stage amplification of the sample, and (iv) a second-stage reaction zone fluidly connected to the first-stage reaction zone, the second-stage reaction zone comprising a plurality of second-stage reaction wells, each second-stage reaction well comprising a pair of primers configured for further amplification of the sample, the second-stage reaction zone configured for contemporaneous thermal cycling of all of the plurality of second-stage reaction chambers. The method further includes (2) adding the sample to the integrated sample preparation zone and sealing the integrated sample preparation zone subsequent to adding the sample, wherein the adding includes adding one or more of a swab, a liquid, or solid sample to the integrated sample preparation zone, (3) injecting the contents of the liquid sample preparation reagent pack into the integrated sample preparation zone and lysing the cells, viruses, or spores, if present, in the sample to generate a lysate, (4) extracting the nucleic acids from the lysate, and moving the extracted nucleic acids to the first-stage reaction zone, (5) subjecting the nucleic acids in the first-stage reaction zone to amplification conditions, (6) fluidly moving a portion of the nucleic acids to each of the additional second-stage amplification chambers, and (7) performing second-stage amplification in the additional second-stage amplification chambers.

In one embodiment, the integrated sample preparation zone may include a chamber that may be provided with a sample collection device (e.g., a swab) for collecting a variety of sample types (e.g., blood, nasopharyngeal swab, sputum, stool, etc.) and transferring the sample to the integrated sample preparation chamber. The sample collection device can be removed from the chamber, used to collect a sample, and returned to the chamber for sample preparation and analysis in the pouch with little or no input from the user. Similarly, the container may include all of the reagents and components for sample preparation, nucleic acid amplification, and analysis so that, after placing a sample to be analyzed in the container, the container can be run in an instrument with little or no additional input from the user.

In yet another embodiment, a method for extracting nucleic acids from a sample is disclosed. The method includes (a) providing a flexible container comprising a multifunction chamber, the flexible container and the multifunction chamber including therein reagents and magnetic particles for sample preparation and nucleic acid recovery, (b) introducing the sample into the multifunction chamber, (c) generating a lysate in the multifunction chamber in the presence of the magnetic particles, and (d) recovering nucleic acids with the magnetic particles by isolating the magnetic particles from the lysate. In one embodiment, the magnetic particles may include silica-coated magnetic particles. In one embodiment, the multifunction chamber also includes lysis particles (e.g., zirconium silicate beads). In one embodiment, the method further includes amplifying nucleic acids in a first-stage multiplex nucleic acid amplification reaction in the multifunction chamber. In one embodiment, the step of amplifying the nucleic acids in the multifunction chamber may be performed in the presence or absence the magnetic particles and/or the lysis particles.

In one embodiment, the flexible container further includes a second-stage reaction zone fluidly connected to with the multifunction chamber. The second-stage reaction zone includes a plurality of second-stage reaction wells with each second-stage reaction well including a pair of primers configured for further amplification of the sample, the second-stage reaction zone configured for contemporaneous thermal cycling of all of the plurality of second-stage reaction chambers. Thus, in one embodiment, the method further includes steps of combining a portion of the first-stage nucleic acid amplification reaction with reagents for a second-stage nucleic acid amplification reaction to form a second-stage nucleic acid amplification mixture, filling each of the second-stage reaction wells with the second-stage nucleic acid amplification mixture, and performing a second-stage nucleic acid amplification reaction in plurality of second-stage reaction wells of the second-stage reaction zone.

In one embodiment, the method may include performing at least two steps in the multifunction chamber, wherein the steps include: (1) contacting the sample and the magnetic beads prior to lysis, (2) generating a lysate in the presence of the magnetic particles, (3) binding nucleic acids with the magnetic particles, (4) isolating the magnetic particles from the lysate, (5) performing at least one wash on the magnetic particles isolated from the lysate, and (6) amplifying nucleic acids in a first-stage nucleic acid amplification reaction.

In yet another embodiment, a method for identifying an organism is disclosed. The method includes steps of obtaining a fluid sample suspected of containing the organism, providing a flexible container comprising a multifunction chamber that contains magnetic particles, adding the fluid sample into the multifunction chamber, generating a lysate in the multifunction chamber by applying at least one of heat and a force to the fluid sample resulting in the lysate, recovering nucleic acids from the lysate with the magnetic particles in the multifunction chamber, performing a first-stage nucleic acid amplification reaction in the multifunction chamber in the presence of the lysis particles and magnetic particles to generate one or more amplicons, and identifying the organism using the amplicons.

In one embodiment, the method of identifying the organism further includes providing a flexible container that further includes a second-stage reaction zone fluidly connected to with the multifunction chamber, introducing a sample into the second-stage reaction zone, and contemporaneously thermal cycling of all of the plurality of second-stage reaction chambers. The second-stage reaction zone includes a plurality of second-stage reaction wells, each second-stage reaction well including a pair of primers configured for further amplification of one of the amplicons. In one embodiment, the method includes prior to contemporaneously thermal cycling, combining a portion of the first-stage nucleic acid amplification reaction with reagents for a second-stage nucleic acid amplification reaction to form a second-stage nucleic acid amplification mixture, and filling each of the second-stage reaction wells with the second-stage nucleic acid amplification mixture.

In one embodiment, the method of identifying the organism further includes melting the second-stage amplicons, if present, in each of the different second-stage reaction wells after the second-stage nucleic acid amplification reaction, thereby generating a melting curve for each of the different second-stage reaction wells, and identifying the organism, if present in the sample.

In yet another embodiment, a flexible container for performing nucleic acid amplification on a sample in a closed system is disclosed. The container includes a first flexible layer and a second flexible layer defining a multifunction chamber, and a second-stage reaction zone disposed between the first flexible layer and the second flexible layer and fluidly connected to the multifunction chamber. The multifunction chamber and the flexible container include therein magnetic particles, optionally, lysis particles, and reagents for sample preparation, nucleic acid recovery, and a first-stage nucleic acid amplification reaction. In one embodiment, the first-stage nucleic acid amplification reaction is a singleplex reaction. In another embodiment, the first-stage nucleic acid amplification reaction is a multiplex reaction. The second-stage reaction zone includes a plurality of second-stage reaction chambers, with each second-stage reaction chamber including a pair of primers configured for further amplification of the sample, the second-stage reaction zone configured for contemporaneous thermal cycling of all of the plurality of second-stage reaction chambers.

In one embodiment, the flexible container further includes a sample receiving chamber in fluid communication with the multifunction chamber. In one embodiment, the sample receiving chamber incudes a sample collection swab that is provided in the sample receiving chamber. In one embodiment, the flexible container is provided with one or more reagent blisters in fluid communication with the multifunction chamber. In one embodiment, one or more of the reagent blisters are fluid-filled reagent blisters (e.g., one or more of a sample lysis buffer, a magnetic bead wash buffer, an elution buffer, a reverse transcriptase, a mixture of first-stage nucleic acid amplification components, or a mixture of second-stage nucleic acid amplification components). In one embodiment, the fluid-filled reagent blisters may be filed filled at the time of manufacture of the flexible container and may be contained therein until the flexible container is used by an end used.

In yet another embodiment, a method for amplifying nucleic acids in a sample is disclosed. The methods includes steps of (a) providing a flexible container comprising a multifunction chamber that includes magnetic particles therein, (b) injecting a fluid sample into the multifunction chamber, (c) generating a lysate by applying at least one of heat and a force to the multifunction chamber, (d) recovering the nucleic acids with the magnetic particles by isolating the magnetic particles from the lysate, and (e) performing the first-stage nucleic acid amplification reaction in the multifunction chamber in the presence of the magnetic beads.

In yet another embodiment, a system for performing nucleic acid amplification on a sample is disclosed. The system may be configured to receive a flexible container and includes thermocycling instrument. In one embodiment, the flexible container includes a first flexible layer and a second flexible layer defining a multifunction chamber, a second-stage reaction zone disposed between the first flexible layer and the second flexible layer and fluidly connected to the multifunction chamber, and one or more reagent blisters formed between the first flexible layer and the second flexible layer in fluid communication with the multifunction chamber. The multifunction chamber and the flexible container include therein magnetic particles, optionally, lysis particles, and reagents for sample preparation, nucleic acid recovery, and a first-stage nucleic acid amplification reaction. The second-stage reaction zone includes a plurality of second-stage reaction chambers, with each second-stage reaction chamber including a pair of primers configured for further amplification of the sample, the second-stage reaction zone configured for contemporaneous thermal cycling of all of the plurality of second-stage reaction chambers. In one embodiment, the flexible container further includes reagents and components for a second-stage nucleic acid amplification reaction in the second-stage reaction zone. In one embodiment, the thermocycling instrument includes a receptacle for positioning the flexible container in the instrument, a heater/cooler positionable in the instrument for heating and/or cooling one or more of the multifunction chamber and the second-stage reaction zone, a cell lysis component configured for generating a lysate in the multifunction chamber, and a fluid movement component configured for moving fluids in the flexible container between at least the one or more reagent blisters, the multifunction chamber, and the second-stage reaction zone. In one embodiment, the first-stage nucleic acid amplification reaction is a singleplex reaction. In another embodiment, the first-stage nucleic acid amplification reaction is a multiplex reaction.

In one embodiment, the heater/cooler includes a first heater adjacent to a first portion of the multifunction chamber for adjusting a first portion of a sample to a first temperature, and a second heater adjacent to a second portion of multifunction chamber for adjusting a second portion of a sample to a second temperature, the second temperature being different from the first temperature. In one embodiment, the heater/cooler further includes a wiper element that moves the first portion of the sample to the second portion of the multifunction chamber while moving the second portion of the sample to the first portion of the multifunction chamber such that portions of the sample are under control of each of the heaters simultaneously. In one embodiment, the wiper element repeatedly moves portions of the sample to opposite portions of the multifunction chamber to thermocycle the sample. In one embodiment, the instrument further includes a translator mechanically coupled to at least one of the receptacle, the flexible container, or the heater/cooler to laterally align at least one portion of the multifunction chamber and/or the second-stage reaction zone relative to the first and second heater elements of the heater/cooler such that the at least one portion is under temperature control of at least one of the first or the second heater elements.

Described herein are:

Embodiment 1. A method for amplifying nucleic acids in a sample comprising:

providing a container comprising a multifunction chamber and a first reaction zone fluidly connected to the multifunction chamber, the container comprising therein magnetic particles and reagents for sample preparation, nucleic acid recovery, and a first-stage nucleic acid amplification reaction, wherein the magnetic particles and the reagents are fluidly connected to the multifunction chamber or the first reaction zone or both;

introducing the sample into the multifunction chamber;

performing at least two steps in the multifunction chamber, wherein the steps include:

(1) contacting the sample and the magnetic beads prior to lysis, (2) generating a lysate in the presence of the magnetic particles, (3) binding nucleic acids with the magnetic particles, (4) isolating the magnetic particles from the lysate, (5) performing at least one wash on the magnetic particles isolated from the lysate, and (6) amplifying nucleic acids in a first-stage nucleic acid amplification reaction.

Embodiment 2. The method of embodiment 1 wherein the multifunction chamber is provided with lysis particles.

Embodiment 3. The method of embodiment 1 or 2, wherein the steps performed in the multifunction chamber are selected from the group of:

steps (1) and (2);
steps (1), (2), and (3);
steps (1)-(4);
steps (2) and (3); and
steps (2), (3), and (4).

Embodiment 4. The method of embodiment 1 or 2, wherein the steps performed in the multifunction chamber are selected from the group of:

steps (3) and (4);
steps (3), (4), and (5);
steps (4), (5), and (6); and
steps (5) and (6).

Embodiment 5. The method of any of embodiments 1-4 wherein the performing step includes step (3) and step (3) further comprises applying heat to the sample while generating the lysate.

Embodiment 6. The method of any of embodiments 1-5 wherein the performing step includes step (2) wherein the lysate is generated under conditions for binding the nucleic acids to the magnetic particles.

Embodiment 7. The method of any of embodiments 1-6 wherein the performing step includes step (2) wherein the lysate is generated at a lysis temperature and the nucleic acids are recovered from the lysate at a controlled temperature, wherein the lysis temperature is in the range of 40-100° C., preferably 50-100° C., or more preferably 70-100° C., and wherein the controlled temperature is below the lysis temperature and is in the range of 0-60° C., preferably 0-50° C., or more preferably 0-40° C.

Embodiment 8. The method of embodiment 1 or 2, further comprising:

wherein the performing step includes steps (3) and (4) and step (4) further comprises moving the magnetic particles from the multifunction chamber to the first reaction zone, wherein the performing step includes step (5) and step (5) is performed in the first reaction zone, wherein the wash includes injecting a wash buffer into the first reaction zone, dispersing the magnetic beads in the wash buffer, recapturing the magnetic beads, and expelling the wash buffer, and wherein the performing step includes step (6) and step (6) is performed in the first reaction zone.

Embodiment 9. The method of any of embodiments 1-8, wherein the lysis particles remain in the multifunction chamber after performing steps (3) and (4).

Embodiment 10. The method of any of embodiments 1-9, further comprising adding nucleic acid amplification reagents to the first reaction zone after step (5), and wherein there is no eluting step prior to step (6).

Embodiment 11. The method of any of embodiments 1-10, the performing step including steps (3), (4), and (5), wherein:

steps (3) and (4) further comprise expelling the lysate to a waste chamber, and step (5) is performed in the multifunction chamber, wherein step (5) includes injecting a wash buffer into the multifunction chamber, dispersing the magnetic beads in the wash buffer, recapturing the magnetic beads, and expelling the wash buffer.

Embodiment 12. The method of any of embodiments 1-11 wherein step (6) is a first-stage multiplex nucleic acid amplification reaction in the multifunction chamber, wherein there is no eluting step prior to the amplifying step.

Embodiment 13. The method of any of embodiments 1-12 wherein the container further comprises a second-stage reaction zone fluidly connected to the multifunction chamber, the second-stage reaction zone comprising a plurality of second-stage reaction wells, each second-stage reaction well comprising a pair of primers configured for further amplification of the sample, the second-stage reaction zone configured for contemporaneous thermal cycling of all of the plurality of second-stage reaction chambers.

Embodiment 14. The method of any of embodiments 1-13, wherein the second-stage reaction zone is fluidly connected to the multifunction chamber via the first reaction zone.

Embodiment 15. The method of any of embodiments 1-14 wherein the performing step include step (6) and further comprising combining a portion of the first-stage nucleic acid amplification reaction with reagents for a second-stage nucleic acid amplification reaction to form a second-stage nucleic acid amplification mixture, filling each of the second-stage reaction wells with the second-stage nucleic acid amplification mixture, and performing a second-stage nucleic acid amplification reaction in plurality of second-stage reaction wells of the second-stage reaction zone to generate one or more amplicons.

Embodiment 16. The method of any of embodiments 1-16 further comprising identifying one or more organisms, if present in the sample, using the one or more amplicons.

Embodiment 17. The method of any of embodiments 1-16 wherein the flexible container further comprises a sample receiving chamber in fluid communication with the multifunction chamber.

Embodiment 18. The method of any of embodiments 1-17 further comprising collecting a sample with a sample swab, inserting the swab into the sample receiving chamber and sealing the sample receiving chamber with the swab therein, dispersing the sample in the sample receiving chamber with a sample lysis buffer injected into the sample receiving chamber, and transferring the sample and the sample lysis buffer into the multifunction chamber.

Embodiment 19. The method of any of embodiments 1-18 wherein the magnetic particles and reagents for sample preparation, nucleic acid recovery, and first-stage nucleic acid amplification are provided in one or more fluid-filled reagent blisters, in one or more dry reagent blisters, or a combination thereof.

Embodiment 20. The method of any of embodiments 1-19 wherein the performing step includes step (2) and further comprising subsequent to step (2), sequestering the lysis particles in the multifunction chamber away from the lysate.

Embodiment 21. The method of any of embodiments 1-20 wherein the performing step includes step (3) and further comprising sequestering the magnetic particles in the multifunction chamber subsequent to step (3).

Embodiment 22. A container for performing nucleic acid amplification on a sample in a closed system, the container comprising:

a first layer and a second layer defining a multifunction chamber therebetween, the container provided with magnetic particles and reagents for sample preparation, nucleic acid recovery, and a first-stage nucleic acid amplification reaction, wherein the magnetic particles are provided in a chamber that is fluidly connected to the multifunction chamber or are provided in the multifunction chamber, and wherein the reagents are provided in chambers that are fluidly connected to the multifunction chamber; and a second-stage reaction zone disposed between the first layer and the second layer and fluidly connected to the multifunction chamber, the second-stage reaction zone comprising a plurality of second-stage reaction chambers, each second-stage reaction chamber comprising a pair of primers configured for further amplification of the sample, the second-stage reaction zone configured for contemporaneous thermal cycling of all of the plurality of second-stage reaction chambers.

Embodiment 23. The container of embodiment 22, wherein the multifunction chamber is provided with cell lysis components and the magnetic particles.

Embodiment 24. The container of any of embodiments 22-23 wherein the cell lysis components comprise lysis particles.

Embodiment 25. The container of any of embodiments 22-24, wherein the container further comprises a sample lysis chamber in fluid communication with the multifunction chamber, wherein the sample lysis chamber is provided with cell lysis components and the magnetic particles, and the multifunction chamber is provided with magnetic bead wash components and first-stage nucleic acid amplification components.

Embodiment 26. The container of any of embodiments 22-25 further comprising a filter positioned between the sample lysis chamber and the multifunction chamber.

Embodiment 27. The container of any of embodiments 22-26, wherein the filter has a porosity sized to retain the lysis particles and allow the magnetic beads to pass through.

Embodiment 28. The container of any of embodiments 22-27, wherein a channel connects the sample lysis chamber and the multifunction chamber and the filter is positioned between the first layer and the second layer across the channel.

Embodiment 29. The container of any of embodiments 22-28, wherein the filter is wider than the channel.

Embodiment 30. The container of any of embodiments 22-29, wherein a channel extends between the sample lysis chamber and the multifunction chamber, and the filter is located in the sample lysis chamber adjacent the channel.

31. The container of any of embodiments 22-30, wherein the channel is smaller than the sample lysis chamber and the filter is wider than the channel.

Embodiment 32. The container of any of embodiments 22-31 wherein the magnetic particles are nucleic acid-binding magnetic particles.

Embodiment 33. The container of any of embodiments 22-32 further comprising a sample receiving chamber in fluid communication with the multifunction chamber.

Embodiment 34. The container of any of embodiments 22-33 wherein the sample receiving container comprises a sample collection swab.

Embodiment 35. The container of c any of embodiments 22-34 wherein the sample collection swab comprises an elongate shaft, wherein the sample receiving chamber and the elongate shaft of the swab are fabricated from chemically compatible materials that can be at least partially fused with a heat seal.

Embodiment 36. The container of any of embodiments 22-35 wherein the magnetic particles and the reagents are provided in one or more reagent blisters in fluid communication with the multifunction chamber.

Embodiment 37. The container of any of embodiments 22-36 wherein one or more of the reagent blisters are fluid-filled reagent blisters and are filled at the time of manufacture of the container.

Embodiment 38. The container of any of embodiments 22-37 wherein one or more of the reagent blisters comprise dry reagents disposed in the reagent blisters.

Embodiment 39. The container of any of embodiments 22-38 further comprising an openable seal between the reagent blisters and the multifunction chamber.

Embodiment 40. The container of any of embodiments 22-39 wherein the openable seal is a burstable seal.

Embodiment 41. The container of any of embodiments 22-40 wherein the openable seal is a tacked together film seal.

Embodiment 42. A self-contained reaction vessel, comprising
a first reaction zone fluidly connected to a second reaction zone, wherein the second reaction zone comprises:
a first layer, a card layer with a plurality of second-stage reaction wells formed therein, and a second layer,
wherein the first layer is disposed over and seals a first end of the plurality of second-stage reaction wells, and the second layer is disposed over and seals a second, opposite side of the plurality of second-stage reaction wells,
a fill channel fluidly connecting the first reaction zone to the plurality of second-stage reaction wells of the second reaction zone;
wherein the fill channel is formed at least in part as a space between the second layer and the card layer, and the fill channel further forms a convoluted flow path into each of the plurality of second-stage reaction wells so as to suppress fluid communication between wells in the second stage reaction zone.

Embodiment 43. The self-contained reaction vessel of embodiment 42, the fill channel comprising a channel formed in the card layer, the second layer, or a combination of the card layer and the second layer, wherein the fill channel individually fluidly connects all of the second-stage reaction wells to the first-stage reaction zone.

Embodiment 44. The self-contained reaction vessel of any of embodiments 42-43, further comprising a third layer bonded to the second layer, wherein the second layer comprises a pierced layer having a plurality of piercings fluidly connected to the plurality of second-stage reaction wells, and wherein the fill channel is formed as a space between the second and third layers.

Embodiment 45. The self-contained reaction vessel of any of embodiments 42-44, wherein the convoluted flow path for each second-stage reaction well comprises an opening in the second layer adjacent to but not aligned with a second-stage reaction well and in fluid communication with a cutout in the card layer adjacent to but not aligned with a second-stage reaction well.

Embodiment 46. The self-contained reaction vessel of any of embodiments 42-45, wherein the convoluted flow path for each second-stage reaction well comprises an opening in the second layer adjacent to but not aligned with a second-stage reaction well, the opening being in fluid communication with a substantially vertical cutout in the card layer extending adjacent to a second-stage reaction well from the second film layer to a substantially horizontal cutout in the card layer adjacent to the first layer and creating a fluid conduit from the opening to the substantially vertical cutout and into the second-stage reaction well.

Embodiment 47. The self-contained reaction vessel of any of embodiments 42-46, wherein the fill channel is heat sealable.

Embodiment 48. The self-contained reaction vessel of any of embodiments 42-47, wherein a single heat seal seals flow from a fill channel to multiple second-stage reaction wells and seals the second-stage reaction wells from each other.

Embodiment 49. The self-contained reaction vessel of any of embodiments 42-48, wherein the fill channel further comprises a dilution zone that includes a dilution well in the fill channel between the first and second reaction zones, wherein the dilution well is configured to receive a volumetric portion of a reaction product from the first reaction zone, combine the volumetric portion with a dilution medium to form a combined volumetric portion, and fill the plurality of second-stage reaction wells of the second reaction zone with the combined volumetric portion.

Embodiment 50. The self-contained reaction vessel of any of embodiments 42-49, the dilution zone further comprising a dilution blister in fluid communication with the dilution well, wherein the dilution blister is configured to receive the dilution medium, combine the volumetric portion with the dilution medium, and fill the plurality of second-stage reaction wells of the second reaction zone.

Embodiment 51. A self-contained reaction vessel, the self-contained reaction vessel comprising:
a sample lysis zone configured for lysis of cells or spores present in a sample,
a first reaction zone fluidly connected to the sample lysis zone, the first reaction zone nucleic acid configured for recovering nucleic acids from a lysed sample and for first-stage amplification of nucleic acids present in the,
a second-stage reaction zone fluidly connected to the first reaction zone, the second-stage reaction zone comprising a plurality of second-stage reaction wells, each second-stage reaction well comprising a pair of primers configured for further amplification of the sample, the second-stage reaction zone configured for contemporaneous thermal cycling of all of the plurality of second-stage reaction chambers, and
a plurality of liquid reagent blisters fluidly connected to one or more of the sample lysis zone, the first reaction zone, or the second-stage reaction zone, wherein liquid reagents are provided in the liquid reagent blisters at time of manufacture.

Embodiment 52. The self-contained reaction vessel of embodiment 51 wherein the sample lysis zone is provided with lysis particles configured for lysing cells or spores located in the sample and magnetic beads configured for recovering nucleic acids from a lysate.

Embodiment 53. The self-contained reaction vessel of any of embodiments 51-52, wherein the lysis particles, magnetic beads, and a lysis buffer are provided in one or more of the liquid reagent blisters that are fluidly connected to the sample lysis zone.

Embodiment 54. The self-contained reaction vessel of any of embodiments 51-53 wherein one of the liquid reagents is provided in a liquid reagent pack within one of the liquid reagent blisters.

Embodiment 55. The self-contained reaction vessel of any of embodiments 51-54, wherein the liquid reagent pack comprises a volume of liquid sealed between a first layer and a second layer.

Embodiment 56. The self-contained reaction vessel of any of embodiments 51-55, wherein at least one of the first layer or the second layer comprises a barrier film.

Embodiment 57. The self-contained reaction vessel of any of embodiments 51-56 further comprising an openable seal between the liquid reagent disposed in the liquid reagent blister and one or more of the sample lysis zone, the first reaction zone, or the second-stage reaction zone.

Embodiment 58. The self-contained reaction vessel of any of embodiments 51-57, wherein the openable seal is a burstable seal.

Embodiment 59. The self-contained reaction vessel of any of embodiments 51-58, wherein the openable seal is a tacked together film seal.

Embodiment 60. A system for performing nucleic acid amplification on a sample, the system comprising:
a reaction vessel that includes:
a first layer and a second layer defining a multifunction chamber therebetween, a second-stage reaction zone disposed between the first layer and the second layer and fluidly connected to the multifunction chamber, the second-stage reaction zone comprising a plurality of second-stage reaction chambers, each second-stage reaction chamber comprising a pair of primers configured for further amplification of the sample, the second-stage reaction zone configured for contemporaneous thermocycling of all of the plurality of second-stage reaction chambers; and
one or more reagent blisters formed between the first layer and the second layer in fluid communication with the multifunction chamber and the second-stage reaction zone, wherein magnetic particles are provided in a blister fluidly connected to the multifunction chamber or are provided in the multifunction chamber;
a thermocycling instrument that includes:
a receptacle for positioning the flexible container in the instrument;
a heater/cooler positionable in the instrument for heating and/or cooling one or more of the multifunction chamber and the second-stage reaction zone;
a cell lysis component configured for generating a lysate in the reaction vessel; and
a fluid movement component configured for moving fluids in the flexible container between at least the one or more reagent blisters, the multifunction chamber, and the second-stage reaction zone.

Embodiment 61. The system of embodiment 60, wherein the multifunction chamber is provided with cell lysis components and the magnetic particles.

Embodiment 62. The system of any of embodiments 60-61 wherein the container further comprises a sample lysis chamber in fluid communication with the multifunction chamber, wherein the sample lysis chamber is provided with cell lysis components and the magnetic particles, and the multifunction chamber is provided with magnetic bead wash components and first-stage nucleic acid amplification components.

Embodiment 63. The system of embodiments 60 or 62 wherein the instrument further comprises a magnet deployable in the instrument for isolating the magnetic beads in a portion of the multifunction chamber.

Embodiment 64. The system of any of embodiments 60-63 wherein the heater/cooler comprises a first heater adjacent to a first portion of the multifunction chamber for adjusting a first portion of a sample to a first temperature, and a second heater adjacent to a second portion of multifunction chamber for adjusting a second portion of a sample to a second temperature, the second temperature being different from the first temperature.

Embodiment 65. The system of any of embodiments 60-64 wherein the heater/cooler is mechanically associated with a wiper element that moves the first portion of the sample to the second portion of the multifunction chamber while moving the second portion of the sample to the first portion of the multifunction chamber such that portions of the sample are under control of each of the heaters simultaneously.

Embodiment 66. The system of any of embodiments 60-65 wherein the wiper element repeatedly moves portions of the sample to opposite portions of the multifunction chamber to thermocycle the sample.

Embodiment 67. The system of any of embodiments 60-66 wherein the instrument further comprises a translator mechanically coupled to at least one of the receptacle, the flexible container, or the heater/cooler to laterally align at least one portion of the multifunction chamber, the second-stage reaction zone, or both relative to the first and second heater elements of the heater/cooler such that the at least one portion of the multifunction chamber or the second-stage reaction zone is under temperature control of at least one of the first or the second heater elements.

Embodiment 68. The system of any of embodiments 60-67 wherein the instrument is configured to repeatedly align the at least one portion with the first heater element and then the second heater element for thermocycling a fluid sample in the at least one portion.

Embodiment 69. An array assembly comprising:
a plurality of wells arranged in an array;
a fluid fill channel in fluid communication with each of the plurality of wells,
at least one of the wells of the array comprising a reaction well with a first diameter and a sub-well recessed below a first surface of the array assembly with a second, smaller diameter, wherein the recessed sub-well is not fluidly connected to the fluid fill channel.

Embodiment 70. The array assembly of embodiment 69, the fluid fill channel comprising a plurality of branch channels in fluid communication with each of the plurality of wells, wherein the recessed sub-well is not fluidly connected to its branch channel.

Embodiment 71. The array assembly of any of embodiments 69-70, the sub-well being recessed below a second surface of the array, wherein the second surface of the array is opposite the first surface.

Embodiment 72. A method for spotting an array comprising:
providing an array assembly that includes a plurality of wells that are arranged in an array, wherein the array assembly and the plurality of wells do not include a backing layer prior to spotting reagents and/or reaction components to the plurality of wells;

positioning the array assembly in a spotting apparatus relative to a spotting assembly that includes a plurality of cannulae arranged in an array that corresponds to the wells of the array assembly, wherein each cannula is fluidly connected to a fluid reagent reservoir;

delivering a droplet of fluid to an end of each cannula;

contacting the droplets and the wells of the array to transfer the droplets to the array assembly; and evaporating fluid from the droplets to yield an array assembly having dried reagents in the wells.

Embodiment 73. The method of embodiment 72 wherein the spotting apparatus includes alignment pins, stops, a frame, or a combination thereof positioned to align the array assembly relative to the cannulae.

Embodiment 74. The method of any of embodiments 72-73 wherein two or more cannulae are fluidly connected to the same fluid reagent reservoir.

Embodiment 75. The method of any of embodiments 72-74 wherein each cannula is fluidly connected to a different fluid reagent reservoir.

Embodiment 76. The method of any of embodiments 72-75 further comprising:

extending the cannulae through the wells of the array assembly prior to the delivering step; and wherein the contacting step comprises retracting the cannula to contact the droplets and the wells of the array to transfer the droplets to the array assembly.

Embodiment 77. The method of any of embodiments 72-76 further comprising:

moving the array assembly relative to the cannulae to extend the cannulae through the wells of the array assembly prior to the delivering step; and wherein the contacting step includes retracting the array assembly relative to the cannulae to contact the droplets and the wells of the array to transfer the droplets to the array assembly.

Embodiment 78. A method of making a reaction pouch comprising:

providing an array assembly spotted according the method or one of embodiments 72-77;

inserting the array assembly into a preformed pocket between two or more film layers;

sealing the film layers to the array assembly to seal the film layers to a top and a bottom surface of the array assembly; and sealing the preformed pocket.

Embodiment 79. The method of embodiment 78 wherein the two or more film layers are laminated together and heat formed prior to positioning the array between the film layers to define defined areas selected from the group consisting of one or more reaction blisters, one or more reagent blisters, and one or more pockets.

Embodiment 80. The method of embodiment 78 wherein the two or more film layers are laminated together and heat formed after positioning the array between the film layers to define defined areas selected from the group consisting of one or more reaction blisters, one or more reagent blisters, and one or more pockets.

Embodiment 81. The method of embodiment 78 wherein the array pocket is fluidly connected to one or upstream fluid blisters so that the array can be flooded with fluid.

Embodiment 82. The method of embodiment 78, wherein the array assembly includes a fluid channel system and a vacuum channel system fluidly connected to each well of the array assembly.

Embodiment 83. A reaction container comprising:

a first layer of material and at least a second layer of material defining the reaction container;

a sample introduction blister and a dilution blister formed between the first and second layers of material, wherein the dilution blister is fluidly connected to the sample introduction blister, and one or more reaction wells fluidly connected to the sample introduction blister and one or more reaction wells fluidly connected to the dilution blister, wherein the dilution blister is configured to make a selected dilution of an aliquot of sample from the sample introduction blister, and wherein the one or more reaction wells include a reagent for performing an assay on the sample.

Embodiment 84. The reaction container of embodiment 83 wherein the dilution blister is provided with a selected volume fluid to perform a selected dilution of the sample added to the sample introduction blister.

Embodiment 85. The reaction container of any of embodiments 83-84 wherein reaction container further comprises a volumetric dilution well sized and dimensioned to receive a selected volume of fluid from a blister and combine it with a selected volume of a diluent to make a diluted sample.

Embodiment 86. The reaction container of any of embodiments 83-85 wherein reaction container further comprises a channel sized and dimensioned to receive a selected volume of fluid from a blister and combine it with a selected volume of a diluent to make a diluted sample.

Embodiment 87. The reaction container of any of embodiments 83-86 wherein the one or more reaction wells contain the same reagent.

Embodiment 88. The reaction container of any of embodiments 83-87 wherein the one or more reaction wells contain a different reagent.

Embodiment 89. The reaction container of any of embodiments 83-88 wherein at least one of the reaction wells comprises a reaction well with two or more co-fillable sub-wells fluidly connected to the same sample blister.

Embodiment 90. The reaction container of any of embodiments 83-90 further comprising a known standard solution blister fluidly connected to one or more reaction wells that include a reagent for performing an assay on the standard solution for providing a reference for the sample the sample introduction blister and the dilution blister.

Embodiment 91. An array assembly, comprising:

a plurality of wells arranged in an array;

a fluid fill channel comprising a plurality of branch channels in fluid communication with each of the plurality of wells, wherein at least one of the wells of the array comprises a reaction well with two or more co-fillable sub-wells fluidly connected to the same branch channel.

Embodiment 92. The array assembly of embodiment 91 wherein the two or more sub-wells each comprise a separate reagent.

Embodiment 93. The array assembly of any of embodiments 91-92 wherein the separate reagents in the sub-wells are combinable when the reaction well is filled with fluid.

Embodiment 94. The array assembly of any of embodiments 91-93 further comprising a card layer having the plurality of wells formed therein.

Embodiment 95. A method for sealing a reaction container comprising:

providing a reaction container comprising a sample receiving chamber and a first reaction zone fluidly connected to the sample receiving zone;

providing a sample collection swab comprising an elongate shaft;

inserting the swab into the sample receiving chamber; and applying a seal to the sample receiving chamber across the elongate shaft of the swab to seal the sample receiving chamber.

Embodiment 96. The method of embodiment 95 wherein the seal is a heat seal that at least partially fuses the sample receiving chamber and the elongate shaft of the sample collection swab at the seal.

Embodiment 97. The method of any of embodiments 95-96 wherein the shaft has a non-circular cross-section.

Embodiment 98. The method of any of embodiments 95-97 further comprising applying additional seal across the elongate shaft to divide the sample receiving chamber into a plurality of chambers that are fluidly connected to the first reaction zone.

Embodiment 99. The method of any of embodiments 95-98 wherein the sample receiving chamber and the elongate shaft of the swab are fabricated from chemically compatible materials that can be at least partially fused with a heat seal.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description that follows, and in part will be obvious from the description, or may be learned by the practice of the invention. The features and advantages may be realized and obtained by means of the instruments and combinations particularly pointed out in the appended claims. These and other features will become more fully apparent from the following description and appended claims, or may be learned by the practice of the invention as set forth hereinafter.

BRIEF DESCRIPTION OF THE FIGURES

FIG. 5A shows another embodiment of a pouch having flexible and rigid portions.

FIG. 5B illustrates a cross-sectional view of a portion of the pouch of FIG. 5A along the line B-B.

FIG. 5C illustrates a cross-sectional view of a portion of the pouch of FIG. 5A along the line C-C.

FIGS. 9A-9E illustrate a series of wells that can be included in a high density array that can be filled under standard atmospheric pressure conditions.

FIG. 10A illustrates a second-stage array showing one embodiment of a point-of-use array evacuation system.

FIG. 10B is a cross-sectional view of a portion of FIG. 10A along the line B-B.

FIG. 12A illustrates an embodiment of a liquid reagent packet that may be included in one or more of the pouches described herein.

FIG. 12B is a cross-sectional view of a portion of FIG. 12A along the line B-B.

FIG. 12C illustrates another embodiment of a liquid reagent packet that may be included in one or more of the pouches described herein.

FIG. 12D illustrates a cross-sectional view of another embodiment of a liquid reagent packet that may be included in one or more of the pouches described herein.

FIG. 15A schematically illustrates a pouch with two reaction blisters and an absorbent member disposed in a channel between the reaction blisters.

FIGS. 15B and 15C illustrate a cut-away view along line B-B of FIG. 15A of the absorbent member in an expanded and compressed state, respectively.

FIGS. 24A-24F illustrate a method for spotting chemistry into the wells of an array.

FIG. 36 depicts the increase in florescence in the wells of the second-stage PCR array as a function of cycle number. FIGS. 37 and 38 depict the results of a melting experiment to ensure that the product being amplified is the correct product. FIG. 37 is a raw melting curve and FIG. 38 depicts a negative first derivative (dF/dt) of the melting curve.

FIG. 39 illustrates the temperature response with an 8 sec. cycle time (4 sec. holds at each temperature), FIG. 40 illustrates another temperature response experiment with an 8 sec. cycle time, FIG. 41 illustrates the temperature response with an 4 sec. cycle time (2 sec. holds at each temperature), and FIG. 42 illustrates the temperature response with a 2 sec. cycle time (1 sec. holds at each temperature).

FIGS. 43A-43D illustrate cross-sectional views of several examples of swab shafts that may be sealed in a sample receiving chamber.

FIGS. 44A and 44B illustrate cross-sectional views of a sample receiving chamber and a swab shaft before sealing across the shaft (FIG. 44A) and after sealing across the shaft (FIG. 44B).

DETAILED DESCRIPTION

Figure 1:
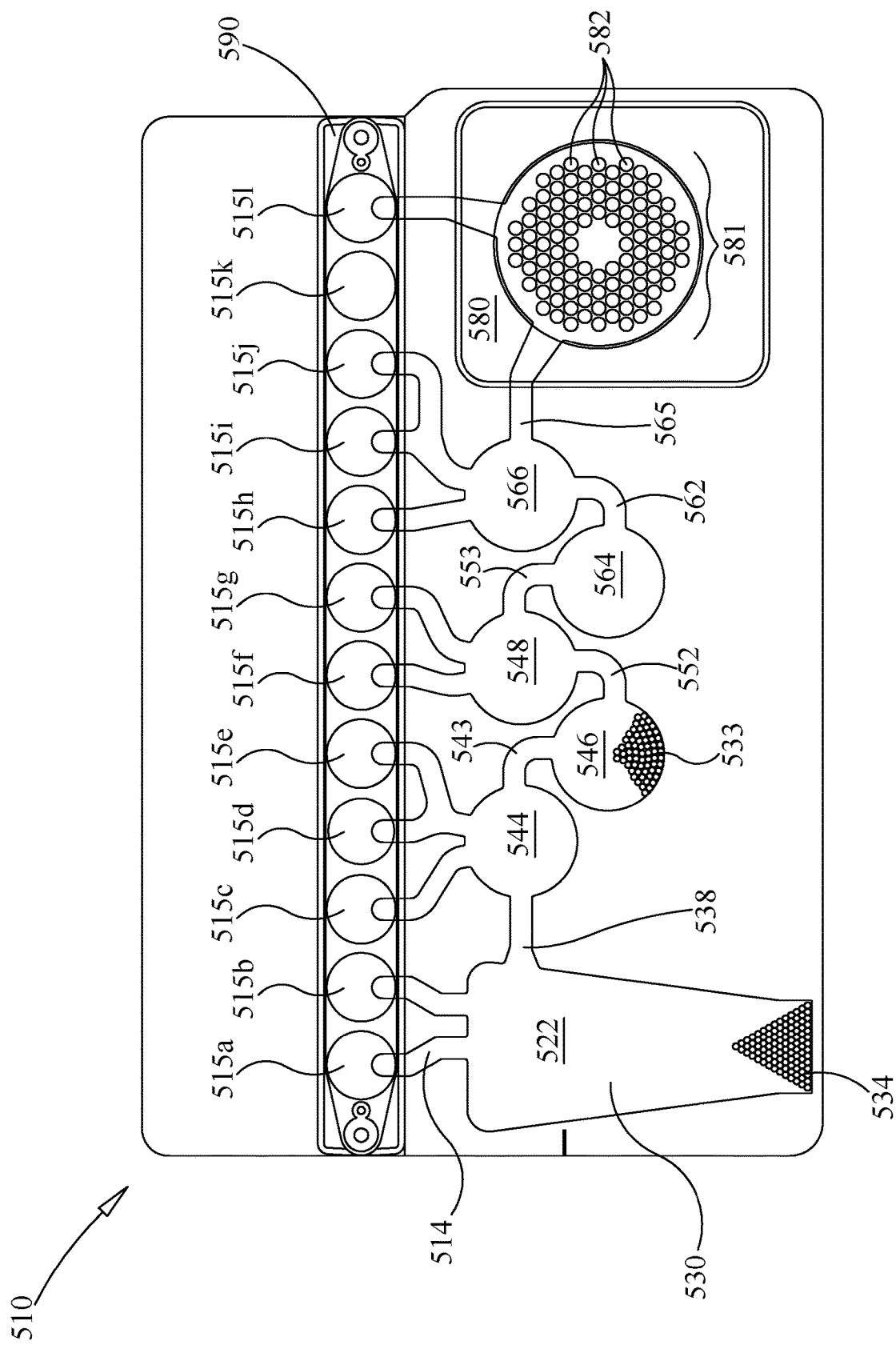
FIG. 1 shows a flexible pouch useful for self-contained PCR.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference for in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatuses, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within that implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal, including, but not limited to, a human animal; a cell (either within a subject (e.g., a human or non-human animal), taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids. Samples may also include environmental samples such as, but not limited to, soil, water (fresh water, waste water, etc.), air monitoring system samples (e.g., material captured in an air filter medium), surface swabs, and vectors (e.g., mosquitos, ticks, fleas, etc.).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, mRNA, rRNA, cDNA, gDNA, ssDNA, dsDNA, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically to occur at about a melting temperature (Tm) minus 5° C. (i.e. 5° below the Tm of the probe). Functionally, high stringency conditions are used to identify nucleic acid sequences having at least 80% sequence identity.

By "lysis particles" is meant various particles or beads for the lysis of cells, viruses, spores, and other material that may be present in a sample. Various examples use Zirconium ("Zr") silicate or ceramic beads, but other lysis particles are known and are within the scope of this term, including glass and sand lysis particles. The term "cell lysis component" may include lysis particles, but may also include other components, such as components for chemical lysis, as are known in the art.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles, doubling time, or crossing point (Cp), and additional reaction time may be added where additional PCR cycles are added in the embodiments described herein. It is understood that protocols may need to be adjusted accordingly.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", "amplification container", or the like are used herein, these terms are meant to encompass wells, tubes, and various other reaction containers, as are used in these amplification systems. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly. While many embodiments herein use a multiplex reaction for the first-stage amplification, it is understood that this is illustrative only, and that in some embodiments the first-stage amplification may be singleplex. In one illustrative example, the first-stage singleplex amplification targets housekeeping genes, and the second-stage amplification uses differences in housekeeping genes for identification. Thus, while various embodiments discuss first-stage multiplex amplification, it is understood that this is illustrative only.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515a through 515l, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, Utah). However, it is understood that the pouch embodiment is illustrative only.

While other containers may be used, illustratively, pouch 510 may be formed of two layers of a flexible plastic film or other flexible material such as polyester, polyethylene terephthalate (PET), polycarbonate, polypropylene, polymethylmethacrylate, mixtures, combinations, and layers thereof that can be made by any process known in the art, including extrusion, plasma deposition, and lamination. For instance, each layer can be composed of one or more layers of material of a single type or more than one type that are laminated together. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding and low protein binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington Del.) of about 0.0048 inch (0.1219 mm) thick and polypropylene films of 0.001-0.003 inch (0.025-0.076 mm) thick perform well. Illustratively, pouch 510 may be made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of the pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material. Thus, it is understood that when the terms "flexible pouch" or "flexible sample container" or the like are used, only portions of the pouch or sample container need be flexible.

Illustratively, a plastic film may be used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Likewise, the plastic film(s) used for pouch 510 may be cut and welded together using a laser cutting and welding device. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction may be hydrated by an aqueous sample. If the aqueous sample has been heated prior to hydration, this creates the conditions for a true hot-start PCR and reduces or eliminates the need for expensive chemical hot-start components. In another embodiment, components may be provided in powder or pill form and are placed into blisters prior to final sealing.

Pouch 510 may be used in a manner similar to that described in U.S. Pat. No. 8,895,295. In one illustrative embodiment, a 300 µl mixture comprising the sample to be tested (100 µl) and lysis buffer (200 µl) may be injected into an injection port (not shown) in fitment 590 near entry channel 515a, and the sample mixture may be drawn into entry channel 515a. Water may also be injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l. Illustrative methods and devices for injecting sample and hydration fluid (e.g. water or buffer) are disclosed in U.S. Patent Application No. 2014-0283945, herein incorporated by reference in its entirety, although it is understood that these methods and devices are illustrative only and other ways of introducing sample and hydration fluid into pouch 510 are within the scope of this disclosure. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

After injection, the sample may be moved from injection channel 515a to lysis blister 522 via channel 514. Lysis blister 522 is provided with beads or particles 534, such as ceramic beads or other abrasive elements, and is configured for vortexing via impaction using rotating blades or paddles provided within the FilmArray® instrument. Bead-milling, by shaking, vortexing, sonicating, and similar treatment of the sample in the presence of lysis particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses. In another embodiment, a paddle beater using reciprocating or alternating paddles, such as those described in PCT/US2017/044333, herein incorporated by reference in its entirety, may be used for lysis in this embodiment, as well as in the other embodiments described herein.

Figure 2:
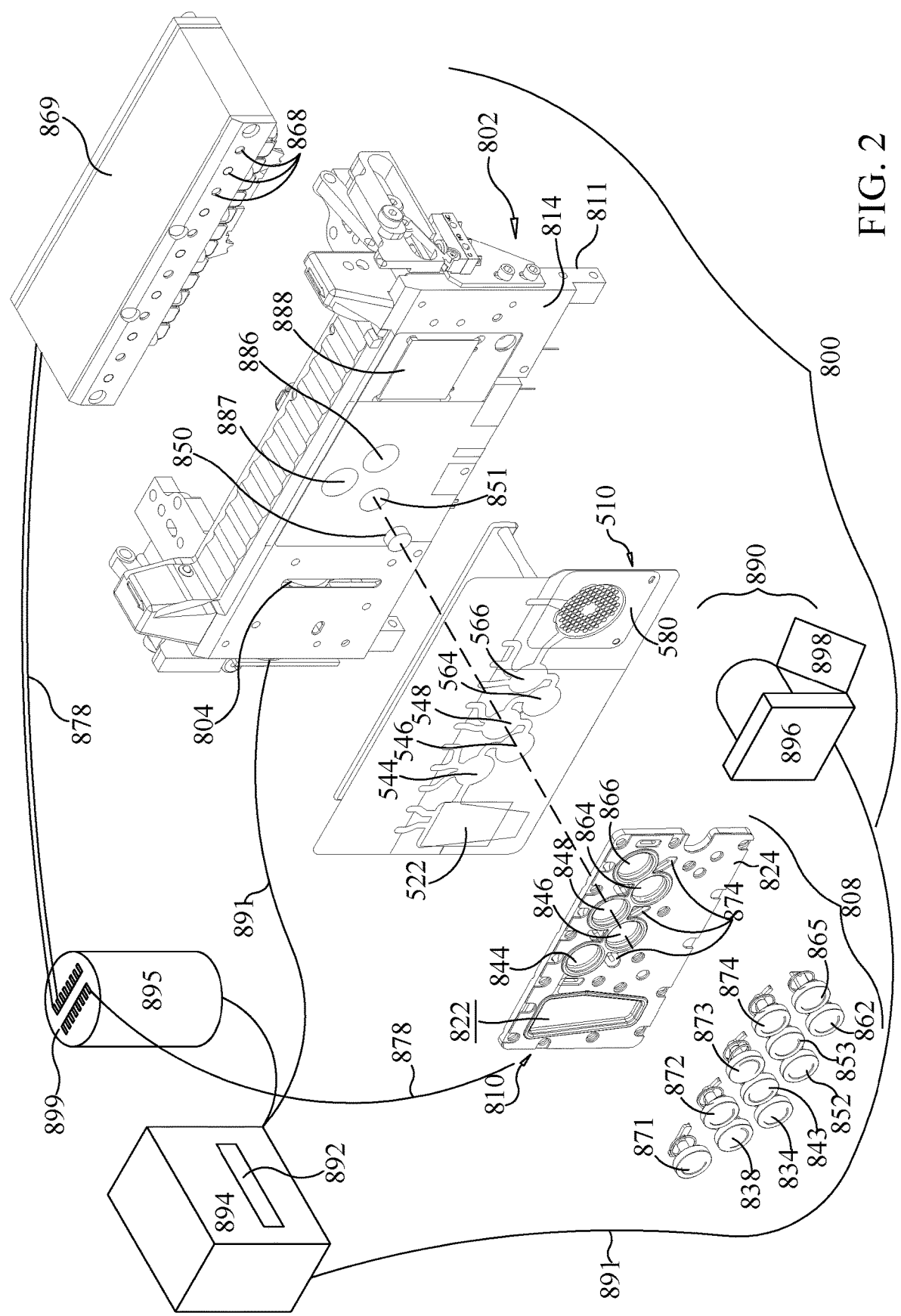
FIG. 2 is an exploded perspective view of an instrument for use with the pouch of FIG. 1, including the pouch of FIG. 1.
Figure 4:
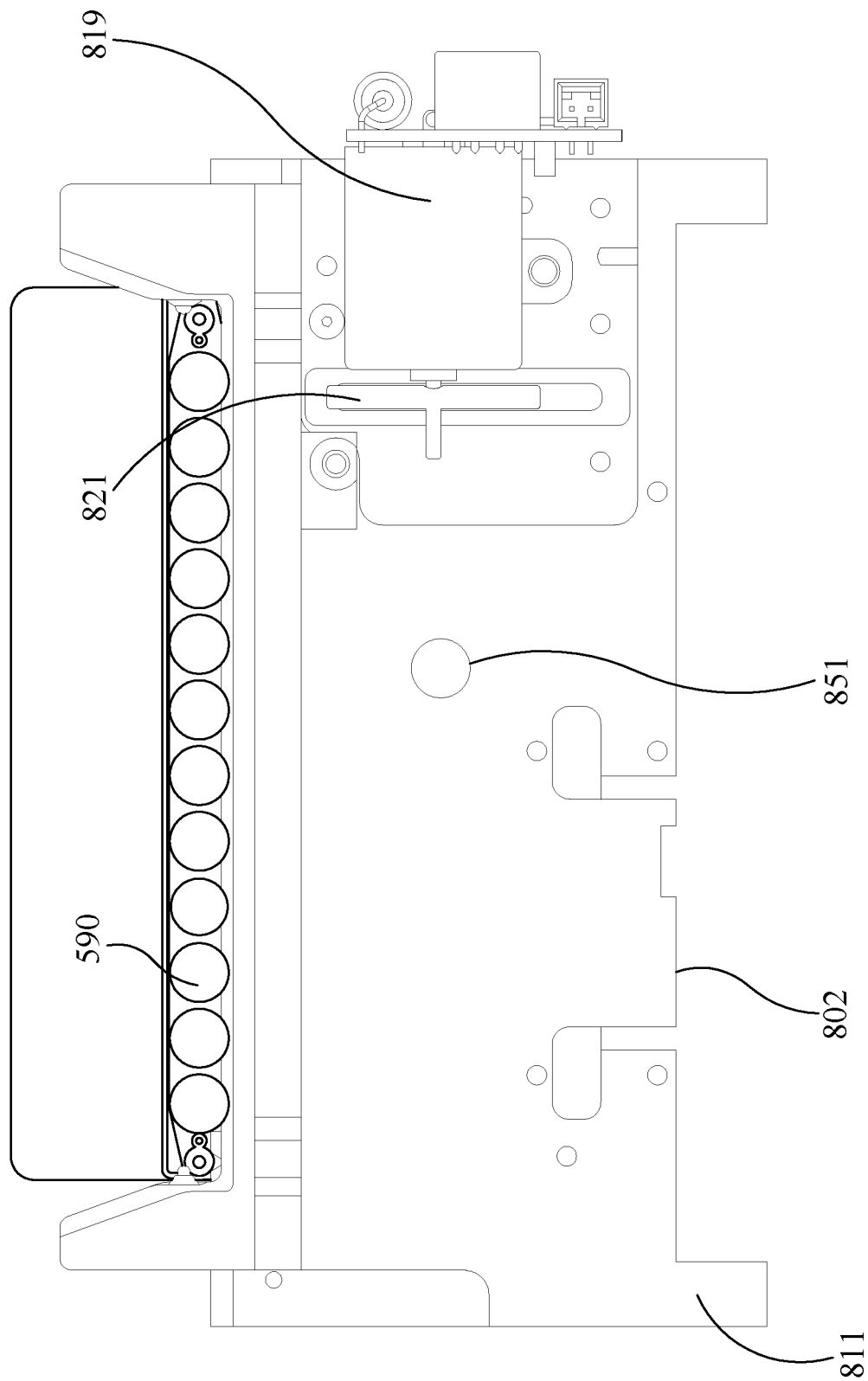
FIG. 4 shows a motor used in one illustrative embodiment of the instrument of FIG. 2.

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, another structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample. In some embodiments, chemicals or heat may be used in addition to or instead of mechanical lysis.

Once the sample material has been adequately lysed, the sample is moved to a nucleic acid extraction zone, illustratively through channel 538, blister 544, and channel 543, to blister 546, where the sample is mixed with a nucleic acid-binding substance, such as silica-coated magnetic beads 533. Alternatively, magnetic beads 533 may be rehydrated, illustratively using fluid provided from one of the entry channel 515c-515e, and then moved through channel 543 to blister 544, and then through channel 538 to blister 522. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. If incubation takes place in blister 522, multiple portions of the solution may need to be moved to blister 546 for capture. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515f is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, a reverse transcription (RT) step may be performed prior to or simultaneously with the first-stage multiplex PCR. First-stage multiplex PCR temperature cycling in the FilmArray® instrument is illustratively performed for 15-20 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in U.S. Pat. Pub. No. US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515i. Alternatively, a dilution buffer from 515i may be moved to blister 566 then mixed with the amplified sample in blister 564 by moving the fluids back and forth between blisters 564 and 566. If desired, dilution may be repeated several times, using dilution buffer from injection channels 515j and 515k, or injection channel 515k may be reserved, illustratively, for sequencing or for other post-PCR analysis, and then adding second-stage PCR master mix from injection channel 515h to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

In one embodiment, the illustrative second-stage PCR master mix is incomplete, lacking primer pairs, and each of the 102 second-stage wells 582 is pre-loaded with a specific PCR primer pair. In other embodiments, the master mix may lack other components (e.g., polymerase, $Mg^{2+}$, etc.) and the lacking components may be pre-loaded in the array. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously or individually thermal cycled, illustratively with one or more Peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
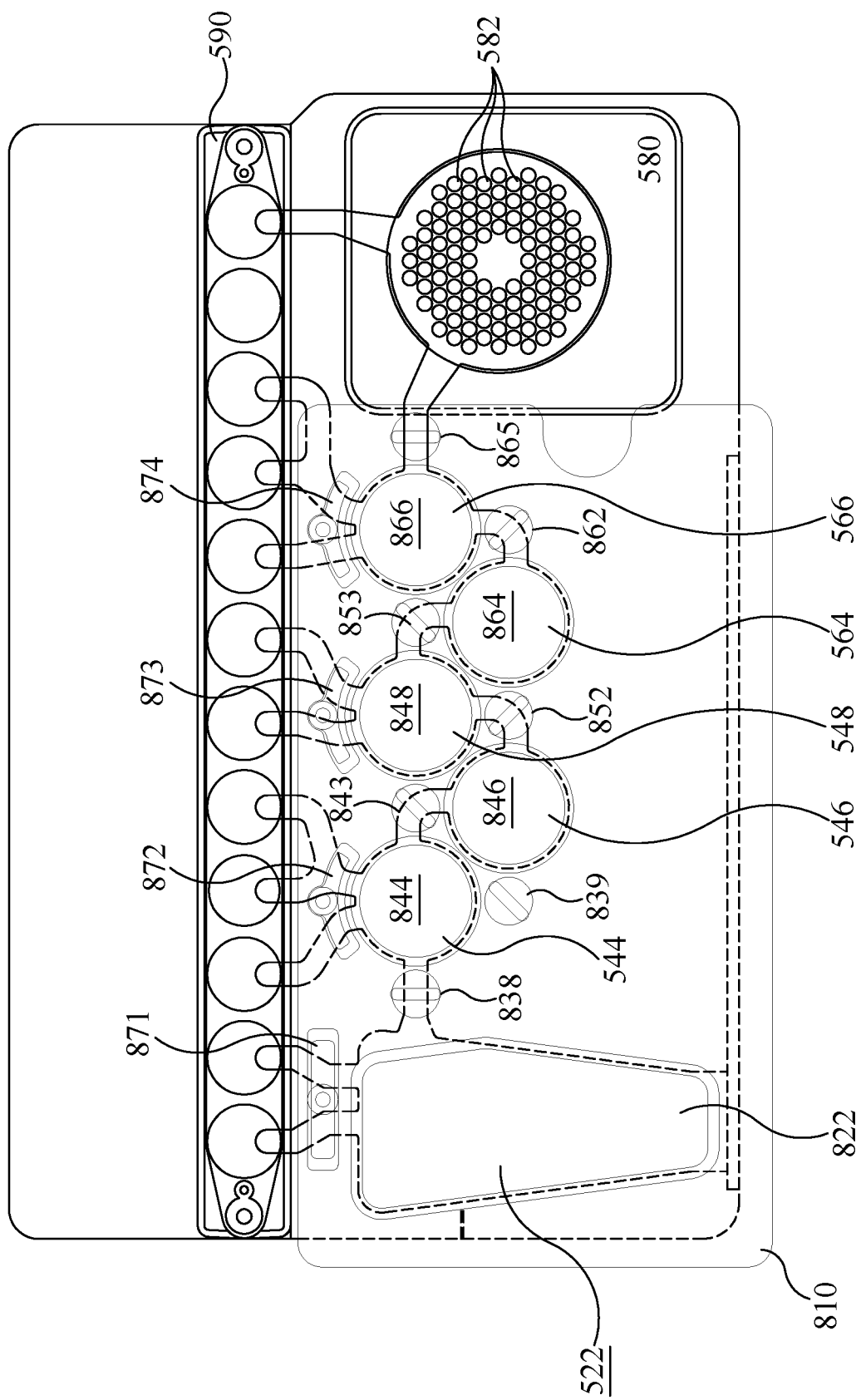
FIG. 3 shows the pouch of FIG. 1 along with the bladder components of FIG. 2.

When pneumatic pressure is used to move materials within pouch 510, in one embodiment, a "bladder" may be employed. The bladder assembly 810, a portion of which is shown in FIGS. 2-3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention. Alternatively, an array or mechanical actuators and seals may be used to seal channels and direct movement of fluids between blisters. A system of mechanical seals and actuators that may be adapted for the instruments described herein is described in detail in PCT/US2017/044333, the entirety of which is already incorporated by reference.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of Taq polymerase enzyme, adjustments in $MgCl_2$ concentration, adjustments in primer concentration, addition of engineered enzymes that are resistant to inhibitors, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2-3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned such that a small number of actuators could be used for several of the processing stations including sample disruption, nucleic-acid capture, first and second-stage PCR, and processing stations for other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Turning back to FIG. 2, each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention. Similar pneumatic control may be provided, for example, in the instrument of FIGS. 28A and 28B, for control of fluid movement in the pouches described herein, or other actuators, servos, or the like may be provided.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is fully retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required. It is understood that similar magnets and methods for activating the magnets may be used in the embodiments of FIGS. 28A and 28B.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of temperature control elements are mounted on a second side 814 of support 802. As used herein, the term "temperature control element" refers to a device that adds heat to or removes heat from a sample. Illustrative examples of a temperature control element include, but are not limited to, heaters, coolers, Peltier devices, resistive heaters, induction heaters, electromagnetic heaters, thin film heaters, printed element heaters, positive temperature coefficient heaters, and combinations thereof. A temperature control element may include multiple heaters, coolers, Peltiers, etc. In one aspect, a given temperature control element may include more than one type of heater or cooler. For instance, an illustrative example of a temperature control element may include a Peltier device with a separate resistive heater applied to the top and/or the bottom face of the Peltier. While the term "heater" is used throughout the specification, it is understood that other temperature control elements may be used to adjust the temperature of the sample.

As discussed above, first-stage heater 886 may be positioned to heat and cool the contents of blister 564 for first-stage PCR. As seen in FIG. 2, second-stage heater 888 may be positioned to heat and cool the contents of second-stage blisters 582 of array 581 of pouch 510, for second-stage PCR. It is understood, however, that these heaters could also be used for other heating purposes, and that other heaters may be included, as appropriate for the particular application.

As discussed above, while Peltier devices, which thermocycle between two or more temperatures, are effective for PCR, it may be desirable in some embodiments to maintain heaters at a constant temperature. Illustratively, this can be used to reduce run time, by eliminating time needed to transition the heater temperature beyond the time needed to transition the sample temperature. Also, such an arrangement can improve the electrical efficiency of the system as it is only necessary to thermally cycle the smaller sample and sample vessel, not the much larger (more thermal mass) Peltier devices. For instance, an instrument may include multiple heaters (i.e., two or more) at temperatures set for, for example, annealing, extension, denaturation that are positioned relative to the pouch to accomplish thermal cycling. Two heaters may be sufficient for many applications. In various embodiments, the heaters can be moved, the pouch can be moved, or fluids can be moved relative to the heaters to accomplish thermal cycling. Illustratively, the heaters may be arranged linearly, in a circular arrangement, or the like. Types of suitable heaters have been discussed above, with reference to first-stage PCR.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible. The embodiment for second-stage heaters shown in FIG. 18 provides the heaters on the opposite side of pouch 510 from that shown in FIG. 2. Such orientation is illustrative only and may be determined by spatial constraints within the instrument. Provided that second-stage reaction zone 580 is provided in an optically transparent material, photodetectors and heaters may be on either side of array 581.

As shown, a computer 894 controls valves 899 of compressed air source 895, and thus controls all of the pneumatics of instrument 800. In addition, many of the pneumatic systems in the instrument may be replaced with mechanical actuators, pressure applying means, and the like in other embodiments. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Other instruments known in the art teach PCR within a sealed flexible container. See, e.g., U.S. Pat. Nos. 6,645,758, 6,780,617, and 9,586,208, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. Still, it is understood that the pouch contents could be removed for further testing.

Turning back to FIG. 2, instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Illustrative heaters include Peltiers and other block heaters, resistive heaters, electromagnetic heaters, and thin film heaters, as are known in the art, to thermocycle the contents of blister 864 and second-stage reaction zone 580. Bladder plate 810, with bladders 822, 844, 846, 848, 864, 866, hard seals 838, 843, 852, 853, and seals 871, 872, 873, 874 form bladder assembly 808, which may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

Self-Contained Reaction Vessels

FIG. 5A shows another illustrative embodiment of a pouch 5000 (also referred to herein as a 'science card') that may be used in various embodiments, or may be reconfigured for various embodiments described herein for PCR, microbial testing, or for a variety of other tests. The pouch 5000 may be configured for use in an instrument described in PCT/US2017/18748, herein incorporated by reference, or in a variety of other instruments. The illustrative pouch 5000 of FIG. 5A includes a number of zones or blisters where sample preparation, nucleic acid amplification, and detection can occur. The illustrative pouch 5000 may include a sample preparation blister 5005 where a sample containing nucleic acids to be amplified and analyzed may be introduced into the pouch 5000, a first-stage PCR blister 5010, a volumetric dilution well 5015 for measuring a portion of the product from first-stage PCR prior to second-stage PCR, and a second-stage PCR array 5081 that includes a number of individual reaction wells 5082. The volumetric well 5015 may also be fluidly coupled to blisters 5020 and 5025, where reagents for second-stage PCR may be introduced and mixed with the contents of the dilution well 5015. Thus, a specific volume (e.g., 1-5 µl) of the product of the first-stage nucleic acid amplification reaction (e.g., a PCR reaction) may be dispensed into the volumetric dilution well 5015 and combined with a specific volume of diluent (e.g., 100 µl) to achieve a more precise dilution of the first-stage PCR amplicon prior to filling the array for the second-stage PCR reaction. In one example, a sample for second-stage PCR may be prepared by repeatedly mixing the contents of volumetric well 5015 with reagents for second-stage PCR between blisters 5020 and 5025. The second-stage array 5081 may also be fluidly connected to a waste receptacle 5035. Alternatively, blister 5010 may be used for both sample preparation and first-stage PCR and blister 5005 may be used as a waste receptacle for, for example, sample preparation waste(s). Other arrangements are possible.

Blisters 5005, 5010, 5020, and 5025, dilution well 5015, and second-stage array 5081 may be fluidly connected by channels 5050a-5050e. Sample and reagent may be entered into the pouch 5000 via entry channels 5040a-5040f and entry ports 5045a-5045f, which may be peelable, frangible, self-sealable, capped, heat-sealable, one-way, or other types of entry ports as are known in the art. Alternatively, pouch 5000 may be fitted with a device similar in form to fitment 590 of FIG. 1 for introduction of sample and reagents into the pouch 5000. In addition, the pouch 5000 may include dehydrated (e.g., freeze dried) reagents in a fitment or a similar structure that may be hydrated with a suitable hydration buffer prior to use of the pouch. In yet another embodiment, liquid reagents may be provided in pouch 5000.

In one embodiment, the pouch 5000 may be fabricated from a number of layers of material (layers of the same material or layers of different types of material) that are sealed together to form the pouch 5000. In FIGS. 5B and 5C, cutaway views are shown along the lines B-B and C-C illustrating layers of material that may be used to fabricate different parts of the pouch 5000. In one region of the pouch 5000 illustrated in FIG. 5B, the illustrative pouch 5000 may be fabricated from a first layer of film 5090 that is bonded to a second layer of film 5098. Layers 5090 and 5098 may be bonded together by any conventional means known in the art such as, but not limited to, adhesive, heat and pressure, sonic welding, or laser welding. FIG. 5B also illustrates that a blister or a channel (e.g., channel 5040c) may be formed in the pouch 5000 by leaving an open area between the film layers 5090 and 5098 and defining the boundaries of the open area with sealed margins along the opening—an illustrative weld is shown at 5084 in FIGS. 5A and 5B. FIG. 5C illustrates another region of the pouch 5000 that includes a thick card material that may be used to form the wells of the second-stage array 5081. This region of the illustrative pouch 5000 may be fabricated from a first film layer 5090, a pressure sensitive adhesive layer 5092, a card layer 5094, a second pressure sensitive adhesive layer 5096, and a second film layer 5098. In one illustrative example, the wells 5082 of the second-stage array 5081 may be formed in the card layer 5094. In an alternative to forming the channels (e.g., channel 5040c) and blisters (e.g., blister 5005) by leaving open space between the film layers (e.g., film layers 5090 and 5098) as illustrated in FIG. 5B, the card 5094 layer could be extended and the blisters and/or the channels could be formed by making appropriate cutouts in the card layer 5094. Likewise, channels 5050a-5050e and entry channels 5040a-5040f may be formed by making appropriate cutouts in the either the first or second pressure sensitive adhesive layers 5092 and 5096. One will appreciate that other configurations are possible. It is understood that while the illustrative blister areas are flexible, the card layer 5094 optionally may be less flexible and may be rigid, and still be part of a flexible sample container. Thus, it is understood that a "flexible pouch" need only be flexible in certain zones. Alternatively or in addition, flow channels between the blister areas can be formed by adding another film layer, tubing, or rigid layer above film layer 5090 or below film layer 5098 and welding the layers together, leaving open blister areas and channels between the layers.

While other materials may be used, illustratively, the film layers of pouch 5000 may be formed from a flexible plastic film or other flexible material similar to the pouch 510 described in FIG. 1. For instance, pouch 5000 may be fabricated from materials such as, but not limited to, such as polyester, polyethylene terephthalate (PET), polycarbonate, polypropylene, polymethylmethacrylate, combinations, mixtures, and laminated layers thereof that can be made by any process known in the art, including extrusion, plasma deposition, and lamination. Similar materials (e.g., polycarbonate) may be used for the card layer 5094. Other materials, including metal foils or plastics with aluminum lamination, may also be used. Other barrier materials are known in the art that can be sealed together to form the blisters and channels. If plastic film is used, the layers may be bonded together, illustratively by heat sealing or laser welding. Illustratively, the material has low nucleic acid binding and low protein binding capacity. If fluorescence detection is used, optically transparent material may be used in the appropriate areas of the pouch (e.g., in the vicinity of the second-stage array).

Pouch 5000 may be used in a manner similar to that described for pouch 510 and/or in a manner similar to that described in U.S. Pat. No. 8,895,295. Referring again to FIG. 5A, two alternative sequences for filling the pouch, preparing a sample, performing first-stage PCR, and performing second-stage PCR are described. In a first example method, sample preparation and first-stage PCR may be performed in separate blisters. This is referred to herein as the "three-zone method," with the three zones being sample preparation, first-stage PCR, and second-stage PCR. In the following examples describing the "three zone method" and the "two-zone method," one will appreciate that pouch 5000 is one embodiment of a pouch and that other pouch configurations (e.g., pouch 510 of FIG. 1, pouch 7000 of FIG. 7, pouch 10000 of FIGS. 11A and 11B, pouch 3900 of FIGS. 17A and 17B, pouch 4000 of FIG. 17C, or pouch 21000 of FIG. 28A) may be adapted to the three- and/or two-zone methods.

In a first step, a sample is injected into blister 5005 via fill channel 5040a. In one embodiment, cells, viruses, and the like may be lysed in blister 5005 using the wiping system described in detail elsewhere herein. Alternatively, cell lysis may be accomplished with an alternative lysis device such as, but not limited to, a sonication device, a bead beater, a paddle beater, or by chemical lysis. Optionally, lysis may be aided by heating the sample (e.g., to about 70-90° C.) with one or more heater elements of the heater assembly described in detail elsewhere herein. Following lysis, the sample may be cooled with a thermoelectric cooler element (i.e., a Peltier element) to a temperature in a range of about 0° C. to about 20° C. (e.g., about 10-15° C.) to aid in nucleic acid recovery with, for example, silica-coated magnetic beads. Other cooler elements include, but are not limited to, fluid or gas heat exchange elements, fan cooled heat sinks, heat pipes, condensation units, and the like.

Magnetic beads may be injected into blister 5005 via fill channel 5040a or 5040b for use in recovering nucleic acids from the lysate. Alternatively, cells to be lysed, lysis particles, magnetic beads, lysis buffer, and the like may be injected together or sequentially into blister 5005 prior to lysis, or magnetic beads may be provided in blister 5005 prior to use. Illustratively, the magnetic beads and the lysate may be mixed cold (e.g., in a range of about 0-10° C., illustratively by adjusting the temperature of one of the heaters). Once the magnetic beads and the lysate have been thoroughly mixed for a sufficient time, the magnetic beads may be gathered in blister 5005 with a magnet illustratively provided in the instrument and the spent lysate may be sent to liquid waste via channel 5040b. Then wash buffer may be injected via fill channel 5040a. The wash buffer and the magnetic beads may be mixed cold (e.g., in a range of about 0-10° C.). The magnetic beads may be gathered again and the spent wash buffer may be flushed to liquid waste via channel 5040b. The wash cycle may be repeated at least one more time. Following the wash, an elution buffer (optionally plus first-stage PCR primers) may be injected into blister 5005 via fill channel 5040a. The elution buffer (plus first-stage PCR primers) and the magnetic beads optionally may be mixed hot (e.g., at about 70-90° C.), illustratively, under control of one or more heaters. It is understood that heating and cooling during lysis and/or washing is illustrative only, and that in some embodiments, temperature need not be regulated during these steps. It is also understood that controlling the temperature during lysis and/or washing may be included in methods incorporating other pouch embodiments described herein or in other sample vessels.

For first-stage PCR, PCR master mix (e.g., a polymerase, dNTPs, and other amplification components known in the art) may be injected into blister 5010 via fill channel 5040c. The PCR master mix may be heated (e.g., to about 57° C.) prior to introduction of the eluate from the magnetic beads, thereby providing a physical "hot-start." In blister 5005, the magnetic beads may be gathered again and the eluate may be sent to blister 5010 via channel 5050*a*.

In one embodiment, first-stage PCR may be performed in blister 5010 with rotary movement of a wiper system illustrated in FIGS. 18-21 and described further in PCT/US2017/18748, already incorporated by reference, illustratively under temperature control of two heaters. Alternatively, first-stage PCR thermocycling may be performed by translating a heater assembly or the pouch 5000 so that blister 5010 may be under control of one heater and then another of a heater assembly that includes two different heaters at two different temperatures (e.g., at an annealing and at a denaturation temperature). The channels leading into and out of blister 5010 may be closed, illustratively with hard seals similar to those described in reference to FIGS. 2 and 3, during first stage PCR. In some embodiments, it may be possible to speed up first-stage PCR in the pouch by employing a volume reduction protocol. For instance, a volume reduction protocol may include performing several cycles (e.g., 5-10) of PCR with an initial volume (e.g., ~100 µL) in blister 5010, purging approximately half the volume of blister 5010, performing several more cycles of PCR (e.g., 5-10), and again purging approximately half the volume of blister 5010. Volume reduction can reduce the cycle time for a PCR reaction because smaller volumes of liquid have less thermal mass and can be thermocycled more quickly than larger volumes.

Following a sufficient number of cycles of first-stage PCR (e.g., 20-30 cycles), a small sample (e.g., ~1-5 µL) of first-stage PCR mixture may be sent to dilution well 5015 via channel 5050*b*; channels 5050*c*-5050*e* may be closed. Illustratively, the volume of first-stage PCR mixture used for dilution may be controlled by forming dilution well 5015 with an appropriate small volume, so that dilution well 5015 can only receive the appropriate small sample. The mixture for second-stage PCR may be prepared by injecting the second-stage PCR master mix into blister 5025 via channel 5040*e*. Seals channels 5050*b* and 5050*e* may be closed, seals 5050*c* and 5050*d* may be opened and the sample in well 5015 may be mixed with the master mix by mixing between blisters 5025 and 5020 and well 5015 to dilute first-stage PCR product for second-stage PCR. Blisters 5020 and 5025 and well 5015 may be heated prior to or during mixing for a physical "hot-start" prior to completion of the second-stage PCR mixture (i.e., when primers are included in each of the second-stage wells). Channel 5050*e* is then opened and seals 5050*c* and 5050*d* may be closed so that the second-stage PCR mix can be transferred into the second-stage PCR array 5081. In another embodiment, the pouch 5000 may include one or more additional dilution wells and sets of mixing blisters downstream from well 5015 and blisters 5025 and 5020 and upstream from array 5081. For example, in some embodiments with concentrated first-stage PCR primers or with highly concentrated product, it may be desirable to dilute the first-stage primers and product to a degree greater than can be achieved with one dilution well. Thermocycling for second-stage PCR in array 5081 may illustratively be accomplished by translating the heater assembly back and forth as described in detail elsewhere herein.

In the second exemplary method, sample preparation and first-stage PCR may be performed in the same blister. This is referred to herein as the "two zone method," wherein sample preparation and first-stage PCR are performed in one zone and second-stage PCR is performed in a second zone. In a first step, a sample may be injected into blister 5010 via fill channel 5040*c*. In one embodiment, cells, viruses, and the like are lysed in blister 5010 using the wiping system described in detail elsewhere herein. Alternatively, cell lysis may be accomplished with an alternative lysis device such as, but not limited to, a sonication device, a bead beater, a paddle beater, or chemical lysis. Lysis may be aided by heating the sample to an elevated temperature (e.g., about 70-90° C.) with one or more heater elements of the heater assembly described in detail elsewhere herein. Following lysis, the sample may optionally be cooled with a thermoelectric cooler element (i.e., a Peltier element) to a reduced temperature (e.g., a temperature below ambient temperature such as, but not limited to, ~0-10° C.).

Magnetic beads may be injected into blister 5010 via fill channel 5040*c* in order to recover nucleic acids from the lysate. In one embodiment, the magnetic beads and the lysate may be mixed cold (e.g., at a temperature in a range of about 0-10° C.) after lysis. In another embodiment, a combination of cells to be lysed, lysis buffer, magnetic beads, and, optionally, lysis particles may be injected together into blister 5010 such that lysis and nucleic acid capture may occur at substantially the same time. Once the magnetic beads and the lysate have been thoroughly mixed for a sufficient time, the magnetic beads may be gathered in blister 5010 with a magnet and the spent lysate may be sent to blister 5005 (i.e., the liquid waste blister in this example) liquid waste via channel 5050*a*. Then wash buffer may be injected into blister 5010 via fill channel 5040*c*. Optionally, the wash buffer and the magnetic beads may be mixed cold (e.g., at a temperature in a range of about 0-10° C.). The magnetic beads are gathered again and the spent wash buffer may be flushed to blister 5005. The wash cycle may be repeated one or more times, if desired. After wash, nucleic acids may be eluted from the beads (optionally at an elevated temperature of, e.g., about 70-90° C.) by injecting an elution buffer (plus first-stage PCR primers) into blister 5010. The magnetic beads and any remaining lysis particles (if present) may be collected into the upstream half of blister 5010, and sent to waste blister 5005 via channel 5050*a*. As discussed above, it is understood that heating and cooling during lysis and/or washing is illustrative only, and that in some embodiments, temperature need not be regulated during these steps.

For first-stage PCR, the wiper system may be set and first-stage PCR master mix may be injected into channel 5040*d* and optionally held at an elevated temperature (e.g., about 57° C.) if a true hot-start may be desired. First-stage PCR master mix may be mixed with primers and template in blister 5010 and first-stage PCR may be performed as described above.

Following first-stage PCR, the protocol may proceed to second-stage PCR as described above for the "three zone method."

When fluorescent detection is desired, an optical array may be provided. An optical array may include a light source, illustratively a filtered LED light source, filtered white light, or illumination, and a camera. The camera illustratively has a plurality of photodetectors each corresponding to a second-stage well in array 5081 of pouch 5000. Alternatively, the camera may take images that contain all of the second-stage wells, and the image may be divided into separate fields corresponding to each of the second-stage wells. Depending on the configuration, the optical array may be stationary, or the optical array may be placed on movers attached to one or more motors and moved to obtain signals from each individual second-stage well. It is understood that other arrangements are possible.

Figure 6A:
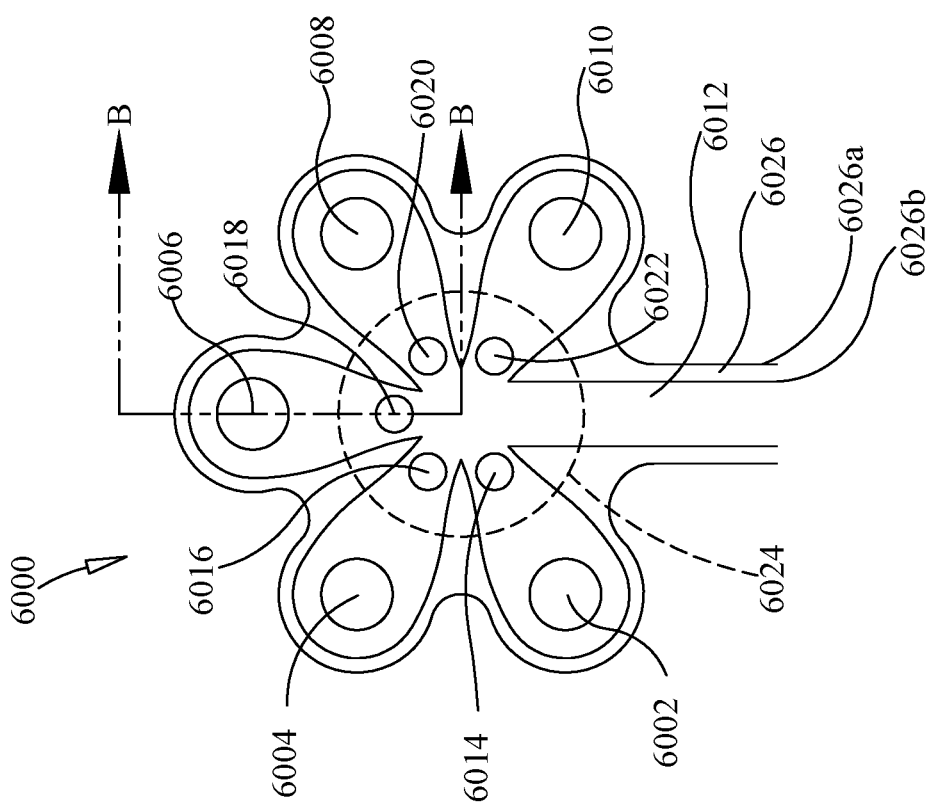
FIG. 6A is a schematic illustration of a second-stage PCR array that may be included in the pouch of FIG. 5A or in various other embodiments herein.

Referring now to FIG. 6A, an array 6000 of wells that may be used for second-stage PCR is illustrated in greater detail. Array 6000 may be a standalone array or it may be included as part of a wider array, such as part of array 5081. Array 6000 includes individual wells 6002, 6004, 6006, 6008, and 6010. Each of wells 6002, 6004, 6006, 6008, and 6010 may be used for a second-stage PCR reaction. In the illustrated embodiment, the wells 6002, 6004, 6006, 6008, and 6010 are fluidly connected to a fill channel 6012; holes 6014, 6016, 6018, 6020, and 6022 are formed in the fill channel 6012 for filling each of the wells. In one embodiment, wells of a second-stage array (e.g., wells 6002, 6004, 6006, 6008, and 6010) may be under a partial vacuum to facilitate drawing fluid from the fill channel 6012 into the wells. In one embodiment, the wells 6002, 6004, 6006, 6008, and 6010 can be sealed off from the fill channel 6012 and from each other (i.e., cross-talk between the well can be prevented) by applying a seal (e.g., a heat seal) or pressure in or around the region illustrated at 6024. Thus, the single seal may be applied in the region indicated at 6024 to close off wells 6002, 6004, 6006, 6008, and 6010 from fill channel 6012 and from each other to prevent well-to-well crosstalk. The cross-sectional structure of the array 6000 and the flow path for filling the wells is illustrated below in FIGS. 6B and 6C. And while array 6000 is illustrated with five wells 6002, 6004, 6006, 6008, and 6010 associated with the fill channel 6012, one will appreciate that more or fewer reaction wells can be associated with a fill channel and that multiple fill channels can be fluidly connected to multiple clusters of wells. Multiple arrays 6000 may be used in combination to create larger arrays.

Figures 6B, 6C:
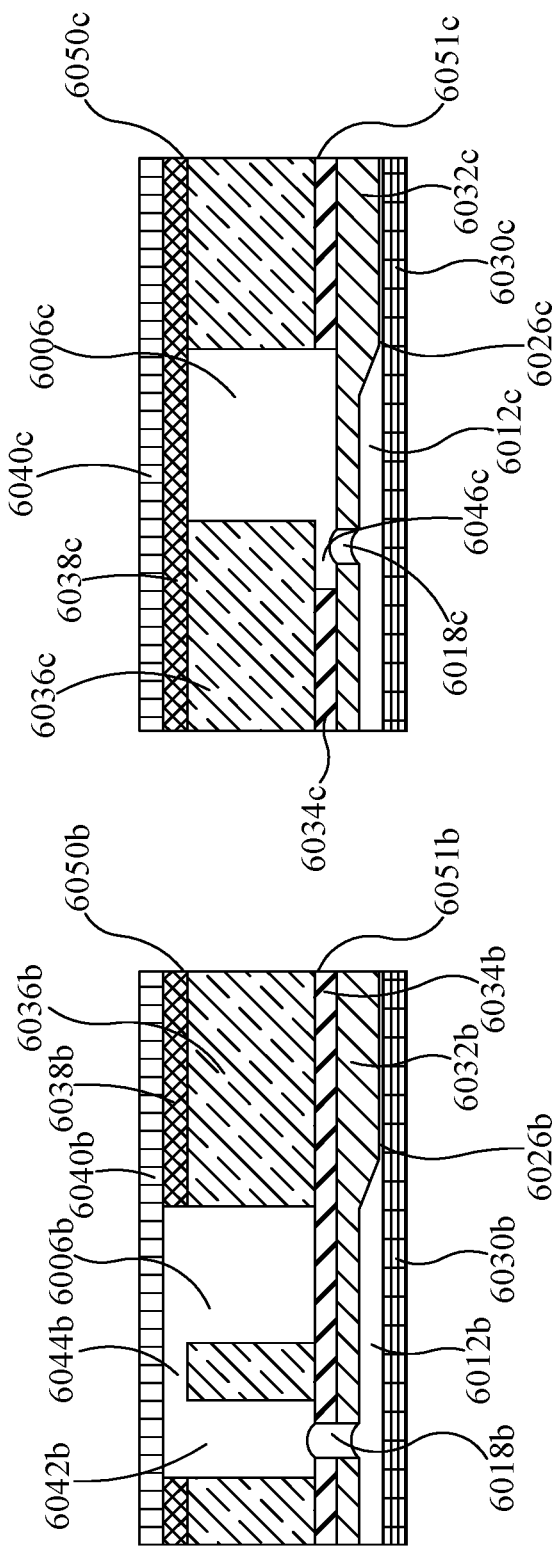
FIG. 6B is a cutaway view of the array of FIG. 6A along the line B-B illustrating one well of the array and a series of channels for filling the well.
FIG. 6C is similar to FIG. 6B, but illustrating one well of the array and an alternate system for filling the well.

Referring now to FIGS. 6B and 6C, FIG. 6B is a cross-sectional view illustrated along the line B-B of FIG. 6A, and FIG. 6C is an alternative embodiment showing different embodiments of well filling systems. The portion of the array 6000 illustrated in cross section in FIGS. 6B and 6C is made of layers similar to those shown in FIG. 5C; it should be noted that the array 6000 may be included as part of the pouch 5000 shown in FIG. 5A instead of array 5081. The well 6006b shown in FIG. 6B may be defined by a first film layer 6030b, a second film layer 6032b, an adhesive layer 6034b, a card layer 6036b having a first side or end 6050b and a second side or end 6051b in which well 6006b may be defined, a second adhesive layer 6038b, and a third (outside) film layer 6040b. The well 6006c shown in FIG. 6C is quite similar and may be defined by a first film layer 6030c, a second film layer 6032c, an adhesive layer 6034c, a card layer 6036c having a first side or end 6050c and a second side or end 6051c in which a well 6006c may be formed, a second adhesive layer 6038c, and a third (outside) film layer 6040c. The key differences between 6B and 6C are in how the wells 6006b and 6006c are formed in the surrounding layers and in how the wells may be filled.

In FIG. 6B, the fill channel 6012b may be formed by leaving a gap between the first and second film layers 6030b and 6032b where liquid can flow. FIG. 6C shows a similar fill channel 6012c formed by leaving a gap between the first and second film layers 6030c and 6032c. The fill channels may be defined by weld lines 6026b or 6026c that seal the first and second film layers together around the array. An example of how these welds may be applied is shown in FIG. 6A at weld region 6026 that includes an outer weld 6026a and an inner weld 6026b defining the fill channel 6012 and the space around the wells. In FIG. 6B, the fill hole 6018b may be formed by making selective cutouts in the second film layer 6032b and in the first adhesive layer 6034b. In FIG. 6C, the fill hole 6018c may be formed by making a selective cutout in the second film layer 6032c that is adjacent to a corresponding cutout in the first adhesive layer 6034c. Fill holes 6018b and 6018c are adjacent to but not aligned with a second-stage reaction wells 6006b and 6006c. That is, the fill holes 6018b and 6018c are fluidly connected to the second-stage reaction wells 6006b and 6006c, but the fill holes 6018b and 6018c are offset relative to the second-stage reaction wells 6006b and 6006c—i.e., the fill holes 6018b and 6018c do not lie over the second-stage reaction wells 6006b and 6006c.

In FIG. 6B, a well filling channel that flows around and over the well 6006b for filling the well may be formed by making a cutout 6042b in the card layer 6036b and a cutout 6044b in the second adhesive layer 6038b, although other ways of forming these channels are possible. The design of the well filling channel of FIG. 6B may, for instance, help to reduce cross-talk or cross-contamination between wells because the flow path in and out of the well 6006b includes a number of twists and turns—i.e., the flow path is convoluted. It is understood that other indirect paths that reduce cross-talk or cross-contamination are contemplated, some of which are illustrated in other embodiments herein, illustratively in FIGS. 8A, 8B, 17A and 17B (see, e.g., spiral well filling paths 3930), and 20A-20E. Because the primers are typically spotted in array wells like well 6006b, amplicon should be found primarily in the well; thus, cutout regions 6042b and 6044b can serve to minimize the leakage of amplicon and primers between or among wells (i.e., cross-talk). In addition, channel 6012b that is formed by layers 6030b and 6032b and that includes fill hole 6018b is easily sealed in situ, essentially blocking off access into or out of the well(s). For example, the fill hole 6018b and access to the well 6006b can be sealed, illustratively with a heat seal device or by pressure, illustratively by a bladder that inflates in the region adjacent to 6024 of FIG. 6A or against all or part of the array 6000. In FIG. 6C, the well filling channel 6018c flows directly into the well 6006c and may be formed by making a cutout 6046c in the first adhesive layer 6034c that fluidly connects the fill hole 6018c to the well 6006c. It is expected that the filling design of FIG. 6C will also generally suppress cross-talk between wells. However, the design of FIG. 6C may be sealed, illustratively, with a heat seal device, which may provide better sealing than pressure alone.

Figure 7:
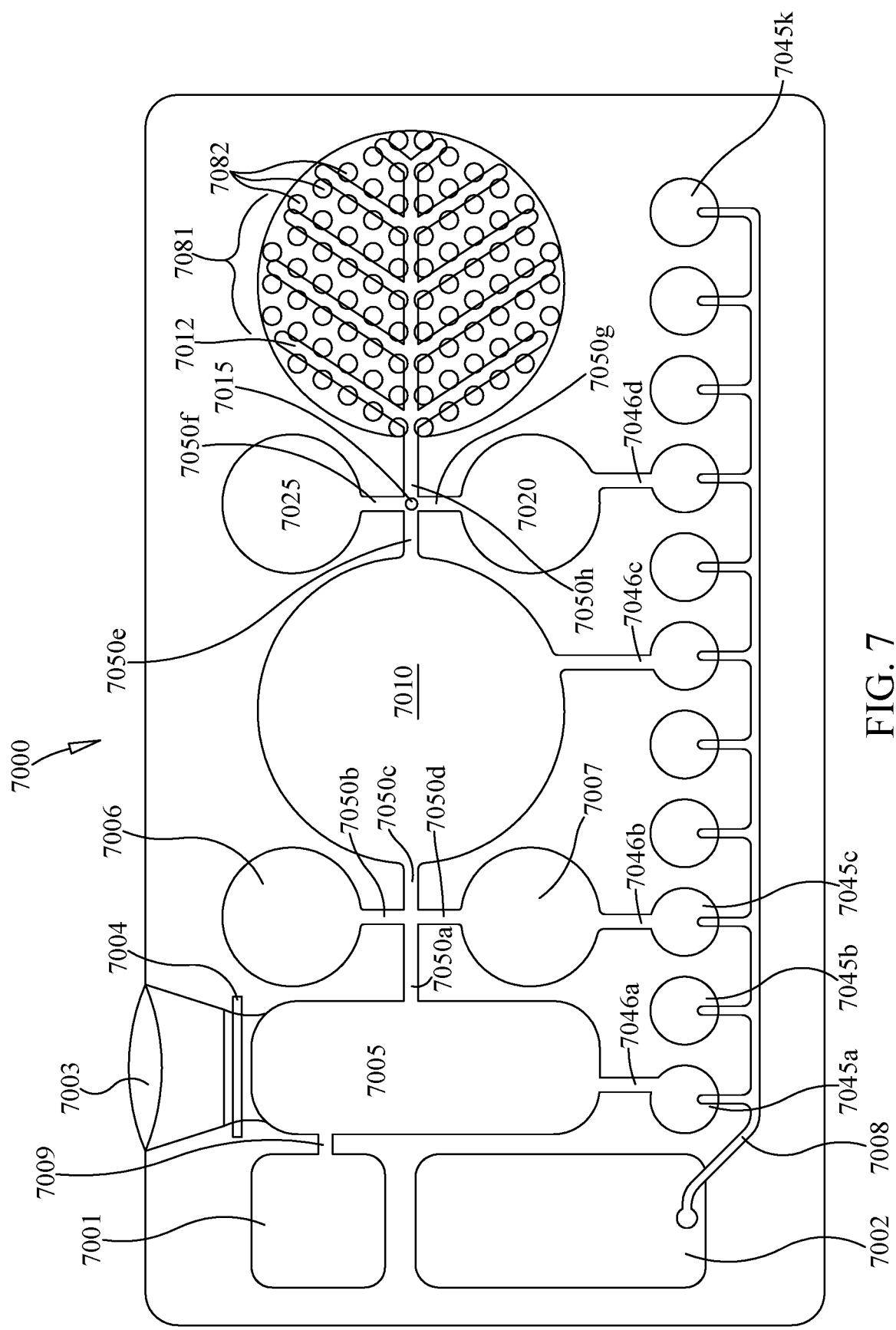
FIG. 7 shows another embodiment of a flexible pouch that includes an integrated sample preparation vessel and one or more fluid reagent packets.

Referring now to FIG. 7, another embodiment of a pouch 7000 is illustrated. Pouch 7000 is similar to pouch 5000 of FIG. 5A and may be used similarly. Differences between pouch 7000 and pouch 5000 include, but are not limited to, providing on-board reagent rehydration solution (e.g., water or buffer) and lysis buffer, and providing an integrated sample preparation chamber. In lieu of a reagent rehydration solution that is intended, for instance, for rehydration of dehydrated reagents (e.g., magnetic beads, PCR components, etc.), some embodiments of pouch 7000 may include ready-to-use liquid reagents that may be included in the pouch at the time of manufacture. Because pouch 7000 is configured for performing steps like sample mixing, sample preparation, reagent rehydration (if needed) in the pouch and without input or manipulation from a technician, pouch 7000 and similar pouches are easy to use. Ease of use can have, for example, a significant effect on how tests are regulated in the US by the FDA and by regulatory agencies in other countries. For instance, if the FDA determines that a test is so simple that there is little risk of error, then the test may be exempted from most Clinical Laboratory Improvement Amendments (CLIA) requirements. Pouch 7000 may be configured for use in an instrument like instrument 800 or instrument 1200 described in detail herein.

Pouch 7000 may be fabricated from two or more material layers (e.g., plastic film layers as discussed elsewhere herein) that are bonded together to form reaction zones, fluid flow channels, and the like. Pouch 7000 includes an integrated sample preparation (ISP) zone 7005 that is configured for receiving a sample to be analyzed (e.g., a sample suspected of containing unknown cells and/or pathogens) and preparing the sample for nucleic acid amplification and analysis using first-stage and second-stage nucleic acid amplification. In the illustrated embodiment, the ISP zone 7005 is fluidly connected to an integrated fluid blister 7001 via channel 7009. In one embodiment, integrated fluid blister 7001 may be a fluid-filled blister having an openable seal (e.g., a tacked together film seal or a burstable seal) that is formed between the pouch material layers and filled with fluid at the time of manufacture. In one embodiment, the integrated fluid blister 7001 may contain a volume of a lysis buffer (e.g., 200 µl) that may be introduced into the ISP zone 7005 with a sample to aid with, for example, sample hydration and/or lysis.

Figure 11A:
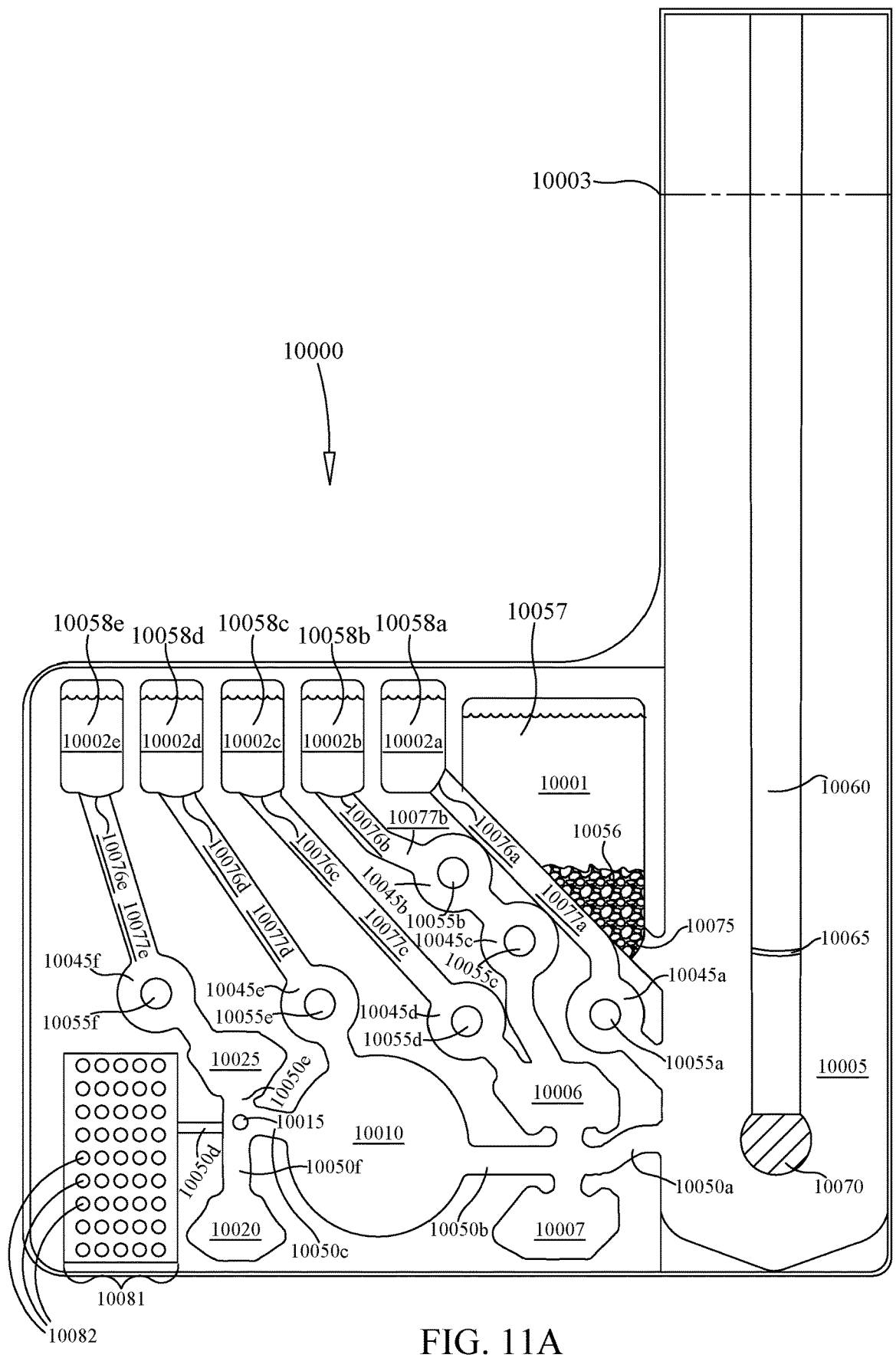
FIGS. 11A and 11B illustrate another embodiment of a flexible pouch, with FIG. 11A showing an unused pouch and FIG. 11B showing the pouch of FIG. 11A after the swab has been used for sample collecting and the pouch is sealed.
Figure 11B:
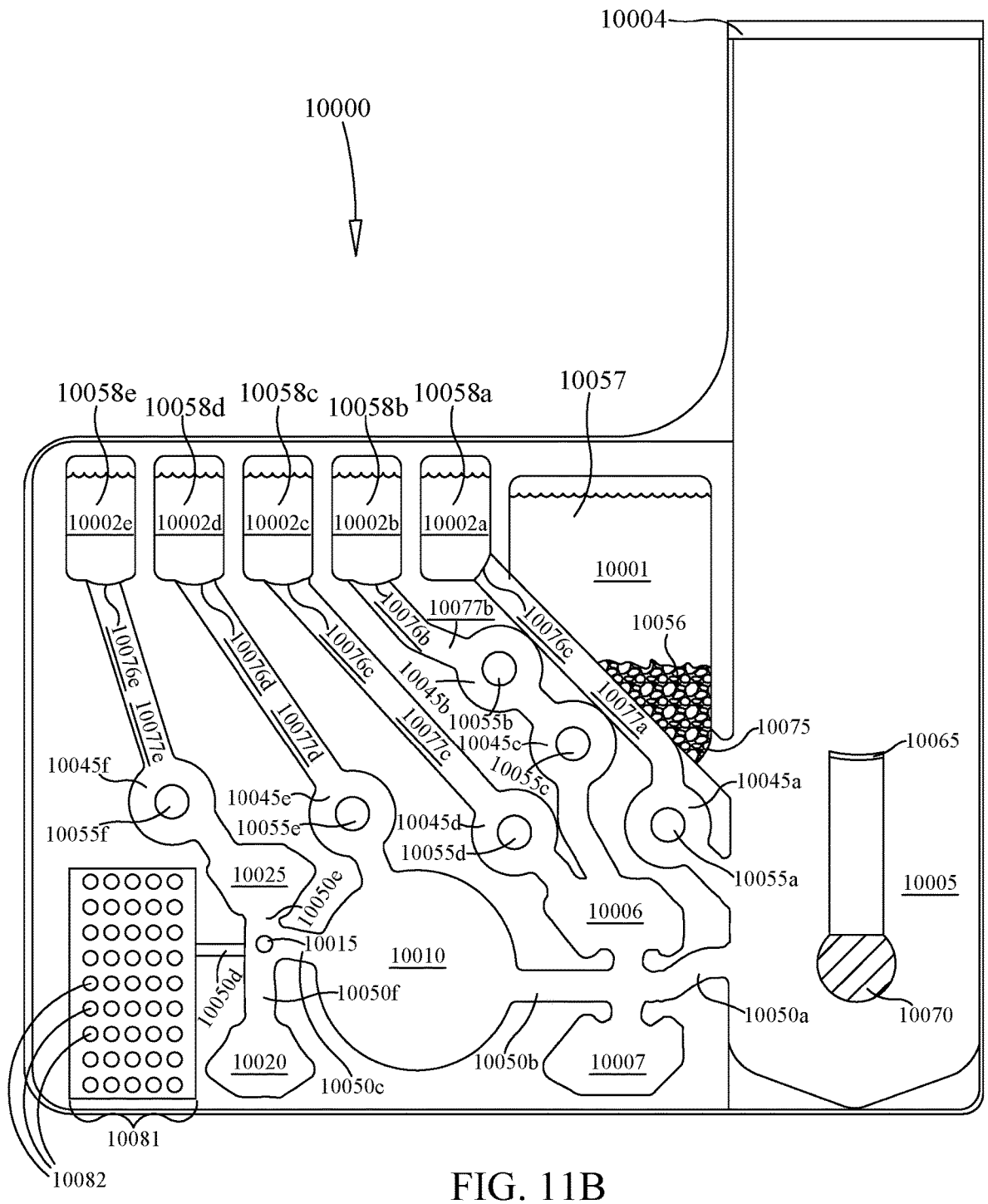

In one embodiment, pouch 7000 may also include an on-board blister 7002 that is fluidly connected to a series reagent wells 7045a-7045k via channel 7008. The on-board blister 7002 may include a volume (e.g., 800 µl) of a reagent rehydration solution (e.g., purified water) that can be introduced into channel 7008 and into reagent wells 7045a-7045k to rehydrate dehydrated reagents or, alternatively, to dilute concentrated reagents therein. Reagent wells 7045a-7045k are provided with entry channels 7046a-7046d that can be used, optionally along with flow between the reagent wells along flow channel 7008, for introduction of reagents into various sample preparation and reaction zones of pouch 7000. While only four entry channels 7046a-7046d are shown, it is understood that additional entry channels are contemplated and that multiple reagent wells may be connected to the various blisters of pouch 7000. In one embodiment, reagent wells 7045a-7045k may be arranged in a structure similar to fitment 590 illustrated in FIG. 1. In another embodiment, reagent wells 7045a-7045k may include blisters or wells formed (e.g., thermoformed) in the material layers of pouch. An illustrative example of such reagent blisters are shown in FIGS. 11A and 11B and specific examples of dried and liquid reagent blisters are discussed in detail below in reference to FIG. 11C and FIGS. 12A-12D, respectively. Illustratively, reagent wells 7045a-7045k may include freeze dried reagents (e.g., dry powders and/or freeze dried reagent pills) that may be rehydrated prior to use, or reagent wells 7045a-7045k may include liquid reagents, or a combination of dried and liquid reagents.

In the illustrated embodiment, ISP zone 7005 is adjacent a sample injection port 7003 that may be formed (e.g., thermoformed) in the material layers used to fabricate pouch 7000. In one embodiment, the sample injection port may be an inverted cone that facilitates addition of liquid samples, sample swabs, solid or semi-solid samples, and the like into ISP zone 7005. Other shapes and configurations are within the scope of this disclosure. In addition, ISP zone 7005 includes a sealable zone 7004 that can be sealed after a sample is introduced into ISP zone 7005. For example, sealable zone 7004 may be sealed with a plastic bag-type zipper seal, a peelable adhesive strip, a heat seal, or another seal. In one embodiment, cells, viruses, and the like may be lysed in ISP zone 7005 using a lysis device such as, but not limited to, a sonication device, a bead beater, a paddle beater, or by chemical lysis. Lysis may be aided by heating the sample (e.g., to about 70-90° C.). In one embodiment, cell lysis may be improved by including lysis particles (e.g., zirconium silicate or metallic beads) in ISP zone 7005. Such beads may be included in ISP zone 7005 at the time of manufacture, or such beads may be introduced into ISP zone 7005 from a downstream blister (e.g., blister 7006 or 7007), from a reagent blister (e.g., blister 7045a), or along with the sample.

For nucleic acid recovery from a lysate, silica-coated magnetic beads may be introduced into ISP zone 7005. Such beads may be included in ISP zone 7005 at the time of manufacture, or such beads may be introduced into ISP zone 7005 from a downstream blister (e.g., blister 7006 or 7007), or from one of the reagent wells 7045a-7045k. In such a case where the beads are introduced from a downstream blister, the magnetic beads may be rehydrated, illustratively using fluid provided from one of reagent wells or with the lysate, and then moved through channel 7050b or 7050d to channel 7050a and in to ISP zone 7005. As explained in detail herein in reference to FIGS. 1 and 2, magnetic beads and the lysate may be allowed to mix together for a sufficient amount of time, then the magnet beads may be captured by activation of magnet in the instrument and moved to blister 7006 or 7007 for at least one washing step followed by elution of the captured nucleic acids from the magnetic beads.

As with various pouches described herein, pouch 7000 includes a first-stage PCR blister 7010, a volumetric dilution well 7015 for measuring a portion of the product from first-stage PCR prior to second-stage PCR, and a second-stage PCR array 7081 that includes a number of individual reaction wells 7082. The first-stage PCR blister 7010 and the second-stage PCR array 7081 may be used for first- and second-stage PCR, as described elsewhere herein.

The volumetric well 7015 may also be fluidly coupled to one or more blisters, illustratively blisters 7020 and 7025, where reagents for second-stage PCR may be introduced and mixed with the contents of the dilution well 7015. In one example, a sample for second-stage PCR may be prepared by repeatedly mixing the contents of volumetric well 7015 with reagents for second-stage PCR between blisters 7020 and 7025. Blisters 7005, 7010, 7020, and 7025, dilution well 7015, and second-stage array 7081 may be fluidly connected by channels 7050a-7050h. In the illustrated embodiment, the wells 7082 of the second-stage array 7081 are fluidly connected to channel 7050h via a branched fill channel 7012 that functions similarly to fill channel 6012 illustrated in FIG. 6a. While array 7081 is shown with a branched fill channel 7012, one will appreciate that other fill channel configurations such as, but not limited to, spiral, serpentine, clusters similar to those shown in FIG. 6A, and the like can also be used.

In one embodiment, the pouch 7000 may be fabricated from a number of layers of material (layers of the same material or layers of different types of material) that are sealed together to form the pouch 7000. While other materials may be used, illustratively, the film layers of pouch 7000 may be formed from a flexible plastic film or other flexible material similar to the pouch 510 described in FIG. 1. For instance, pouch 7000 may be fabricated from materials such as, but not limited to, such as polyester, polyethylene terephthalate (PET), polycarbonate, polypropylene, polymethylmethacrylate, combinations, mixtures, and laminated layers thereof that can be made by any process known in the art, including extrusion, plasma deposition, and lamination. Other materials, including metal foils or plastics with aluminum lamination, may also be used. Other barrier materials are known in the art that can be sealed together to form the blisters and channels. If plastic film may be used, the layers may be bonded together, illustratively by heat sealing or laser welding. Illustratively, the material has low nucleic acid binding and low protein binding capacity. The second-stage array may be fabricated with a card material, as discussed elsewhere herein. If fluorescence detection is used, optically transparent material may be used in the appropriate areas of the pouch (e.g., in the vicinity of the second-stage array).

Figure 8:
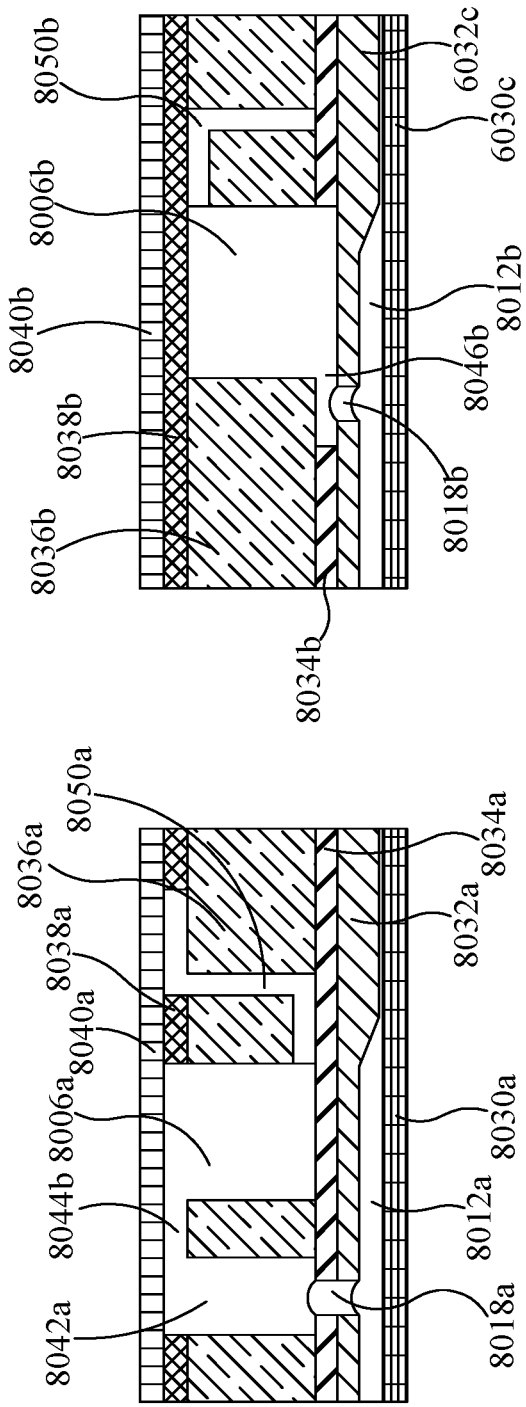
FIG. 8A a cutaway view of a well of that may be included in a high density array illustrating an air pressure expansion chamber that allows the well to be filled under standard atmospheric pressure conditions.
FIG. 8B a cutaway view of another embodiment of a well of that may be included in a high density array illustrating an air pressure expansion chamber that allows the well to be filled under standard atmospheric pressure conditions.

In some embodiments, the wells of the second-stage array may be under a partial vacuum to facilitate filling of the wells with fluid for second-stage PCR. Generally, this may mean that the pouch is stored under a partial vacuum from the time of manufacture until packaging surrounding the sample pouch is opened at the time of use. FIGS. 8A, 8B, 9A-9E, and 10A and 10B illustrate second-stage array configurations that may be used as an alternative to vacuum storage while still allowing reliable well filling in the second-stage array. As will be discussed in detail below, FIGS. 8A and 8B illustrate cutaway views of wells of a second-stage array that include areas 8050*a* and 8050*b* that can allow air and excess fluid to escape from wells 8006*a* and 8006*b* so that fluid can flow from the fill channel 8012*a* and 8012*b* and into the wells without having to maintain the pouch and the array under vacuum. As will be discussed in detail elsewhere herein, FIGS. 10A and 10B schematically illustrate an array that includes a vacuum way that may, illustratively, be formed in a liquid filling channel that allows a partial vacuum to be pulled on the array in situ—e.g., while an assay is being performed in the pouch in an instrument.

Referring now to FIGS. 8A and 8B, cross-sectional views of two designs of well filling systems are illustrated. These views are similar to the views illustrated in FIGS. 6B and 6C. The well 8006*a* shown in FIG. 8A may be fabricated from a first film layer 8030*a*, a second film layer 8032*a*, an adhesive layer 8034*a*, a card layer 8036*a* in which a well 8006*a* may be formed, a second adhesive layer 8038*a*, and a third (outside) film layer 8040*a*. The well 8006*b* shown in FIG. 8B is quite similar and may be fabricated from a first film layer 8030*b*, a second film layer 8032*b*, an adhesive layer 8034*b*, a card layer 8036*b* in which a well 8006*b* may be formed, a second adhesive layer 8038*c*, and a third (outside) film layer 8040*b*.

In FIG. 8A, the fill channel 8012*a* may be formed by leaving a gap between the first and second film layers 8030*a* and 8032*a* where liquid can flow. FIG. 8B shows a similar fill channel 8012*b* formed by leaving a gap between the first and second film layers 8030*b* and 8032*b*. The fill hole 8018*b* may be formed by making a selective cutout in the second film layer 8032*b* that is adjacent to a corresponding cutout in the first adhesive layer 8034*b*.

In FIG. 8A, air in well 8006*a* that may be pressurized by flow of liquid through the well filling channel into well 8006*a* through cutout 8042*a* and cutout 8044*a* may be allowed to escape into chamber 8050*a* that is formed by making cutouts in card layer 8036*a* and second adhesive layer 8038*a*. In FIG. 8B, air in well 8006*b* that may be pressurized by flow of liquid through the well filling channel into well 8006*b* through fill hole 8018*b* and cutout 8046*b* may be allowed to escape into chamber 8050*b* that is formed by making cutouts in card layer 8036*b*. While air escape chambers like 8050*a* and 8050*b* are shown connected to one well each, it is understood that such air escape chambers may be connected to multiple adjacent wells in some embodiments. Likewise, while air escape chambers like 8050*a* and 8050*b* are shown as blind holes, it is understood that air escape paths may be connected to other layers and even to outside air or a vacuum source in some embodiments. While FIGS. 6B-6C are shown in relation to pouch 5000 and FIGS. 8A-8B are shown in relation to pouch 7000, it is understood that the second-stage wells may described herein may be used in the various pouches described herein, limited only by the needs of the specific application.

Referring now to FIGS. 9A-9E, another embodiment of second-stage wells for use in various science cards or pouches described herein are shown. Wells 9004*a*-9004*c*, that illustratively can be filled without vacuum, are illustrated. Wells 9004*a*-9004*c* may be formed in a first plastic layer, illustratively spotted with primer pairs for second-stage amplification, and then the open ends of the wells may be covered with a second plastic layer. Wells 9004*a*-9004*c* may then be flattened and provided with a support layer that may surround the wells and that, among other things, may prevent the wells from being reflattened during use.

In the embodiment illustrated in FIG. 9A, wells 9004*a*-9004*c* may be formed (e.g., thermoformed) in a first film layer 9002 (e.g., a thermoplastic polymer layer). Wells 9004*a*-9004*c* may be spotted with primers for second-stage PCR (schematically shown at 9005*a*-9005*c*) after forming, illustratively done while first film layer 9002 is upside down. In one embodiment, a fixture for forming the wells may include fluid connections for spotting the primers at the time of well formation. In a second step illustrated in FIG. 9B, a second film layer 9006 may be bonded (e.g., laser welded) to the first film layer 9002. In one embodiment, the second film layer 9006 may be a single film layer with filling holes 9020*a*-9020*c* formed in the film layer corresponding to the second-stage wells 9004*a*-9004*c*. In another embodiment, the second film layer 9006 may be formed from one or more layers with a fill channel (or channels), fill holes, and other optional flow structures for filling the second-stage wells 9004*a*-9004*c* and, preferably, preventing cross-talk between the wells.

In a third step illustrated in FIG. 9C, the wells 9004*a*-9004*c* formed in FIG. 9A may be compressed substantially flat with a fixture 9008. Following flattening, as illustrated in FIG. 9D, a layer 9010, which may be opaque, may be added between the wells to prevent optical cross-talk between the wells during fluorescence data acquisition. In one embodiment, the opaque layer 9010 may be a fabricated from a rigid or semi-rigid material (e.g., the thick, card material used to fabricate array 581 or 5081) that can protect the wells of the array from being re-flattened after they have been filled for second-stage PCR cycling. Although FIG. 9D shows the opaque layer 9010 being added after well formation and flattening, one will appreciate that the opaque layer 9010 could be added prior to well formation or flattening. In one embodiment, opaque layer 9010 may be fabricated from a reflective material (e.g., a foil or a metalized plastic material like aluminized Mylar). For instance, a reflective material may be capable of preventing optical cross-talk between wells while providing reflection within individual wells to increase optical signal. In some embodiments, a reflective material layer may be added in addition to a rigid or semi-rigid layer. Likewise, a reflective material layer may be added before or after well formation and/or flattening.

In one embodiment, previously flattened wells 9004*a*-9004*c* may be re-expanded by filling with fluid as shown in the embodiment illustrated in FIG. 9E. Because the flattened wells contain substantially no trapped air, the wells 9004*a*-9004*c* may be fillable without having the array under partial vacuum, illustratively by filling wells 9004*a*-9004*c* with gentle pressure. Wells 9004*a*-9004*c* may be thermocycled for nucleic acid amplification according to one or more of the methods described herein.

FIGS. 10A and 10B illustrate another embodiment of a second-stage array 11000 that that may be filled without having the pouch manufactured and stored under partial vacuum. Second-stage array 11000 is similar to second-stage array 6000 illustrated in FIG. 6A. Second-stage array 11000, which is defined in part by weld line 11026, includes second-stage wells 11002, 11004, 11006, 11008, and 11010 that can each be provided with a specific second-stage primer pair and that can be filled with component for second-stage PCR (e.g., diluted product from first-stage PCR, polymerase, dNTPs, etc.) and be thermal cycled for second-stage analysis, as described in detail elsewhere herein. The second-stage wells are fillable from fill channel 11012, which is in fluid communication with fill holes 11014, 11016, 11028, 11020, and 11022 and fluidic vias 11052a-11052e that are associated with each second-stage well. Integrally formed in the fill channel and in fluid communication with each of the fill holes, vias, and second-stage wells is an illustrative vacuum way 11050. Vacuum way 11050 is in turn in fluid communication with port 11051 that may be placed on a portion of the pouch away from the array. In one embodiment, port 11051 may include an opening 11051a that can be pre-formed or formed in situ to provide fluid access to the vacuum way. Illustratively, opening 11051a may be formed in either layer 11030 or 11032. Vacuum way 11050 can illustratively be used to pull a partial vacuum on the second stage wells in situ (e.g., by a vacuum pump in the instrument during a pouch run) so that the pouch does not need to be manufactured or stored under vacuum. In one embodiment, vacuum channel 11050 may illustratively be connected to a remote vacuum hub on the pouch that can be connected to a vacuum source.

Referring now to FIG. 10B, a cross-section of the fill channel 11012 and the vacuum way 11050 is illustrated. In the illustrated embodiment, the fill channel 11012 is formed as an open space between two film layers 11030 and 11032 that are joined together (e.g., heat or laser welded) on their edges at 11026. Illustratively, the vacuum way 11050 may be formed as a sub-channel in one or both of layers 11030 or 11032. In the illustrated embodiment, the vacuum way 11050 has an arch shape that is designed to hold channel 11012 open and connect the fill holes, vias, and second-stage wells to the vacuum source via vacuum way 11050 and port 11051. Without the vacuum channel 11050, channel 11012 may tend to "kiss" shut when a vacuum is applied to the channel 11012 and prevent evacuation of the second-stage array 11000. In one embodiment, the vacuum channel 11050 may be formed in one of the layers with a heat forming fixture (e.g., an appropriately shaped hot 'debossing' wire). In other embodiments, the vacuum channel 11050 may be formed by molding, laser etching, xurography, or the like. As illustrated in FIG. 10B, vacuum way 11050, which is an example of a heat formed channel, includes a channel that is formed in the plastic layer. Preferably, the channel 11050 has an arch shape that supports the plastic and holds the channel open so that the vacuum can draw air out of the second-stage wells. Nonetheless, the vacuum way 11050 can be sealed by, for example, bonding layers 11030 and 11032 to one another by applying a heat seal over the vacuum way 11050, illustratively, near port 11051 and away from the array wells.

In one embodiment, a vacuum of at least 1-150 millibar (e.g., 2-10 millibar or, more preferably, 2-5 millibar) may be pulled on the second stage array for 10-120 seconds in the instrument. Following pulling a vacuum, the vacuum channel may be sealed (e.g., heat seated) and the vacuum may be released at port 11051, which leaves the wells of the array under a partial vacuum. Experiments on prototype arrays with vacuum channels similar to what is described above have shown that pulling a vacuum in situ can be at least as effective as and perhaps more effective than manufacturing and storing the pouch under vacuum.

Referring now to FIGS. 11A and 111B, another embodiment of a pouch 10000 is illustrated. Pouch 10000 can be used similarly to the other pouches described herein. Pouch 10000 includes an integrated sample preparation (ISP) zone 10005, which is similar to ISP zone 7005 of FIG. 7. ISP zone 10005 includes a swab 10060 with an absorbent tip 10070 that can be used for sample collection (e.g., from blood, sputum, stool, saliva, soil, and the like). In use, ISP zone 10005 may be opened (e.g., torn open or by opening a seal) at 10003 and swab 10060 may be removed for sample collection. After collection, swab 10005 may be reinserted into ISP zone 10005 and may be broken off at a score line 10065 as illustrated in FIG. 11B. In one embodiment shown in FIG. 11B, ISP zone 10005 may include a seal 10004 (e.g., a zipper seal, a peelable seal, a screw-top seal, or the like) that may be used to seal ISP 10005 prior to completion of sample preparation. Alternatively, a heat seal or the like may be applied to ISP zone 10005 to seal the container prior to completion of sample preparation. Optionally, a heat seal bar may be provided in the instrument configured to run pouch 10000 to seal ISP zone 10005 at the location of seal 10004.

For sample preparation and further sample processing, pouch 10000 includes on-board fluid reservoirs 10001 and 10002a-10002e. In one embodiment, the fluid reservoirs may be filled at the time of manufacture or, alternatively, by a user prior to pouch use. In one embodiment, fluid reservoir 10001 may include a sample lysis buffer 10057 and sample lysis components 10056. Sample lysis components 10056 may include sample lysis particles (e.g., zirconium silicate beads) and/or silica-coated magnetic beads that can be used for nucleic acid recovery from a sample lysate. In the illustrated embodiment, fluid reservoir 10001 includes an openable seal 10075 such as a peelable or frangible seal that separates the contents of reservoir 10001 from ISP zone 10005. In one embodiment, openable seal 10075 may be a burstable seal that may be emplaced during pouch fabrication, or, because the film layers used to fabricate pouch 10000 may have some natural affinity for one another and may tend to bond loosely together, seal 10075 may be formed by film layers in a channel that are tacked together. For instance, film layers can be tacked together by applying heat to the film layers (e.g., by rolling between heated rollers) sufficient to transiently (e.g., peelably) bond the films together but not sufficient to melt the layers and form a permanent bond. This and other seals discussed herein may be peelable, frangible, tacked together, one-way, pressure, or other seals, as are known in the art.

In use, contents 10056 and 10057 of reservoir 10001 may be emptied into ISP zone 10005 for sample lysis. Contents 10056 and 10057 of reservoir 10001 may be emptied into ISP zone 10005 by manual manipulation of reservoir 10001 by a user or an instrument may include a pressure applying device that can empty the contents 10056 and 10057 of reservoir 10001 after inserting the pouch 10000 into an instrument.

Lysis and nucleic acid recovery may proceed (in the presence of swab 10060) as previously described elsewhere herein. In one embodiment, lysis and nucleic acid recovery may proceed simultaneously (i.e., lysis particles and magnetic beads may be introduced together into ISP zone 10005). In another embodiment, reagent blister 10045a may include a "pill" 10055*a* of magnetic beads that may be introduced into ISP zone 10005 through channel 10077*a*, before, during, or subsequent to lysis. The pill of magnetic beads 10055*a* may be formed by pressure or provided in a dissolvable material and may be introduced into ISP zone 10005 by rehydrating with fluid 10058*a* from fluid reservoir 10002*a* by, for example, opening a peelable seal or bursting frangible seal 10076*a*. In yet another embodiment, magnetic beads may be included in reservoir 10001 and pill 10055*a* may include another lysis or cell preparation reagent, such as a protease, a nuclease inhibitor, or the like. Other combinations are contemplated, and it is understood that the component(s) provided in reagent blister 10045*a* and other blisters may be provided to the blister in forms other than as a pill.

Magnetic beads may be captured and recovered from ISP zone 10005 with an actuatable magnet provided in an associated instrument, as described elsewhere herein. Magnetic beads may be transferred to blisters 10006 and/or 10007 for washing and elution. Wash reagent pills 10055*b* and 10055*c* (e.g., an acidic buffer component, such as but not limited to Na citrate, having a pH of about 4-5), which are shown in reagent blisters 10045*b* and 10045*c*, may be rehydrated with fluid 10058*b* from reservoir 10002*b* by opening seal 10076*b* and introducing the rehydrated reagents into blisters 10006 and 10007 via channel 10077*b*. Pouch 10000 is shown with reagent pills 10055*b* and 10055*c* that can be used for two washes, but one will appreciate that the pouch could contain reagents for only one wash or for more than two. Likewise, reagent pills 10055*b* and 10055*c* may be rehydrated and used for one, two, three, or more wash steps. Pouch 10000 also includes an elution reagent pill 10055*d* in reagent blister 10045*d* that can be used to elute nucleic acids from the magnetic beads. In one embodiment, the elution reagent pill may include a buffering component that, when rehydrated, makes buffer having a pH of about 8-9. In another embodiment, the elution reagent pill may include a buffering component having a pH of about 8-9 and one or more components (e.g., dNTPs, Mg, BSA, etc.) of a first-stage PCR reaction. Pill 10055*d* can be rehydrated with the fluid 10058*c* in reservoir 10002*c* by, for example, opening a peelable seal or bursting frangible seal 10076*c* and introducing the elution reagent via channel 10077*c*. The actuatable magnet may be used to capture the magnetic beads for washing and elution as described elsewhere herein.

Pouch 10000 also includes a first-stage PCR blister 10010, a volumetric dilution well 10015 for measuring a portion of the product from first-stage PCR prior to second-stage PCR, and a second-stage PCR array 10081 that includes a number of individual reaction wells 10082. Reagents for first-stage PCR may be included in reagent pill 10055*e* in reagent blister 10045*e*. Reagent pill 10055*e* may be rehydrated with fluid 10058*d* in reservoir 10002*d* via burstable seal 10076*d* and channel 10077*d*. The volumetric well 10015 may also be fluidly coupled to blisters 10020 and 10025, where reagents for second-stage PCR may be introduced and mixed with the contents of the dilution well 10015. Reagents for second-stage PCR may be included in reagent pill 10055*f* in reagent blister 10045*f*. Reagent pill 10055*f* may be rehydrated with fluid 10058*f* in reservoir 10002*f* via burstable seal 10076*f* and channel 10077*f*. As with seal 10075, seals 10076*a*-10076*e* may be, for example, frangible seals or openable or peelable seals formed by, for example, tacking the films together in channels 10077*a*-10077*e* by, for example, hot rolling or similarly treating the films to bond them together without melting them together to form permanent seal. In one example, a sample for second-stage PCR may be prepared by repeatedly mixing the contents of volumetric well 10015 with reagents for second-stage PCR between blisters 10020 and 10025. In some embodiments, liquid reagents instead of reagent pills 10055*a*-10055*f* may be provided in pouch 10000. For instance, fluid blisters 10001 and 10002*a*-10002*e* may include liquid reagents for nucleic acid recovery, magnetic bead washes, elution, first-stage PCR, second-stage PCR, and the like and some or all of reagent pills 10055*a*-10055*f* may be omitted in lieu of ready to use liquid reagents.

Blisters 10005, 10006, 10007, 10010, 10020, and 10025, dilution well 10015, and second-stage array 10081 may be fluidly connected by channels 10050*a*-10050*f*. Fluid movement within pouch 10000 from the entry channels 10077*a*-1077*e* and via the inter-blister channels 10050*a*-10050*f* may, for example, be controlled and directionalized with the use of seals that act on the channels, as described, for example, in reference to FIG. 2. Movement of fluid between blisters may be actuated with pistons, or the like, as described in reference to FIG. 2, for example.

In one embodiment, the pouch 10000 may be fabricated from a number of layers of material (layers of the same material or layers of different types of material) that are sealed together to form the pouch 10000. While other materials may be used, illustratively, the film layers of pouch 10000 may be formed from a flexible plastic film or other flexible material similar to the pouch 510 described in FIG. 1. For instance, pouch 10000 may be fabricated from materials such as, but not limited to, such as polyester, polyethylene terephthalate (PET), polycarbonate, polypropylene, polymethylmethacrylate, combinations, mixtures, and laminated layers thereof that can be made by any process known in the art, including extrusion, plasma deposition, and lamination. Similar materials (e.g., polycarbonate) may be used for array 10081. Other materials, including metal foils or plastics with aluminum lamination, may also be used. Other barrier materials are known in the art that can be sealed together to form the blisters and channels. If plastic film may be used, the layers may be bonded together, illustratively by heat sealing or laser welding. Illustratively, the material has low nucleic acid binding and low protein binding capacity. If fluorescence detection is used, optically transparent material may be used in the appropriate areas of the pouch (e.g., in the vicinity of the second-stage array).

Figure 11C:
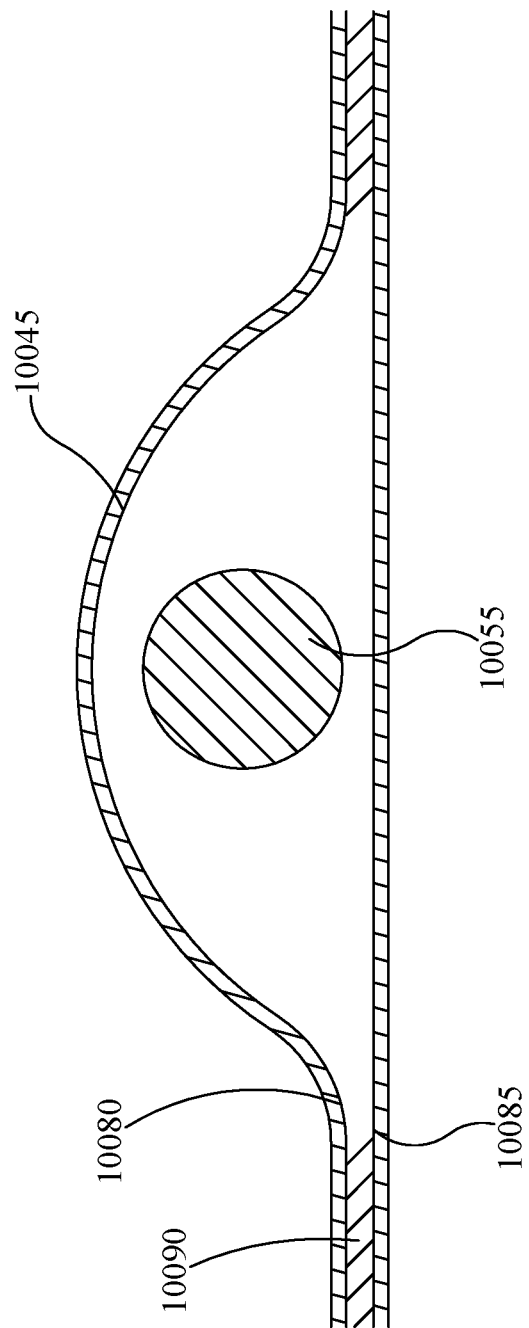
FIG. 11C illustrates a blister and a dried reagent pill that may be included in one or more of the pouches illustrated herein.

Referring now to FIG. 11C, a cross sectional view of an illustrative reagent blister 10045 is shown. In the illustrated embodiment, the reagent blister 10045 is fabricated from a first layer of film material 10080 and a second layer of film material 10085. In the illustrated embodiment, the first film layer 10080 may be molded (e.g., thermoformed) to form a blister shape. The first film layer 10080 and the second film layer 10085 may be bonded together around at least a portion of the periphery of the blister with a weld line (e.g., a laser weld line), which is shown schematically at 10090. As is illustrated, for example, in FIGS. 11A and 111B, the weld line 10090 may not be continuous, to allow fluid flow into and out of reagent blister 10045.

The reagent pill 10055 may include suitable chemicals, enzymes, and the like for use in pouch 10000 and in the methods described herein. Reagent pill 10055 may also include additives known in the art for stabilizing chemicals, enzymes, and the like, for freeze drying. In one embodiment, pill 10055 may be flash frozen and freeze dried prior to adding to the blister 10081 formed in layer 10080. For instance, freeze dried reagent pills may be placed in a hopper or the like and added to formed blisters like 10081 in an automated or semi-automated manufacturing process. The inventors in this case have found that such reagent pills rehydrate readily upon exposure to aqueous media, such as from reservoirs 10002*a*-10002*e* illustrated in FIGS. 11A and 11B. While FIG. 11C shows a reagent pill 10055, reagents may also be dispensed into reagent blisters as dry powders in some embodiments. For instance, reagents may be formed into reagent pills, freeze dried, ground into powder, and then dispensed into reagent blisters in powder form. In an alternative embodiment, some reagent (e.g., reverse transcriptase enzyme and, optionally, buffers and stabilizers) may instead be applied to a medium (e.g., filter paper), air dried, divided into pieces, and then dispensed into reagent blisters as pieces of the medium with the dried reagent. In another alternative embodiment, liquid reagents (e.g., droplets of liquid reagent, optionally with buffer, stabilizers, and the like) may be added directly to the film used to form the reagent blisters and then be allowed to air dry in place in or around the region of the reagent blisters or, alternatively, directly in or around the reaction blisters.

FIGS. 7, 11A, and 11B illustrate pouches that may include on-board water, lysis buffer, or other liquid reagents. In some embodiments, water, lysis buffer, and the like can be added to the pouch between pouch film layers at the time of manufacture. Having on-board water, lysis buffer, and the like may, for example, make the pouches easy to use. That is, so the operator does not necessarily need to be a highly trained technician. In the example of FIGS. 11A and 111B, all a user has to do is collect a sample (e.g., blood, saliva, sputum, or an environmental sample) with the provided swab, place the swab with the sample back in the provided sample preparation chamber (i.e., ISP zone 10005), optionally break off the swab, seal the sample preparation chamber, and place the pouch in the instrument. The instrument can be programmed to perform the rest of the steps needed to prepare and analyze the sample, including, but not limited to, sample and reagent hydration, sample preparation, nucleic acid recovery, first-stage PCR, and second-stage PCR. While water, lysis buffer, and the like can be added to the pouch between pouch film layers, FIGS. 12A-12D illustrate several other possibilities for placing on-board water and buffers in the various pouch embodiments.

FIGS. 12A and 12B illustrate views of an embodiment of an aqueous media packet 12000 that may, in one embodiment, be placed in a reservoir 10001*a*, similar to reservoir 10001 illustrated in FIGS. 11A and 11B. Aqueous media packet 12000 may, for example, may be filled with purified water, buffer, or the like and may fabricated to fit in reservoir 10001*a*. In one embodiment, aqueous media packet 12000 may be double sealed 12002 around a portion of aqueous media packet 12000 and may be single sealed 12004 around another portion. In such an embodiment, aqueous media packet 12000 is sealed around its entire periphery to maintain the integrity and preselected volume of the contents of aqueous media packet 12000 while the single sealed portion 12004 provides a more readily burstable portion so that the contents of the packet can be dispensed into the pouch. In one embodiment, aqueous media packet 12000 may also be shaped such that pressure applied to dispense the contents of the packet is focused on the burstable seal portion. In the illustrated embodiment, for example, the packet 12000 narrows towards the burstable seal portion 12004 such that pressure applied will tend to be relieved by bursting at portion 12004 and not around the double sealed portion 12002. FIG. 12A depicts one possible design for an aqueous media packet with a selectively burstable seal. Other burstable seals are possible and within the scope of this disclosure.

FIG. 12B illustrates a cross sectional view of reservoir 10001*a* and aqueous media packet 12000. Aqueous media packet 12000 may be fabricated from a first layer of material 12010 and a second layer of material 12012. In one embodiment, the first and/or second layers of material 12010 and 12012 may be fabricated from materials such as, but not limited to, such as polyester, polyethylene terephthalate (PET), polycarbonate, polypropylene, polymethylmethacrylate, combinations, mixtures, and laminated layers thereof. In another embodiment, the first and/or second layers of material 12010 and 12012 may be fabricated from a metal foil materials such as, but not limited to, aluminum foil, plastic/metal films, and metalized plastic films (e.g., aluminized Mylar film). Such metal foils (e.g., aluminum foil) can preserve the contents 12014 (e.g., buffer, water, and the like) of aqueous media packet 12000 for extended storage (e.g., up to one or two years) under vacuum. Thus, aqueous media packets can be disposed in the appropriate portions of the pouch at the time of manufacture and the pouch can be subsequently shipped and stored under vacuum.

In one embodiment, the aqueous media packet 12000 may be a packet of aqueous media that is fabricated separately from the pouch that is sized and shaped to fit snugly into a selected pocket formed in a pouch—e.g., like reservoir 10001 of pouch 10000. In another embodiment, the aqueous media packet 12000 may fabricated contemporaneously with the pouch and may be formed in and sealed between the material layers used to fabricate the pouch. As illustrated in FIG. 12B, for example, reservoir 10001*a* is fabricated from layers 12006 and 12008 and the aqueous media packet 12000 may be bonded (e.g., heat sealed or laser welded) to layer 12006 and 12008 in the region indicated at 12016. This may ease manufacture because the aqueous media packet 12000 can be fabricated and filled separately and can then be fitted and sealed into the pouch during the fabrication of the reservoir. Likewise, sealing the aqueous media packet 12000 between pouch layers may help direct the flow of fluid that is expelled from the packet when pressure is applied.

FIGS. 12C and 12D illustrate another aqueous media packet for reservoir 10001*b*. The aqueous media packet 12020 in FIG. 12C is similar to aqueous media packet 12000 of FIG. 12A. Aqueous media packet 12020 may be a foil or plastic film container that contains water, buffer, or the like and may be configured to dispense its contents into a pouch at the appropriate time in response to, for example, external pressure. Aqueous media packet 12020 may be double sealed 12022 around the periphery of the packet 12020 to protect the contents of packet 12020. Aqueous media packet 12020 may be provided with an openable seal (not shown) to prevent free flow of fluid from packet 12020. For dispensing of fluid, aqueous media packet 12020 is provided with an outlet tube 12024 that may be plumbed, for example, into a pouch channel illustrated at 12028. In one example, pouch channel 12028 may be similar to one of channels 10077*a*-10077*e* illustrated in FIGS. 11A and 11B. To prevent back flow of fluid into the reservoir (e.g., reservoir 10001) and to ensure that fluid flows into channel 12028, the outlet tube 12024 may be sealed (e.g., heat sealed or laser welded) to the pouch material, as indicated in the region of 12026.

FIG. 12D illustrates an aqueous media packet 12030 that is fabricated from a thin, readily burstable material layer 12034 and thicker material layer 12036. Bursting layer 12034 in response to pressure will dispense fluid 12038. In one example, layer 12034 may be a thin foil layer and layer 12036 may be a thicker foil layer. Because layer 12034 is burstable, layers 12034 and 12036 may, for example, be single sealed or double sealed 12032 around the entire periphery of packet 12030 as opposed to 12A that includes a single sealed portion at 12004 where packet 12000 will preferably burst and dispense its fluid.

Figure 13:
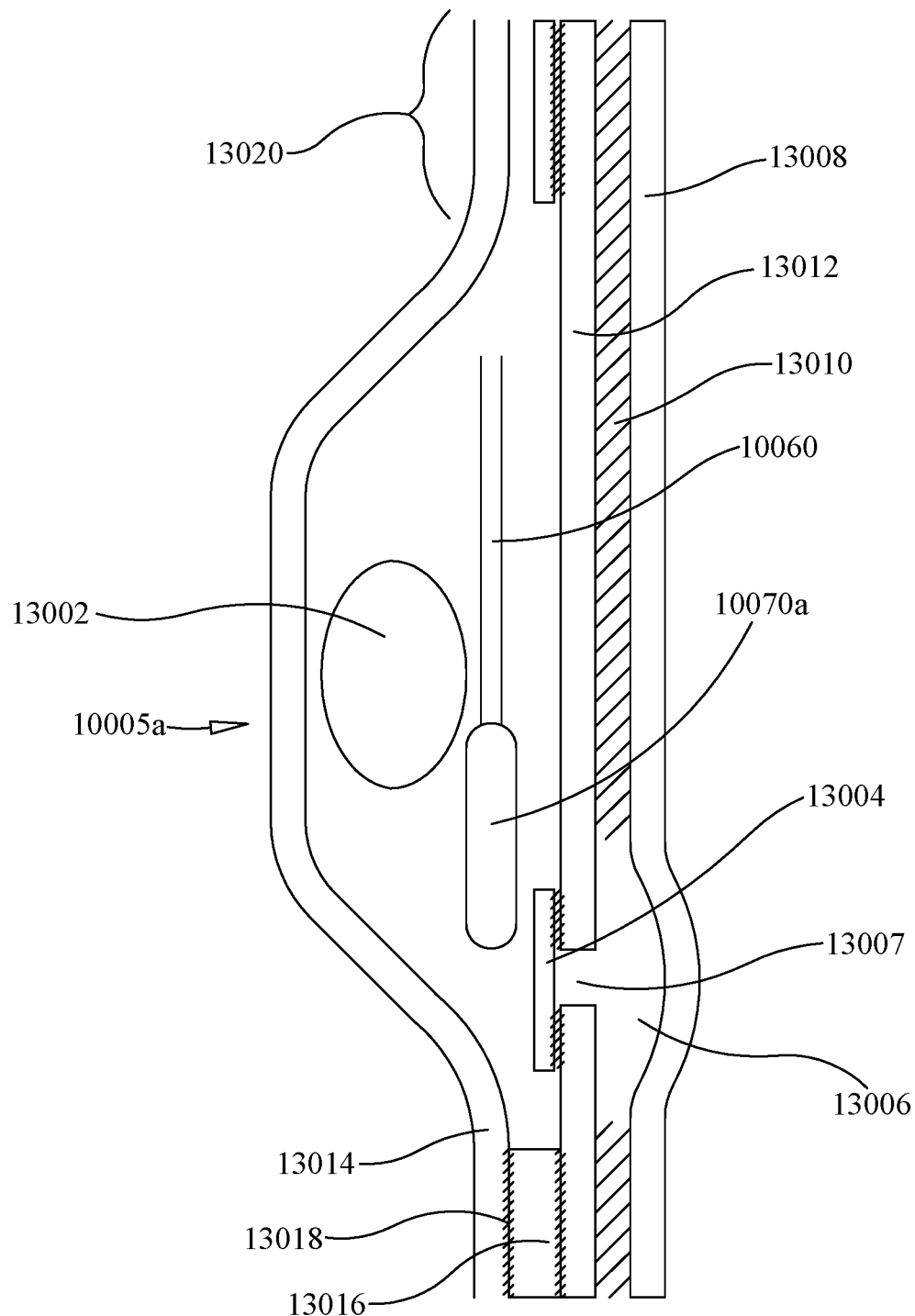
FIG. 13 illustrates a cross-sectional view of an integrated sample preparation blister and associated channels that may be included in one or more of the pouches described herein.

Referring now to FIG. 13, a cross-sectional view of one embodiment of a sample preparation chamber 10005a is illustrated, similar to the sample preparation chamber 10005a of FIGS. 11A-11B. The illustrated embodiment of the sample preparation chamber 10005a is fabricated from first and second film layers 13008 and 13012 that are bonded together at 13010 to form a back surface of the sample preparation chamber 10005a, and third and fourth film layers 13014 and 13016 that are bonded together at 13018 to form a front surface of the sample preparation chamber 10005a. A fill channel 13006 and a fill hole 13007, that can be used for filling sample preparation chamber 10005a with lysis buffer and for withdrawing lysate, are formed in layer 13012 to connect channel 13006 to chamber 10005a. A region where a seal can be provided for sealing the sample preparation chamber 10005a is illustrated at 13020.

A method for using sample preparation chamber 10005a was described in reference to FIGS. 11A and 11B. In FIG. 13, sample preparation chamber 10005a includes an optional filter 13004. In use, lysis buffer may be introduced into sample preparation chamber 10005a via channel 13006 to hydrate the sample on swab 10060 and absorbent swab end 10070a. In the embodiment illustrated in FIG. 13, sample preparation media (e.g., lysis particles and/or silica-coated magnetic beads) are disposed in pill 13002 in sample preparation chamber 10005a. When lysis buffer is introduced into sample preparation chamber 10005a, the buffer hydrates and disperses the sample and disperses the sample preparation media. Sample preparation may proceed, for example, by striking sample preparation chamber 10005a with a bead beater motor or by other methods, as described in detain elsewhere herein. After lysis, the lysate may be expelled from sample preparation chamber 10005a through filter 13004 and channel 13006.

In one embodiment, the filter 13004 is sized such that lysis particles cannot flow through the filter but magnetic beads can readily pass. For instance, the lysis particles typically used in the embodiments described herein have a size of about 100-200 μm and the magnetic beads used in the embodiments described herein have a size of about 1-5 μm. Thus, in one embodiment, magnetic beads can be included in the lysis mixture and, after lysis, the lysate and magnetic beads can be expelled from sample preparation chamber 10005a while leaving the larger lysis particles behind. In other embodiments, the lysis may proceed as described elsewhere herein with zirconium silicate beads and, after bead beating, the lysate can be expelled from sample preparation chamber 10005a though filter 13004, leaving the lysis particles behind, and nucleic acid recovery can proceed with magnetic beads introduced downstream, as described elsewhere herein.

Figure 14A:
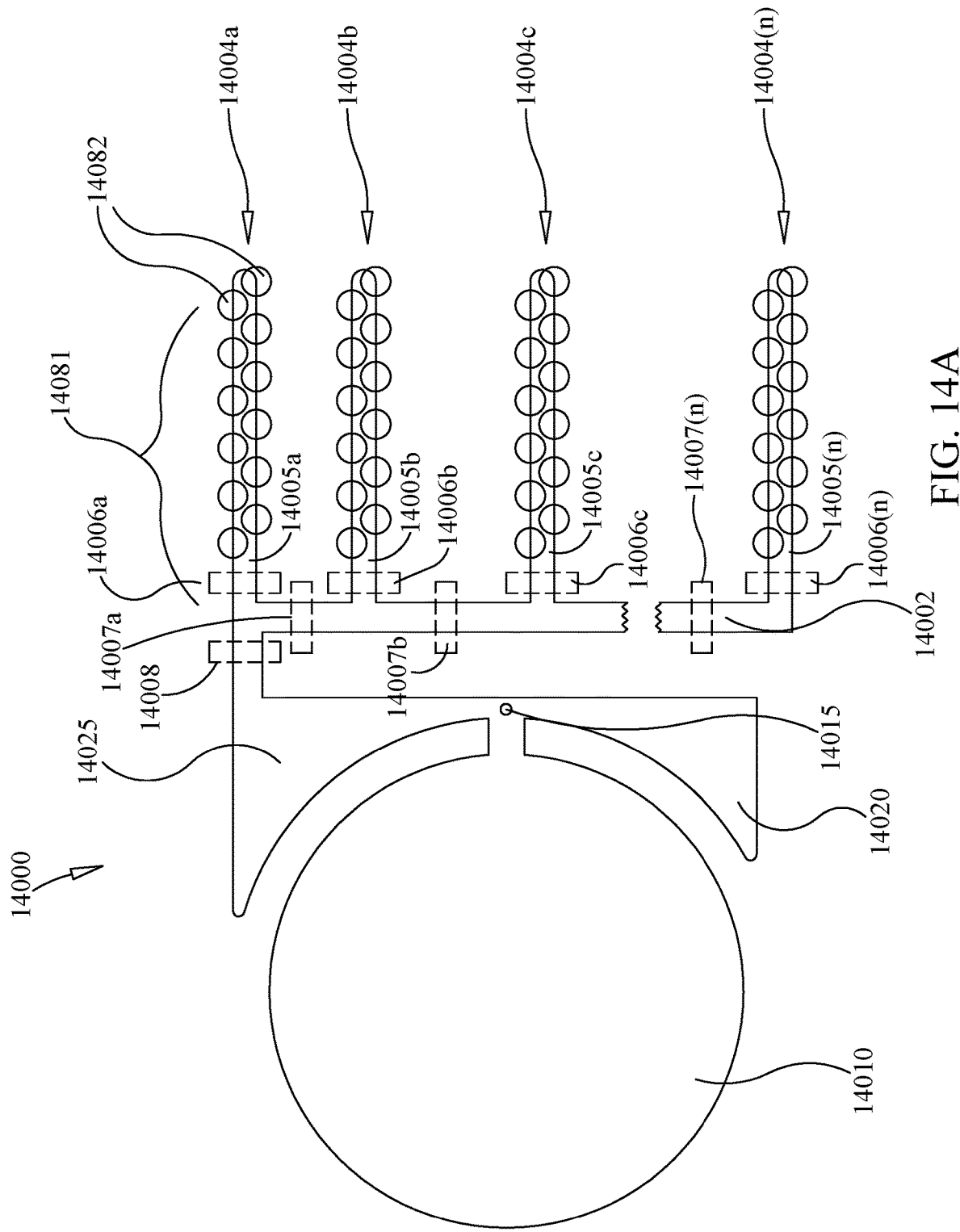
FIG. 14A illustrates a second-stage array with multiple independently fillable arrays of second-stage reaction wells.

Referring now to FIG. 14A, an alternative embodiment of a second-stage PCR array 14081 is illustrated. It is understood that FIG. 14A may show only portions of a pouch, and the features shown in FIG. 14A may be incorporated in the various illustrative pouches described herein. Second-stage PCR array 14081 includes 'n' rows 14004a, 14004b, 14004c, . . . 14004(n) of second-stage reaction wells 14082 that are respectively fluidly connected to array fill channels 14005a, 14005b, 14005c, . . . 14005(n). Second-stage PCR array 14081 is fluidly connected to a first-stage PCR reaction zone 14010, a dilution well 14015, and second-stage reagent mixing blisters 14020 and 14025. Second-stage PCR array 14081, the dilution well 14015, and the second-stage reagent mixing blisters 14020 and 14025 are fluidly connected to a fill channel 14002 that, in one embodiment, can be selectively opened and closed to allow filling of the wells of rows 14004a, 14004b, 14004c, . . . 14004(n) one at a time. Seal 14008 may be placed between blister 14025 and fill channel 14002, seals 14006a, 14006b, 14006c, . . . 14006(n) may be positioned across respective array fill channels 14005a, 14005b, 14005c, . . . 14005(n), and/or seals 14007a, 14007b . . . 14007(n) may be placed across fill channel 14002 to control the filling of each row of second-stage reaction wells 14082. The seals may be retractable seals or they may be heat seals or they may be a combination of retractable and heat seals, or other seals as known in the art. Likewise, the seals may be manually applied or they may be applied in an instrument.

In one embodiment, the wells 14082 connected to fill channel 14005a may be filled with fluid from blister 14010 (either using dilution well 14015 and mixing blisters 14020 and 14025, or with fluid direct from blister 14010) by retracting seal 14008 and keeping seal 14007a in place and moving a fluid sample from blister 14010 into fluid channel 14002. Seal 14006a may be placed after the wells 14082 connected to fill channel 14005a are filled. The wells 14082 connected to fill channel 14005b may be filled by opening seal 14007a, keeping seals 14007b and 14006a in place and moving a fluid sample from blister 14010 into fluid channel 14002. Seal 14006b may be closed after the wells 14082 connected to fill channel 14005b are filled. The wells 14082 connected to fill channel 14005c may be filled by opening seal 14006c and keeping seals 14007(n), 14006a and 14006b in place and moving a fluid sample from blister 14010 into fluid channel 14002. Seal 14006c may be closed after the wells 14082 connected to fill channel 14005c are filled. The wells 14082 connected to fill channel 14005(n) may be filled by opening seals 14006(n) and 14007a-14007(n) and keeping seals 14006a-14006c in place and moving a fluid sample from blister 14010 into fluid channel 14002. Seal 14006(n) may be closed after the wells 14082 connected to fill channel 14005c are filled.

In another embodiment, the wells 14082 connected to array fill channels 14005a, 14005b, 14005c, . . . 14005(n) may be filled in a reversed order from the previous example. The wells 14082 connected fill channel 14005(n) may be filled by keeping seals 14006a-14006c in place and opening seal 14006(n) while moving a fluid sample from blister 14010 into fluid channel 14002. Seal 14006(n) may be closed after filling the wells 14082 connected fill channel 14005(n). The wells 14082 connected fill channel 14005(c) may then be filled by keeping seals 14006a, 14006b, and 14006(n) in place and opening seal 14006(c) while moving a fluid sample from blister 14010 into fluid channel 14002. Seal 14006(c) may be closed after filling the wells 14082 connected fill channel 14005(c). The wells 14082 connected fill channel 14005(b) may then be filled by keeping seals 14006a, 14006c, and 14006(n) in place and opening seal 14006(b) while moving a fluid sample from blister 14010 into fluid channel 14002. Seal 14006(b) may be closed after filling the wells 14082 connected fill channel 14005(b). The wells 14082 connected fill channel 14005(a) may then be filled by keeping seals 14006b, 14006c, and 14006(n) in place and opening seal 14006(a) while moving a fluid sample from blister 14010 into fluid channel 14002. Seal 14006(a) may be closed after filling the wells 14082 connected fill channel 14005(a). While the wells 14082 connected to array fill channels 14005a, 14005b, 14005c, . . . 14005(n) are filled in these example in rank (a, b, c, . . . (n)

or (n) . . . c, b, a), one will appreciate that other fill orders may be used by opening and closing selected seals, as described in these examples.

In one embodiment, the contents of second-stage reaction wells 14082 in rows 14004a thru 14004(n) are substantially identical to one another (i.e., the second-stage primers in corresponding wells are the same). Thus, for example, the second-stage PCR could be initiated in row 14004a after a selected number of cycles of first-stage PCR (e.g., 10 cycles), row 14004b could be filled and second-stage PCR could be initiated in row 14004b after a selected additional number of cycles of first-stage PCR (e.g., 15 cycles total), row 14004c could be filled and second-stage PCR could be initiated in row 14004c after a selected further number of cycles of first-stage PCR (e.g., 20 cycles total), and so on. With multiple consecutive second-stage PCR reactions separated by the number of first-stage PCR reaction cycles contributing to the number of template molecules in the reaction, the number of second-stage PCR reaction cycles needed to reach a crossing point (Cp) or saturation in the parallel reactions can, for example, be used to back calculate the relative concentration of the organisms in the original sample or the concentration of the original template recovered from the lysate.

In another embodiment, the contents of second-stage reaction wells 14082 in rows 14004a thru 14004(n) may not be the same. The wells of row 14004a could, for example, be provided with different primer pairs in each of the second stage wells of row 14004a for amplifying target nucleic acid sequences from organisms that are expected to be present in the highest titers in the starting sample and that have highest risk for unexpected positives, the wells of row 14004b may, for example, be provided with different primer pairs in each of the second stage wells of row 14004b for amplifying target nucleic acid sequences from organisms present at high titers and that have a medium risk for unexpected positives, and wells of row 14004c may, for example, be provided with different primer pairs in each of the second stage wells of row 14004c for amplifying target nucleic acid sequences from organisms present at lower titers and that have a lower risk for unexpected positives. Additional rows through 'n' could be provided with primer pairs in their well for identifying different sets of organisms in the sample with different characteristics and different titers. In this embodiment, wells of rows 14004a thru 14004(n) may be filled and temperature cycled for second-stage PCR substantially simultaneously. Melts for detection of organisms in the sets in rows 14004a thru 14004(n) may be performed after different numbers of second-stage PCR cycles. For example, a melt to detect amplification of nucleic acids from organisms in the set of 14004a may be performed after 20 second-stage PCR cycles, a melt to detect amplification of nucleic acids from the organisms of the set in 14004b may be performed after 26 second-stage PCR cycles, a melt to detect amplification of nucleic acids from the organisms of the set in 14004c may be performed after 32 second-stage PCR cycles, and so on. See, e.g. U.S. Pat. Pub. No. 2015/0232916, herein incorporated by reference, for additional discussion. It is understood that such an arrangement of a second-stage array may be used with any of the pouches described herein, as appropriate.

Figure 14B:
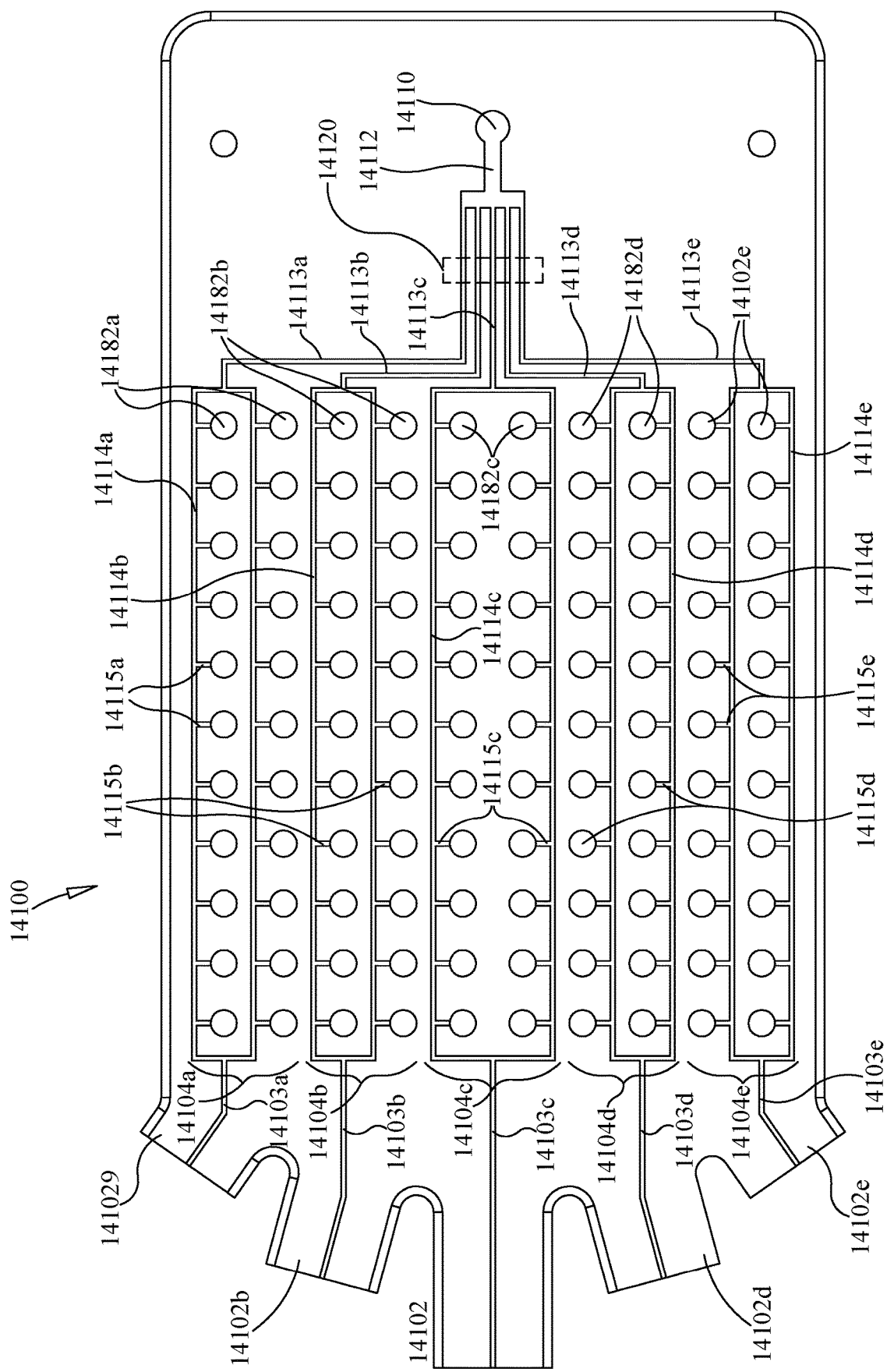
FIG. 14B illustrates another embodiment of a second-stage array with multiple independently fillable arrays of second-stage reaction wells.

FIG. 14B illustrates another embodiment of an array card 14100 that can be used in an assay device. Array card 14100 has many of the features of the array in assay apparatus 14000 illustrated in FIG. 14A. Array card 14100 may be used as a standalone array or may be incorporated as a second-stage array in the various illustrative pouches described and illustrated herein. Array card 14100 may be used in an assay pouch for PCR analysis, examples of which were discussed in reference to FIG. 14A, or array card may be used for other assays. One example of an application that array card 14100 may be used in is described below in reference to FIG. 14C.

Array card 14100 includes five separately fillable rows of wells 14104a-14104e that, respectively, include wells 14182a-14182e. However, one will appreciate that five rows of wells is merely illustrative and that an array card may include more or fewer separate rows of wells. The wells in the rows are accessible via fill channels 14102a-14102e, which can be connected to one or more fluid reservoirs (e.g., a first stage amplification zone), as described in other embodiments herein, and fluidic vias 14103a-14103e that fluidly connect wells grouped in rows 14104a-14104e to their respective fill channels. Specifically, fluidic vias 14103a-14103e are fluidly connected to wells 14182a-14182e via fluid channels 14114a-14114e and well fill channels 14115a-14115e. For instance, fluid entering fill channel 14102a may fill the wells 14182a of row 14104a through an interconnected fluid system that includes fluidic via 14103a, fluid channel 1411a, well fill channels 14115a, and wells 14182a. Wells 14182b-14182e of rows 14104b-14104e may be filled similarly.

As was discussed in reference to FIGS. 10A and 10B, some embodiments of assay apparatuses described herein include vacuum systems that permit a vacuum to be applied in situ to one or more the wells of an array. Array card 14100 includes such a vacuum system. The vacuum system includes a vacuum port 14110, vacuum channel 14112, and vacuum channels 14113a-14113e. Vacuum channels 14113a-14113e are fluidly connected to array wells 14182a-14182e via fluid channels 14114a-14114e and well fill channels 14115a-14115e. When included in an assay pouch, array card 14100 may be sealed between two or more layers of plastic film that seal the top and bottom surfaces of the array. Thus, if vacuum port 14110 is opened (e.g., by piercing the film covering the port) and a vacuum is applied to the port, the vacuum may partially evacuate all of the fluidly connected wells of the array 14100. A seal (e.g., a heat seal) applied in the region of 14120 over channels 14113a-14113e may simultaneously seal all of the channels from vacuum port 14110 and vacuum channel 14112 and seal all of the channels from each other so that fluid flowing into, for example, row 1414a may not access other rows through the vacuum channels. Further discussion of in situ application of a vacuum to an array or another portion of an assay pouch is described in PCT/US18/34194, the entirety of which is incorporated herein by reference.

Figure 14C:
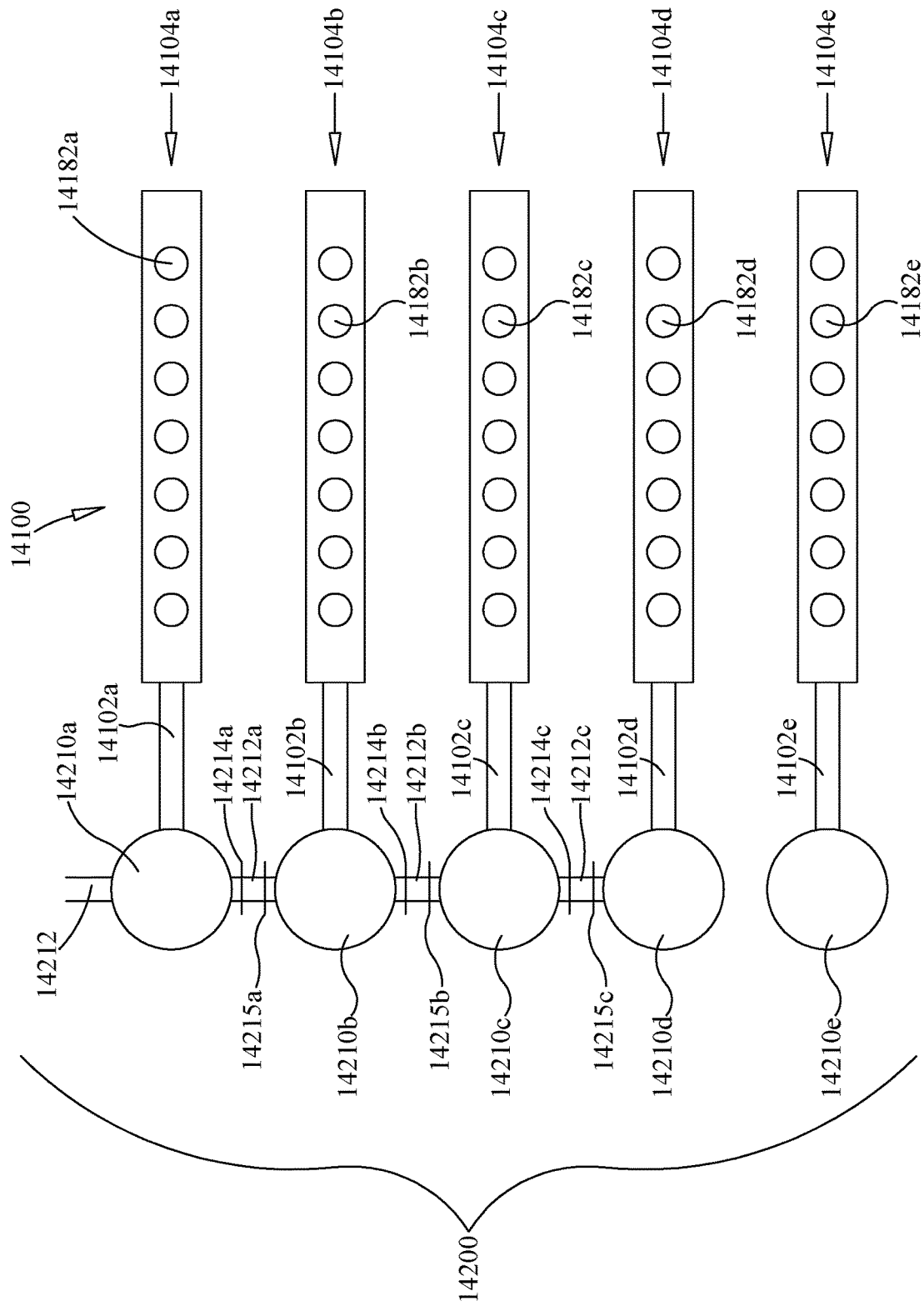
FIG. 14C is a schematic drawing illustrating how the second-stage array of FIG. 14B may be connected a series of fluid blisters for performing an analytical method.

In one embodiment, array 14100 of FIG. 14B may be incorporated into a pouch like 14000 illustrated in FIG. 14A, or array 14100 may be integrated into another pouch illustrated herein, such as, but not limited to, the pouches of FIG. 1, FIG. 5A, FIG. 7, FIGS. 11A and 11B, FIGS. 17A-17C, or FIG. 21A. FIG. 14C schematically illustrates an embodiment showing how array card 14100 may be incorporated into an assay article 14200. For purposes of simplicity, FIG. 14C does not show many of the details of array card 14100. Assay article 14200 shows array card 14100 fluidly connected to a series of fluid blisters 14210a-14210e that may be used for performing an assay. For instance, fluid blisters 14210a-14210e may be used for performing an assay with a series of serial dilutions (blisters 14210a-14210d) and a standard 14120e. Fluid blister 14120a includes a sample entry point 14212 through which a fluid sample may be injected into blister 14210a. Blister 14210a is connected to blisters 14210b-14201d by a series of fluid channels 14212a-14212c. Fluid flow into and out of channels 14212a-14212c may be controlled by seals 14214a-14214c and 14251a-14215c. The seals may be retractable seals or they may be heat seals or they may be a combination of retractable and heat seals, or other seals, as are known in the art. Likewise, seals may be manually applied or they may be applied automatedly inside an instrument.

In one embodiment, a sample may be added to blister 14210a, for example, through channel 14212 and fluid blisters 14210b-14210d may be provided with a selected volume fluid to perform a series of dilutions of the sample added to blister 14210a. In one embodiment, fluid channels 14212a-14212c may include volumetric dilution wells similar to well 14105 illustrated in FIG. 14A, or, in another embodiment, channels 14214a-14214c may be sized and dimensioned to receive a selected volume of fluid. For instance, sample from blister 14210a may be aliquoted into channel 14212a (either into a dilution well or into the channel itself) by opening seal 14214a, dispensing a volume of fluid into channel 14121a, closing seal 14214a and opening seal 14215a, and mixing the contents of the channel with the fluid in blister 14210b. Such a sequence may be repeated for 14210c and 14210d to perform a series of dilutions of the original sample in blister 14210a (e.g., a 0.1×, 0.01×, and 0.001× dilution series). In one optional embodiment, fluid blister 14210e may be pre-filled with a known standard solution for providing a reference for the sample in blisters 14210a-14210d.

Fluid in blisters may be introduced in to wells of rows 14104a-14104e by moving fluid from blisters 14210a-14210e through their respective fill channels 14102a-14102e and in to wells 14182a-14182e. In one embodiment, wells 14182a-14182e may be provided with reagents (e.g., dried reagents) for performing a selected assay. In one embodiment, wells 14182a-14182e may be provided with components for performing a PCR-based assay. In another embodiment, wells 14182a-14182e may be provided with reagents and reaction components for performing any of a variety of chemical- or biological-based assays. For instance, wells 14182a-14182e may be provided with one or more dried reagents for performing a turbidimetric or chromogenic endotoxin assay, as known to persons of skill in the art. In one embodiment, wells 14182a-14182e may be provided with the same reagents and/or components or they may be provided with a series of dilutions of the one or more reagents or components of the assay.

Referring now to FIGS. 15A-15C, a "sponge pump" for moving fluid from blister to blister in the pouches described herein is illustrated. Illustrated in FIG. 15A is a pair of blisters 15002 and 15004 of an illustrative pouch 15000. A channel 15003 connects blisters 15002 and 15004. Channel 15003 has an absorbent member 15006 (e.g., a sponge or another absorbent medium) that can be used to move volumes of fluid from one blister to another, as illustrated at 15008 and 15010. It is understood that FIG. 15A shows only portions of a pouch, and the features shown in FIG. 15A may be incorporated in the various illustrative pouches described herein, or in other embodiments.

As illustrated in FIGS. 15B and 15C, the absorbent member 15006a may be bonded to film layers 15012 and 15014. As seen in FIG. 15B, absorbent member 15006a can expand to absorb fluid and then, as seen in FIG. 15C, the adsorbent member 15006a may be compressed to dispense the fluid. The ends 15005a and 15005b of the channel 15003 can be closed (e.g., with seals in an instrument) to impose directionality on the fluid moved by the absorbent member. For example, in the illustrated embodiment, end 15005a of channel could be opened and end 15005b could be closed to draw fluid 15008 from blister 15002, and end 15005a could be closed and end 15005b could be opened to move the fluid to volume 15010 in blister 15004. In addition, because the absorbent member 15006 will absorb and dispense a predictable volume of fluid, the system illustrated in FIGS. 15A-15C can be used to move selected volumes of fluid in the pouches described herein. For example, a "sponge pump" may be used for performing the dilution between first- and second-stage PCR, or may be used for dispensing predetermined volumes of fluid for washing the magnetic beads and the elution of nucleic acids from the magnetic beads, as described elsewhere herein. In addition, reagents (e.g., buffers, polymerase, etc.) may be dried in the absorbent material 15006 as an alternative to dried reagent pills (see, e.g., FIG. 11C). Since the absorbent material 15006 can absorb and dispense a predictable and known volume of liquid, the absorbent material 15006 can be used for rehydrating a reagent with the predetermined volume of liquid.

Figure 16:
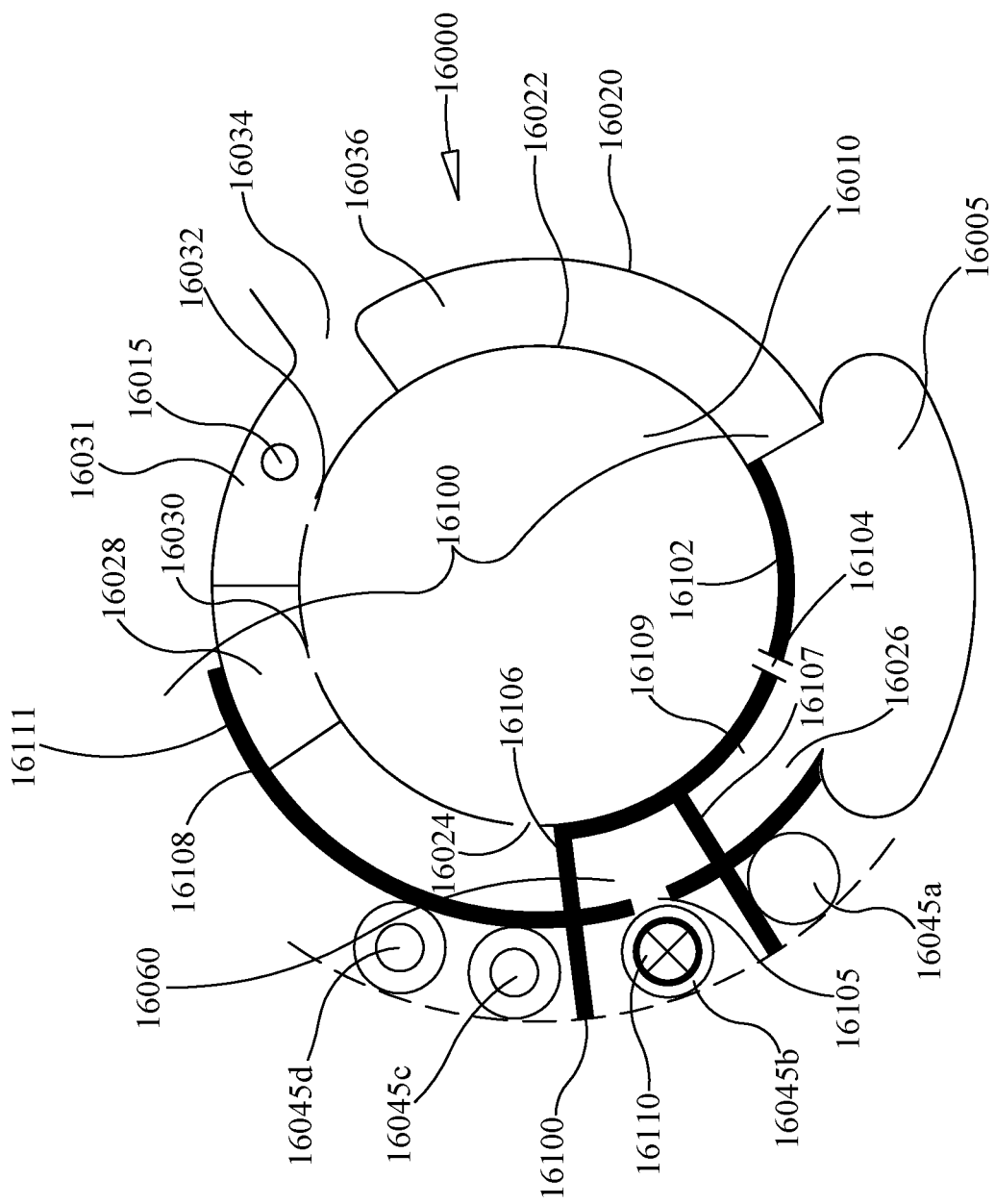
FIG. 16 illustrates another embodiment of a flexible pouch and features of an instrument configured for use with the pouch.

FIG. 16 illustrates another embodiment of a pouch 16000 that can be used for sample preparation and PCR in an enclosed chemistry card. The layout of pouch 16000 is different than other pouches and chemistry cards described herein, but pouch 16000 is similar in that it includes different blister areas where different processes can be performed.

Illustratively, pouch 16000 comprises a pair of nested rings defined by an outer wall 16020 and an inner wall 16022. Illustratively, outer wall 16020 and inner wall 16022 may be defined by laser weld lines. In the space between outer wall 16020 and inner wall 16022, a number of blisters, channels, and spaces are defined that may be used as work spaces in cooperation with an instrument configured to work with pouch 16000. Illustratively, blister 16005 may be a sample preparation blister, upstream blister 16036 may be used for introducing a sample into pouch 16000 and/or as a waste receptacle, channel 16026 may be a zone for further sample preparation including, but not limited to nucleic acid recovery, wash, and elution, and blister 16010 may be used for first-stage PCR. Additionally, blister 16028 may be used for introduction of reagents (e.g., reverse transcriptase, polymerase, etc.) into first-stage PCR blister 16010, and channel 16031, which may include dilution well 16015, may be used for transferring product of first-stage PCR to a downstream second-stage PCR array (not shown). Pouch 16000 illustratively also includes reagent blisters 16045a-16045d located outside of outer wall 16020 that are positioned to deliver reagents into the blisters and channels of pouch 16000. Pouch 16000 includes four reagent blisters, but this is illustrative only and other embodiments may include more or fewer reagent blisters. Use of these blisters, zones, and channels for sample preparation, first-stage PCR, etc. will be described in greater detail below.

FIG. 16 also schematically illustrates elements of an instrument 16100 that may act on pouch 16000 to accomplish functions like sample preparation and fluid movement. Element 16102 is an instrument inner wall that is concentric with inner wall 16022 of pouch 16000 and 16108 is an instrument outer wall that is concentric with to outer wall 16020 of the pouch 16000. Instrument inner wall 16102 includes an opening 16104 that can be aligned with openings in the inner wall 16022 (e.g., openings 16024, 16030, and 16032) that can be opened to create flow paths into and out of first-stage PCR blister 16010. Likewise, inner wall 16102 can also be aligned over the openings in the inner wall 16022 (e.g., openings 16024, 16030, and 16032) to cut off flow paths. Similarly, instrument outer wall 16108 includes an opening 16105 that can be aligned with openings, illustratively, between the reagent blisters 16045a-16045d and the sample preparation channel 16026.

Instrument 16100 also includes a first wiper 16106 and a second wiper 16107 that can be used to wipe fluid from space to space in the pouch 16000 and to define various work spaces in the pouch 16000. In one illustrative embodiment, wiper 16106 may be positioned to close the sample preparation blister 16005 at the entrance to the sample preparation channel 16026 and wiper 16107 may 'squeegee' a sample from blister 16036 into sample preparation blister 16060. As with the other sample preparation blisters described herein, sample preparation blister 16060 may contain lysis particles and cell lysis may be accomplished illustratively by contacting sample preparation blister 16060 with a bead beater or paddle beater apparatus. Following cell lysis, wiper 16106 may be moved upstream to define a work space adjacent to one of reagent blisters 16045a-16045 and wiper 16107 may be used to move fluid to the appropriate work space. Illustratively, reagent blister 16045a may contain magnetic beads for nucleic acid recovery, reagent blisters 16045b and 16045c may contain a reagent for washing the magnetic beads, and reagent blister 16045d may contain a reagent for elution of nucleic acids from the magnetic beads.

The use of wipers 16106 and 16107 to define a work space is schematically illustrated in the vicinity of reagent blister 16045b. That is, wipers 16106 and 16107 are positioned to confine a region of sample preparation channel 16026 to define a work space 16060 where fluid, reagents, and material can be contained in the vicinity of reagent blister 16045b. As illustrated, wipers 16106 and 16107 also define a channel 16105 between reagent blister 16045b and work space 16060. Illustratively, instrument 16100 includes a device 16110 that can compress the reagent blisters and dispense the reagent into the work space 16060. While movement of the wipers 16106 and 16107 is discussed in the foregoing, one will appreciate that one or more of wipers 16106 and 16107 may be stationary and that the pouch 16000 may be rotated to define works spaces, wipe fluid from region to region, etc. Thus, wipers 16106 and 16107 form portions of a selector ring 16111, where rotation of the selector ring 16111 allows materials to move to various regions within pouch 16000, illustratively through channel 16034. Thus, the numbers of channels and compressors may be reduced compared to other layouts for a pouch.

Illustratively, following elution of nucleic acids, opening 16104 may be aligned with opening 16024 to create flow path from the sample preparation channel 16026 into the first-stage PCR blister 16010. Reagents for first-stage PCR may illustratively be contained in blister 16010 or they may be contained in compartment 16028 or some reagents may be contained in both. Reagents for first-stage PCR may be hydrated by introduction of fluid from the sample preparation channel 16026 into blister 16010 and 16028. First-stage PCR may illustratively proceed in blister 16010 with a wiper and a heater with two temperature zones, as described elsewhere herein, illustratively in FIGS. 25, 26, 27A-27D, and 28A-28B. Likewise, first-stage PCR may be conducted in blister 16010 with a conventional thermocycling heater/cooler device cycling between denaturation, annealing, and elongation temperatures. Following first-stage PCR, at least a portion of the product of the reaction may be expelled through opening 16032 into channel 16031. A portion of the product may be measured in well 16015 and the rest may be sent to a waste chamber (not shown) or back into blister 16010, which may then be used as a waste blister. The measured product may be combined with reagents for second-stage PCR and may be sent via channel 16034 to a second-stage PCR reaction zone (not shown), illustratively a second-stage PCR array like array 581 of FIG. 1, or like other array embodiments described herein.

Figure 17A:
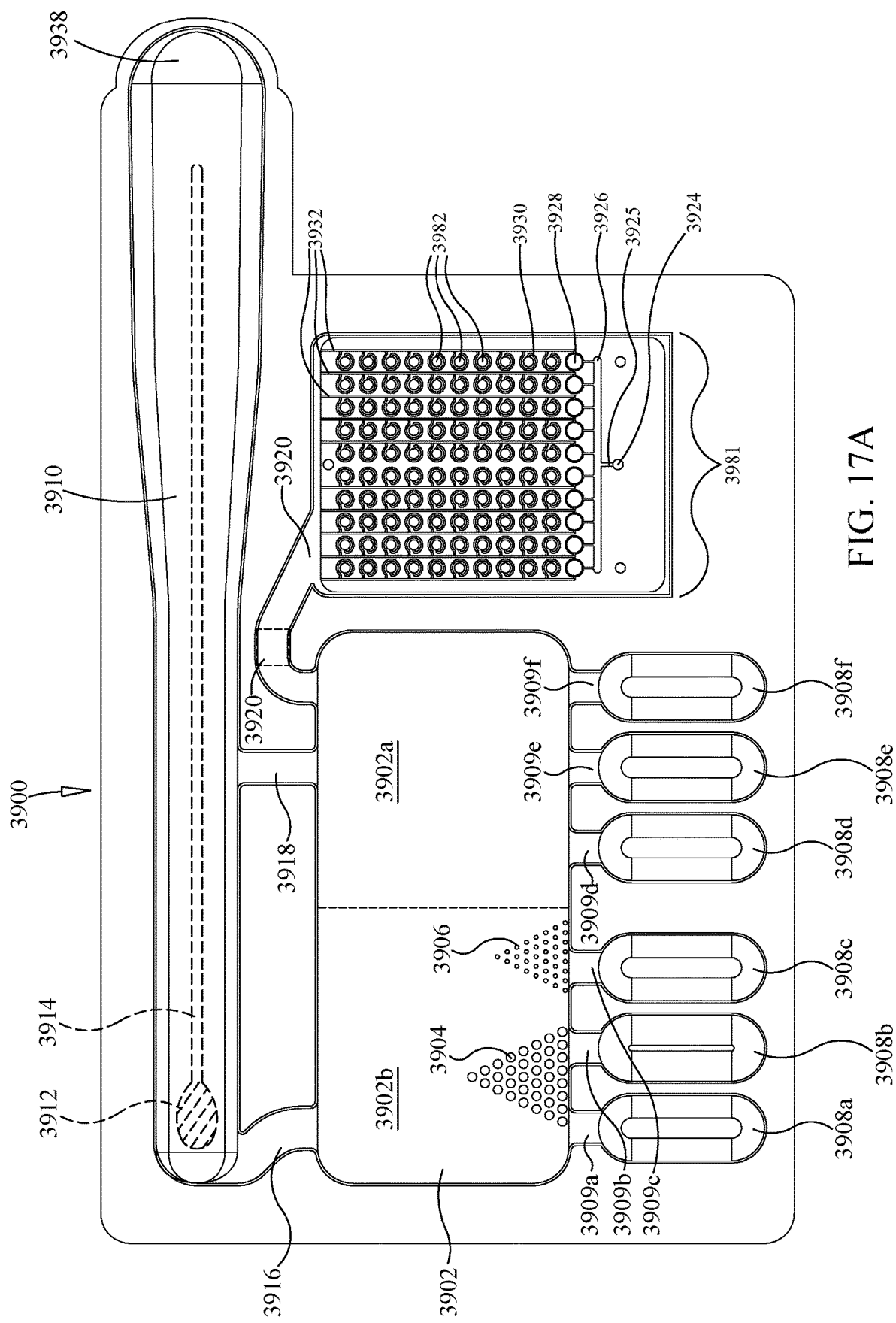
FIG. 17A illustrates another embodiment of a pouch, wherein the pouch includes reagents and components for sample preparation, nucleic acid recovery, and, optionally, a first-stage nucleic acid amplification reaction in a single compartment.
Figure 17B:
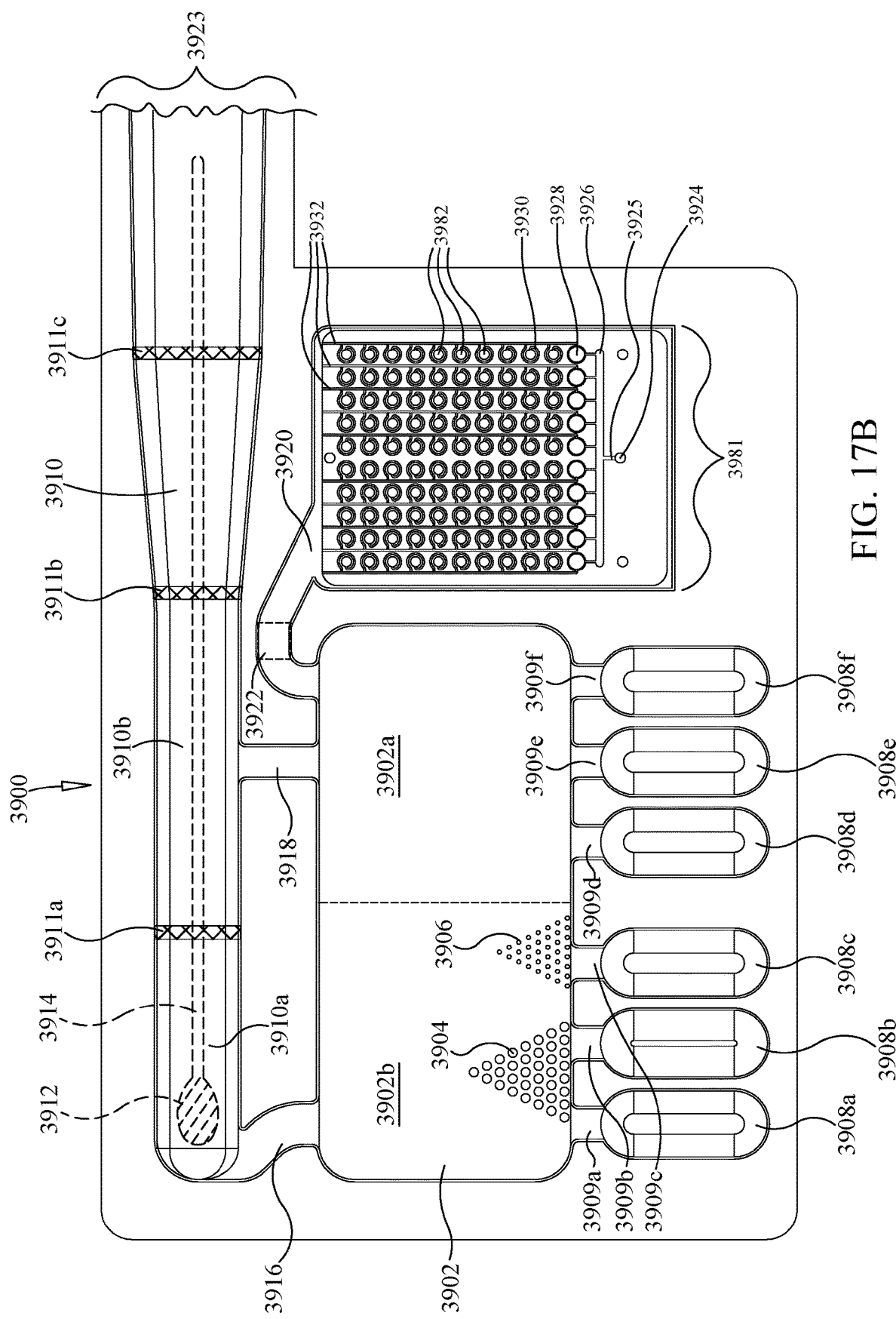
FIG. 17B illustrates the pouch of FIG. 17B with a sample introduction chamber opened for, in one embodiment, removal and insertion of a swab for introducing a sample into the pouch.

Referring now to FIGS. 17A and 17B, another embodiment of a flexible pouch 3900 that may be used with the methods and instruments is described herein. Flexible pouch 3900 includes a single chamber 3902 (referred to herein as a 'multifunction chamber') that can be used for sample preparation, nucleic acid recovery, and a first-stage multiplex nucleic acid amplification reaction or, alternatively, directly into a singleplex, real-time nucleic acid amplification reaction in a fluidly connected second-stage reaction zone. Performing these functions in a single chamber can simplify the pouch and simplify instruments used to run the pouch. Use of a single multifunction chamber can also save time for an assay that may be run in the pouch because many fluid movement steps can be simplified or eliminated, or multiple steps may be performed contemporaneously. Likewise, performing sample preparation and nucleic acid recovery in the same chamber can save time and instrument execution steps because the nucleic acid recovery medium (typically silica-coated magnetic beads) that is used for nucleic acid recovery in the methods described herein is rehydrated and dispersed in the lysate before or as the lysate is formed. As an added benefit, such a process can also increase sensitivity and shorten the time to detection because the nucleic acid recovery medium is dispersed in the whole volume of lysate.

As in the previous examples, flexible pouch 3900 may be formed of two layers of a flexible plastic film or other flexible material such as polyester, polyethylene, polyethylene terephthalate (PET), polycarbonate, polypropylene (PP), polymethylmethacrylate, mixtures, combinations, and layers thereof that can be made by any process known in the art, including extrusion, plasma deposition, and lamination. For instance, each layer can be composed of one or more layers of material of a single type or more than one type that are laminated together. One operative example is a bilayer plastic film that includes a PET layer and a PP layer, as discussed elsewhere herein. Metal foils or plastics with aluminum lamination also may be used. Illustratively, the material has low nucleic acid binding and low protein binding capacity. If plastic film is used, the layers may be bonded together, illustratively by heat sealing.

In some embodiments, a barrier film may be used in one or more of the layers used to form the flexible pouch 3900. For instance, barrier films may be desirable for some applications because they have low water vapor and/or oxygen transmission rates that may be lower than conventional plastic films. For example, typical barrier films have water vapor transmission rates (WVTR) in a range of about 0.01 $g/m^2/24$ hrs to about 3 $g/m^2/24$ hrs, preferably in a range of about 0.05 $g/m^2/24$ hrs to about 2 $g/m^2/24$ hrs (e.g., no more than about 1 $g/m^2/24$ hrs) and oxygen transmission rates in a range of about 0.01 $cc/m^2/24$ hrs to about 2 $cc/m^2/24$ hrs, preferably in a range of about 0.05 $cc/m^2/24$ hrs to about 2 $cc/m^2/24$ hrs (e.g., no more than about 1 $cc/m^2/24$ hrs). Examples of barrier films include, but are not limited to, films that can be metallized by vapor deposition of a metal (e.g., aluminum or another metal) or sputter coated with an oxide (e.g., $Al_2O_3$ or $SiO_x$) or another chemical composition. A common example of a metallized film is aluminized Mylar, which is metal coated biaxially oriented PET (Bo-PET). In some applications, coated barrier films can be laminated with a layer of polyethylene, PP, or a similar thermoplastic, which provides sealability and improves puncture resistance. As with conventional plastic films, barrier films layers used to fabricate a pouch may be bonded together, illustratively by heat sealing. Illustratively, the material has low nucleic acid binding and low protein binding capacity. Other barrier materials are known in the art that can be sealed together to form the blisters and channels.

In the embodiment illustrated in FIGS. 17A and 17B, multifunction chamber 3902 may be provided with lysis particles 3904 and nucleic acid recovery beads 3906 (typically silica-coated magnetic beads). For purposes of illustration, the lysis particles 3904 and nucleic acid recovery beads 3906 are shown separately. However, one will appreciate that the lysis particles 3904 and nucleic acid recovery beads 3906 may be provided intermixed in multifunction chamber 3902. Likewise, while the multifunction chamber 3902 is shown provided with lysis particles 3904 and nucleic acid recovery beads 3906, one will appreciate that one or both of lysis particles 3904 and nucleic acid recovery beads 3906 may be provided in the reagent blisters in the flexible pouch 3900, such as in reagent blister 3908a, or one or both may be provided with the sample. In some embodiments, lysis particles 3904 may be omitted. For many analytes, agitation with or without heat in the presence of a lysis buffer (e.g., a buffering agent, a chaotrope, and a detergent) may be sufficient to induce lysis and the lysis bead may be omitted. For other analytes, the recovery beads may serve both lysis and recovery functions. In one embodiment, a lysis buffer may be provided in multifunction chamber 3902, or in a reagent blister, such as blister 3908a. It is understood that the magnetic beads may be present during lysis in any of the embodiments discussed herein.

In the illustrated embodiment, the multifunction chamber 3902 of the flexible pouch 3900 is fluidly connected to a number of reagent blisters 3908a-3908f that can be provided with various reagents at the time of manufacture and can be used for introducing reagents for, for example, sample preparation, nucleic acid recovery, one or more washes, first-stage PCR, and second-stage PCR into the multifunction chamber 3902. However, one will appreciate that in another embodiment a flexible pouch may be provided with one or more empty reagent blisters into which reagent can be introduced at some later time, illustratively by an end user just before use. In one embodiment, one or more of the reagents in reagent blisters 3908a-3908f may be provided in dried form (see, e.g., FIG. 11C). In another embodiment, one or more of the reagents in reagent blisters 3908a-3908f may be provided in liquid form (see, e.g., FIGS. 11A and 11B). In the illustrated embodiment, reagents from reagent blisters 3908a-3908f may be introduced into multifunction chamber 3902 via channels 3909a-3909f by applying an external pressure to the reagent blisters to force fluid from the blisters and into chamber 3902. In one embodiment, the channels 3908a-3908f may be openably sealed at the time of manufacture to prevent leakage of reagents from the blisters into multifunction chamber 3902, or the contents of the reagent blisters 3908a-3908f may be provided in packets similar to packet 12020 of FIG. 12C.

Also in the illustrated embodiment, pouch 3900 includes a sample receiving chamber 3910. In one embodiment, the sample receiving chamber 3910 may comprise a cavity (e.g., a tubular well or blister) configured to receive a sample. Such a cavity may be formed by methods known in the art, such as, but not limited to, heating the material used to fabricate pouch 3900 and forming the material around a form (e.g., a mold). In another embodiment, the sample receiving chamber 3910 may be formed by sealing a sample tube (e.g., a plastic tube) in the film layers at the time of manufacture. In any case, the sample receiving chamber 3910 may be fluidly connected to the multifunction chamber 3902 so that sample can be introduced in and waste can be ejected from the multifunction chamber 3902. In the illustrated embodiment, the sample receiving chamber 3910 is connected to the multifunction chamber 3902 by channels 3916 and 3918. One will appreciate, however, that this is merely illustrative and that the flexible pouch may include more or fewer channels connecting multifunction chamber 3902 to the sample receiving chamber 3910.

In one embodiment, the sample receiving chamber 3910 may include a sample collection swab 3912. The sample collection swab may be used to collect a sample (e.g., nasal discharge, sputum, blood, stool, soil, etc.) and deliver the sample to the sample receiving chamber 3910. In another embodiment, a liquid, solid, or semi-solid sample may be injected directly into the sample receiving chamber 3910 in lieu of or in addition to using the sample collection swab 3912. In another embodiment, a transfer pipette, a capillary tube (e.g., a blood collection capillary tube), a facial tissue that includes a sample (i.e., a soiled tissue), or the like may be received in the sample receiving chamber 3910. In the illustrated embodiment, the swab 3912 includes a shaft 3914 that may be used to hold the swab, for manipulating the swab for collecting a sample, and to return the swab to the sample receiving chamber 3910. As illustrated in FIG. 17B, the top 3935 of the sample receiving chamber 3910 may be opened or removed to create an opening illustrated at 3923 so that the swab 3912 can be removed for sample collection and returned for analysis.

In one embodiment, shaft 3914 and sample receiving chamber 3910 are configured so that one or more seals (e.g., heat seals) can be placed across the shaft 3914 to seal sample receiving chamber 3910. Sealing across the shaft may simplify use of the pouch for the user and, for example, obviate the need for a breakable swab shaft such as the shaft used on the swab of FIGS. 11A and 11B. In the illustrated embodiment, three seals 3911a-3911c may be placed across the shaft 3914. Nevertheless, one will appreciate that this is merely illustrative and that more or fewer seals may be placed. In one embodiment, the seals may be placed to create different sub-chambers in the sample receiving chamber 3910. In the illustrated embodiment, for example, seal 3911a may be placed to create a sample rehydration/dispersal chamber 3910a and seals 3911a and 3911b may form a waste chamber 3910b. As such, channel 3916 may be used for sample rehydration/dispersal and introduction of the sample into multifunction chamber 3902 and channel 3918 may be used for expelling waste (e.g., spent lysate and wash buffer) from multifunction chamber 3902. Seal 3911c may, for example, be placed to guard against leakage. Seal 3911c may be placed as shown over a portion of the swab shaft 3914, however, one will appreciate that seal 3911c may also be placed above the end of the shaft. In one embodiment, excess air may be expelled from multifunction chamber 3902 and the sample receiving chamber 3910 prior to placing one or more of seals 3911a-3911c. It is understood that features of sample receiving chamber 3910 may be used with pouch 10000, and that features of sample preparation zone 10005 may be used with pouch 3900. Also features of sample receiving chamber 3900 and sample preparation zone 10005 may be used with any of the other pouches described herein.

In the case of heat sealing the sample receiving chamber 3910 across shaft 3914, the shaft may be at least partially softened or melted and fused, stuck, tacked, or adhered to the material used to fabricate flexible pouch 3900 and sample receiving chamber 3910. Incorporating the shaft into the seal(s) may, for example, prevent leakage around the seals. Likewise, sealing the swab in the sample receiving chamber allows the use of a swab with a full-length shaft and no breakable tip and reduces the number of manual manipulations that an operator has to perform with the swab to collect a sample and return it to the sample receiving chamber. In addition, omitting a breakable tip reduces the chance of an adverse event of breaking off the tip accidentally, e.g., in a patient. Referring now to FIGS. 43A-43D, several examples of shafts that may be used are illustrated. In one embodiment, FIG. 43A is a cross-section of a substantially round shaft 4114a. Substantially round shaft 4114a includes an outer layer 4102 and an inner lumen 4103. In another embodiment, FIG. 43B illustrates a cross-section of a substantially diamond-shaped shaft 4114b. Like shaft 4114a, shaft 4114b includes a hollow inner lumen 4105 and an outer layer 4104. In one embodiment, one or more of the corners 4104a-4104d of shaft 4114b may be rounded as shown, or may be elongated. FIG. 43C illustrates another shaft 4114c with an oval shape and a solid profile 4106. The oval shape of shaft 4114c may be flattened and/or elongated for better sealing. For instance, swabs with shafts like 4114b and 4114c having non-circular cross-sections may provide a better seal than circular cross-sections, as circular cross-sections may leave a gap or void adjacent the shaft. FIG. 43D illustrates yet another shaft 4114d with an outer layer 4107 disposed over a solid core 4108. In one embodiment, core 4108 may be a wire or another stiffening and/or shapeable member that can allow the swab to be pushed and guided into a cavity for sample collection. Swabs with shafts made from wire or other thin, stiff, shapeable materials are known in the art and may be used for collecting certain sample types. One will appreciate, of course, that shafts 4114a-4114d are merely exemplary and that other shaft shapes and lumen shapes (e.g., the shape of the lumen need not necessarily reflect the shape of the outer layer and other outer layer or solid shapes may be used) are possible and within the scope of this disclosure.

In one embodiment, the material(s) used to fabricate shafts 4114a-4114d are selected to be compatible with the film materials used to fabricate the pouch, and more specifically, the sample receiving chamber. As used herein, the term 'compatible' refers to materials that can be fused together to form a stable bond. The two polymers to be joined can, but are not required to, be the same type of material. That being the case, the plastics used to form the pouch and the swab shaft are expected to share similar properties to be good candidates for bonding. The factors that make plastics compatible include, but are not limited to, the chemical make-up of the polymer chains, similar and overlapping melting temperatures of the polymers, and the surface energy of the plastics. The more similar the plastics are in these characteristics the better the bond. Most common thermoplastics are easily bonded to themselves as well as a variety of other combinations known in the art.

For instance, the pouch 3900 and sample receiving chamber 3910 may be fabricated from a bilayer film that includes a polyethylene terephthalate (PET) outer layer and a polypropylene (PP) inner layer. Such a bilayer material allows the inner PP layers of the pouch films to be heat sealed together (e.g., laser or heat welded) without compromising the integrity of the higher melting outer PET layers. Plastic shaft materials that may be 'compatible' with the PP material include, but are not limited to, polyethylene (PE), PP or PE co-polymers and block copolymers, other thermoplastic copolymers like ethylene vinyl acetate (EVA), ethylene ethyl acetate (EEA), and the like. Fabrication of the pouch from PET/PP bilayer material and the foregoing examples of compatible shaft materials are merely illustrative. It is thus understood that the pouch can be fabricated from other materials, as discussed elsewhere herein above, and that swab shaft materials compatible with other pouch film materials are known to persons of ordinary skill in the art.

Referring now to FIG. 44A, an example of a shaft 4214a that can be sealed in a sample receiving chamber 3910a is illustrated in cross-section. Sample receiving chamber 3910a in the illustrated embodiment is fabricated from a first layer of material 4202 and a second layer of material 4204; the layers are bonded together on the edges at 4206 and 4208 to form chamber 3910a. FIG. 44B illustrates the sample receiving chamber 3910b after forming a seal 3911 across the shaft. In the seal 3911, shaft 4114a may be completely collapsed to form sealed shaft 4214b and layers 4202 and 4204 may be completely sealed to each other and to shaft 4214b as indicated at 4210. In one embodiment, the shaft shape, the shaft material, and the sealing procedure are selected so that there are preferably no voids in the cross-section of the seal 3911. For instance, shafts with an inner lumen like shafts 4114a and 4114b may be preferred in some embodiments because they include less material and they may be easier to melt. Shafts like 4114c may readily melt and spread to form the seal. Likewise, one or more of the corners 4104a-4104d of substantially diamond-shaped shaft 4114b may be rounded or may be elongated for better sealing. It is also possible that rounding one or more corners may reduce the likelihood of the formation of hot spots on the film or shaft that can lead to holes in the seal region.

Referring again to FIGS. 17A and 17B, multifunction chamber 3902 is configured for sample preparation (e.g., lysis), nucleic acid recovery (e.g., recovery of nucleic acids from the lysate with a nucleic acid-binding substrate such as silica-coated magnetic beads, expelling the spent lysate, washing the magnetic beads with a wash buffer, elution of the nucleic acids from the beads), and a first-stage multiplex nucleic acid amplification reaction. In a typical work flow, the sample receiving chamber 3910 of pouch 3900 may be opened, illustratively by opening the pouch open at opening 3923, the swab 3912 may be removed, used to collect a sample, and the swab 3912 with the sample may be returned to the sample receiving chamber 3910. The pouch 3900 may then be inserted into an instrument and the sample receiving chamber 3910 may be sealed as described above. Lysis buffer, which may be provided in the multifunction chamber 3902, in blister 3908a or other blister, or may be injected along with or prior to loading a sample, may be forced from the multifunction chamber 3902 into the sample rehydration/dispersion chamber 3910a by application of an external force to chamber 3902, agitated, and returned to the multifunction chamber 3902 by application of an external force to chamber 3910a. Following introduction of the sample into chamber 3902, silica-coated magnetic beads 3906 and, optionally, lysis particles 3904 may be introduced into chamber 3902 from reagent blister 3908a via channel 3909a by applying an eternal force to blister 3908a. Optionally, silica-coated magnetic beads 3906 and the optional lysis particles 3904 may be provided in chamber 3902 in the lysis buffer and reagent blister 3908a may be used for another component.

In one embodiment, lysis in the multifunction chamber 3902 may occur, for example, by vortexing via impaction using rotating blades as provided within the FilmArray® instrument or by a paddle beater using reciprocating or alternating paddles, such as those described in PCT/US2017/044333, herein incorporated by reference in its entirety. In one embodiment, lysis may include agitation (e.g., vortexing) while heating the sample (e.g., to a temperature in a range of 40° C. to 100° C.). In another embodiment, agitation may be omitted and lysis may occur through a combination of heat and chemical action.

Following lysis, the magnetic beads 3906 may be isolated in the multifunction chamber 3902 by activation of an external magnet in the instrument (similar to magnet 850 of FIG. 2) and the lysate may be expelled to the waste chamber 3910b via channel 3918 by application of an external pressure to chamber 3902. In one embodiment, the lysate may be set to a controlled temperature (e.g., to a temperature in a range of 60° C. to 0°) to encourage nucleic acid binding to the silica-coated magnetic beads prior to activating the magnet and expelling the lysate. After expelling the lysate, the magnet may be moved away and the magnetic beads, the optional lysis particles, and the multifunction chamber itself may be subjected to at least one wash with a wash buffer. In one embodiment, the wash buffer is an acidic buffer (e.g., around pH 5); the wash (or washes) may be conducted a controlled temperature (e.g., to a temperature in a range of 60° C. to 0°). The wash buffer may be introduced into chamber 3902 from reagent blisters 3908b and, optionally, 3908c via channels 3909b and 3909c. The magnetic beads may be isolated by activation of the magnet and the spent wash buffer may be expelled to waste chamber 3910b. In one embodiment, the wash (or washes) may include agitation of chamber 3902 to disperse the magnetic beads and the optional lysis particles in the wash buffer.

Following the wash (or washes), reagents for the first-stage nucleic acid amplification reaction may be introduced into chamber 3902. In one embodiment, reagents for the first-stage nucleic acid amplification reaction may be introduced from one or more of the reagent blisters. In one embodiment, the first-stage amplification reagents are provided in liquid form with some reagents in each of reagent blisters 3908d and 3908e, so that each of reagent blisters 3908d and 3908e contain incomplete amplification reactions to avoid primer dimer formation, or the like. Reagents from blisters 3908d and 3908e are provided via channels 3909d and 3909e. In one embodiment, the reagents for the first-stage nucleic acid amplification reaction may elute the nucleic acids recovered from the lysate from the magnetic beads. In one embodiment, the pH of the reagents for the first-stage nucleic acid amplification reaction may be around pH 7-9 (e.g., pH 8.5). In one embodiment, the recovered nucleic acids may include RNA and, as such, a reverse transcription step may be performed in multifunction chamber 3902 prior to or simultaneous with the first-stage multiplex nucleic acid amplification reaction. In one embodiment, the reagents from blisters 3908d and 3908e include reagents for the reverse transcriptase step and the first-stage multiplex nucleic acid amplification reaction. In one embodiment, reagent blister 3908d may include components for the reverse transcriptase step and blister 3908e may include components for a first-stage multiplex PCR reaction. In one embodiment, multifunction chamber 3902 is configured for amplification by thermocycling using a Peltier or another heater that can thermocycle to heat and cool the contents of multifunction chamber 3902, or by translating a pair of heaters, such as heaters 1286 and 1287 of FIG. 28B, set, for example, to an annealing temperature and a denaturation temperature to heat and cool the contents of chamber 3902 or, alternatively, by translating pouch 3900 relative to the heaters.

In one embodiment, the reverse transcription step may be performed in chamber 3902 in the presence of lysis particles and magnetic beads, or one or both of the magnetic beads and lysis particles may be sequestered prior to performing the reverse transcription step. In one embodiment, magnetic beads may be sequestered by activation of a magnet similar to magnet 850 of FIG. 2 adjacent to chamber 3902. In one embodiment, lysis particles, if present, may be sequestered by allowing them to settle in chamber 3902 and then, for example, activating a pressure member to, for example, isolate the lysis particles in 3902b and to expel the fluid to 3902a. It is understood that lysis particles are often larger than other components in multifunction reaction chamber 3902 and this size may aid in settling. Magnetic beads may be isolated with the lysis particles, if present, by activation of a magnet in 3902b or in one discrete area of 3902a. In one embodiment, the first-stage multiplex nucleic acid amplification reaction may be conducted in the multifunction chamber 3902 in the presence of both the magnetic beads and the lysis particles. It is understood that if magnetic beads are present during first-stage amplification, an elution step may be omitted and some of the first-stage amplification may occur with target nucleic acid still bound to the magnetic beads. In such an embodiment, a component that aids in neutralizing the inhibitory effect on amplification in the presence of magnetic beads may be needed. Such components may include buffers, a coating molecule such as BSA, or other components as are known in the art. In another embodiment, the magnetic beads and the lysis particles may, for example, be sequestered in 3902b by the activation of a magnet and a pressure member, and the eluate may be expelled to 3902a for the first-stage multiplex nucleic acid amplification reaction.

After the first-stage multiplex nucleic acid amplification reaction has proceeded for a desired number of cycles, the sample may optionally be diluted by, illustratively, expelling a portion of the product of the first-stage multiplex nucleic acid amplification reaction, illustratively to chamber 3910a or 3910b, leaving only a small amount of the product in multifunction chamber 3902. The product may then be diluted by adding reagents for a second-stage nucleic acid amplification reaction from, illustratively, reagent blister 3908f into multifunction chamber 3902. Product may be expelled and reagents may be introduced to, for example, yield a 1:10 to 1:100 dilution of the product of the first-stage multiplex nucleic acid amplification reaction. In one embodiment, reagent blister 3908f may be reserved and primary dilution may be performed with reagents for a second-stage nucleic acid amplification reaction from reagent blister 3908e and dilution may be repeated with reagents from blister 3908f. In another illustrative embodiment, one of the reagent blisters (e.g., blister 3908e) may include a diluent (e.g., a buffer) and another reagent blister (e.g., blister 3908f) may include reagents for a second-stage nucleic acid amplification reaction. It is understood that the level of dilution may be adjusted by altering the number of dilution steps or by altering the percentage of the sample discarded prior to mixing with the reagents for the second-stage nucleic acid amplification reaction. In some embodiments, a volumetric dilution chamber may be used.

In one embodiment, reagents for the second-stage nucleic acid amplification reaction may comprise a master mix for amplification, illustratively a polymerase, dNTPs, and a suitable buffer, although other components may be suitable. In another embodiment, the reagents for the second-stage nucleic acid amplification reaction may comprise an incomplete reaction mix that is lacking at least one of the components for the second stage amplification with the lacking component(s) being dried in each of the second stage wells 3982. In one illustrative embodiment, the reagents for the second-stage nucleic acid amplification reaction is lacking primer pairs, and each of the second-stage wells 3982 is pre-loaded with a specific PCR primer pair. Each primer pair may be similar to or identical to a first-stage PCR primer pair or may be nested within the first-stage primer pair. In one illustrative embodiment, the reagents for the second-stage nucleic acid amplification reaction may be lacking primer pairs and one or more of polymerase (e.g., klentaq), Mg++, or buffer, and the lacking component(s) (e.g., polymerase (plus stabilization reagent), Mg++, or buffer) may be dried in the second-stage wells 3982. This may allow for greater stability of the dried components as well as a cost reduction for more expensive reagents like polymerase because the array wells are spotted with only as much of the component (s) needed for the reaction in the each well, rather than flooding the array with excess volume containing the component(s) and expelling the excess. If desired, this mixture of the sample and the reagents for the second-stage nucleic acid amplification may be pre-heated in multifunction chamber 3902 prior to movement to second-stage wells 3982 for second-stage amplification. Such preheating may obviate the need for a hot-start component (antibody, chemical, or otherwise) in the second-stage PCR mixture. If real-time or post-amplification detection is desired, the mixture or the second-stage wells may include a dye or other suitable detection component, and the associated instrument may include a fluorimeter or other detection mechanism.

In the illustrated embodiment, multifunction chamber 3902 is fluidly connected to an array 3981 that includes a number of wells 3982 for a second-stage nucleic acid amplification reaction. Array 3981 and wells 3982 may be filled via channel 3920. Well filling of the second-stage array is discussed in detail elsewhere herein. In brief, filling each of wells 3982 is generally accomplished by placing the array under partial vacuum. This may be done at the time of manufacture (the level of vacuum may be maintained by storing the pouch in a container under vacuum) or a vacuum may be applied to the array in situ—e.g., in an instrument while the pouch is in use. Array 3981, which may be configured for the latter, includes a vacuum port 3924, a vacuum way 3926, vacuum reservoirs 3928, array flow channels 3932, and spiral paths 3930, although other direct of convoluted paths may be used. Several illustrative examples of well filling paths are illustrated herein in reference to FIGS. 20A-20E. A vacuum applied at vacuum port 3924 prior to filling the array will evacuate the wells 3982 via the vacuum way 3926, vacuum reservoirs 3928, array flow channels 3932, and illustrative spiral paths 3930; the vacuum can be preserved, for example, by applying a heat seal in the region of 3925 to close off the vacuum way 3926. Additional discussion of in situ application of a vacuum to a second-stage array and second-stage array designs configured for in situ application of a vacuum can be found in PCT/US18/34194, the entirety of which was previously incorporated herein by reference.

Similar to other embodiments described herein, each of wells 3982 may be in fluid communication with the multifunction chamber 3902 via fill channel 3920, which is in turn in fluid communication with a series of array flow channels 3932. In one embodiment, fill channel 3920 may include a filter 3922 (or the like) to prevent magnetic beads, lysis particles, and the like from traveling from the multifunction chamber 3902 and into the array 3981. In the illustrative example shown in FIGS. 17A-17B, wells 3982 are fluidly connected to the multifunction chamber 3902 via the array flow channels 3932 that connect to each well via spiral paths 3930 that spiral around each of the wells 3982. This is another example of a "convoluted" array well filling path that may help prevent unwanted mixing of fluids (i.e., cross-talk) between array wells. However, it is understood that these array flow channels 3932 and spiral paths 3930 are only one illustrative example of a well filling path and that other convoluted well filling paths may be used Other convoluted well filling paths are shown in FIGS. 6B, 6C, 8A, 8B, and 20B-20E. Other ways of filling wells 3982 without cross-contamination are also contemplated. See, e.g. U.S. Pat. No. 8,895,295, herein incorporated by reference. Contents of the second-stage array 3981 may be thermocycled with the heater/cooler (e.g., a Peltier) position in the instrument for heating and cooling second stage array 3981, or by translating a pair of heaters, such as heaters 1286 and 1287 of FIG. 28B, set, for example, to an annealing temperature and a denaturation temperature to heat and then cool the contents of chamber second stage array 3981 or, alternatively, by translating pouch 3900 relative to the heaters.

In one embodiment, channels 3909a-3909f, 3916, 3918, and 3912 may be sealed, illustratively with burstable, peelable, or other openable seals formed by the addition of binding material such as wax or adhesive that may be placed during pouch fabrication, or, using the film layers to fabricate pouch 3900 that have some natural affinity for one another and may tend to bond loosely together, such seals may be formed by film layers in a channel that are tacked together. For instance, film layers can be tacked together by applying heat to the film layers (e.g., by rolling between heated rollers) sufficient to transiently bond the films together but not sufficient to form a permanent bond. This and other seals discussed herein may be peelable, frangible, tacked together, one-way, pressure, or other seals, as are known in the art. Channels 3909a-3909f, 3916, 3918, and 3912 may also be sealed with hard seals in an instrument used to run an assay in flexible pouch 3900. Examples of hard seals are illustrated in the channels of the pouch shown in FIG. 3.

Figure 17C:
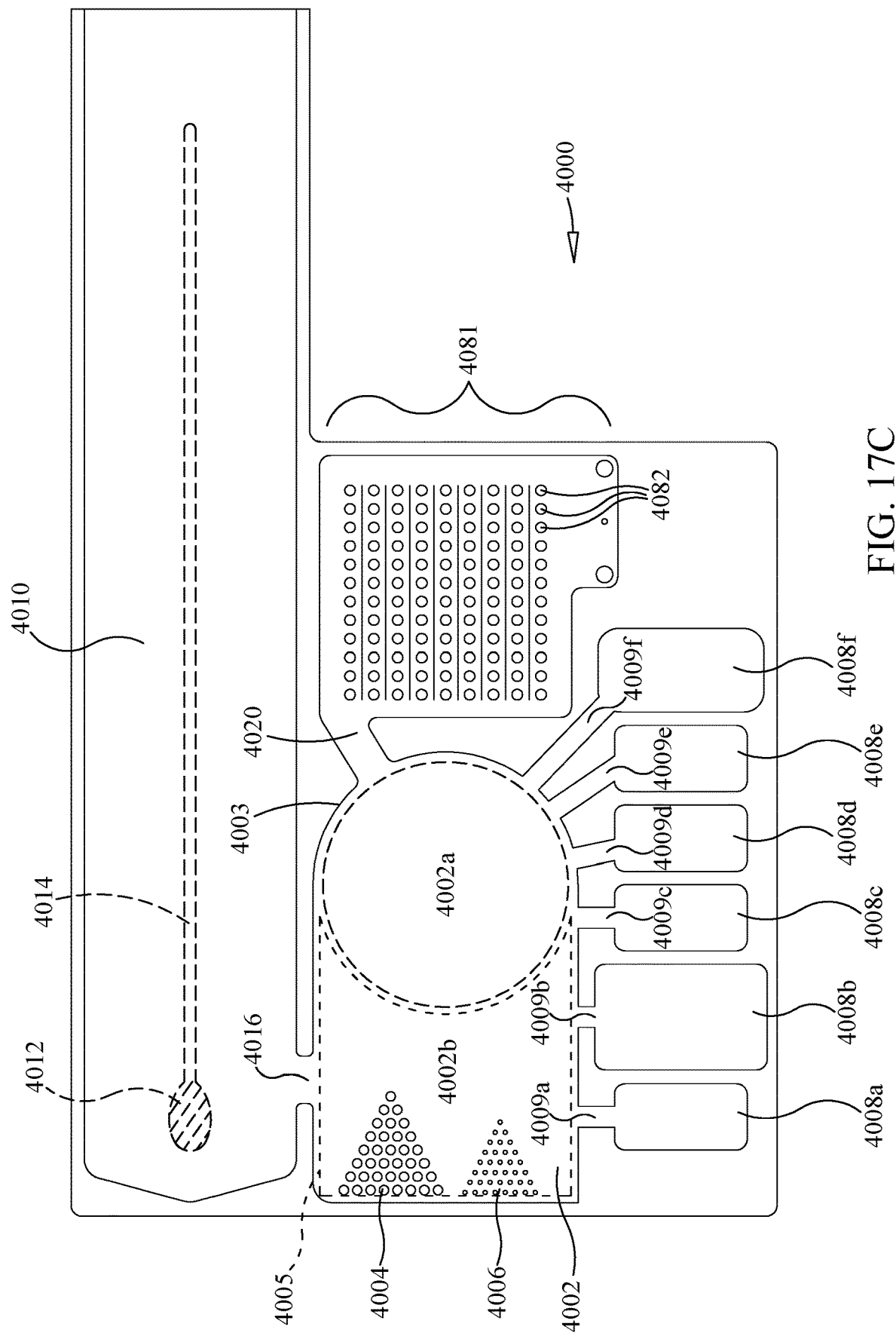
FIG. 17C illustrates yet another embodiment of a flexible pouch, wherein the flexible pouch includes reagents and components for sample preparation, nucleic acid recovery, and, optionally, a first-stage nucleic acid amplification, optionally by wiper cycling.

Referring now to FIG. 17C, another embodiment of a flexible pouch 4000 is illustrated. Pouch 4000 is similar to pouch 3900 and similar elements are given similar numbers. For example, the multifunction chamber is numbered 3902 in FIGS. 17A and 17B and is numbered 4002 in FIG. 17C, and the sample receiving chamber is numbered 3910 in FIGS. 17A and 17B and is numbered 4010 in FIG. 17C. The primary difference between the embodiment of FIGS. 17A-17B and the embodiment of FIG. 17C is that the embodiment of FIG. 17C is configured for first-stage nucleic acid amplification with a wiper device such as the wiper described with respect to FIGS. 25-27D.

Referring specifically to the multifunction chamber 4002, the multifunction chamber 4002 may be provided with lysis particles 4004 and nucleic acid recovery beads 4006. Lysis and nucleic recovery may proceed in the multifunction chamber 4002 in the presence of the lysis particles 4004 and nucleic acid recovery beads 4006 as was described in reference to FIGS. 17A and 17B. In some embodiments, however, it may be preferable to perform the first-stage multiplex nucleic acid amplification reaction in the absence one or both of the lysis particles 4004 and nucleic acid recovery beads 4006. Multifunction chamber 4002 may be configured accordingly.

Following nucleic acid recovery from the lysate, one or both of the lysis particles 4004 and nucleic acid recovery beads 4006 may, for example, be allowed to settle where they may be sequestered in a second portion 4002*b* of the multifunction chamber 4002 by, for example, the activation of a pressure device (e.g., an external pressure plate in the instrument positioned adjacent to chamber 4002), which is illustrated schematically at 4005. Meanwhile, the eluate may be sequestered in a first portion 4002*a* of the multifunction chamber 4002 for first-stage multiplex nucleic acid amplification. In one embodiment, a ring having a curved portion that corresponds to the arched end 4003 of the multifunction chamber 4002 may be provided in an accompanying instrument and used to sequester the eluate in the first portion 4002*a*. Thermal cycling in the first portion may proceed with a wiper and two heaters set at high and low temperatures as described below in reference to, for example, FIGS. 25, 26, and 27A-27D. Other methods are provided in PCT/US2017/018748, already incorporated by reference. In one embodiment, a compression member like 4005 may be used to expel the eluate from the second portion 4002*b* and isolate the lysis particles 4004 and nucleic acid recovery beads 4006 away from the eluate in the second portion 4002*b* and the eluate may be thermally cycled in the first portion 4002*a*. In another embodiment, the silica-coated magnetic beads may be sequestered or isolated for one or more steps by the activation of an external magnet in the instrument adjacent to chamber 4002. In one embodiment, the compression member may have a profile like compression member 4005 that forms the illustrated circular first portion 4002*a*. In such a case, thermal cycling may occur with a wiper as mentioned above with reference to FIGS. 25, 26, and 27A-27D. In another embodiment, the compression member may have a profile that is not necessarily compatible with the thermal cycling system illustrated in FIGS. 25, 26, and 27A-27D. In such a case, the contents of the first portion may be thermally cycled, for example, with a translating heater assembly like the one illustrated in FIG. 28B or with a stationary heater that configured for three temperature thermal cycling or two temperature thermal cycling.

In one embodiment, flexible pouches 3900 or 4000 may be used in an assay method, for example, for extracting nucleic acids from a sample and/or for identifying an unknown organism in a sample. In one embodiment, a method includes (a) providing a flexible container that includes a multifunction chamber that includes therein magnetic particles, wherein the multifunction chamber is configured for sample preparation and nucleic acid recovery, (b) introducing the sample into the multifunction chamber, (c) generating a lysate in the multifunction chamber in the presence of the magnetic particles, and (d) recovering nucleic acids with the magnetic particles by isolating the magnetic particles from the lysate. In one embodiment, the magnetic particles may be isolated from the lysate by placing an external magnet adjacent to the multifunction chamber. In one embodiment, the multifunction chamber may also include lysis particles (e.g., zirconium silicate beads). In one embodiment, the method further includes a step of (e) amplifying nucleic acids in a first-stage multiplex nucleic acid amplification reaction in the multifunction chamber.

In one embodiment, the flexible container further comprises a sample receiving chamber in fluid communication with the multifunction chamber. In one embodiment, the flexible container may be provided with a sample swab in the sample receiving chamber. In one embodiment, the method may further include collecting a sample with a sample swab, inserting the swab into the sample receiving chamber and sealing the sample receiving chamber with the swab therein. The method may further include introducing a lysis buffer from the multifunction chamber into the sample receiving chamber, agitating the lysis buffer and dispersing the sample in the sample receiving chamber with the sample lysis buffer, and transferring the sample and the sample lysis buffer back into the multifunction chamber. In one embodiment, the multifunction chamber may be provided with the lysis buffer, or, alternatively, the lysis buffer may be introduced into the multifunction chamber prior to inserting the sample swab into the sample receiving chamber. In one embodiment, the swab comprises an elongate shaft and the sealing further comprises sealing the sample receiving chamber across the elongate shaft of the swab (e.g., with a heat sealing device). In one embodiment, the method further includes applying more than one seal across the elongate shaft to divide the sample receiving chamber into at least a sample rehydration/dispersion chamber and a waste chamber. In one embodiment, the multifunction chamber includes channels fluidly connected to the sample rehydration/dispersion chamber and to the waste chamber. In one embodiment, the method further includes purging air from the sample receiving chamber and the multifunction chamber by applying pressure to the multifunction chamber and/or the sample receiving chamber prior to sealing the sample receiving chamber.

In one embodiment, generating the lysate further includes applying heat to the sample while generating the lysate. In one embodiment, generating the lysate includes applying a force or energy external to the multifunction chamber to move the magnetic particles and the fluid sample together to generate the lysate. In one embodiment, the multifunction chamber further includes lysis particles (e.g., Zr silicate particles or other hard and/or abrasive elements) and is configured for vortexing via impaction using rotating blades or paddles. As such, in one embodiment, applying the force moves the lysis particles and magnetic particles and the fluid sample to generate high velocity impacts resulting in the lysate. Bead-milling, by shaking, vortexing, sonicating, and similar treatment of the sample in the presence of lysis particles such as zirconium silicate (ZS) beads 3904 or 4004, is an effective method to form a lysate. It is understood that, as used herein, terms such as "lyse," "lysing," and "lysate" are not limited to rupturing cells, but that such terms include disruption of non-cellular particles, such as viruses. In another embodiment, a paddle beater using reciprocating or alternating paddles, such as those described in PCT/US2017/044333, herein incorporated by reference, may be used for lysis in this embodiment, as well as in the other embodiments described herein.

In one embodiment, the method further includes, subsequent to generating the lysate, sequestering the lysis particles in the multifunction chamber away from the lysate. In one embodiment, the method may further include allowing the lysis particles to settle in the multifunction chamber and applying an external pressure to the multifunction chamber to isolate the lysis particles and expel the fluid away from the lysis particles. In one embodiment, the method further includes sequestering the magnetic particles in the multifunction chamber subsequent to recovering the nucleic acids from the lysate. In one embodiment, the magnetic beads may be sequestered by placing an external magnet adjacent to the multifunction chamber to capture the magnetic beads. In one embodiment, the magnetic beads may be sequestered with the lysis particles.

In one embodiment, generating the lysate further includes applying heat to the sample while applying the force. In one embodiment, the lysate is generated under conditions for binding the nucleic acids to the magnetic particles. Preferably, the nucleic acids are capable of binding to the magnetic beads as the lysate is being generated in the multifunction chamber. In one embodiment, the lysate is generated at an elevated temperature and the nucleic acids are recovered from the lysate at a controlled temperature below the lysis temperature. Temperature may be controlled in the multifunction chamber by positioning the multifunction chamber adjacent to a heater/cooler device (e.g., a Peltier device) that can heat and cool the contents of the multifunction chamber. In one embodiment, the elevated temperature for generating the lysate is in the range of 40-100° C., preferably 50-100° C., or more preferably 70-100° C. In one embodiment, the controlled temperature below the lysis temperature for nucleic acid recovery is in the range of 60-0° C., preferably 50-0° C., or more preferably 40-0° C. (e.g., 40° C.-20° C.).

In one embodiment, recovering nucleic acids with the magnetic particles further includes: capturing the magnetic particles from the lysate by positioning a magnet adjacent to the multifunction chamber, expelling the lysate (e.g., to waste chamber 3910b shown in FIG. 17B), performing at least one wash of the magnetic beads in the multifunction chamber, wherein the wash includes introducing a wash buffer into the multifunction chamber (e.g., from one of reagent blisters 3908a-3908f shown in FIGS. 17A and 17B), dispersing the magnetic beads in the wash buffer (e.g., by removing the magnet and agitating the contents of the multifunction chamber), recapturing the magnetic beads with the magnet, expelling the wash buffer (e.g., to waste chamber 3910b), and eluting the nucleic acids from the magnetic beads, wherein the eluting includes introducing an elution buffer into the multifunction chamber (e.g., from one of reagent blisters 3908a-3908f shown in FIGS. 17A and 17B). In one embodiment, the elution buffer includes reagents for the first-stage multiplex nucleic acid amplification reaction.

In one embodiment, the nucleic acids recovered from the lysate include RNA and the method further comprises performing a reverse transcription step in the multifunction chamber to convert the RNA to DNA. In one embodiment, reagents for the reverse transcription step may be introduced into the multifunction chamber from one or more of reagent blisters 3908a-3908f shown in FIGS. 17A and 17B. In one embodiment, the multifunction chamber may be under temperature control of a heater/cooler for adjusting the temperature of the contents of the multifunction chamber for the reverse transcription step. In one embodiment, the method may further include sequestering the magnetic particles in the multifunction chamber (e.g., with a magnet provided external to the multifunction chamber) prior to performing the reverse transcription step. In one embodiment, the method includes performing the first-stage multiplex nucleic acid amplification reaction in the multifunction chamber subsequent to or simultaneous with the reverse transcription step. In one embodiment, the multifunction chamber may be under temperature control of a heater/cooler for thermally cycling the temperature of the contents of the multifunction chamber for the first-stage multiplex nucleic acid amplification reaction. In one embodiment, the magnetic particles may be sequestered (e.g., with the magnet) for the first-stage multiplex nucleic acid amplification reaction, or the first-stage multiplex nucleic acid amplification reaction may be performed in the presence of the magnetic particles.

In one embodiment, the flexible container further includes a second-stage reaction zone fluidly connected to the multifunction chamber, the second-stage reaction zone comprising a plurality of second-stage reaction wells, each second-stage reaction well comprising a pair of primers configured for further amplification of the sample, the second-stage reaction zone configured for contemporaneous thermal cycling of all of the plurality of second-stage reaction chambers. In one embodiment, the method further includes expelling all but a fraction of the product (e.g., amplicon) of the first-stage nucleic acid amplification reaction to a waste chamber (e.g., chamber 3910b), combining the remaining fraction of the product of the first-stage nucleic acid amplification reaction with reagents (provided, e.g., from one or more of reagent blisters 3908a-3908f shown in FIGS. 17A and 17B) for a second-stage nucleic acid amplification reaction to form a second-stage nucleic acid amplification mixture, filling each of the second-stage reaction wells with the second-stage nucleic acid amplification mixture, and performing a second-stage nucleic acid amplification reaction in the plurality of second-stage reaction wells of the second-stage reaction zone to generate one or more second-stage amplicons.

In one embodiment, the method may further include sealing the plurality of second-stage reaction wells of the second-stage reaction zone subsequent to filling. Methods of sealing the plurality of second-stage reaction wells of the second-stage reaction zone are discussed in detail elsewhere herein. In brief, methods for sealing the wells include, but are not limited to, inflating an inflatable bladder over the array of second-stage reaction wells to compress the outside layer pouch plastic against the array to seal the wells and/or applying a heat seal or seals to seal off the fill channels in and out of the wells. For example, fluid flow in and out of wells 3982 may be stopped by placing a series of heat seals between well 3982 substantially perpendicular to channels 3932. In one embodiment, performing a second-stage nucleic acid amplification reaction in the plurality of second-stage reaction wells includes thermocycling the temperature of the contents of the second-stage wells with a heater/cooler device. Heater cooler devices are discussed elsewhere herein, but, in brief, a heater/cooler for thermocycling the temperature of the contents of the second-stage wells may include a Peltier device that thermocycles to heat and cool the contents of the second-stage wells, or a heater assembly with at least two fixed point heaters that may translate to heat and cool the contents of the second-stage wells (one will appreciate that the heater assembly may be stationary and the pouch may be translated instead).

In one embodiment, the method may further include melting the second-stage amplicons in each of the different second-stage reaction wells after the second-stage nucleic acid amplification reaction to generate a melting curve for each of the different second-stage reaction wells. In one embodiment, each of the second-stage wells includes a dsDNA binding dye that can be used to detect the presence of amplicon in each of the second-stage wells. Because the fluorescence of dsDNA binding dyes typically changes in response to melting of dsDNA to ssDNA, dsDNA binding dyes can be used to detect the characteristic melting temperatures of the DNA amplicons in the second-stage wells. Thus, the heater/cooler device(s) used to control the temperature of the second stage reaction wells may be configured to perform a slow temperature ramp to cause melting of the amplicons in the second-stage wells, and the instrument used to run the pouch assay may include excitation and detection optics for producing and detecting fluorescence from the second-stage amplicons and for detecting the melt temperatures and melt curves. It is understood that any of the second-stage reaction zones described and illustrated herein may be used with the embodiment of FIG. 17C.

Figures 18A, 18B:
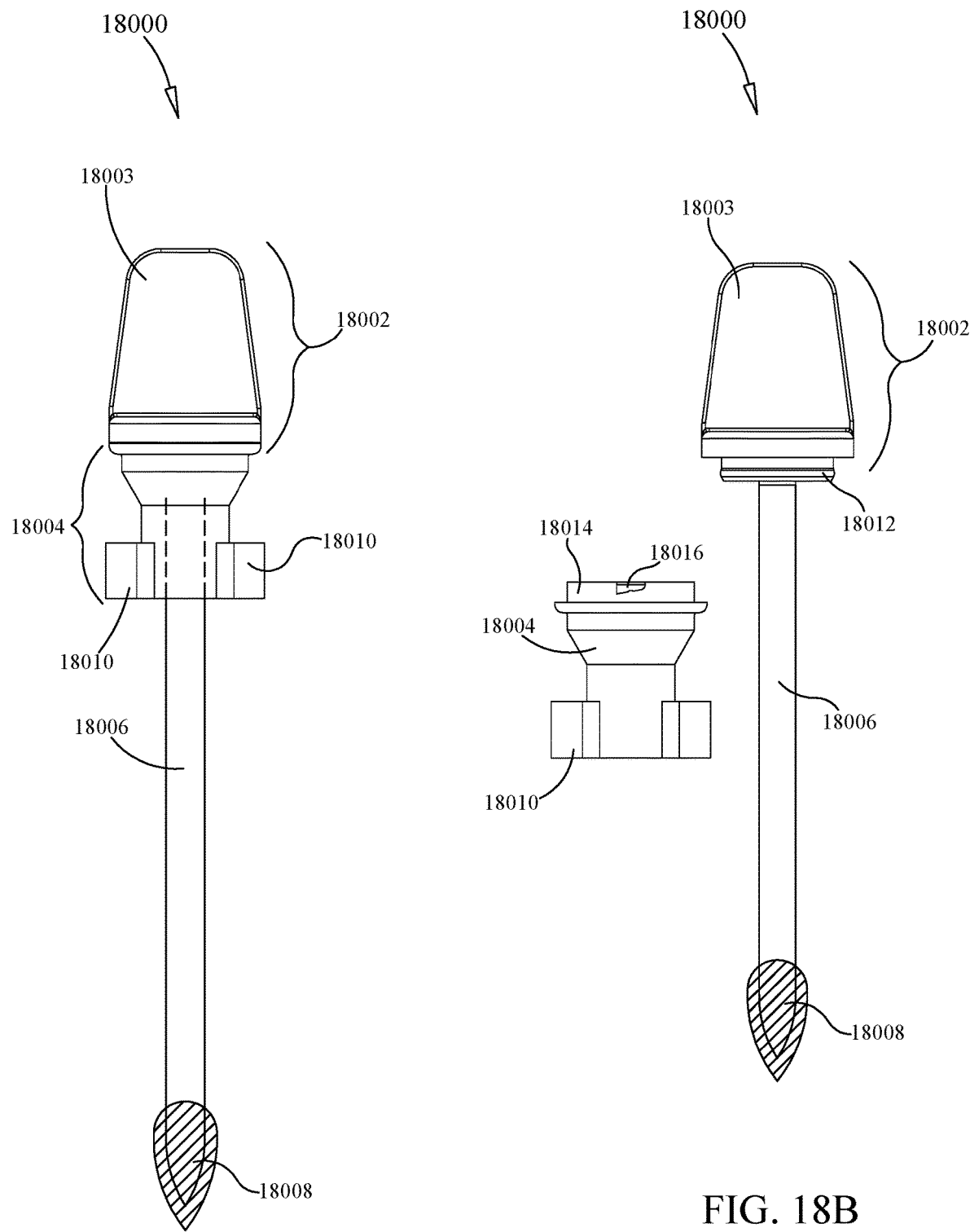
FIGS. 18A and 18B show an embodiment of a swab that may be integrated into a pouch like the pouches of FIGS. 17A-17C in perspective (FIG. 18A) and partially exploded (FIG. 18B) views.

FIGS. 11A, 111B, 17A, 17B, and 17C illustrate general embodiments of swabs 10060, 3912, and 4012, respectively, that may be inserted or incorporated in a pouch with a swab/sample chamber. FIGS. 18A and 18B illustrate an embodiment of a swab 18000 that may be integrated into a pouch like those illustrated in FIGS. 11A, 111B, 17A, 17B, and 17C. Swab 18000 includes a top 18002 and a base 18004 that the top 18002 may be inserted into. Swab 18000 further includes a swab shaft 18006 and a swab tip 18008. In one embodiment, the swab shaft 18002 is integrated or received into the top 18002. In the illustrated embodiment, the top 18002 includes handle 18003 that a user may use to hold and manipulate the swab. In one embodiment, the base 18004 may be integrated into a pouch. For instance, tabs 18010 may be inserted into the swab chamber (e.g., chamber 3910 of FIGS. 17A and 17B) and sealed in the swab chamber so that the swab 18000 is integrated into the pouch. In FIGS. 17A and 17B, for instance, swab 18000 may replace swab 3912 and may be inserted into the swab chamber 3910 in the vicinity of opening 3923. In one embodiment, tabs 18010 may be heat sealed to the film layers used to fabricate the pouch or the tabs 18010 may be adhesed in the opening of the swab chamber with an adhesive placed on tabs 18010 or on the film layers at the opening.

FIG. 18B illustrates a partially exploded view of swab 18000. Base 18004 illustratively includes an acceptor ring 18014 that ring 18012 of the top 18002 may be inserted into. In the illustrated embodiment, acceptor ring 18014 of the base 18004 may include locking tabs 18016 that may removably lock into complementary tabs (not shown) in the ring 18012 of the top 18002 when the top 18002 is twisted into the base 18004. Other swab systems may illustratively include a threaded arrangement, a snap fit, a friction fit, or the like.

Figures 19A, 19B:
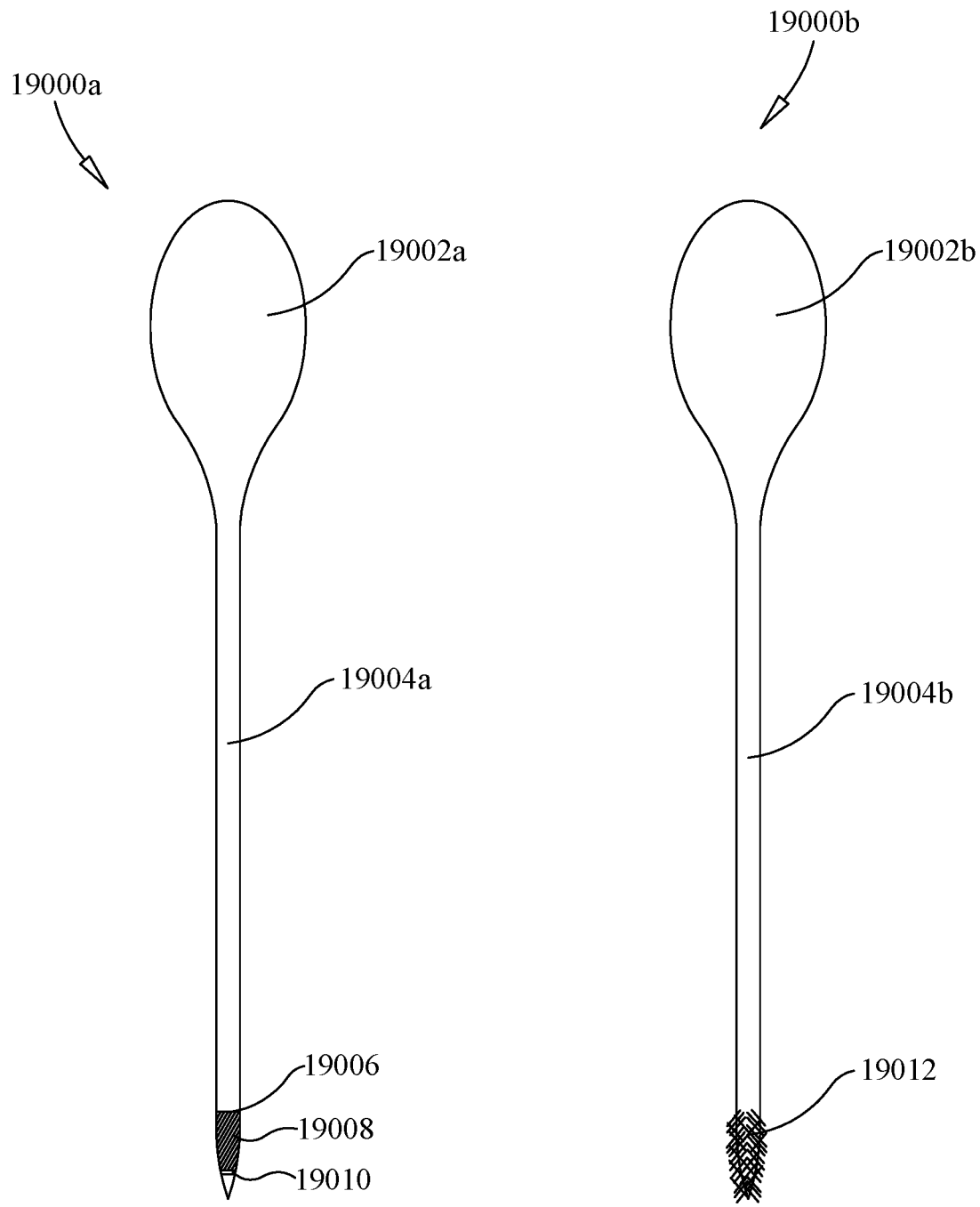
FIG. 19A shows a transfer pipet that includes media in the shaft.
FIG. 19B shows a transfer pipet that includes swab-like fibers on the shaft.

In other embodiments, a transfer pipet or the like may be used instead of a swab for introducing a sample into the pouch. While a transfer pipet of the type well known in the art may be used, FIGS. 19A and 19B illustrate two embodiments of transfer pipets 19000a and 19000b that may be used for capturing and transferring a sample. Transfer pipet 19000a includes a bulb 19002a, a shaft 19004a, and a plug of media 19008 that may be positioned at a distal end of the shaft 19004a. In the illustrated embodiment, the media 19008 may be held in place with a pair of frits 19006 and 19010. Transfer pipet 19000b includes a bulb 19002b and shaft 19004b and a swab-like material 19012 at the distal end of the shaft 19004b. In one embodiment, a transfer pipet may combine the media 19008 of transfer pipet 19000a and the swab-like material 19012 of transfer pipet 19000b. An insertion ring similar to insertion ring 18012 may be provided, illustratively below the bulb 19002a or 19002b, to allow the transfer pipets 19000a or 19000b to the bused to seal the pouch, in a manner similar to the swabs of FIGS. 18A and 18B.

Media 19008 may, for example, be ion exchange media, size exclusion media, hydrophobic media, affinity media (e.g., antibody capture, histidine tag, or the like), etc. to trap and concentrate a selected analyte (or analytes) from the sample. Swab-like material 19012 may have many of the same features of media 19008, i.e., it may include ion exchange groups, hydrophobic groups, or affinity groups, or the like to trap and concentrate a selected analyte (or analytes) from the sample. In some embodiments, a sample may be pipetted back and forth through the media 19008 or the swab-like material 19012 to trap and concentrate a selected analyte (or analytes) from the sample. In the case of the swab-like material 19012, the transfer pipet may also be swished in a sample to trap and concentrate a selected analyte (or analytes) from the sample. Depending on the capture chemistry and the nature of the analyte(s) being trapped, the analyte(s) may also be washed with the action of the pipets prior to insertion into a pouch for analysis. Transfer pipets 19000a and 19000b may be particularly helpful when analyzing samples like urine or blood that have interfering matrices. Capture properties may be used to concentrate analytes (e.g., bacteria or viruses) from sample with low organism loads prior to analysis. For instance, affinity capture may be used to capture and concentrate bacteria and viruses direct from blood or from blood culture after only a few hours of culturing. This could, for example, significantly shorten the time to diagnosis for sepsis patients.

Figure 20A:
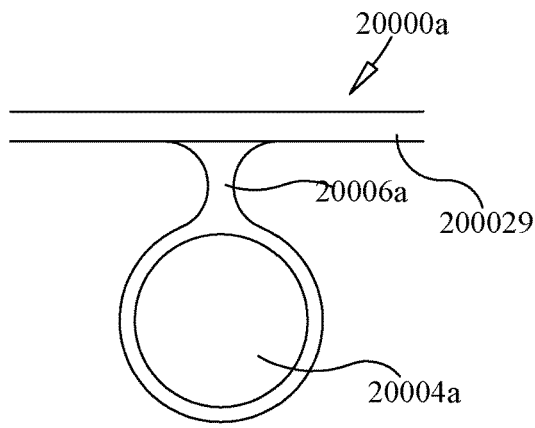
FIGS. 20A-20E show various array well and channel configurations.
Figure 20B:
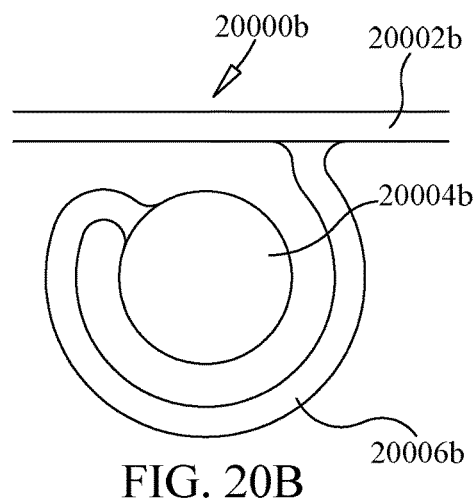
Figure 20C:
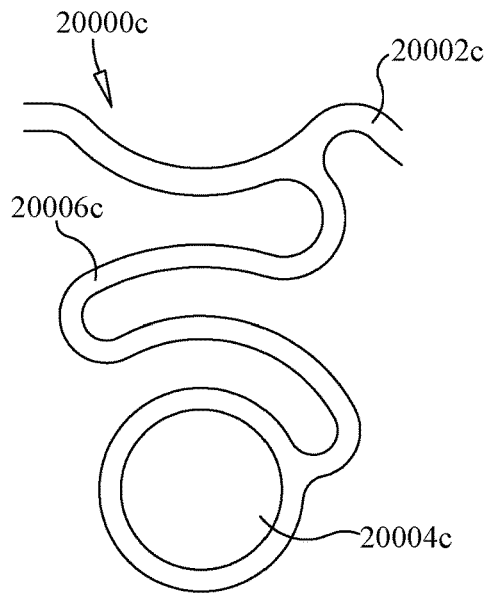
Figure 20D:
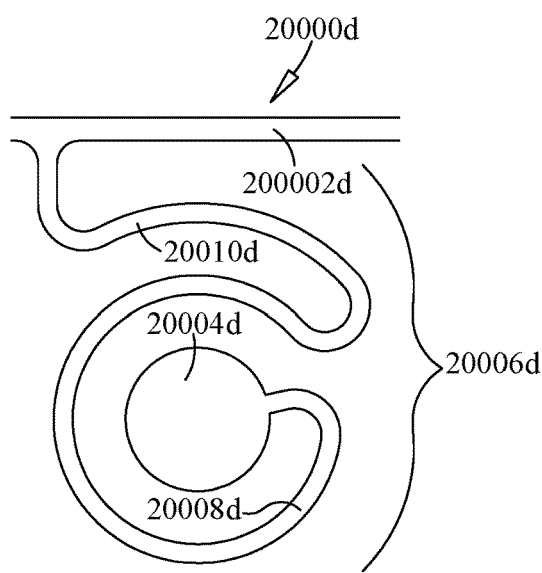
Figure 20E:
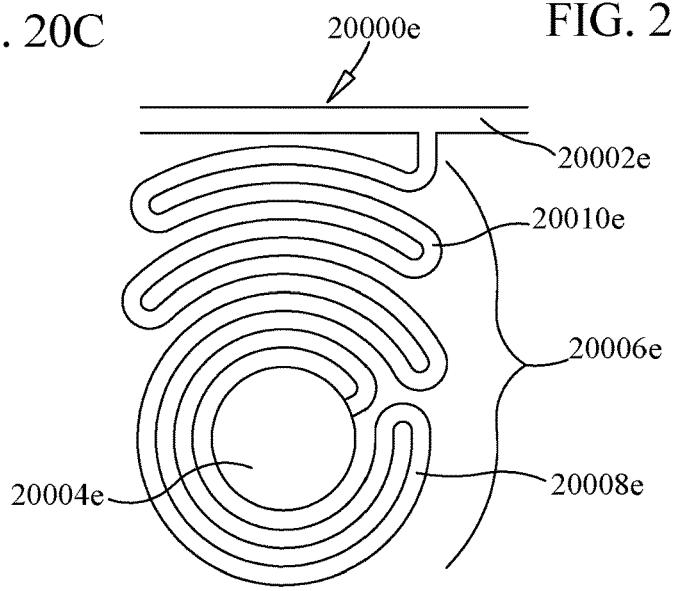

Referring now to FIGS. 20A-20E, examples of various well filling paths for wells in an array are shown. FIGS. 17A and 17B show one example of a "convoluted" array well filling path that includes array flow channels 3932 and spiral paths 3930. FIGS. 20A-20E illustrate other examples of well filling paths. Each example in FIGS. 20A-20E includes a well 20004a-20004e and an array flow channel 20002a-20002e. FIG. 20A illustrates a straight channel 20006a leading into well 20004a. FIG. 20B illustrates an embodiment of a spiral channel 20006b leading into well 20004b. FIG. 20C illustrates a switchback channel 20006c leading into well 20004c. FIG. 20D illustrates a channel 20006d that includes a spiral portion 20008d and a switch back portion 20010d leading into well 20004d. FIG. 20E illustrates a channel 20006e with a spiral switchback portion 20008e and a parallel switchback portion 20010e leading into well 20004e. When placed in a pouch, the wells and the channels illustrated in FIGS. 20A-20E would be sealed on the top and bottom with at least one layer of film. Thus, the only flow paths into the wells is through the flow channels and the well channels. While some paths are more "convoluted" than others, the combination of the flow channels and the well channels generally isolates the well from one another and suppresses mixing (i.e., cross talk) between wells. The foregoing examples are merely illustrative examples of convoluted well filling paths and one will appreciate that other well filling paths may be used.

One of the problems associated with the use of beads in a closed system is that the beads can sometimes be carried downstream along with the desired sample components. For instance, bead beating beads (e.g., Zr silicate beads) or magnetic beads used in, for example, pouch 510 can sometimes be carried downstream into the blisters used for nucleic acid recovery or PCR amplification, or into channels where the beads may affect the seals. Likewise, lysis particles and magnetic beads have an associated void volume and, as such, it may be desirable in some embodiments to separate lysis particles and/or magnetic beads from processes like PCR in a pouch like pouch 3900. Magnetic beads can be isolated with magnets and lysis particles settle due to their size and mass, but these processes do not always eliminate bead movement through the pouch and they do not always address the volume of liquid that may be trapped in the beads.

Figure 21A:
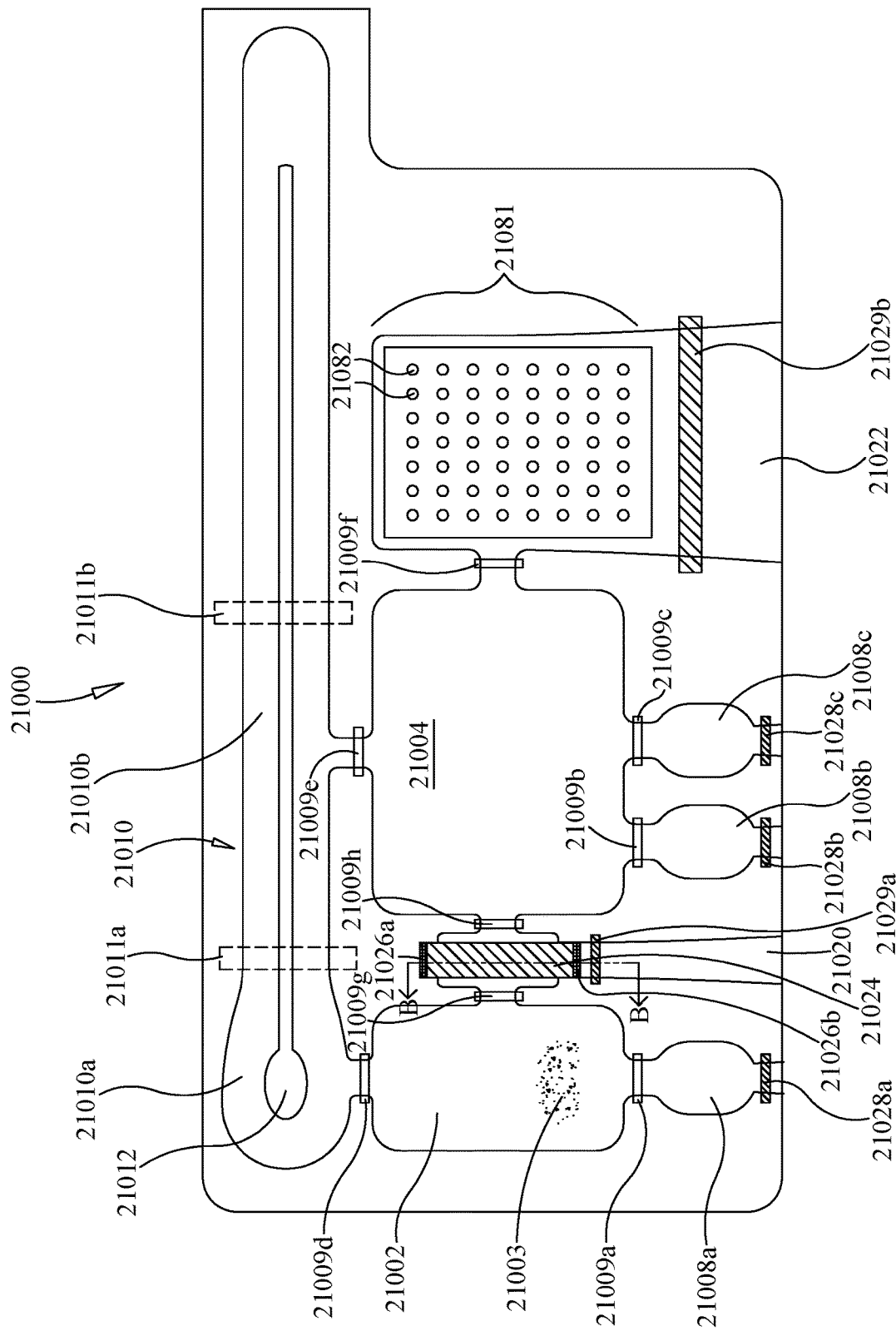
FIG. 21A shows a flexible pouch with a number of fluid zones and a filter between two zones.
Figure 21B:
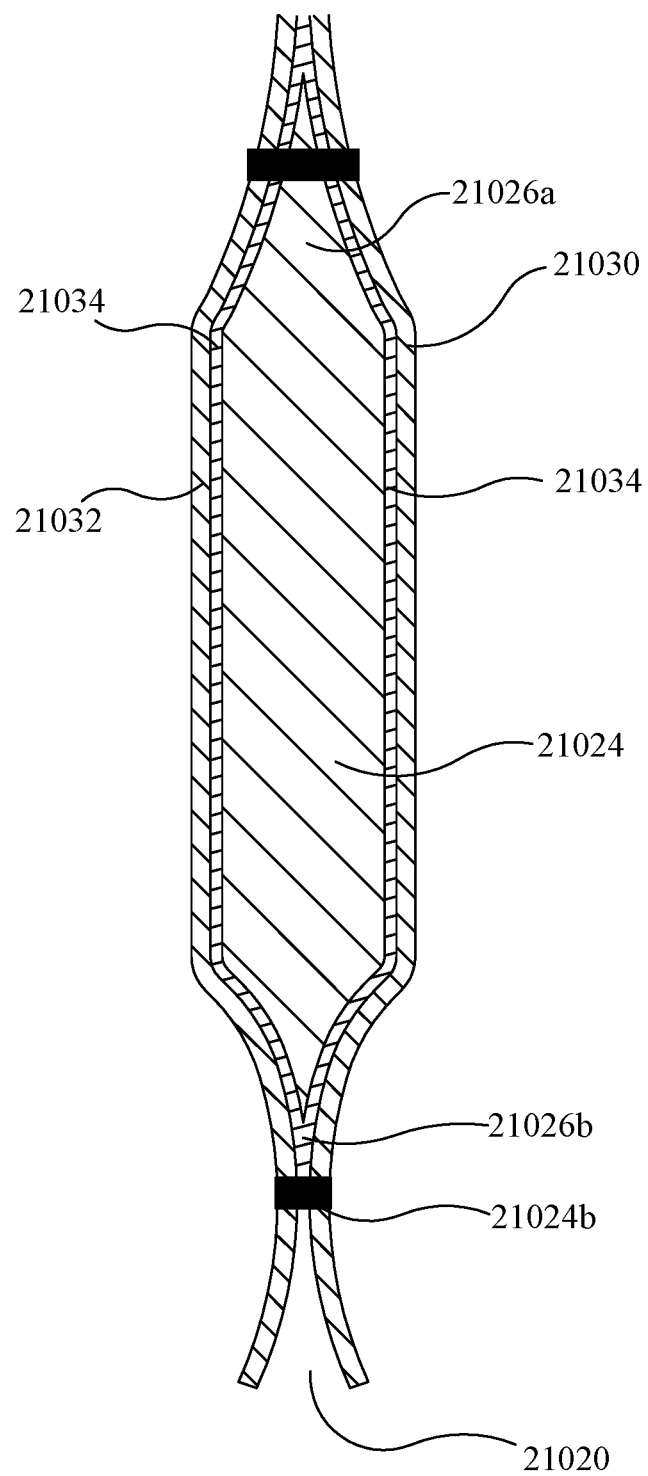
FIG. 21B shows a cross-sectional view of the filter included in the pouch of FIG. 21A FIGS. 21C and 21D illustrate alternative embodiments of in-pouch filters.

In one embodiment, beads (e.g., lysis particles) can be prevented from flowing from blister to blister (and through the channels in between) by inserting a filter element between one or more chambers in the pouch. An embodiment of such a pouch that includes a filter element is illustrated in FIG. 21A. FIG. 21B illustrates a cross-sectional view of a filter and FIGS. 21C and 21D show alternative embodiments of an in-pouch filter. The pouch 21000 illustrated in FIG. 21A is similar to the pouch illustrated in FIGS. 17A and 17B, except the multifunction chamber is divided into a lysis zone 21002 and a reaction zone 21004. It is understood, however, that, while pouch 21000 shows a filter, the filter may be omitted in some pouch embodiments. Similar to the embodiments illustrated in FIGS. 17A-17C, a sample may be introduced into pouch 21000 by collecting a sample with swab 21012 and inserting the swab into sample chamber 21010. Alternatively, a sample may be pipetted into sample chamber 21010. In either case, sample chamber may be sealed to form a sample chamber 21010a by seal 21011a and a waste chamber 21010b by seal 21011b. More seals may be placed in some embodiments. Sample buffer may be moved from 21008a to sample chamber to rehydrate sample and/or prepare it for lysis. In one embodiment, sample lysis may be performed in the lysis zone 21002 (e.g., by bead beating) with the sample, zirconium lysis particles 21003, and the lysis buffer. Following lysis, a lysate may be expelled from lysis zone 21002 through filter 21024 and into reaction zone 21004. The filter 21024 may be sealed in place such that the lysis particles 21003 cannot be carried from lysis zone 21002 to reaction zone 21004.

Following lysis in the lysis zone 21002 and expelling the lysate to reaction zone 21004, pouch 21000 may be used in a way similar to the description for pouch 3900. Processes such as nucleic acid recovery with magnetic silicate beads, washing the beads to remove unwanted lysate components, elution, first stage PCR, and dilution of the first-stage PCR product may be performed in the reaction zone 20004. Diluted first-stage reaction product may be used to fill wells 21082 of array 21081 for second-stage PCR. Reagents for steps performed in the reaction zone 21004 may be provided from reagent blisters 21008b, 21008c, ... 21008(n). Fluid movement in pouch may be controlled with some or all of seals 21009a-21009h.

Illustratively, pouch 21000 may be formed of two layers of a flexible plastic film or other flexible material such as polyester, polyethylene terephthalate (PET), polycarbonate, polypropylene (PP), polymethylmethacrylate, and mixtures thereof. In one embodiment, the pouch 21000 is fabricated by laminating at least two layers of plastic film together in such a way that the blisters and channels are formed—e.g., by heat laminating the film layers together and then laser welding to define various regions such as, but not limited to, blisters, reagent chambers, and the sample chamber. In one embodiment, fabrication of pouch 21000 includes forming a pocket 21020 or a similar structure that a filter 21024 can be inserted into. In one embodiment, the ends of filter 21024 may be heat sealed to the pouch film layers, as shown at 21026a and 21026b. After inserting the filter 21024 into the pocket 21020, the filter pocket may be closed off with seal 21029a.

FIG. 21B shows a cross-section of filter 21024 as it is positioned in the pocket 21020 between film layers 21030 and 21032. Seals 21026a and 21026b can be seen at the ends of the filter 21024. In one embodiment, seals 21026a and 21026b crimp the ends of the filter and fuse the filter material and the film layers together. Seal 21029a is also illustrated. Seal 21029a may be formed away from the filter to close the pocket to keep liquid from flowing out of the pocket. In the illustrated embodiment, the filter 21024 and the film layers 21030 and 21032 are heat sealed 21034 on the face of the filter parallel to the film layers. This keeps material from flowing around the filter, e.g., fluid from lysis zone 21002 to reaction zone 21004 flows through the filter 21024 but not around the filter 21024. In an alternative embodiment (not shown), the filter may not be heat sealed in the pocket and fluid may be prevented from flowing around the filter by tightly compressing the faces of the filter and the ends in an instrument. In either case, the filter is placed across a channel and is illustratively wider than the channel, which presents a filter with a relatively large surface area so that lysate can flow through the filter without becoming clogged.

The selection of filter material depends on the sample type and desired pore size. In general, the pore size of the filter is chosen to be large enough to be able to pass all material in the liquid except the lysis particles. In one embodiment, the pore size of the filter ranges from about 5 to 100 μm (e.g., 50-90 μm or 7-12 μm). Preferably, the filter element is made from a material that is compatible with the material(s) used to form the pouch such that the filter can be heat sealed in the pocket without compromising either the pouch or the filter. Suitable filters include, but are not limited to, various polyethylene filters made by Porex (e.g., POR-4903 and XS-POR-7744).

Similar to the installation and positioning of the filter, the array 21081 can be inserted into a pocket 21022, heat sealed between the pouch film layers, and then sealed at the end 21029b to close the array pocket. Again similarly, reagent blisters 21008a-21008c (more or fewer reagent blisters may be used in other embodiments) may be formed as pockets between the film layers. Liquid or dry reagents or a combination may be placed into the reagent pockets and then seals 21028a-21028c may be applied to seal the ends of the reagent blisters.

FIGS. 21C and 21D show alternative embodiments of placing a filter in a pouch. The embodiments of FIGS. 21C and 21D are similar to the embodiment illustrated in FIGS. 21A and 21B. The embodiments of FIGS. 21C and 21D each include a lysis zone 21002a and 21002b, lysis particles 21003a and 21003b in the respective lysis zones, and reaction chambers 21004a and 21004b. The differences between FIGS. 21C and 21D and 21A are in the way the filter is placed in the pocket and the way the lysis zone and filter are sealed. In FIG. 21C, the filter 21024a is placed into a pocket 21020a at one end 21029e of the lysis zone 21002a. The ends and faces of the filter parallel to the film may be sealed as illustrated in FIG. 21B. The lysis zone 21002a is sealed at 21029c opposite to the filter. In FIG. 21D, a filter pocket 21020b may be formed to receive a filter 21024b at one end of the lysis zone 21002b. Seal 21029d may be placed to close the lysis zone 21002b and to seal the filter in the pocket 21020b.

In FIG. 21C, the lysis zone 21002a is positioned relative to the reaction chamber 21004a such that the beads 21003a can settle on the filter 21024a by gravity and a lysate can flow through the filter 21024a by a combination of gravity and pressure applied to the lysis zone 21002a. In FIG. 21D, the lysis zone 21002b is positioned relative to the reaction chamber 21004b such that the beads 21003b may settle by gravity to the end 21029f of the lysis zone 21002b (away from the filter 21024b) and fluid may be moved from the lysis zone 21002b to the reaction zone 21004b through the filter 21024b (laterally from left to right, as shown in the FIG. 21D) by pressure applied to the lysis zone 21002b. In both embodiments shown in FIGS. 21C and 21D, the large surface area of the filter allows fluid to flow through the filter reduced risk of clogging by cell debris and other material in the lysate.

Figure 22A:
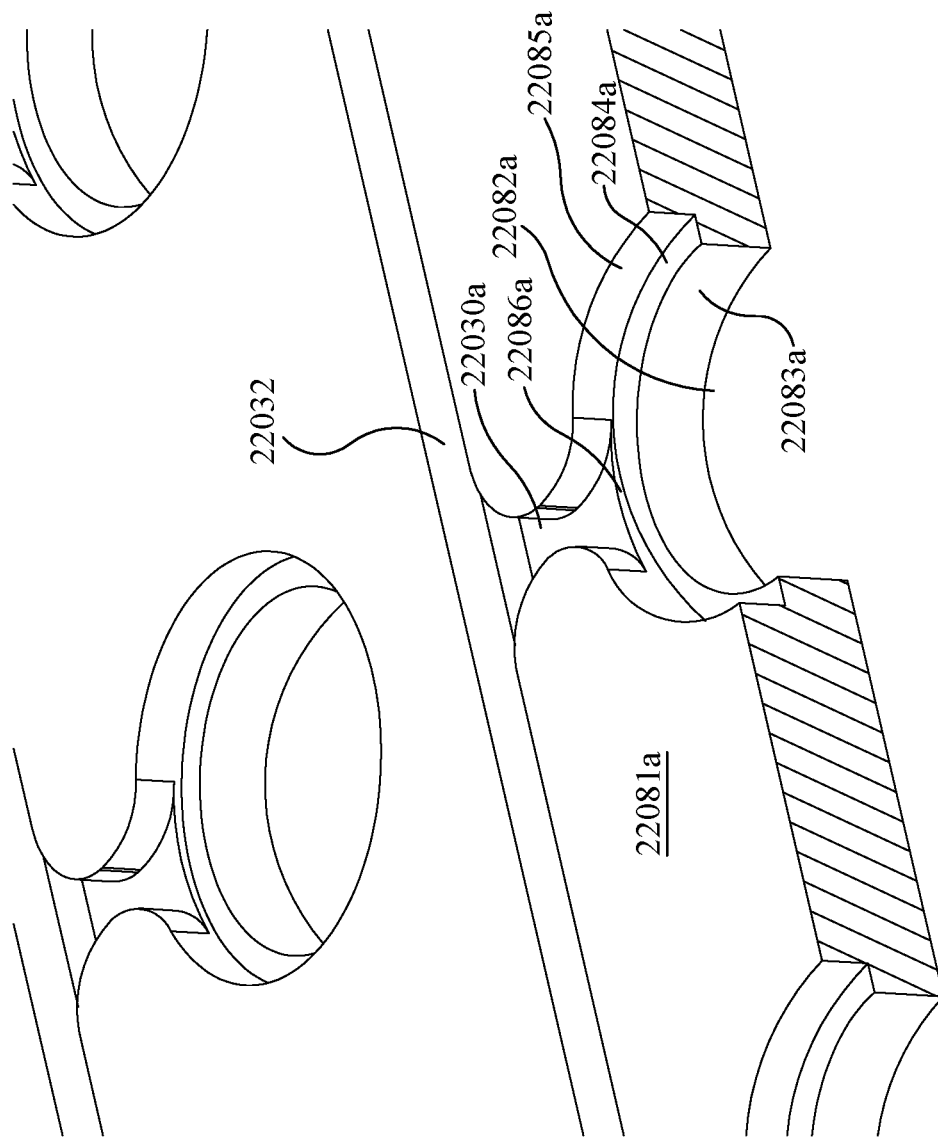
FIG. 22A shows a cut-away view of an array well that may be included in an array card.
Figure 22B:
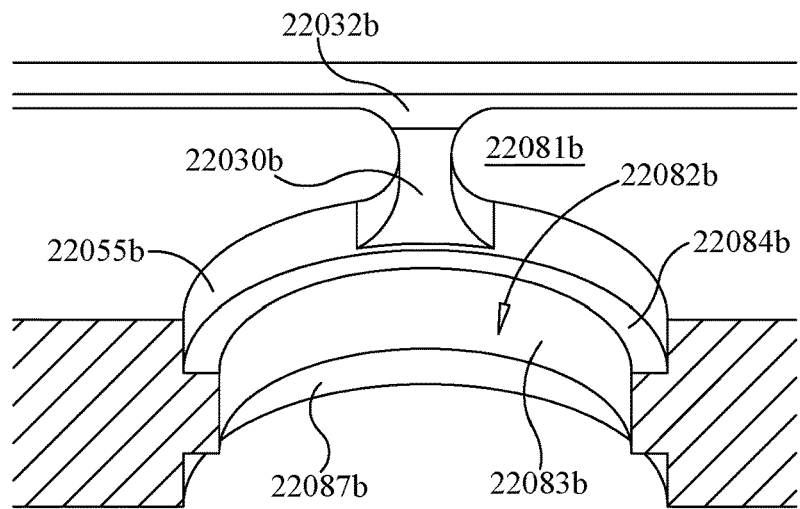
FIG. 22B shows a cut-away view of another embodiment of an array well that may be included in an array card.

Referring to FIGS. 22A and 22B, additional embodiments of wells 22082a and 22082b are illustrated. Well 22082a of FIG. 22A is part of an array card 22081a and well 22082b of FIG. 22B is part of an array card 22081b. The wells 22082*a* and 22082*b* are shown cut-away views to better illustrate the features inside the wells. Wells 22082*a* and 22082*b* are accessed by a fill channel 22030 and a well fill channel 22032. Well 22082*a* of FIG. 22A includes a first wall 22083*a* defined by a first diameter less than the diameter of the well 22082*a*, a step 22084*a*, a second wall 22085*a* defined by a second diameter substantially equal to the diameter of well 22082*a*, and a step 22086*a* into well fill channel 22032. Well 22082*b* of FIG. 22B includes a first wall 22083*b* that is isolated from the top and bottom of the card 22081*b*, second upper and lower walls 22085*b* and 22087*b*, and an upper step 22084*b* and a lower step (not shown).

In one embodiment, because the first walls 22083*a* and 22083*b* may be isolated from at least one surface of the card, chemistry can be provided in the wells without the reagents and/or reaction components contacting either one or both of the top and bottom of the array cards. For instance, it was observed in some instances that droplets applied to the wells could sometimes wick out into the fill channels 22030 and well fill channels 22032 if the droplet could contact the channels. By applying the droplets to areas of the wells isolated from the fill channels 22030 and well fill channels 22032 (e.g., to first walls 22083*a* or 22083*b*) the droplets can be applied without the liquid wicking out into fill channel 22030 and well fill channel 22032 and into other wells. Because first wall 22083*b* of well 22082*b* is isolated from the top and bottom surfaces of the card, the reagents and/or reaction components may be further isolated and even less prone to contamination.

Figure 23A:
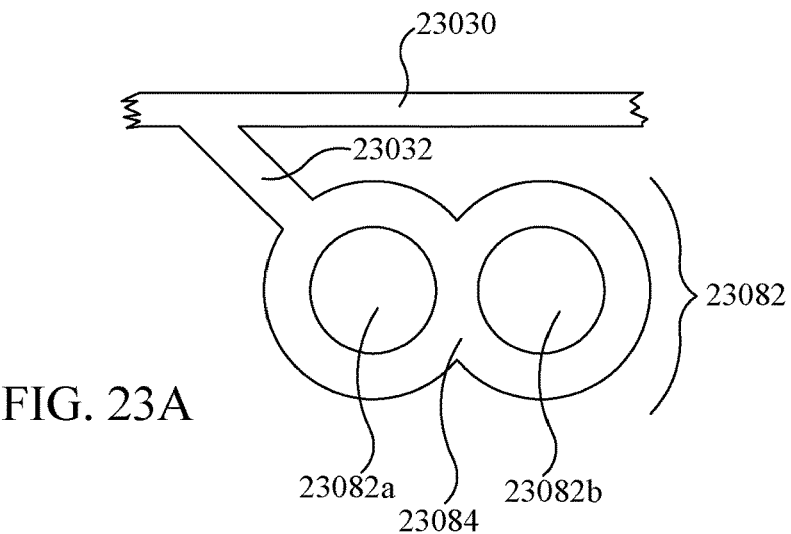
FIGS. 23A and 23B show a plan (FIG. 23A) view and a cut-away view (FIG. 23B) of an array well with two co-fillable wells that may be included in an array card.
Figure 23B:
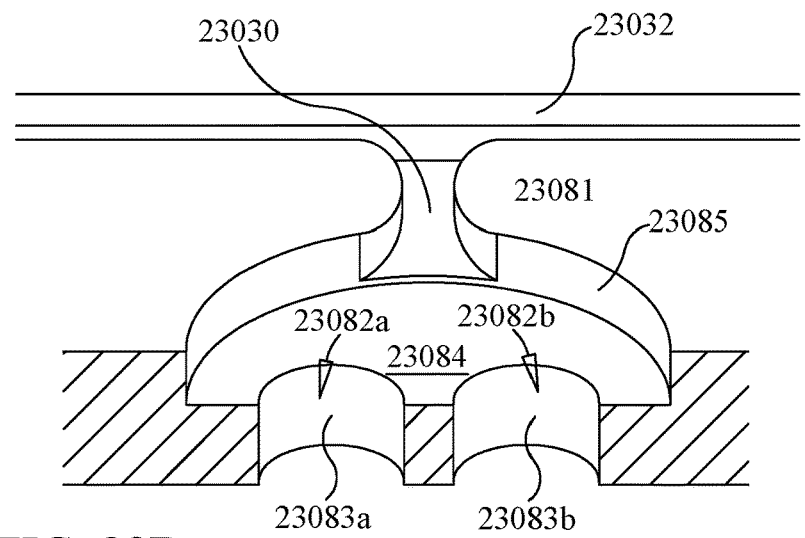

FIGS. 23A and 23B illustrate an embodiment of a reaction well that includes two inter-connected, co-fillable wells that can be spotted with separate reagents and/or reaction components that can combine when the reaction well is flooded with fluid. Reaction well 23082 may be part of an array of well on array card 23081, or reaction well may be individual. The reaction well 23082 is shown in plan view in FIG. 23A and in a cut-away view in FIG. 23B to better illustrate the features inside the wells. Reaction well 23082 may be accessed by a fill channel 23030 and a well fill channel 22032. Reaction well 23082 includes a first sub-well 23082*a* and a second sub-well 23082*b* and a step 23084 that forms a common surface between the first and second sub-wells. Referring to FIG. 23B, the first sub-well 23082*a* includes a first substantially cylindrical wall 23083*a* and the second sub-well 23082*a* includes a second substantially cylindrical wall 23083*b*. The first and second walls 23083*a* and 23083*b* connect to the step 23084 and a second wall 23085 that surrounds the reaction well 23082.

In one embodiment, the first sub-well 23082*a* may include first dried reagents and/or reaction components and the second sub-well 23082*b* may include second dried reagents and/or reaction components. The reagents and/or reaction components may be combined when the reaction well 23082 and the shelf space 23084 are flooded with fluid. In one embodiment, the reagents and/or reaction components in the first and second sub-wells 23082*a* and 23082*b* may be components intended to work together in an analytical method but, nevertheless, it may be desirable to keep them separate until they are needed. For instance, the reagents and/or reaction components in the first sub-well 23083*a* may comprise a DNA polymerase (e.g., Taq DNA polymerase) and the reagents and/or reaction components in the second sub-well 23083*b* may comprise dNTPs. Such a reaction well may be suited for use without need for a "hot start" method because components to complete the reaction mixture (i.e., polymerase and dNTPs) are kept in separate compartments until the reaction begins. In another instance, the reagents and/or reaction components in the first sub-well 23083*a* may comprise an enzyme and the reagents and/or reaction components in the second sub-well 23083*b* may comprise a substrate. Likewise, the reagents and/or reaction components in the first and second sub-wells 23083*a* and 23083*b* may comprise an antibody binding pair for detection of the presence of an epitope or epitopes in a reaction. While FIGS. 23A and 23B show an embodiment of a reaction well that includes two inter-connected, co-fillable wells, one will appreciate that such reaction wells may include more than two (e.g., three or four or five) interconnected, co-fillable wells and that each of the more than two interconnected, co-fillable wells may be provided with reagents and/or reaction components that may be combined in situ for an analytical method.

Method of Spotting an Array

FIGS. 24A-24F illustrate a method for applying (i.e., spotting) reagents and/or reaction components into a well 24082 of an array card 24081. While only one well is shown for the sake of simplicity, persons of ordinary skill will appreciate that the method can be used to spot two or more (e.g., 10 s to 100 s) of well simultaneously. In one embodiment, spotting multiple wells simultaneously may employ an apparatus similar to the spotting apparatus described in U.S. Pat. Pub. No. 2015/0283531, the entirety of which is incorporated herein by reference. Likewise, while the well 24082 depicted in FIGS. 24A-24E is similar to the well described in reference to FIG. 22A, persons of ordinary skill will appreciate that this is merely illustrative and that the well(s) being spotted may have other configurations.

Figure 24A:
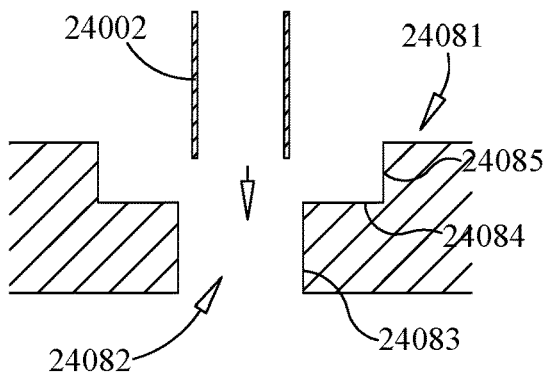

FIG. 24A illustrates an initial state. Array card 24081 includes a well 24082, a first wall 24083, a step 24084, and a second wall 24085. Interestingly, the array card 24081 and the well 24082 do not have a backing film or the like applied prior to spotting the reagents and/or reaction components to the array well(s). Cannula 24002 is positioned relative to the well 24082 for delivering a droplet of reagent and/or reaction components to the well 24082. In one embodiment, cannula is sized and dimensioned so that it can pass through well 24082. In one embodiment, an apparatus for spotting a well (not shown) may include alignment pins or the like to align the card 24081 relative to the cannula 24002. As described in U.S. Pat. Pub. No. 2015/0283531, cannula 24002 may be plumbed to a reservoir of liquid reagents and/or reaction components that can be pumped on demand to apply a spot of liquid to the well 24082. In an apparatus that includes two or more cannulae for spotting two or more wells, each cannula may be plumbed to a reservoir of reagents and/or reaction components unique for that cannula or some or all cannulae may be plumbed to a common reservoir or to reservoirs with the same reagents and/or reaction components.

Figure 24B:
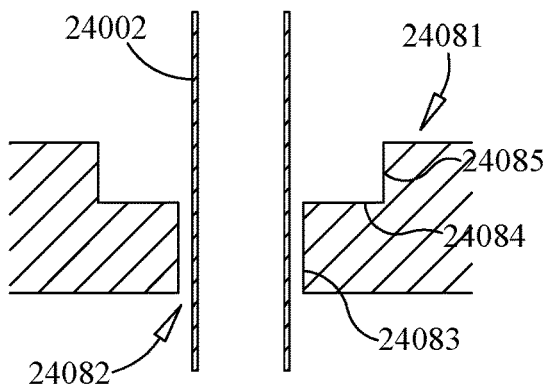

In FIG. 24B, cannula 24002 has been lowered relative to the card 24081 so that the cannula 24002 extends through the well 24082. Alternatively, the card may be moved relative to the cannula and, while reference is made in the following description to moving the cannula relative to the card, one will appreciate that the card may be moved relative to the cannula without departing from the spirit of this description. Also, while card 24081 is shown horizontally, with the cannula 24002 positioned above the card 24018, other orientations are possible, including providing card 24081 vertically with cannula 24002 positioned to enter from a side of the card 24081.

Figure 24C:
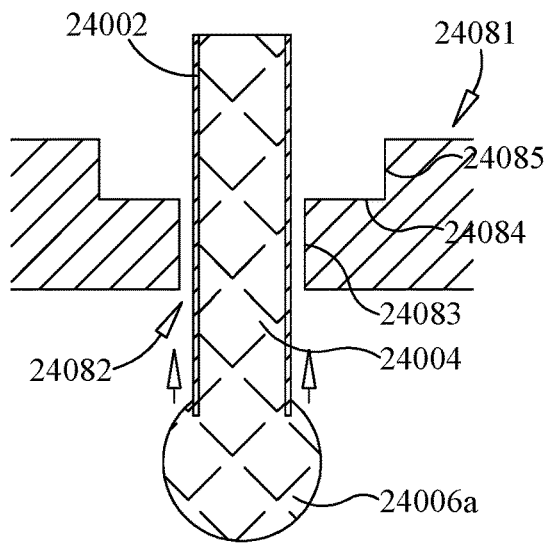
Figure 24D:
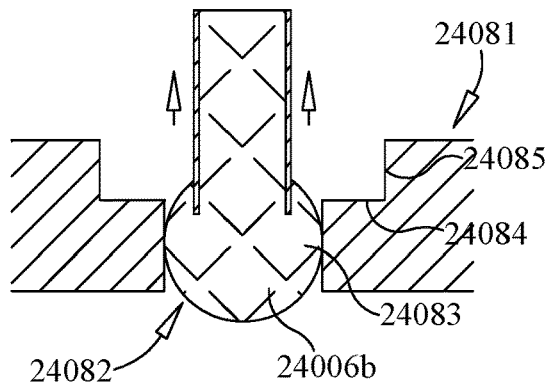
Figure 24D:
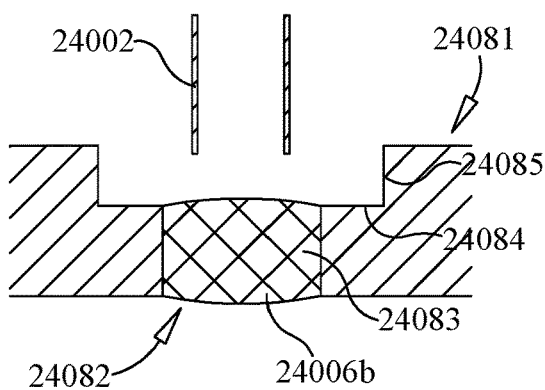
Figure 24F:
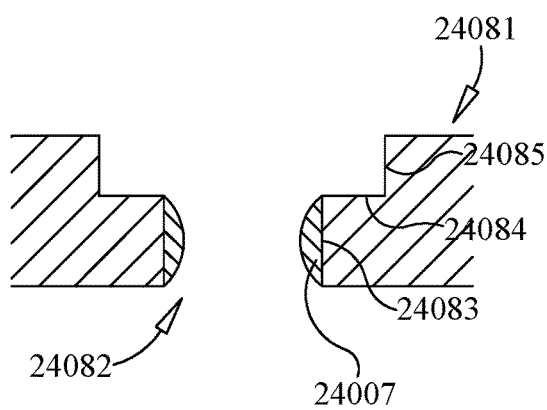

With the cannula extending through the card, as depicted in FIG. 24C, reagents and/or reaction components 24004 may be pumped through cannula 24002 and a droplet 24006*a* may be formed at the end of the cannula 24002. As depicted in FIG. 24D, the cannula 24002 may then be retracted. As the cannula 24002 is being retracted, the droplet 24006*b* may be captured on wall 24083 so that the droplet 24006*b* remains in the well 24082 when the cannula 24002 is fully retracted (FIG. 24E). Following spotting, the solvent in the reagents and/or reaction components droplet 24006*b* may be allowed to evaporate, leaving dried reagents and/or reaction components in a film or ring 24007 in the well 24082 (FIG. 24F). One will appreciate, however, that the film or ring 24007 shown in FIG. 24E is merely illustrative and that the reagents and/or reaction components may dry in other forms depending on the composition and concentration of the reagents and/or reaction components. In one embodiment, the reagents and/or reaction components spotted in the well may include one or more of a reaction buffer, a stabilization buffer, polymerase, dNTPs, a nucleic acid binding dye, Mg++, or assay-specific primers. However, in the case of a PCR reaction mixture, at least one of component of the reaction mixture (e.g., dNTPs or polymerase) may generally be omitted so that the reaction mixture is not complete until the well is at a higher temperature and the well is flooded with fluid—that is, the fluid generally contains the missing component(s) so that the reaction mixture is only complete when the well is flooded with fluid.

In one embodiment, an array card like 24081 (either with provided reagents and/or reaction components or without) may be used to fabricate a pouch (e.g., pouch 3900 or 21000) by inserting the array into a preformed pocket between two or more film layers, sealing the film to the array (e.g., by heat sealing) to seal the top and bottom surfaces of the wells, and sealing (e.g., by heat sealing, sonic welding, or laser welding) the preformed pocket. In one embodiment, the two or more film layers may laminated together and defined areas (e.g., reaction blisters, reagent blisters, pocket(s), etc.) may be formed prior to positioning the array between the film layers. In another embodiment, the array card may be positioned between the at least two film and the defined areas (e.g., reaction blisters, reagent blisters, pocket(s), etc.) may be formed around the card.

In one embodiment, the array pocket may be fluidly connected to one or upstream fluid blisters so that the array can be flooded with fluid. In one embodiment, the array may include a fluid channel system like the one depicted, for example, in FIGS. 17A and 17B so that the individual well of the array can be filled with fluid. In one embodiment, the array may include a vacuum port and a vacuum channel system like one depicted, for example, in FIGS. 17A and 17B so that the array can be partially evacuated in situ.

Instrumentation

The pouches described herein, for example, in reference to FIGS. 1, 5A, 7, 11A, 11B, 17A and 17B, 17C, or 21A may be configured to be used in an instrument similar for the instrument illustrated in FIG. 2. Described below are alternative embodiments of instruments and instrument components that may be used with the pouches described herein. Additional embodiments of instruments that may be used with the pouches described herein can be found, for example, in PCT/US17/18748, the entirety of which is incorporated herein by reference.

Typically, thermocycling for PCR and similar processes is accomplished with a heater cycles up and down in temperature to thermally regulate the temperature of one or more samples that are in thermal contact with the heater. See, for example, heaters 886 and 888 of FIG. 2. By thermocycling heaters 886 and 888, run time for the PCR portions necessarily needs to be at least as long as the heater takes to get to a suitable temperature at each transition. It is understood that run time could be reduced if the temperatures of the heaters do not need to be changed. FIGS. 25-27D show another embodiment for the first-stage PCR amplification. In this illustrative embodiment, blisters 548 and 564 may be replaced with a single blister 549, and the illustrative instrument may be provided with a temperature control element that includes heaters 986 and 987. However, it is understood that one of blisters 548 or 564 may be used and smaller heaters 986, 987 may be used. It is also understood that blister 549 may be used by itself in or combination with other embodiments that may or may not include components for cell lysis and/or additional amplification such as in, but not limited to, the pouches described in reference to in reference to FIGS. 5A, 7, 11A, 111B, 17A and 17B, and 17C. The embodiments of FIGS. 25-27D are particularly well suited for thermocycling the contents of multifunction chamber 4002*a* of FIG. 17C.

Heaters 986, 987 may be Peltier devices, resistive heaters, induction heaters, electromagnetic heaters, thin film heaters, printed element heaters, positive temperature coefficient heaters, other heaters as are known in the art, or combinations of heater types (e.g., a heater element that includes a Peltier thermoelectric heater/cooler device and a resistive heater). However, unlike heater 886 that is provided to thermocycle between an annealing and a denaturation temperature, in one example, heater 986 may be provided at a suitable denaturation temperature, illustratively 94° C., and heater 987 may be provided at a suitable annealing temperature, illustratively 60° C., although other illustrative denaturation and annealing temperatures may be used, as are known in the art. In some embodiments, it may be desirable to set heater 986 higher than 94° C. and set heater 987 at a temperature lower than 60° C., as fluid may be circulated through control of each of these heaters quickly as the fluid reaches temperature, thereby increasing ramp rate. Such embodiments may be suited for use with enhanced primer and polymerase concentrations. Illustratively, an insulating spacer 983 may be provided between heater 986 and heater 987. Any suitable insulating material may be used, including foam, plastic, rubber, air, vacuum, glass, or any other suitable material illustratively of low conductivity. In embodiments where heaters 986 and 987 are held at a generally constant temperature, run time and energy usage may be substantially reduced.

In the illustrative example, a wiper head 910 comprising a wiper 989 engages top surface 549*b* of blister 549. When fluid is moved into blister 549, wiper 989 is moved so that body 913 of wiper 989 forces blister 549 into contact with heaters 986, 987, so that a portion of blister 549 is in contact with each of the heaters, to permit thermal transfer from each of the heaters to a portion of blister 549. One or more blades 949 may then be used to move the sample 572 from one area of blister 549 to another area of blister 549.

Figure 27A:
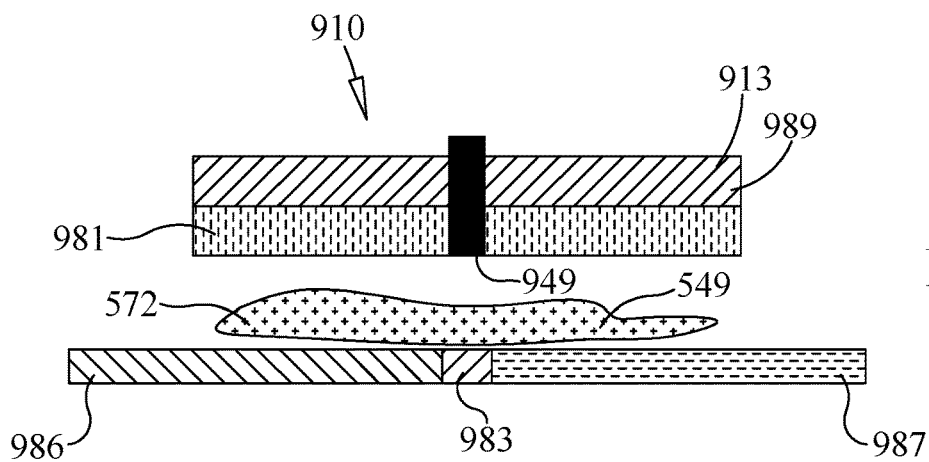
FIGS. 27A-27D show a cross-sectional view of FIG. 26 and also illustrate how a wiper may contact a fluid-filled blister, according to one embodiment of the present disclosure.
Figure 27B:
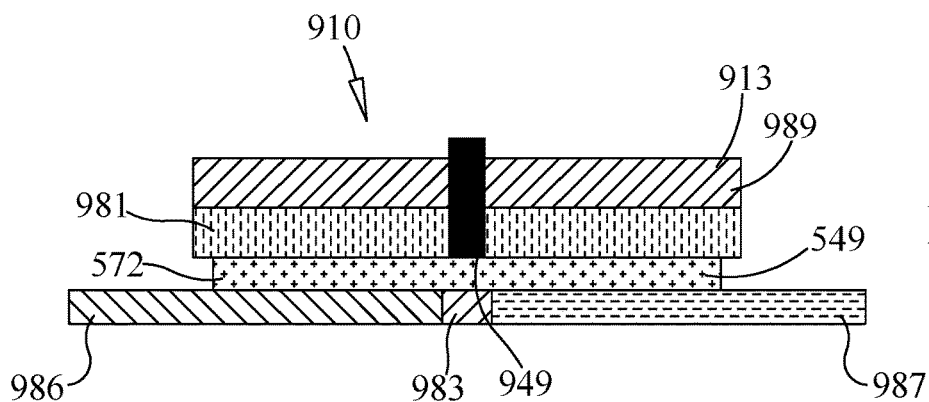

Often when a fluid enters a compartment, the fluid may remain near the entry to that compartment or the contents of a compartment may not be fully mixed. This is schematically illustrated in FIG. 27A where the illustrated blister 549 has adopted an irregular shape and may not be in good contact with the heaters 986 and 987. Depending on the volume of the blister 549, the volume of sample 572 added, the contents of the sample, etc., the fluid 572 may be irregularly shaped with the bulk of the fluid collected near where the sample is injected into the blister. This may be particularly true where the compartment is expandable and is partially or fully collapsed prior to the addition of the fluid, or in other situations when the fluid may be less than sufficient to fill the compartment completely. One can imagine an embodiment wherein sample 572 enters blister 549 through channel 552*a* and remains near channel 552*a* so that engagement of blade 949 traps most or all of sample 572 in section 549*c*. Accordingly, it may be desirable to spread the fluid across the compartment prior to engagement of a blade. Thus, as illustrated in FIG. 27B, wiper head 910 may lowered until it contacts the blister 549 to spread sample 572 across blister 549 to evenly distribute the fluid 572 in the blister 549, to cause the blister 549 to adopt a regular shape, and to press the blister 549 into good, consistent contact with the heaters 986 and 987.

In one embodiment, the wiper head 910 may be provided with a pressure member 981 that places pressure on blister 549 and spreads sample 572 across blister 549. Illustratively, use of member 981 has several benefits. One is that more of sample 572 may be spread across heaters 986, 987 in a thinner layer, thus increasing the surface area to volume ratio, which should improve heat transfer to and from sample 572. Likewise, since the fluid is being rapidly thermocycled—i.e., the liquid of sample 572 is rapidly being raised and lowered in temperature by heaters 986 and 987, spreading the liquid into a thin layer in blister 549 may decrease the dwell time at any given temperature and allow more of the sample to hit the target temperature more quickly. Also, depending on the shape of wiper 989, as discussed below, pressure from member 981 onto blister 549 spreads sample 572 so that engagement of blade 949 of wiper 989 divides the sample 572 in blister 549 into relatively even or proportional volumes. Pressure from member 981 prior to engagement of blade 949 would force some of sample 572 into each of the sections of blister 549.

In one embodiment, member 981 is compressible or semi-compressible (e.g., formed of or comprising a compressible or semi-compressible material). Such materials include compressible or semi-compressible foams, plastics, or rubbers, or may be a more solid material but have a spring-loaded, elastomeric, or other biasing member or force between member 981 and wiper body 913, such that when sample 572 is moved into blister 549, sample 572 is spread across blister 549 but member 981 compresses appropriately to permit sufficient space for sample 572. Other compressible or semi-compressible materials may be used as are known in the art. Alternatively, member 981 may be substantially rigid and set to a position such as to provide only a sufficient space between member 981 and heaters 986, 987 to force the sample 572 to spread across blister 549.

Figure 27C:
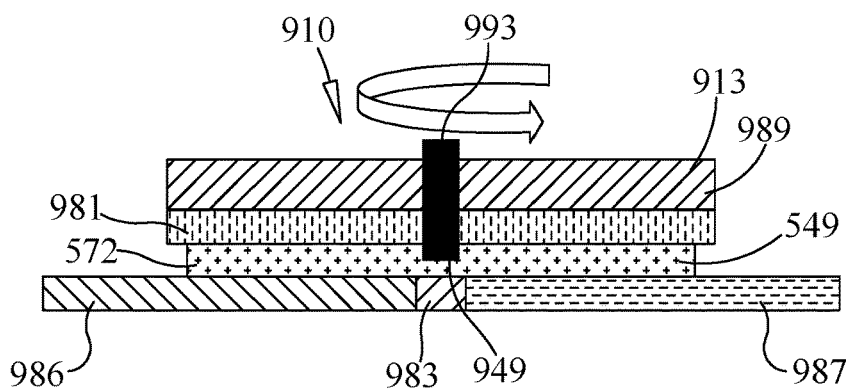
Figure 27D:
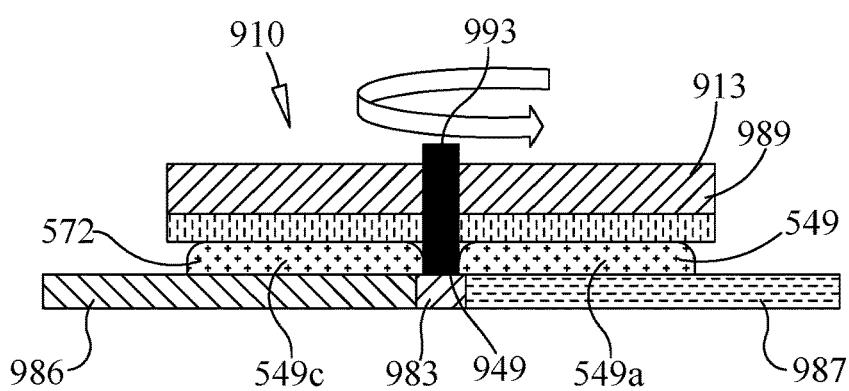

In the illustrative embodiment, wiper 989 has an x-shaped blade 949 that extends through member 981 and divides wiper 989 into four sections 945, 946, 947, 948, as illustrated in FIG. 6. As illustrated in FIGS. 27C and 27D, the wiper 989 and the blade 949 may contact the blister in at least two modes. As illustrated in FIG. 27C, the wiper 989 may be lowered until member 981 is compressed partially and the blade 949 impinges partially on the blister 549. If the wiper head 910 is rotated in the mode of FIG. 27C, the action of the blade 949 can be used to provide a stirring action to thoroughly mix the contents 572 of the blister 549.

If the wiper head is lowered further, as illustrated in FIG. 27D, such that member 981 is further compressed and the blade 949 fully impinges in the blister 549, then the blade may divide the blister into discrete sections. For example, with an x-shaped blade 949, as illustrated in FIG. 7, the blade 949 may contact blister 549 with enough pressure such that blade 949 divides blister 549 into corresponding four sections, 549*a*, 549*b*. 549*c*, 549*d*. Rotation of wiper 989 around axis 993 forces fluid within blister 549 into a circular motion around blister 549. In one embodiment, blade 949 allows portions of the fluid to be heated by each of the heaters 986 and 987 simultaneously, and moves portions of fluid from temperature control of one heater while permitting other portions of fluid to be under control of the other heater. Member 981 compresses the contents of blister 549. Thus, in addition to spreading out the fluid 572 in the blister 549 and improving contact between the blister 549 and the heaters 986 and 987, member 981 may also plunge the contents of blister 549 to another blister. For example, after first-stage thermal cycling is complete, an exit channel may be opened, which opens a path for fluid to flow out of the blister as member 981 returns to its original shape. In one embodiment, fluid may only flow out of the quadrant of the blister that is fluidly connected with the channel. Wiper 989 may be rotated so that each quadrant is connected with the exit channel in turn.

Illustratively, blade 949 may be a rubber or elastomeric material, or a non-stick material such as Teflon or Delrin having enough stiffness to divide blister 549 into sections and to move fluid within blister 549, but not puncture or tear blister 549, although it is understood that such materials are illustrative only and that other materials may be used, as are known in the art. Blade 949 alternatively may be replaced by rollers or other configurations to allow movement of fluid within blister 549. Wiper head 910, including wiper 989 and blade 949, may be moved into position and rotated by any motor, cam, crank, gear mechanism, hydraulics, pneumatics, or other means, as are known in the art. Such movement may be continuous or wiper 989 and blade 949 may be moved step-wise with pauses, illustratively 0.1 seconds to a minute or more, thus holding portions of the sample in control of each of the heaters 986, 987 before being moved to its next position and holding different portions of the sample in control of each of the heaters 986, 987. The motion of wiper 989 may be circular, in a clockwise or counter-clockwise motion, or may reverse directions, alternating between clockwise and counter-clockwise. It is understood that wiper body 913 and blade 949 may be a single fixed unit and move as a single fixed unit, or body 913 may be moved into and out of contact with blister 549 independently of movement of blade 949. It is also understood that the circular shape of blister 549 and rotational motion is illustrative only, and that other sample vessel shapes are possible, as are non-rotational movement of the blade or rollers, such as linear, curvilinear, and semi-circular motions.

Figure 25:
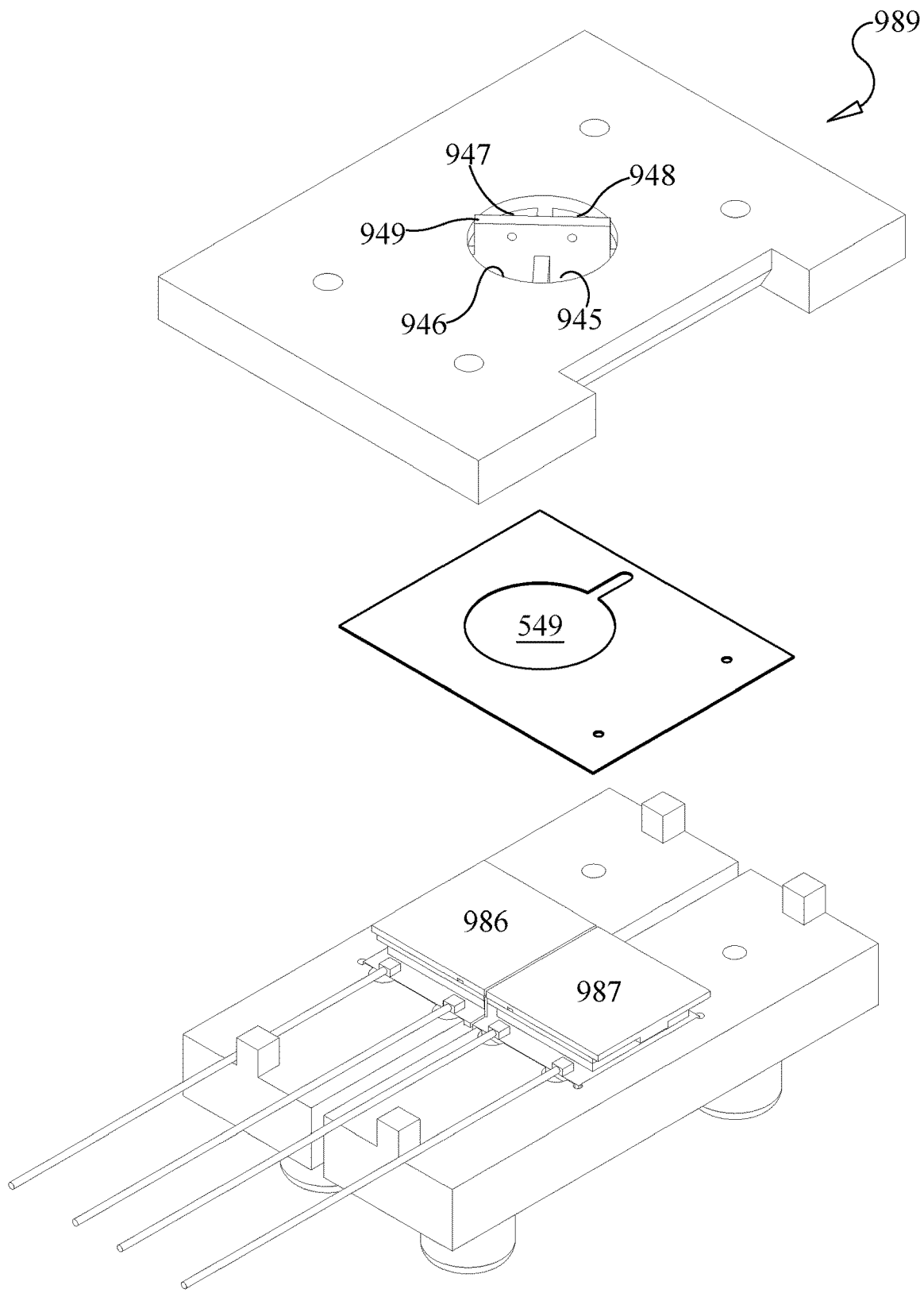
FIG. 25 is an exploded view of an alternative heating embodiment for first-stage PCR that can be used with one or more pouch embodiments in one or more of the instruments described herein.
Figure 26:
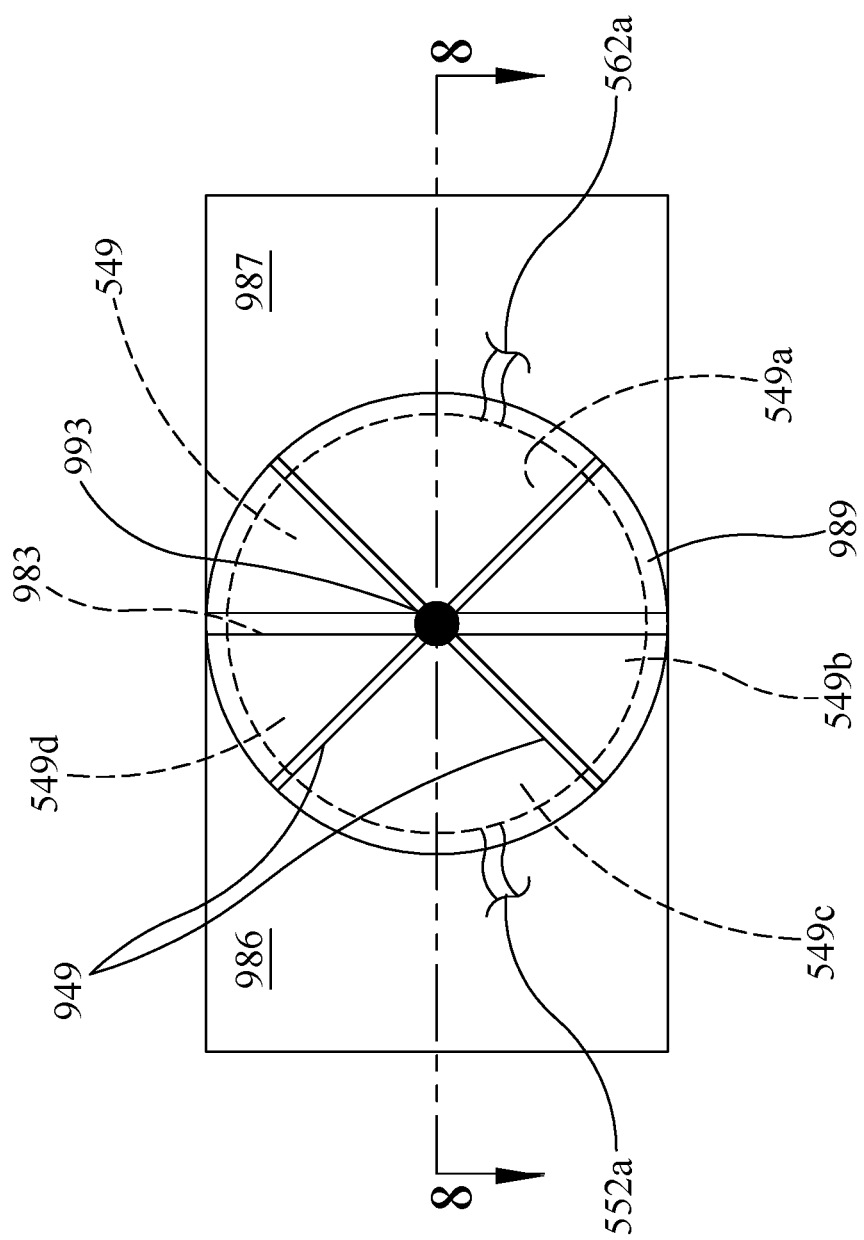
FIG. 26 is a top view of the heating format of FIG. 25.

As discussed above, wiper 989 is provided with an x-shaped blade 949, thereby partitioning wiper into four segments 945, 946, 947, 948, as best seen in FIG. 25, and similarly dividing blister 549 into four segments 549*a*, 549*b*, 549*c*, and 549*d*, as best seen in FIG. 26. However, it is understood that this is illustrative only, and that any shape of blade 949 may be used, including a single linear blade illustratively substantially corresponding to a diameter of blister 549, a single or multiple non-linear blade including an s-shaped blade or a spiral blade, a single blade corresponding to a radius of blister 549 (similar to a clock hand), and multiple blades that divide blister 549 into multiple segments. It is understood that blades that divide blister 549 into multiple similar segments likely provide more controlled heating between different segments where entire segments will be at the annealing and denaturation temperatures at one time, whereas s-shaped, spiral, and radial blades may generate multiple vortexes, eddies, and varied mixing patterns, to move the sample across the thermal surface created by heaters 986, 987. It is also understood that less blade material allows for more of the sample to be in close contact with the heaters, while more blade material better controls fluid movement. Whatever the blade pattern, it is understood that portions of the fluid in blister 549 will be at the annealing temperature, while other portions will be at the denaturation temperature, and yet other portions may be in transition between the temperatures, all within a single sample container. The choice of shape for blade 949 may depend on size and thickness of the blister and size of the heaters, and the desirability of using wiper 989 for expelling material from blister 549 once first-stage thermal cycling has been completed.

In the illustrative embodiment, heaters 986 and 987 are each provided at fixed temperatures, illustratively 94° C. and 60° C. respectively. However, it may be desirable to adjust the temperature of heaters 986 and 987 during use, in some embodiments. For example, it may be desirable to increase the temperature of one or both heaters when the sample is first introduced to blister 549, to compensate for a cooler temperature of the fluid as it enters blister 549. In another example applicable to the following discussion, it may be desirable to "overdrive" the heaters to allow the heaters to achieve the target temperature of the fluid in the blister more rapidly. For instance, if the target temperatures for thermocycling are 940 and 60°, then the heaters may be set above the high temperature (e.g., in a range of 95-110° C.) and below the lower temperature (e.g., in a range of 59-50° C. to more rapidly heat and cool the fluid in the sample. Additionally, while two heaters are shown, any number of heaters may be used. One illustrative example uses three heaters, with one set at a denaturation temperature, one set at an annealing temperature, and the third set at an elongation temperature. In another illustrative example, a first heater may be larger than a second heater, so that the sample stays at the first temperature for a longer portion of the cycle. Moreover, it is understood that blister 549 and its contents may remain stationary, and heaters 986, 987 may be rotated or translated laterally.

Illustratively, fluid may enter blister 549 through channel 552a from a nucleic acid extraction zone, illustratively similar to blister 546 of the pouch of FIG. 1, and channel 552a may then be closed. Member 981 then presses on blister 549, promoting contact of blister 549 with heaters 986 and 987, and then blade 949 is moved toward heaters 986, 987 and divides blister 549 into segments 549a, 549b, 549c, and 549d. As wiper 989 is rotated, sample in each of the four segments 549a, 549b, 549c, and 549d is moved from contact with heater 986 to contact with heater 987, and back again. The amount of time needed to heat and cool the sample in each of the segments is dependent on a number of factors, including thickness of film on blister 549, thickness of the fluid layer within blister 549, mixing of the sample within blister 549, and amount of contact with the heaters. However, it is understood that one full revolution of wiper 989 generally corresponds to one cycle of PCR in this illustrative embodiment.

In addition to the thermal cycling devices described above, the heater and mixer systems described herein can also be used for automated sample preparation in an enclosed pouch. For instance, as will be described in greater detail below, heating a blister like 549 with one or both of heaters 986 and 987 while blending the contents of a sample preparation blister with, for example, wiper 949 can be used to lyse cells (e.g., bacterial and mammalian cells) and release the nucleic acids therein. Alternatively or in addition, a blister may include a chaotropic agent, a detergent, and/or lysis particles (see, e.g., lysis blister 522 of pouch 510 of FIG. 1). Likewise, heating and cooling with thermoelectric cooling devices (i.e., Peltier devices) and mixing can be used to increase the efficiency of other sample preparation processes. For example, nucleic acids bind more efficiently to magnetic beads (e.g., magnetic beads 533 of FIG. 1) at lower temperatures (e.g., ~0-10° C.) and are eluted more efficiently from the magnetic beads at higher temperatures (e.g., ~60-90° C.). Thus, lysing may illustratively occur when blister 549 is in contact with heater/cooler 986, while magnetic bead binding may illustratively occur when blister 549 is in contact with heater/cooler 987, and these heaters may move laterally, as discussed below.

Figure 28A:
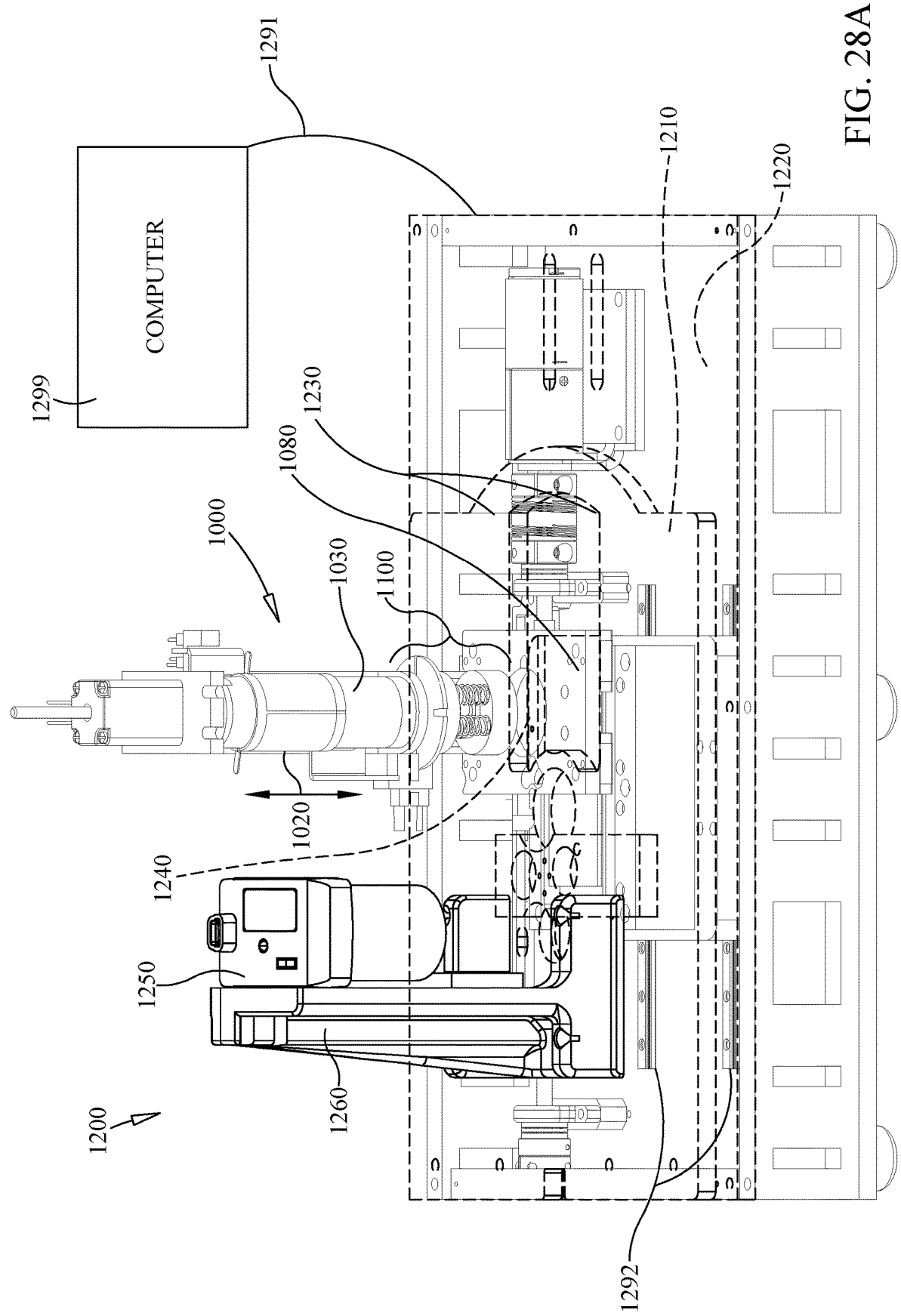
FIGS. 28A and 28B illustrate a thermocycling instrument that incorporates a wiper system and a heater that includes at least two temperature zones that can be used with one or more pouch embodiments described herein, according to one embodiment of the present disclosure.
Figure 28B:
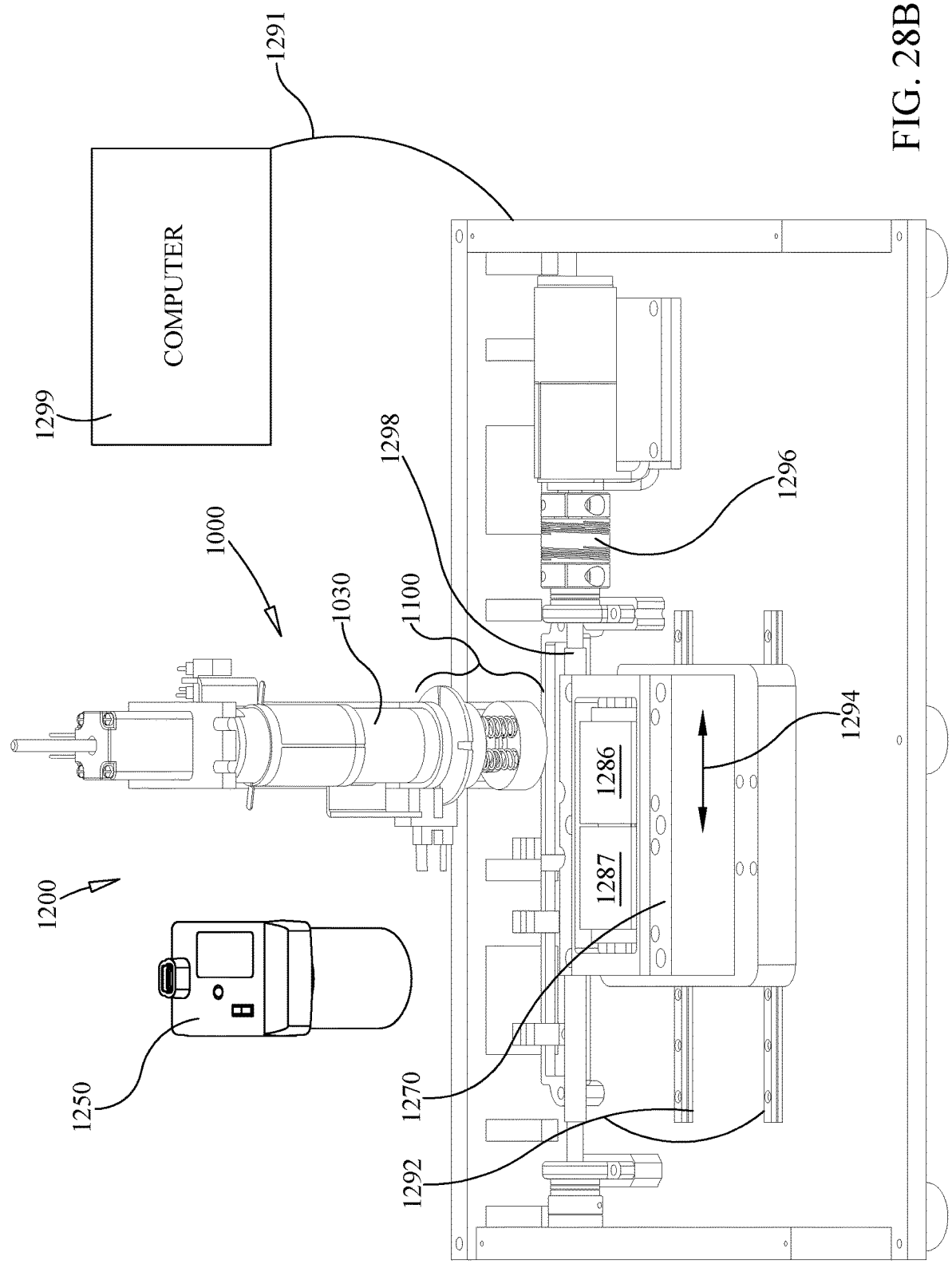

Referring now to FIGS. 28A and 28B, an instrument 1200 is illustrated that may be configured to be used with the pouches described herein in reference to, for example, FIGS. 5A, 7, 11A, 11B, 17A and 17B, and 17C. Instrument 1200 includes a wiper system 1000 similar to wiper 949 discussed, for example, in reference to FIG. 25, and many of the features of the heaters 986 and 987 of FIG. 25. In the illustrative example, instrument 1200 also includes a hinged cover 1210 and a chassis cover 1220. The hinged cover 1210 can be opened for insertion of a flexible pouch for self-contained PCR into the instrument between the hinged cover 1210 and the chassis cover 1220. The chassis cover 1220 lies over the internal components of the instrument 1200 and may define a receptacle for positioning a flexible pouch such as one illustrated in FIGS. 5A, 7, 11A, 111B, 17A and 17B, and 17C in the instrument, wherein the receptacle may be coextensive with a portion of the pouch. The receptacle may be configured to receive the flexible pouch in the instrument and align the flexible pouch so that various components of the instrument can interact with the flexible pouch. Likewise, the receptacle may include openings and the like so that the internal components of the instrument can contact the flexible container. Likewise, the hinged cover 1210 may include openings and the like so that external components of the instrument can interact with the flexible container. Above the covers 1210 and 1220, the instrument 1200 includes a wiper system 1000, which includes a drive motor 1030 and a wiper head 1000, and camera/fluorimeter 1250 and a mount 1260 for collection of fluorimetric data. The wiper system 1000 can be moved up and down as indicated by arrows 1020 through a hole 1240 in the base 1080 and through one or more holes in the hinged cover 1210 in order to contact the pouch.

In the illustrated embodiment, the wiper system 1000 may be translated side-to-side, illustratively on rails 1230, so that the wiper system 1000 can contact different regions of a pouch inserted into the instrument 1200. In one embodiment, the wiper system 1000 may be translated so that the wiper 1100 can interact with different portions of the pouch. For instance, the wiper system 1000 may be used for in-pouch sample preparation and first-stage PCR steps. In an alternative embodiment, the wiper system 1000 may be held stationary and the pouch may be moved so that the wiper can contact different portions of the pouch. It is understood, however, that this arrangement is illustrative, and other arrangements of moving and aligning wipers, heaters, and sample containers are contemplated. It is understood that any combination of wipers, heaters, and pouches may be placed on movable elements and that when translation of wipers, heaters, pouches, and the like is discussed, such movement may be replaced with opposite translation of the wiper, heater, or pouch, working in concert with that element, in any embodiment where such opposite translation is consistent with the arrangement of other elements. In some embodiments, rotary motion of the pouch and other instrument elements is also contemplated.

Referring now specifically to FIG. 28B, the covers 1210 and 1220 are removed so that the interior of the instrument 1200 can be seen more clearly. The interior of the instrument 1200 illustratively includes a heater assembly 1270 that can be translated back and forth by a translator as shown by arrow 1294, for example, on rails 1292. The heater assembly 1270 includes a first heater element 1286 and a second heater element 1287. In the illustrated embodiment, the heater assembly may be mechanically coupled to a translator that illustratively includes a drive motor 1296 and drive member (e.g., a threaded screw) 1298. Heater assembly 1270 may be translated back and forth, for example, on rails 1292 so that the heaters 1286 and 1287 can interact with different regions of a pouch installed in the instrument. For instance, heaters 1286 and 1287 may be positioned as illustrated in FIGS. 25-27D for a first-stage PCR reaction. Likewise, an entire blister may be controlled by one heater at a time, and the blister (e.g., a first-stage PCR blister or a second-stage PCR blister) can be thermocycled by moving the heater assembly 1270 back and forth with the translator so that a selected blister is repeatedly under temperature control of the first heater 1286 and then the second heater 1287, etc. However, it is understood that a motor and rails are illustrative only, and that other linear and non-linear translators may be used. One will appreciate that while the illustrated embodiment includes a heater that can move, the same effect(s) can be accomplished by translating the pouch relative to the heaters instead of moving the heater assembly and that this motion can be along linear, arcilinear, or rotational paths, for example. While heaters 1286 and 1287 are shown in this example for heating and cooling the contents of the pouches described herein—either by translating heaters 1286 and 1287 below a portion of a pouch or in combination with wiper system 1000—it is understood that other ways of heating and cooling the contents of the pouches described herein are contemplated. For example, the system described in U.S. Pat. No. 9,586,208 may be used for compressing the contents (e.g., 150-300 µl) of a fluid-filled blister back and forth between two heaters. The entirety of U.S. Pat. No. 9,586,208 is incorporated herein by reference.

Heaters 1286 and 1287 may be Peltier devices, resistive heaters, induction heaters, electromagnetic heaters, thin film heaters, printed element heaters, positive temperature coefficient heaters, or other heaters as are known in the art. One will appreciate that heater types may also be combined in a single unit (e.g., a heater unit may include a Peltier device with a resistive heater on the front and/or backside of the Peltier to help with maintaining a fixed temperature and/or to increase the efficiency and speed of heating and cooling). While the term "heater" is used to refer to elements 1286 and 1287, it is understood that other temperature control elements or combinations of elements may be used to adjust the temperature of the sample. Unlike heaters typically included in a PCR device that are provided to thermocycle between an annealing and a denaturation temperature, heaters 1287 and 1286 may be held at a fixed temperature or may be thermocycled in a limited temperature range (e.g., between an annealing temperature and an elongation temperature). For instance, as explained in detail above in reference to FIGS. 25-27D, a sample may be thermocycled by moving the contents of a liquid-filled blister between two static temperature zones. In one example, heater 1287 may be provided at a suitable denaturation temperature, illustratively 94° C., and heater 1286 may be provided at a suitable annealing temperature, illustratively 60° C., although other illustrative denaturation and annealing temperatures may be used, as are known in the art. Also, three or more heaters may be desirable for certain protocols.

In one embodiment, one or both of heaters 1286 and 1287 may include a Peltier element. While heaters 1286 and 1287 may not be thermocycled, it may, for instance, be desirable to include a Peltier element in one or both of heater 1286 and 1287. Unlike a typical resistance heater, Peltier elements can actively cool as well as heat samples. For example, in moving a sample from a denaturation temperature (e.g., 94° C.) to an annealing temperature (e.g., 60° C.), the sample has to be cooled down to the annealing temperature. This will happen by radiation/conduction, but these processes are relatively slow. For rapid thermocycling, it may be preferable, for example, to actively cool the sample with Peltier device with the "cool" side of the Peltier set to 60° C. and the "hot" side, where excess heat may illustratively be pumped and disposed of through a heat sink, may be set to a higher temperature.

Instrument 1200 also includes a computer 1299 that may be configured to control one or more of the wiper 1100, the heaters 1286 and 1287, thermocycling parameters (e.g., movement of the wiper, temperatures of the heaters, alignment of the wiper and heaters with the sample container, etc.), fluid movement in the sample container, etc. Likewise, the computer 1299 may be configured for data acquisition and analysis from the instrument 1200, such as from optical system 1250. Each of these components is connected electrically, illustratively via cable 1291, although other physical or wireless connections are within the scope of this invention. It is understood that computer 1299 may be housed within instrument 1200 or may be external to instrument 1200. Further, computer 1299 may include built-in circuit boards that control some or all of the components, and may also include an external computer, such as a desktop or laptop PC, to receive and display data from the instrument 1200. An interface, illustratively a keyboard interface, may be provided including keys for inputting information and variables such as temperatures, cycle times, etc. Illustratively, a display may also be provided. The display may be an LED, LCD, or other such display, for example.

Figure 29A:
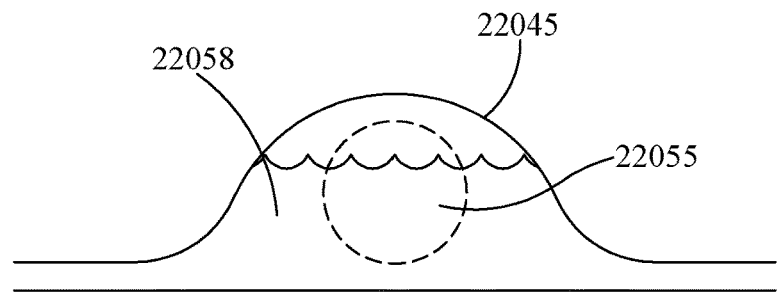
FIG. 29A schematically illustrates a rehydrated blister and a dried reagent pill that may be included in one or more of the pouches illustrated herein.

Some embodiment of the pouches described herein (see, e.g., FIGS. 11A and 111B) may include blisters that, in one embodiment, may include dehydrated reagent pills that may be rehydrated and then dispensed into various reaction zones in the pouch. An example of a blister 22045 that includes a reagent pill 22055 and a rehydration fluid (e.g., water, buffer, or the like) 22058 is shown in FIG. 29A. In one embodiment, the reagent pill 22055 may disperse almost instantaneously as soon as the hydration fluid 22058 is added to the blister 22045. Thus, it is understood that the representation in FIG. 29A is merely schematic and that the pill 22055 may not be configured to remain as shown for any appreciable amount of time after the hydration fluid 22058 is added. In another embodiment, pouch blisters like 22045 may include liquid reagents (e.g., polymerase, dNTPs, and the like) and the reagent pills like 22055 may be omitted for at least some reaction components used in the pouch.

Figure 29B:
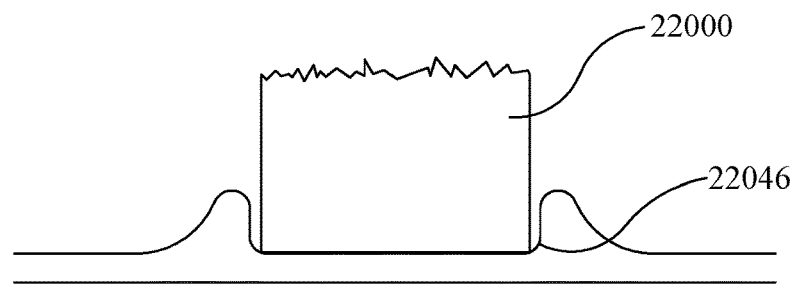
FIG. 29B illustrates a device that may be used to plunge a fluid-filled blister such as the blister in FIG. 29A.

In either pouch embodiment, instruments configured to run pouches like the ones illustrated in FIGS. 7, 11A, and 11B may include a device or devices to predictably and, preferably, volumetrically dispense liquid from liquid filled blisters like blister 22045 shown in FIG. 29A. In one embodiment, liquid filled blisters like blister 22045 may be crushed, collapsed, or compressed by crusher 22000 of FIG. 29B. In one embodiment, blisters may be sized and shaped so that they can be collapsed to predictably and, preferably, volumetrically dispense their fluid when they are crushed, as shown at 22046. Likewise, crusher 22000 may be sized and shaped to predictably and, preferably, volumetrically dispense the fluid in a fluid filled blister.

Figure 29C:
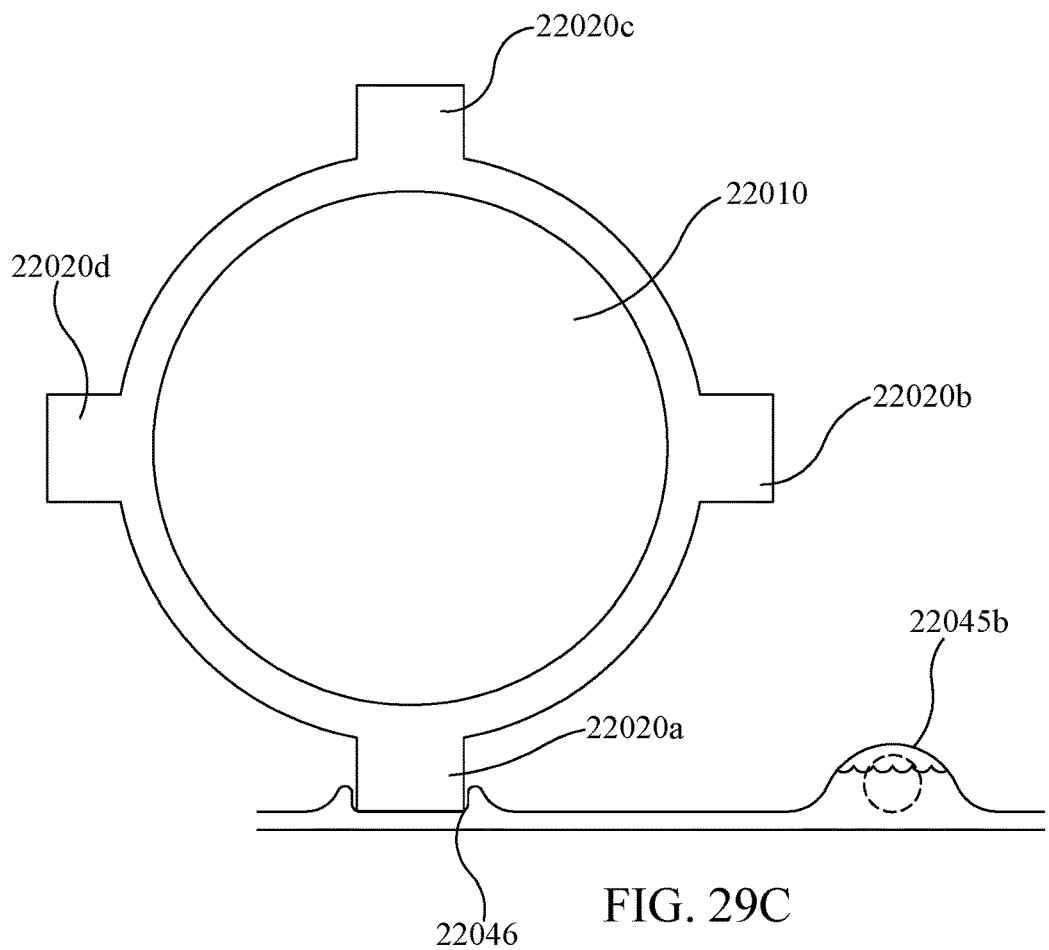
FIG. 29C illustrates a wheel device that may be used to plunge a series of fluid-filled blisters like the blister in FIG. 29A.

In one embodiment, an instrument that includes crusher 22000 may be configured such that crusher 22000 can be moved relative to a pouch to dispense selected fluids from selected blisters at selected times. Similarly, crusher 22000 may be configured to move up and down to crush selected blisters and the pouch may be moved relative to the crusher so that the fluid can be dispensed from selected blisters at selected times. FIG. 22 illustrates an exemplary embodiment of a crusher wheel 22010 that may, for instance, be used to dispense fluid from a series of blisters that are positioned in a line. In the illustrated embodiment, the crusher wheel 22010 of FIG. 29C includes crushers 22020a-22020d that may be used to crush a series of spaced apart blisters when the wheel is turned. Illustratively, blister 22046a has been crushed by the action of crusher 22020a; crusher 22020b is spaced relative to blister 22045b such that blister 22045b may be crushed when wheel 22010 is turned. Wheel 22010 is shown with an illustrative spacing for four equally spaced crushers, but one will appreciate that a crusher wheel may include more or fewer crushers and that spacing may be adjusted for dispensing the fluid contents of blisters with a variety of spacing(s) on a selected pouch.

Additional discussion and embodiments of instruments that may be used with the pouches described herein can be found, for example, in PCT/US17/18748, the entirety of which was incorporated by reference elsewhere herein.

Below are presented Examples of experiments that were performed with pouches and instruments like those described herein. The Example generally illustrate the utility of one or more of the pouches and instruments described herein. However, the Examples are illustrative and are not intended to limit or alter the scope of the invention(s) described herein.

Example 1: High Density PCR

In one example, it is known that standard commercial immunofluorescence assays for the common respiratory viruses can detect seven viruses: adenovirus, PIV1, PIV2, PIV3, RSV, Influenza A, and Influenza B. A more complete panel illustratively would include assays for other viruses including: coronavirus, human metapneumovirus, rhinovirus, and non-HRV enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The FilmArray® Respiratory Panel (BioFire Diagnostics, LLC of Salt Lake City, Utah) includes Adenovirus, Coronavirus HKU1, Coronavirus NL63, Coronavirus 229E, Coronavirus OC43, Human Metapneumovirus, Human Rhinovirus/Enterovirus, Influenza A, Influenza A/H1, Influenza A/H3, Influenza A/H1-2009, Influenza B, Parainfluenza Virus 1, Parainfluenza Virus 2, Parainfluenza Virus 3, Parainfluenza Virus 4, and Respiratory Syncytial Virus. In addition to these viruses, the FilmArray® Respiratory Panel includes three bacteria: *Bordetella pertussis, Chlamydophila pneumoniae*, and *Mycoplasma pneumoniae*. The high density array 581 is able to accommodate such a panel in a single pouch 510. Other panels are available for the FilmArray®, each assaying for at least 20 pathogens.

Example 2: Fast PCR

A prototype instrument using the pouch and heater configuration of FIGS. 25-27D was used to amplify DNA. A 75 µl sample comprising 10,000 copies of a 110 bp synthetic DNA molecule and a 10× higher primer (5 µM each primer) and DNA polymerase (2 U/µL) concentrations (as compared to standard PCR concentrations, as taught in US 2015-0118715, already incorporated by reference), with dNTPs at 0.45 mM and 5 mM Mg++. 1× LCGreen was used for detection. It is understood that the reaction mixture is illustrative only. Depending on cycling times, enhanced primer and polymerase concentrations may be beneficial. See U.S. Patent App. No. 2015-0118715, already incorporated by reference, for more information on enhanced primer and polymerase concentrations. For example, for cycling times of less than 20 sec, it is desirable to have at least 0.5 µM polymerase and at least 1 µM of each primer in a multiplex reaction or 2 µM of each primer in a single-plex reaction. Heater 986 was set to 90° C. and heater 987 was set to 57° C. This mixture was sealed into blister 549 and run with wiper 989 rotating at a speed of one full rotation every 10 sec. It is understood that the rotational speed corresponds to cycle time.

As a control, PCR chemistry reactions (with boosted primer and polymerase concentrations) were cycled in a standard block thermocycler between 96° C. and 60° C. as fast as the hardware would allow (1 second holds, 48 seconds per cycle). To compare the efficiency of amplification for the two systems, identical PCR reactions were amplified in each instrument over a "cycle course" of 5, 10, 15 and 20 cycles. After the first-stage PCR, these reactions were diluted 100-fold into a nested second-stage PCR reaction and amplified in a Roche LC480 real time PCR instrument.

Figure 30:
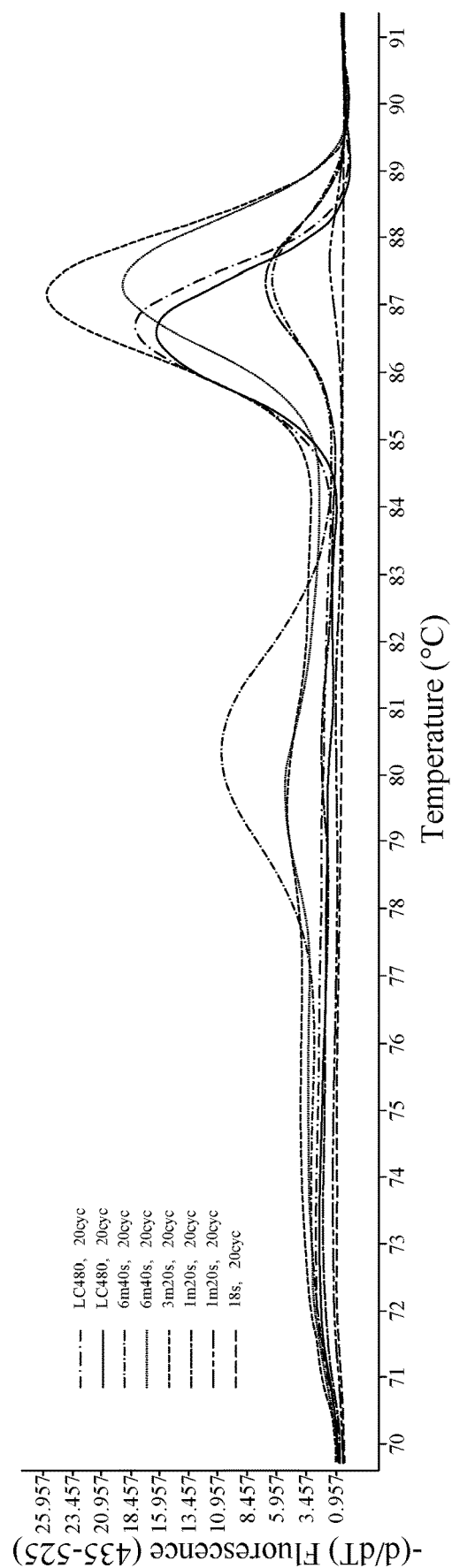
FIG. 30 shows results of amplification using a prototype of the instrument of FIGS. 28A and 28B in comparison to amplification using a standard plate-based thermocycler.
Figure 31:
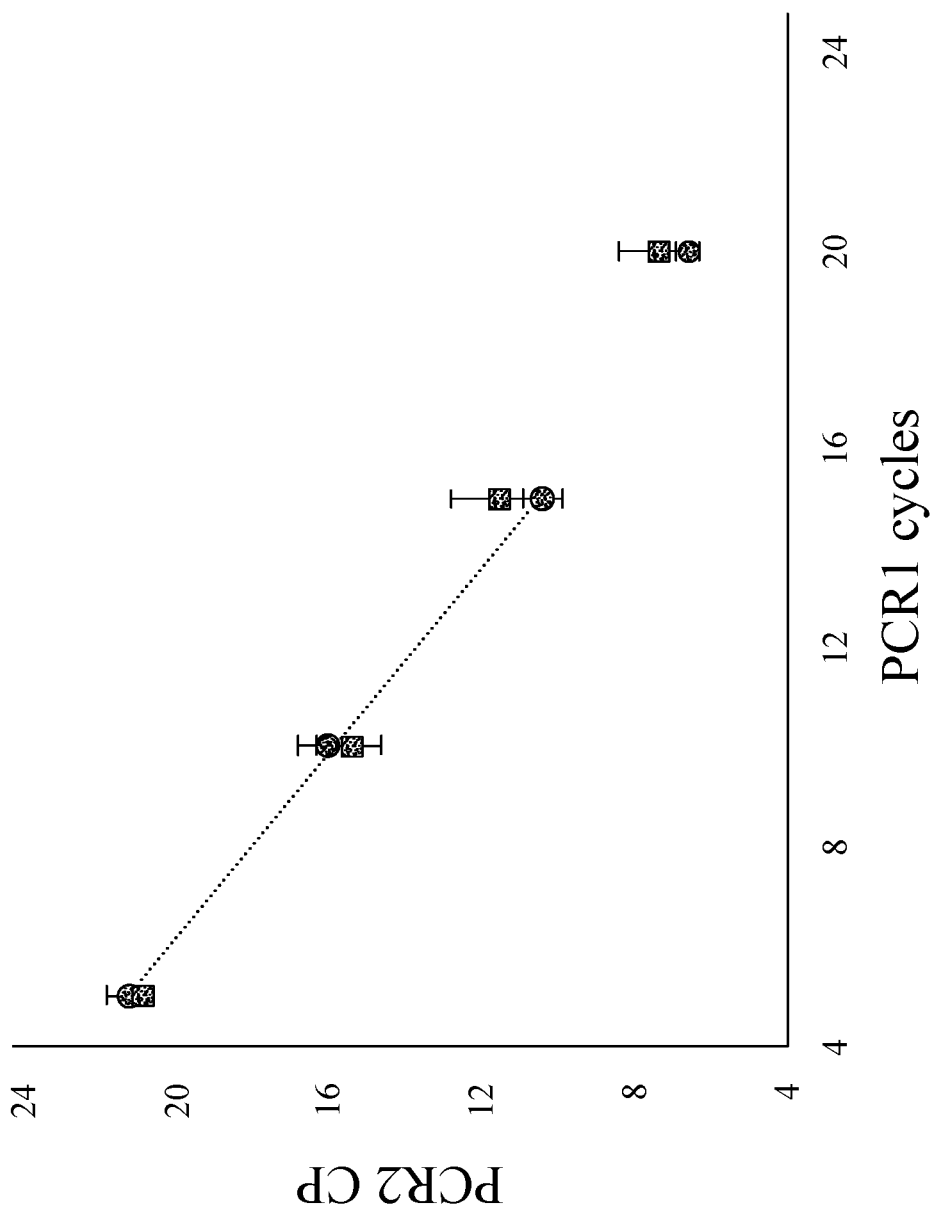
FIG. 31 shows a graph of the second-stage PCR Cp that results from running different numbers of cycles for first-stage PCR in a block thermocycler (circle) and the prototype wiper blade setup (square).

FIGS. 30 and 31 show results of the PCR in the prototype instrument of FIGS. 25-27D. In FIG. 30, melting curves for the first stage reactions in the wiper system at different speeds are compared to melting curves for amplification in the LC480. FIG. 31 shows the results of the cycle course. Amplification in the prototype of FIGS. 25-27D and in the LC480 block thermocycler overlap and are fit by lines with R2 values >0.99). In FIG. 31, the slopes of these lines show the relative efficiency of one cycle in the LC480 compared to one cycle in the prototype. The efficiency of the block cycler (slope of 1.08) is slightly greater than that of the wiper blade system (0.93) indicating slightly less than the full efficiency of a block thermocycler, in approximately 3 min, 20 sec.

Example 3: Three Temperature PCR Using Two Temperature Zones

As discussed above, some PCR protocols use three temperatures, a first temperature for annealing, a somewhat higher temperature for extension that is illustratively chosen based on enzyme activity, and a third highest temperature for denaturation. While it is typical to thermocycler one heater for the three temperatures, in some embodiments it may be desirable to thermocycle larger volumes quickly. Illustratively, it may be desirable to thermocycle first-stage PCR through three temperatures, wherein a heater such as heater assembly 988 may not be able to heat and cool the contents of blister 564 as rapidly as desired.

In one such embodiment, it may be desirable to use a three-step PCR protocol in first-stage PCR in the pouch 510 of FIG. 1. As discussed above, first-stage heater 886 of FIG. 2 is positioned to heat and cool the contents of blister 564 for first-stage PCR. In one embodiment, heater 887 may be provided to control the temperature of the contents of blister 548, where heaters 886 and 887 are controlled together and cycle together. In another embodiment, heaters 886 and 887 may be under separate control, illustratively heater 887 may be provided to maintain a suitable annealing temperature, while blister 886 may be provided to maintain a suitable denaturation temperature, although it is understood that this is illustrative only and that the heaters may be reversed. Other configurations are possible. Two temperature PCR using two heating zones is discussed more fully in U.S. Patent Application No. 2014-0038272, herein incorporated by reference in its entirety.

In one embodiment, Peltier heaters or heaters such as those disclosed in U.S. patent application Ser. No. 15/099,721, herein incorporated by reference, may be used for heaters 887, 888 and other heaters discussed herein, although other heaters or heater assemblies as are known in the art may be used to obtain three-temperature cycling in two temperature zones, provided that the temperature of these heaters is adjustable. In one embodiment, active control of these heaters is desirable.

Figure 32:
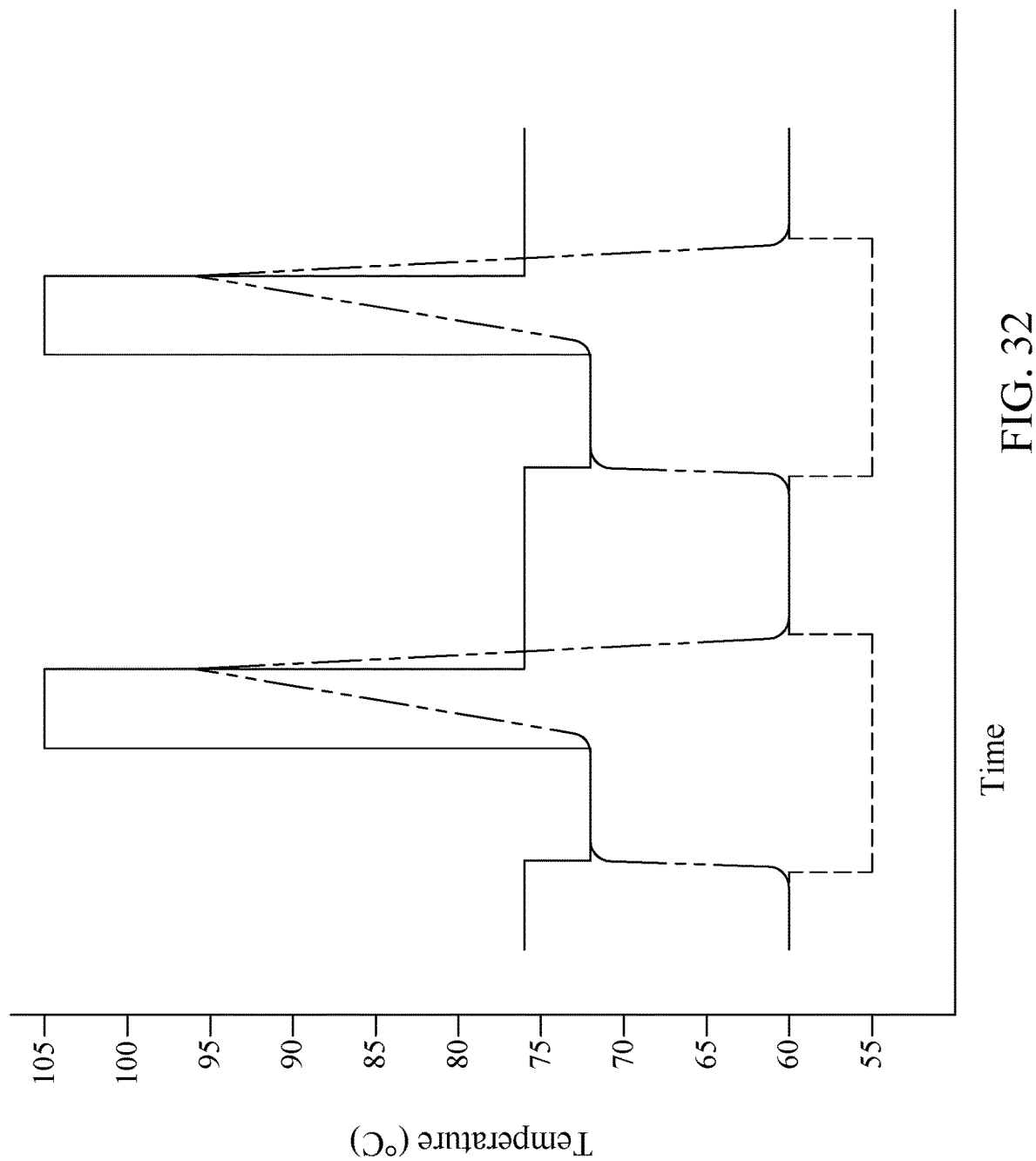
FIG. 32 shows a heating profile for a three-temperature PCR protocol using two heaters. The extension/denaturation heater temperature is shown as a solid line, the annealing heater temperature is shown as a dashed line, and the sample temperature is shown as a dotted line.

One example is illustrated in FIG. 32, wherein the dotted line illustrates the temperature of the sample. In this example, where heater 887 may be used for the annealing temperature, the temperature of heater 887 may be set at the desired annealing temperature, illustratively 60° C., although it is understood that this temperature is illustrative only and that other annealing temperatures may be used, depending on the length and GC content of the primers. When the sample is moved into blister 548, the sample may be held in blister 548 until the entire sample reaches the annealing temperature. In some illustrative protocols, it may be desirable to hold the sample in blister 548 for a period of time after the sample reaches the annealing temperature. In another illustrative embodiment, as illustrated in FIG. 32 by the dashed line, heater 887 may be held at a temperature a few degrees below the annealing temperature, illustratively 2 to 20 degrees below the annealing temperature (the "low annealing temperature"), illustratively 55° C., although other temperatures may be suitable. When the sample is moved from blister 564, which is under control of heater 886 and is substantially hotter than the annealing temperature, the sample may be cooled down to the annealing temperature more quickly because heater 887 is below the annealing temperature. Optionally, movement of bladder 848 may mix the fluid sample in blister 548 to obtain a more uniform temperature within blister 548. Once the sample fluid has been in blister 548 for a length of time that substantially all of the fluid is at or near the annealing temperature, heater 887 may be adjusted to the annealing temperature, as shown by the dashed lines (- - -) in FIG. 32. A hold, illustratively for 2 seconds to 5 seconds may allow for proper annealing, although a hold may be unnecessary, depending on the chemistry used. The sample may then be moved to blister 564. Once the sample has exited blister 548, as shown in FIG. 32, the temperature of heater 887 may then be adjusted back to the low annealing temperature to be ready for the next cycle. It is understood that many heaters take more time to cool than to heat, and it may be faster to cool heater 887 when blister 546 is empty and there is minimal thermal load on heater 887.

In one example, a suitable extension temperature is chosen, illustratively 72° C., although other extension temperatures may be suitable, depending on amplicon length, GC content, and choice of polymerase. As shown by the solid line (-) in FIG. 32, while the sample is still in blister 548, heater 886 may be adjusted to a temperature that is a few degrees above the extension temperature, illustratively 2 to 10 degrees above the extension temperature (the "high extension temperature"). Once the sample fluid has been in blister 564 for a length of time that substantially all of the fluid is at or near the extension temperature, heater 887 may be adjusted from the high extension temperature to the extension temperature, as shown by the solid line in FIG. 32. As discussed above with respect to blister 548, optional movement of bladder 864 may mix the fluid sample in blister 564 to obtain a more uniform temperature within blister 564. A hold, illustratively for 0 second to 5 seconds may allow for proper extension, depending on the protocol. After this hold, heater 886 may then be adjusted to or a few degrees above the denaturation temperature to denature the nucleic acids. It is understood that if heater 886 is adjusted to a temperature above the denaturation temperature, the fluid sample may reach denaturation more quickly. Again, optional movement of bladder 864 may mix the fluid sample in blister 564 to obtain a more uniform temperature within blister 564. Once the sample has been denatured, optionally with or without a hold at the denaturation temperature, the sample may be moved back to blister 548, the temperature of heater 886 may be adjusted to the high extension temperature, which may be more efficient to obtain without the sample in blister 564, and the cycle repeated a sufficient number of times for amplification. If this is first-stage PCR, it is understood that a reduced number of cycles may be desirable, the number of cycles sufficient for enrichment of the targets, whereas if this is second-stage or single-stage, one may desire to thermocycle to or past plateau phase.

Three temperature cycling may be performed using standard PCR chemistry at a standard PCR cycling protocol, illustratively 20 seconds per cycle or longer. If desired, extreme PCR chemistry using enhanced concentrations of polymerase or primer may be added, and faster thermocycling protocols may be used, as disclosed in U.S. Patent Publication No. 2015-0118715, herein incorporated by reference. It is understood that enhanced concentrations of polymerase or primer may result in formation of increased primer-dimer and other non-specific amplification products, unless cycle time is reduced, and that the greater the concentration of polymerase or primer used, the faster the cycle times, where the polymerase and primer may be increased with roughly proportional reductions in cycle time. Cycle times of ten seconds or less should be possible.

Example 4: Fast Multiplex PCR

A prototype instrument using the pouch and heater configuration similar to that of FIGS. 25-27D was used for multiplexed amplification of DNA in a sample. The templates were a mix of natural and synthetic templates—the templates were a synthetic amplicon with a length of 105 bp (referred to as 'mephisto'), a synthetic amplicon with a length of 164 bp (referred to internally as 'Baal3'), a *S. cerevisiae* sequence (natural, amplicon length 364 bp, referred to internally as 'beer'), M13 (natural, amplicon length 264 bp), and MS2 (natural, amplicon length 309 bp).

150 µl and 75 µl samples were prepared comprising 1000 copies of each template, forward and reverse primers unique to each template (5 µM each primer), DNA polymerase (2 U/µL), dNTPs at 0.45 mM, and 5 mM Mg++. 1× LCGreen was used for detection. It is understood that the reaction mixture is illustrative only and that other mixes may be used. These mixtures were sealed into a blister (e.g., blister 549) in 150 µl and 75 µl aliquots. For the 150 µl reactions, the first heater (e.g., heater 986) was set to 103° C. and the second heater (e.g., heater 987) was set to 55° C. For the 75 µl reactions, the first heater (e.g., heater 986) was set to 102° C. and the second heater (e.g., heater 987) was set to 55° C. These reactions were thermocycled according to the procedure described in, for example, FIGS. 25-27D with the wiper blade(s) 949 in contact with the blister and with the wiper head 989 rotating at a speed of one full rotation every 8 seconds (e.g., cycles of rotation of 180°, hold for 4 seconds, rotate 180°, hold for 4 seconds, etc.; or rotate 90°, hold for 2 seconds, rotate 90°, hold for 2 seconds, etc., wherein the rotation time was negligible). It is understood that the rotational speed corresponds to cycle time, with each full revolution representing one cycle. Also, while holds after each quarter turn are used in this example, such is illustrative only and continuous rotation is contemplated. After the first-stage PCR, these reactions were diluted 100-fold into a nested second-stage PCR reaction and amplified in a Roche LC480 real time PCR instrument.

Figure 33:
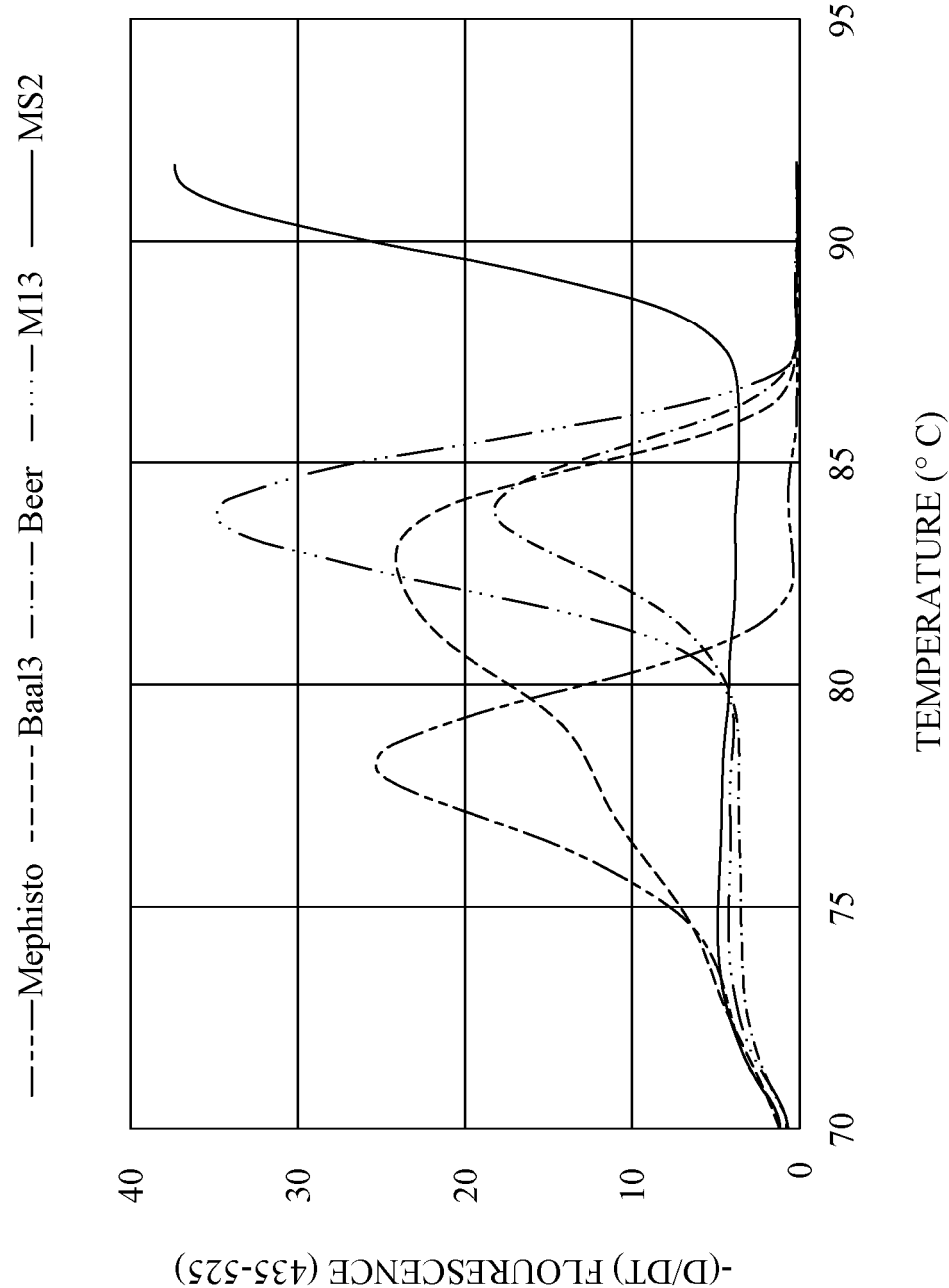
FIG. 33 shows DNA melting curves for multiplexed amplification using a prototype instrument similar to the instrument of FIGS. 28A and 28B for first-stage amplification. Following first-stage amplification, the amplification product was diluted and amplified for second-stage PCR and melting in a Roche LC480 real time PCR instrument.

FIG. 33 shows results of a melting experiment in second-stage PCR showing that all of the first-stage PCR reactions were successful. All of the templates were amplified in first-stage PCR and second-stage PCR and all of the products melted at their expected temperature. This demonstrates that the prototype system can be used for multiplex first-stage PCR.

Example 5: Fast PCR

In this Example, a synthetic DNA template (mephisto) was amplified for first-stage PCR in an LC480 instrument according to standard PCR protocols. The amplification product from the first-stage reaction was diluted 1:100 with a second-stage amplification mixture (e.g., unique forward and reverse primers (5 µM each primer), DNA polymerase (2 U/µL), dNTPs at 0.45 mM, 5 mM Mg++, and 1× LCGreen dye for detection) and injected into a 5-well array similar to array 5081 of FIG. 5A or array 6000 of FIG. 6A. The volume of each well of the array is approximately 0.5 µL. The samples were thermocycled for second-stage PCR in a prototype instrument similar to the instruments shown in FIGS. 28A-28B. The array was thermocycled with a two element heater similar to heater assembly 1270 with a first heater set at 96° C. and a second heater set at 60° C. Second-stage PCR was carried out on the array by translating the heaters so that the array was under control of the first heater, the second heater, the first heater again, and so on. The array with the second-stage PCR sample was thermocycled for 40 cycles at 8 sec/cycle (4 sec. at 96° C., 4 sec. at 60° C., etc.).

Figure 34:
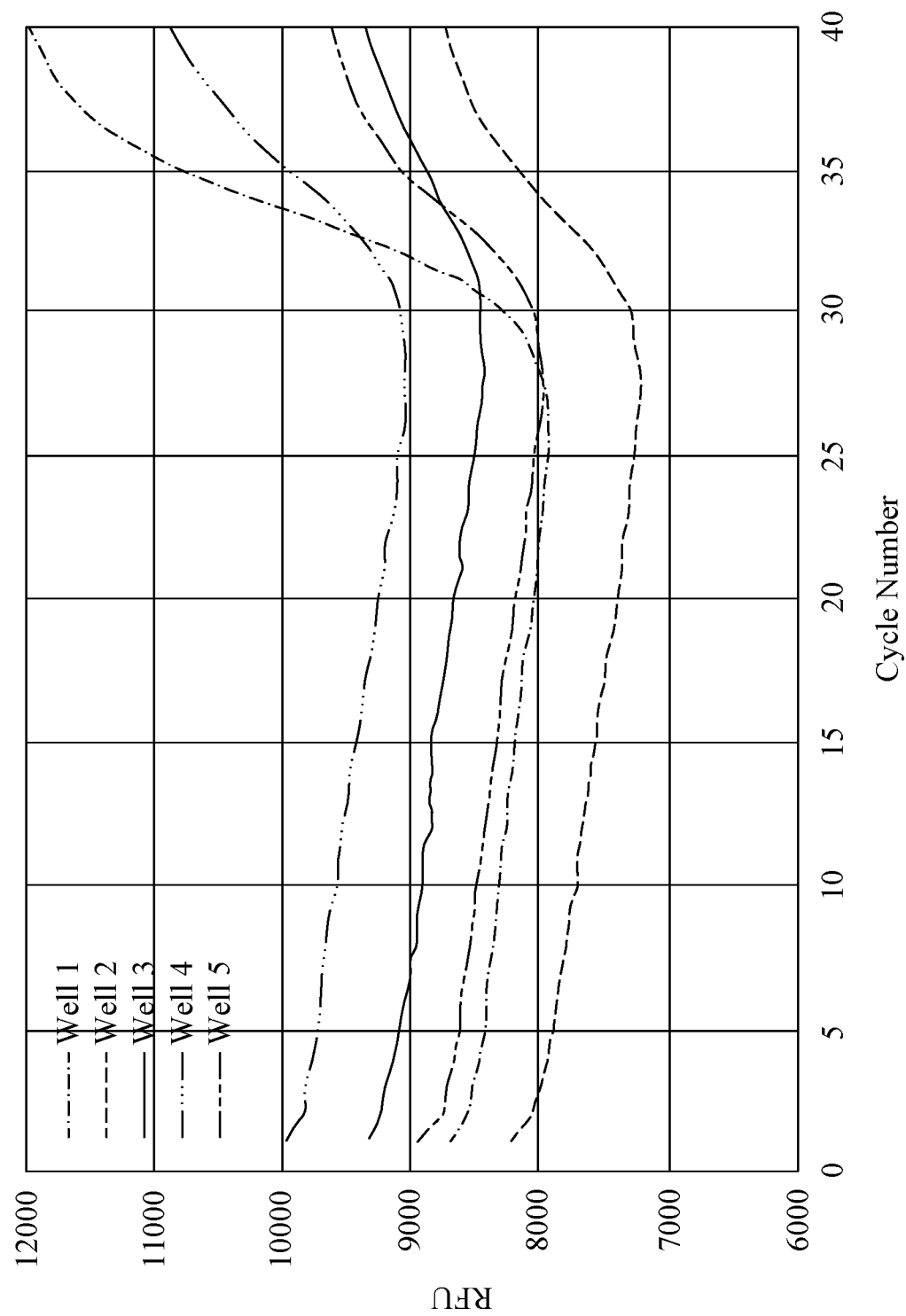
FIG. 34 shows real-time DNA amplification data for a second-stage single-plex DNA amplification reaction. A Roche LC480 real time PCR instrument was used for first-stage PCR; the amplification product from first-stage PCR was diluted, mixed with a second-stage PCR master mix, and injected into an array similar to array 5081 of FIG. 5A for second-stage amplification. Thermocycling for amplification was performed using a procedure similar to the second-stage PCR procedure described in reference to FIGS. 28A and 28B.
Figure 35:
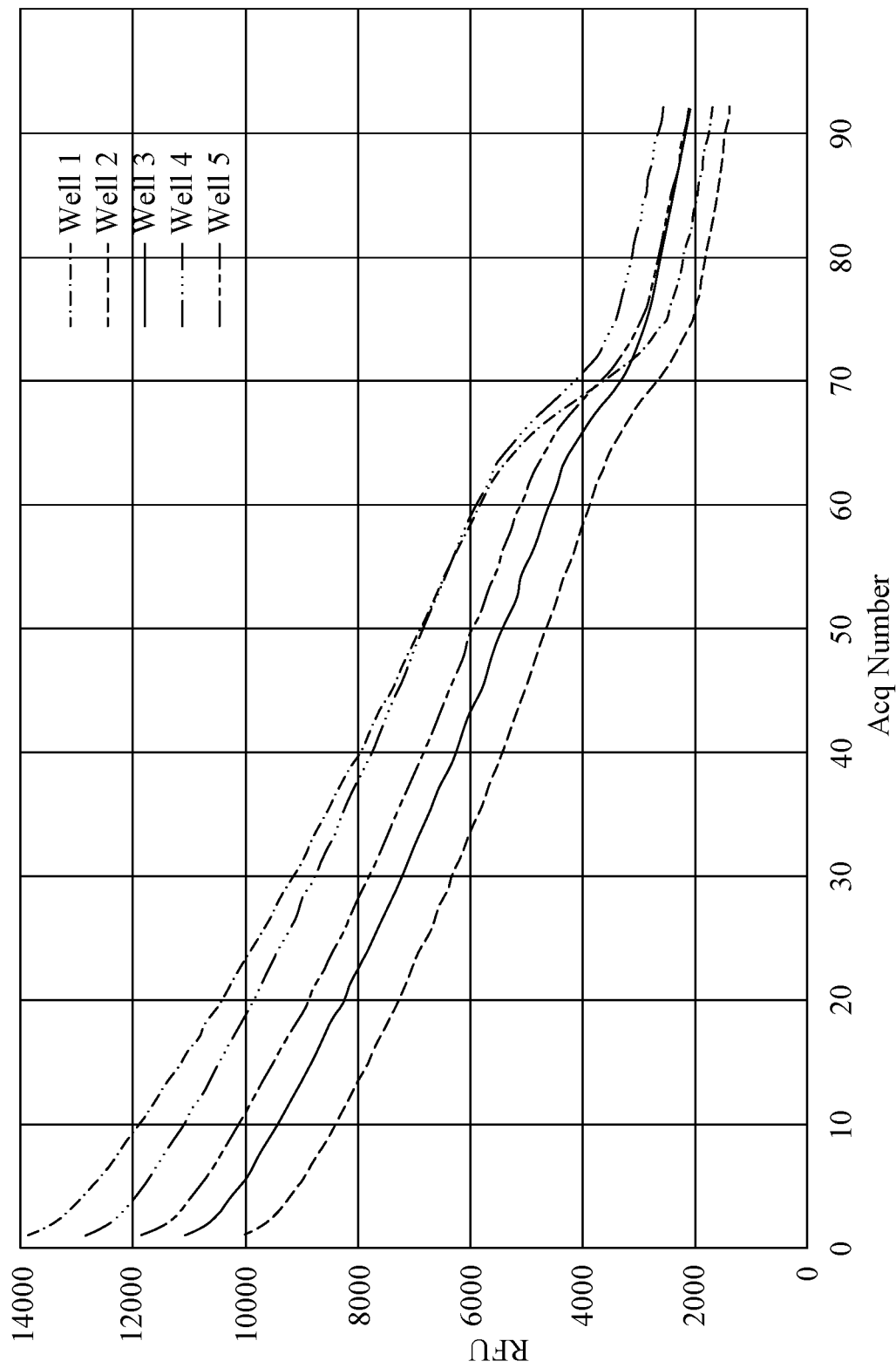
FIG. 35 shows DNA melting curves for second-stage amplification of FIG. 34.

FIGS. 34 and 35 illustrate the results of the second-stage PCR reaction. FIG. 34 shows the change in fluorescence in each of the wells of the array as a function of cycle number and FIG. 35 shows a melting curve for DNA product (if present) in each of the wells of the array. FIGS. 34 and 35 show that the reaction was most successful for well 1 of the array (FIG. 34) and that the product had a melting transition at the expected temperature for the mephisto product (FIG. 35). This Example illustrates that second-stage PCR can be successfully carried out by a two temperature heater unit with the heater transitioning the array from temperature to temperature by moving the heater assembly relative to the array. One will appreciate that thermocycling may also be accomplished by moving the array relative to the heater elements by, for example, laterally translating the sample container or the receptacle that positions the sample container in the instrument.

Example 6: Fast First-Stage and Second-Stage PCR

In this Example, a synthetic DNA template (mephisto) was amplified for first-stage PCR and second-stage PCR in a reaction container similar to pouch 5000 illustrated in FIG. 5A. For first-stage PCR, ~75,000 copies of the template DNA, forward and reverse primers unique to the template (5 µM each primer), DNA polymerase (2 U/µL), and dNTPs at 0.45 mM, and 5 mM Mg++ were combined and 75 µL were injected into and sealed in a blister (e.g., blister 5010) for the first stage PCR reaction. The reaction container was placed in an instrument similar to instrument 1200 for PCR amplification.

For first-stage PCR, the first heater (e.g., heater 1287) was set to 58° C. and the second heater (e.g., heater 1286) was set to 106° C. The heater assembly (e.g., heater assembly 1270) was positioned so that the temperature of approximately one half the reaction blister could be controlled by the first heater and the temperature of the remainder could be controlled by the second heater. The contents of the reaction blister were thermocycled in the instrument according to the procedure described in, for example, FIGS. 25-27D with the wiper blade(s) (e.g., like wiper blades 949) in contact with the blister and with the wiper head (e.g., wiper head 1100) rotating with a cycle time of 8 seconds (e.g., cycles of rotation of 90°, hold for 2 seconds, rotate 90°, hold for 2 seconds, etc.). It is understood that the rotational speed corresponds to cycle time, with one full rotation being equivalent to one cycle.

Following 20 cycles of first-stage PCR in the first-stage PCR reaction blister (e.g., blister 5010), a portion of the first-stage PCR reaction (e.g., ~1 µL) was moved to a volume measuring well (e.g., volumetric well 5015) and mixed with second-stage PCR reagents (DNA polymerase (2 U/µL), dNTPs at 0.45 mM, 2 mM Mg++, and 1× LC Green for detection) by mixing between two larger volume blisters of the pouch (e.g., blisters 5020 and 5025). It is understood that the level of dilution may be adjusted by altering the volume of the volume measuring well or by altering the volume of the diluting reagents (illustratively a polymerase, dNTPs, and a suitable buffer; although other components may be suitable, particularly for non-PCR amplification methods) added to the sample from first-stage PCR. If desired, this mixture of the sample and second-stage PCR master mix may be pre-heated in the volumetric well 5015 and blisters 5020 and 5025 prior to movement to second-stage array for second-stage amplification. Such preheating and separation of the primers from the master mix may obviate the need for a hot-start component (antibody, chemical, or otherwise) in the second-stage PCR mixture.

Following preparation of the sample for second-stage PCR in, for example, volumetric well 5015 and blisters 5020 and 5025, the sample may be moved to an array similar to array 5081 for second stage PCR. Each of the wells of the array is pre-loaded with specific forward and reverse PCR primers. Primers were spotted in the wells of the array at either 2.5 µM or 5 µM. The wells of the array are filled by flooding the array with the second-stage PCR master mix.

The wells of the array may be heat sealed and/or sealed by inflating a clear, flexible bladder over the array to seal off access to the fill channels. Excess second-stage PCR master mix may also be purged from the array by inflating the clear, flexible bladder over the array. In this case, the clear, flexible bladder was inflated to a pressure of approximately 20 psi. Thermocycling for second-stage PCR may be accomplished by translating heater assembly 1270 back and forth under the array so that the array and the contents of the individual wells are under temperature control of the second heater (e.g., heater 1286 for denaturation), then the first heater (e.g., heater 1287 for annealing and elongation), then the second heater (for denaturation again), etc. In this Example, the second heater was set to 102° C. with a hold at the second heater of 2 seconds and the first heater was set at 65° C. with a hold of 6 seconds. The second-stage reaction was thermocycled for a total of 30 cycles. Nucleic acid amplification and DNA melting in the array were monitored with a camera similar to camera 1250 depicted in FIGS. 28A and 28B.

Figure 36:
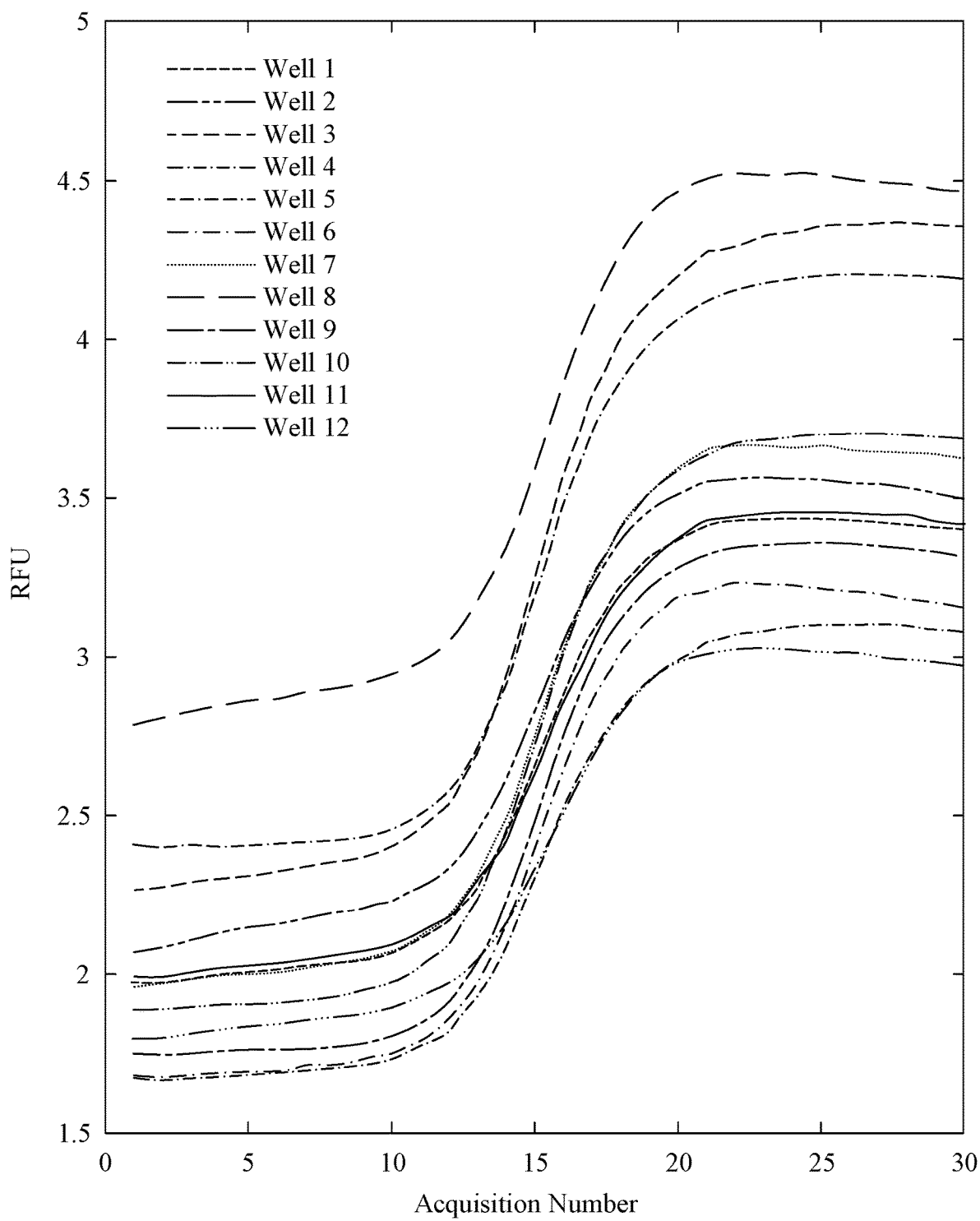
FIGS. 36-38 depict the results of first-stage and second-stage amplification using an instrument similar to the instrument depicted in FIGS. 28A and 28B.
Figure 37:
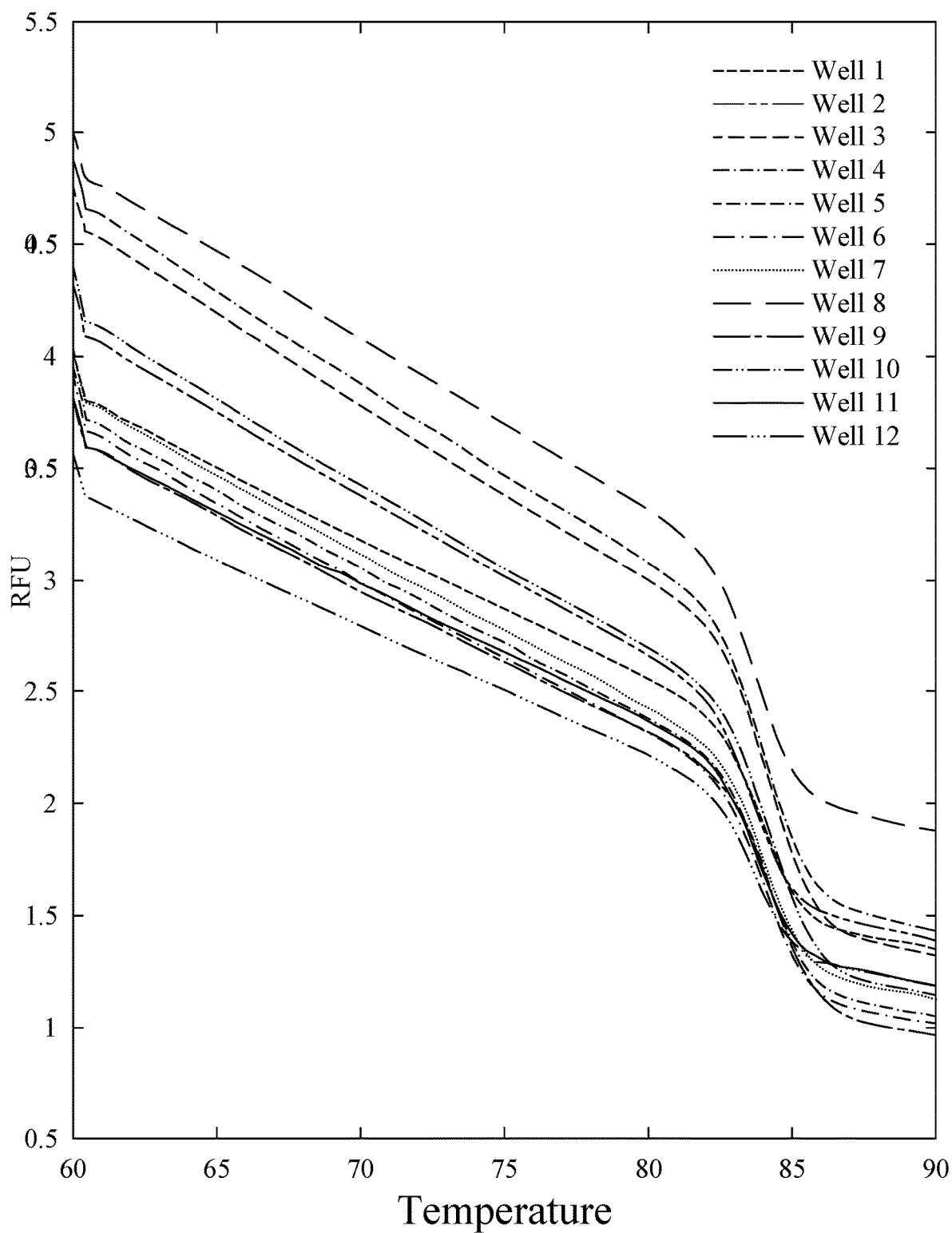
Figure 38:
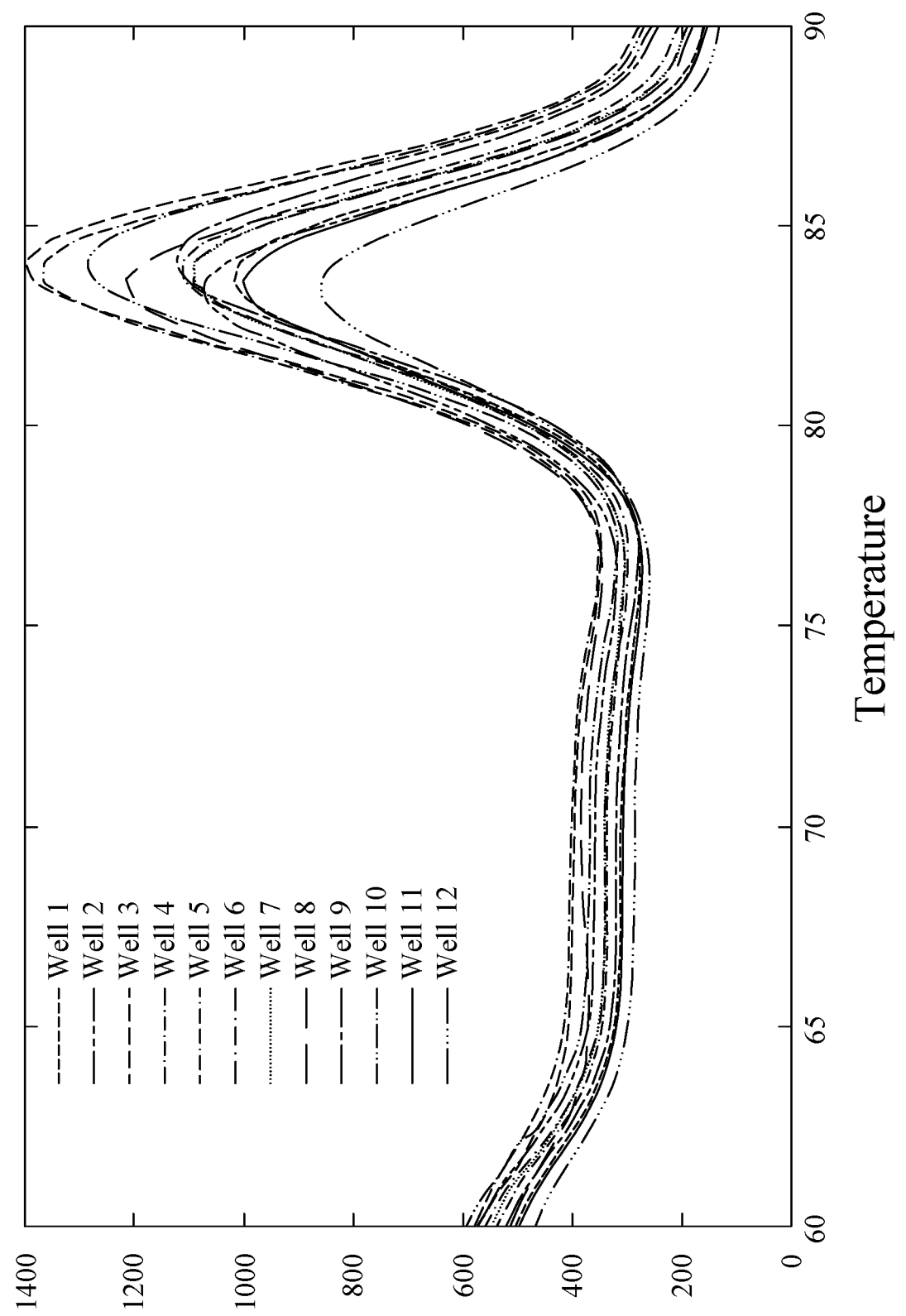

FIGS. 36-38 depict the results of the second-stage PCR reaction. FIG. 36 depicts the increase in fluorescence in the wells of the array as a function of cycle number. As can be seen, DNA amplification occurred in all wells of the array. Likewise, a similar time course (e.g., crossing point) for amplification was observed in each of the wells. FIGS. 37 and 38 depict the results of a melting experiment to ensure that the product being amplified is the correct product. FIG. 37 is a raw melting curve and FIG. 38 depicts a negative first derivative (dF/dt) of the melting curve. As can be seen in FIGS. 37 and 38, the product in all of the wells has a melting transition at essentially the same temperature. The melting transition for all of the wells occurs at approximately 84° C., which is the anticipated melting temperature for this particular synthetic amplicon.

Example 7: Temperature Calibration and Thermocycling Speed in the Second-Stage PCR Array Referring now to FIGS. 39-42, results are illustrated of a series of experiments designed to test the temperature response of the fluid in the well(s) of an array similar to array 5081 or array 6000. In the experiments, a small thermocouple was inserted into one or more wells of the array and sealed between the film layers. For thermocycling, the array was filled with aqueous PCR buffer, inserted into an instrument similar to instrument 1200, and subjected to thermocycling by translating the heater assembly back and forth so that the array was under temperature control of a first heater, a second heater, the first heater again, and so on. For these experiments, a clear, flexible bladder in the instrument was inflated over the array to approximately 20 PSI. These experiments show the temperature response of the fluid in the array with different dwell times at the high and low temperature heaters; regardless of the dwell time in the illustrated examples, the transition time of the heaters (e.g., high temperature to low temperature or low temperature to high temperature) is rapid relative to the dwell time. These data and other data not shown are being used to develop a temperature model that includes the set points of the heaters, the dwell time at each temperature, and the thermal response of the array and the fluid therein so that users can reliably set high and low target temperatures for the fluid in the array for thermal cycling and amplification of various templates with various primer sets.

Figure 39:
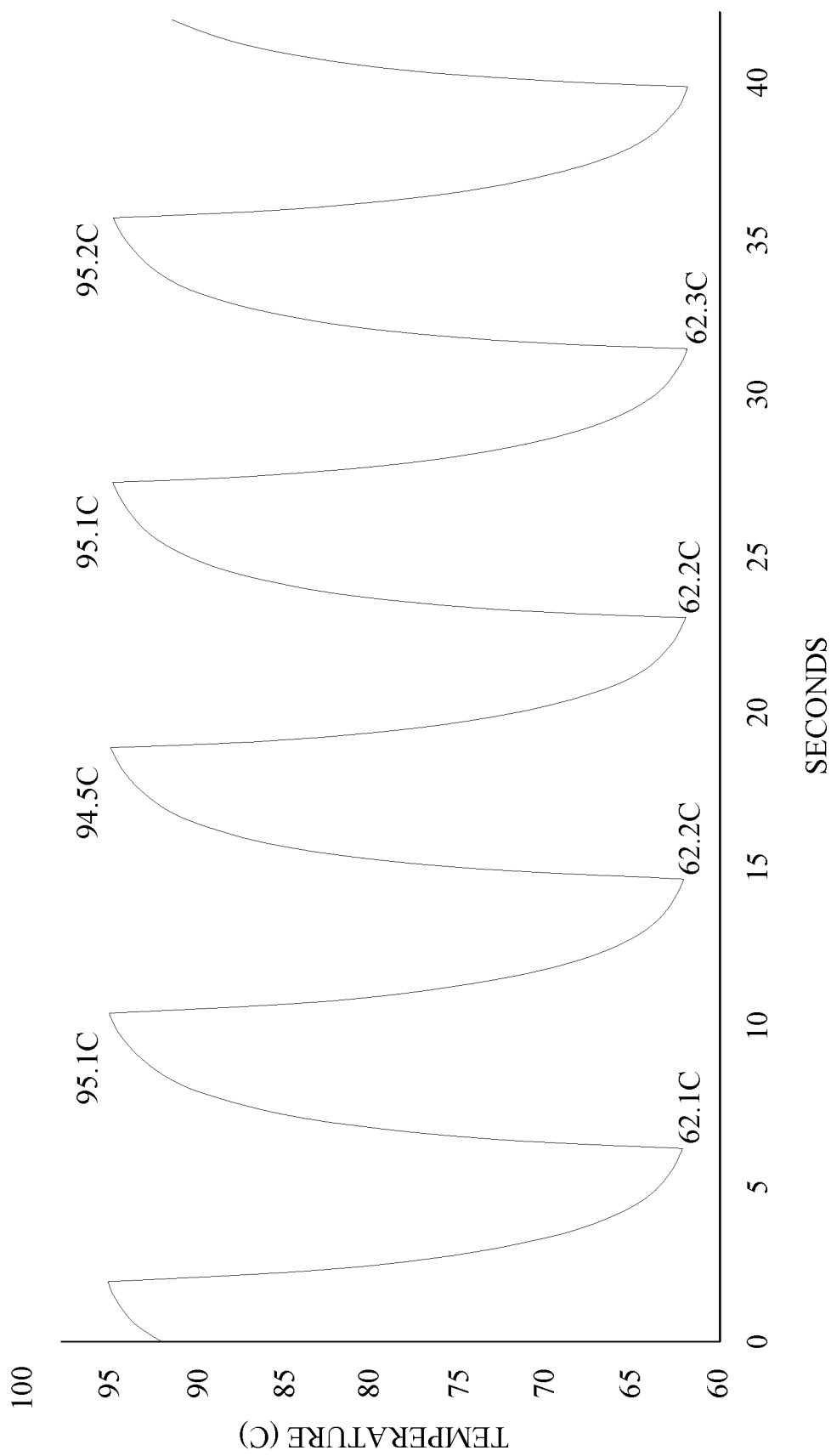
FIGS. 39-42 illustrate the results of a series of experiments designed to test the temperature response of fluid in the well(s) of an array similar to array 5081 or array 6000 with a thermocycling procedure similar to the procedure illustrated in reference to FIGS. 28A and 28B.

In the experiment illustrated in FIG. 39, the target end point temperatures were 95° C. and 62° C. The heaters were set at 98° C. and 62° C. with 4 second hold times (i.e., dwell times) at each temperature zone. The target end point temperatures were 95° C. and 62° C. Because this experiment includes a relatively long hold time, the set points for the heaters and the target temperatures are relatively close together. As can be seen in FIG. 39, the fluid in the well(s) (~0.5 µL) could be thermocycled between ~95° C. and ~62° C. with these heater set points, hold times, and the translating heater protocol described elsewhere herein.

Figure 40:
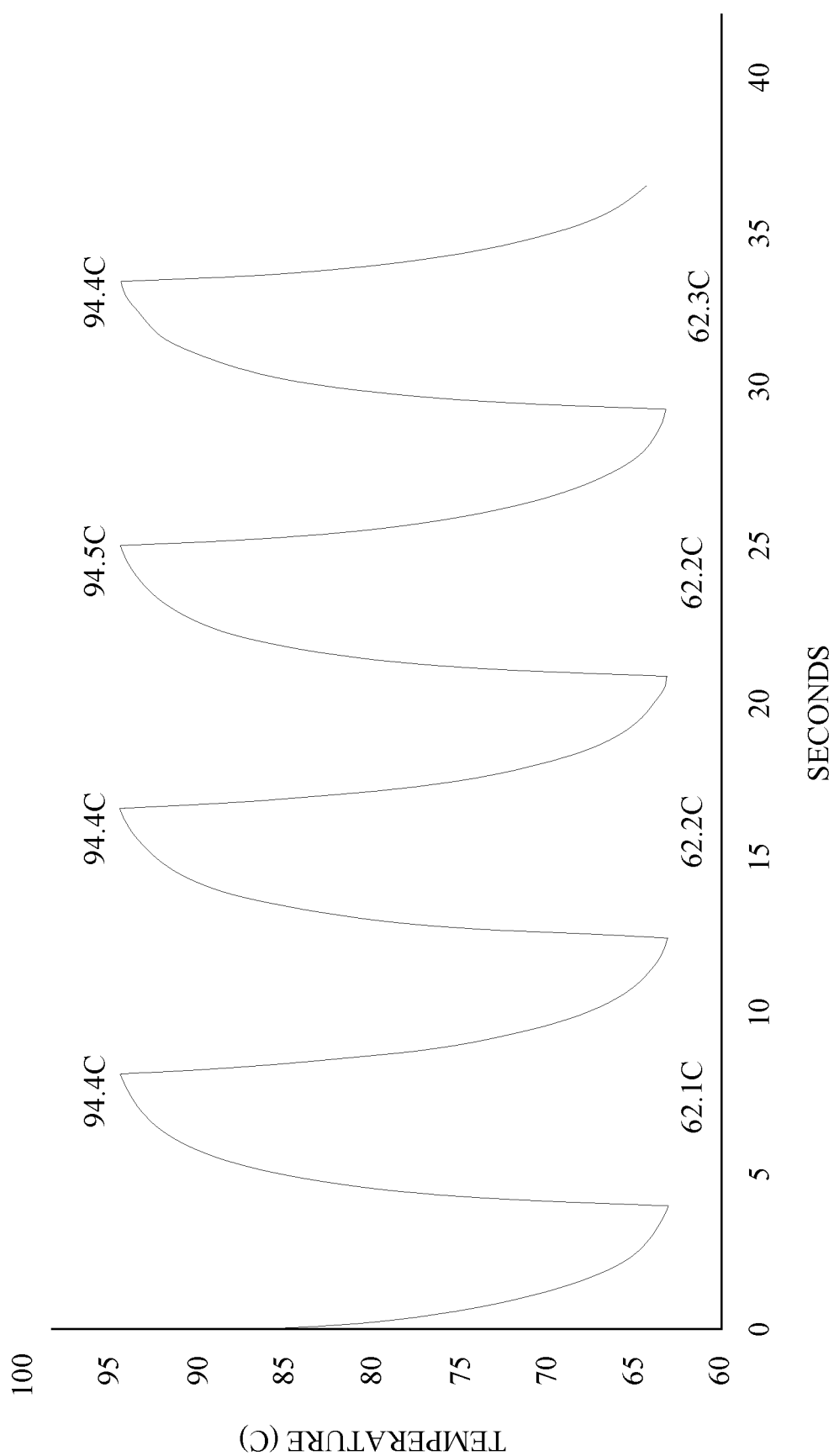

In the experiment illustrated in FIG. 40, the heaters were set at 97° C. and 62° C. with 4 second hold times at each temperature zone. The target end point temperatures being aimed for in this experiment were 94° C. and 62° C. As can be seen in FIG. 40, the fluid in the well(s) (~0.5 µL) could be thermocycled between ~94° C. and ~63° C. with these heater set points, hold times, and the translating heater protocol.

Figure 41:
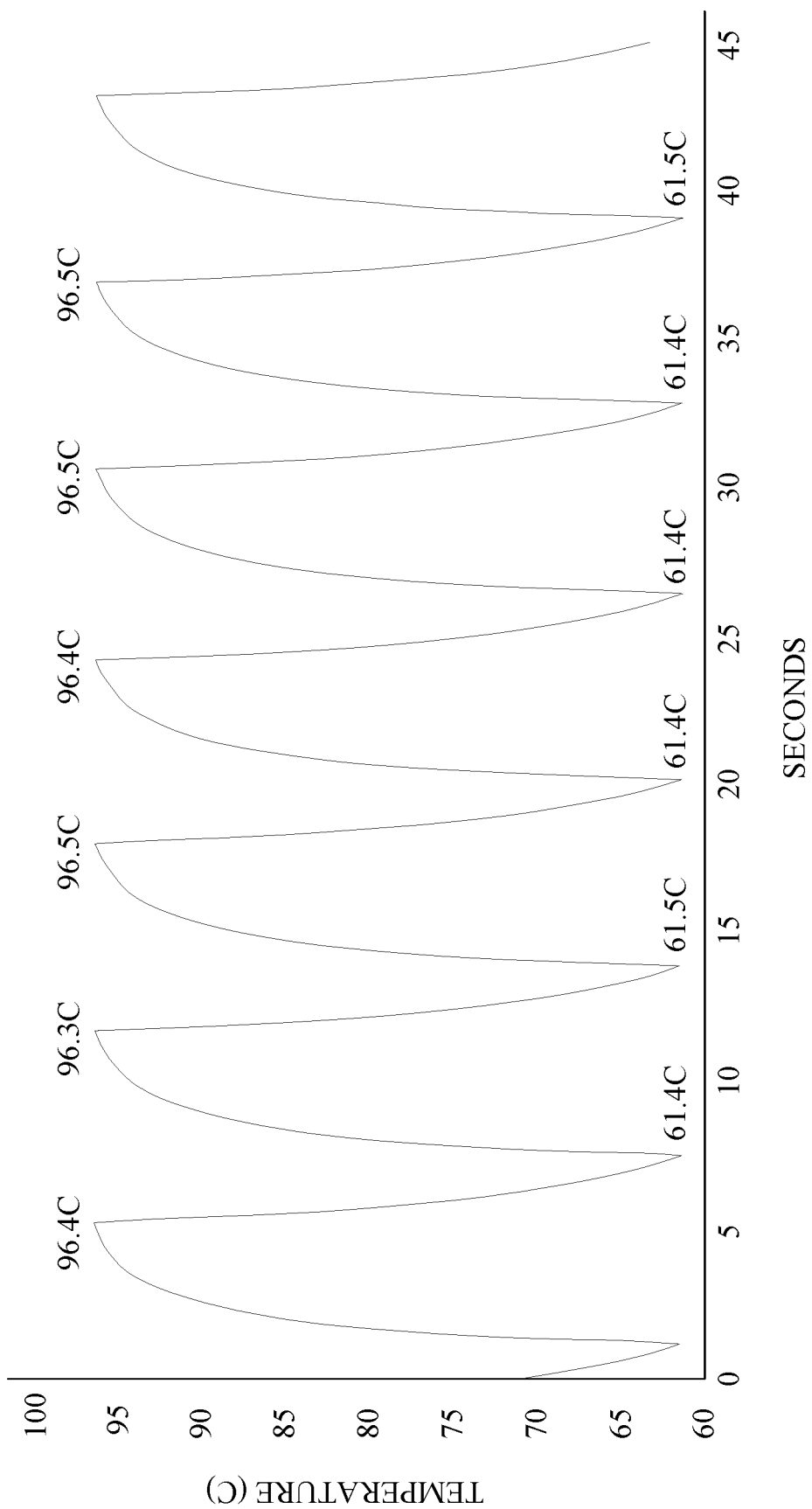

In the experiment illustrated in FIG. 41, the heaters were set at 99° C. and 56° C. with 2 second hold times at each temperature zone. The target end point temperatures were 96° C. and 61° C. As can be seen in FIG. 41, the fluid in the well(s) (~0.5 µL) could be thermocycled ~96° C. and ~61° C. with these heater set points, hold times, and the translating heater protocol.

Figure 42:
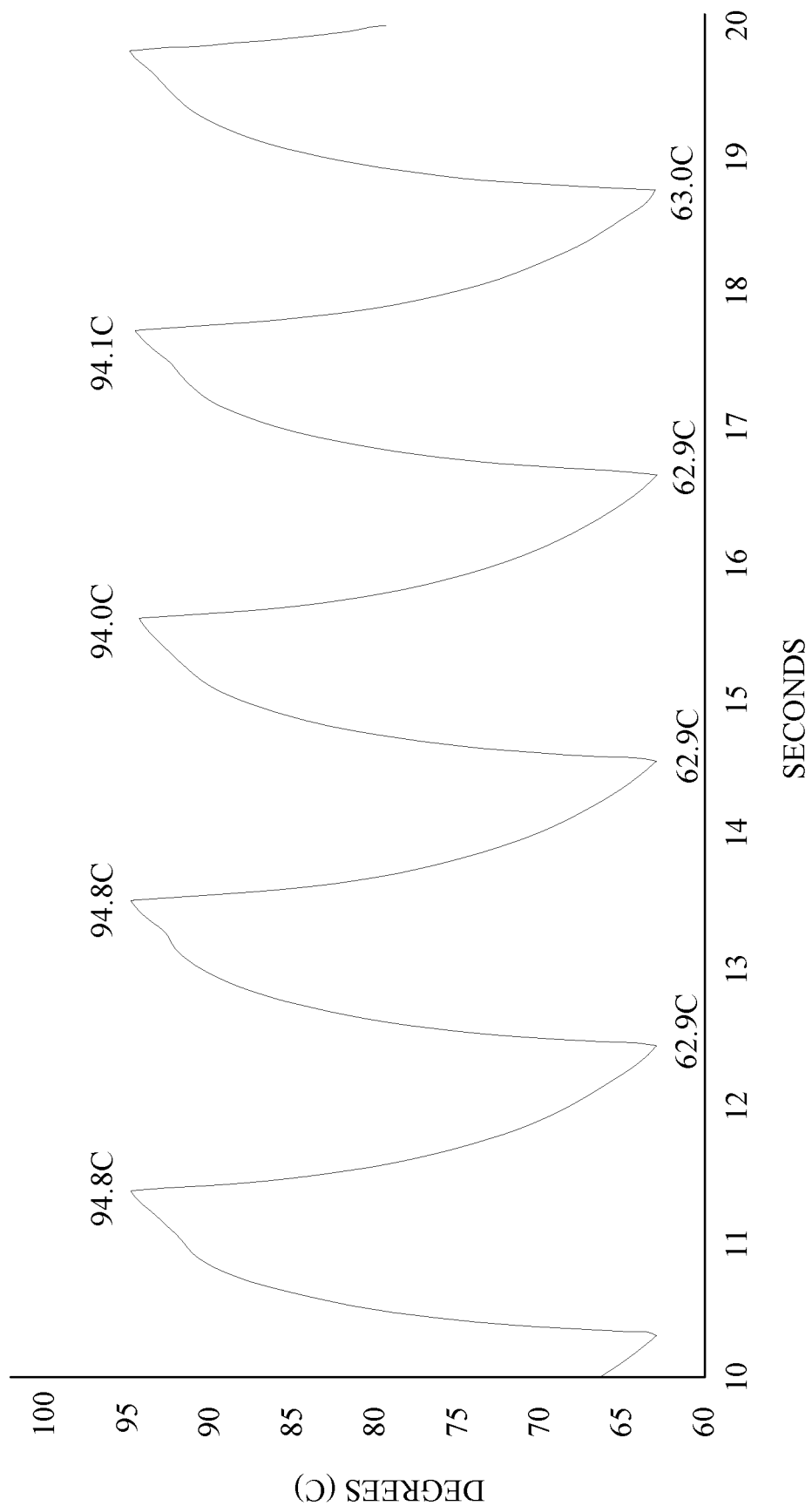

In the experiment illustrated in FIG. 42, the heaters were set at 108° C. and 52° C. with 1 second hold times at each temperature zone. The target end point temperatures were 95° C. and 63° C. As can be seen in FIG. 42, the fluid in the well(s) (~0.5 µL) could be thermocycled between ~95° C. and ~63° C. with these heater set points and the translating heater protocol even with hold times as low as 1 second. As described in, for example U.S. Pat. Pub. No. 2015/0118715 and U.S. Pat. Pub. No. 2016/0289736, which were incorporated herein above in their entireties, adjustments in chemistry, wherein polymerase and primer concentration are increased, can permit the polymerase chain reaction to proceed at rates compatible with 8 second, 4 second, 2 second, or shorter cycle times.

Example 8: Lysis Particles and Nucleic Acid Capture Beads in A Single Container Referring now to FIGS. 45A-47B, results are illustrated of a series of experiments designed to show that PCR amplification is compatible with the presence of silica-coated magnetic beads (i.e., nucleic acid capture beads) in the PCR reaction, that negatively-charged Zr silicate beads apparently bind nucleic acid, which was unexpected, and that nucleic acid capture efficiency can be greatly enhanced by performing lysis in the presence of silica-coated magnetic beads.

In the first experiment, *Staphylococcus aureus* cells were grown overnight on a TSA plate (bioMerieux, France). Then a calibrated bacterial suspension (MF 0.5) was obtained by adding colonies in a suspension medium, using a Densitometer (bioMerieux, France). Coronavirus strain 229E viral suspension was obtained from internal biobank (Verniolles, France). *S. aureus* and Coronavirus were co-spiked in 800 µl of Sample Buffer (see U.S. Pat. No. 9,758,820, herein incorporated by reference) by adding 100p of each pathogen suspension. The concentrations used were $10^5$ CFU/ml for *S. aureus* and 5 TCID50/ml for Coronavirus. Each suspension was transferred to a lysis blister containing 600 mg of Zirconium beads (Biospec Products, USA) and 1.5 mg of magnetic silica (bioMerieux, France). Mechanical lysis was achieved using paddle lysis described in U.S. patent application Ser. No. 15/769,044, herein incorporated by reference. After lysis, the magnetic silica pellet was captured with a magnet (QuickPick (Proteigene, France)) and transferred to a tube containing 140 µl of wash buffer (described in U.S. Pat. No. 9,758,820). The wash buffer was removed, and 100 µl of a first-stage PCR mastermix was added on the silica pellet and a first-stage PCR reaction was performed. After completion of first-stage PCR, a second-stage PCR reaction was set-up. In order to evaluate the effect of the PCR on the presence of magnetic silica, controls were done by eluting from the magnetic silica in and elution buffer and then adding the first-stage PCR mastermix to the eluate.

Figure 45A:
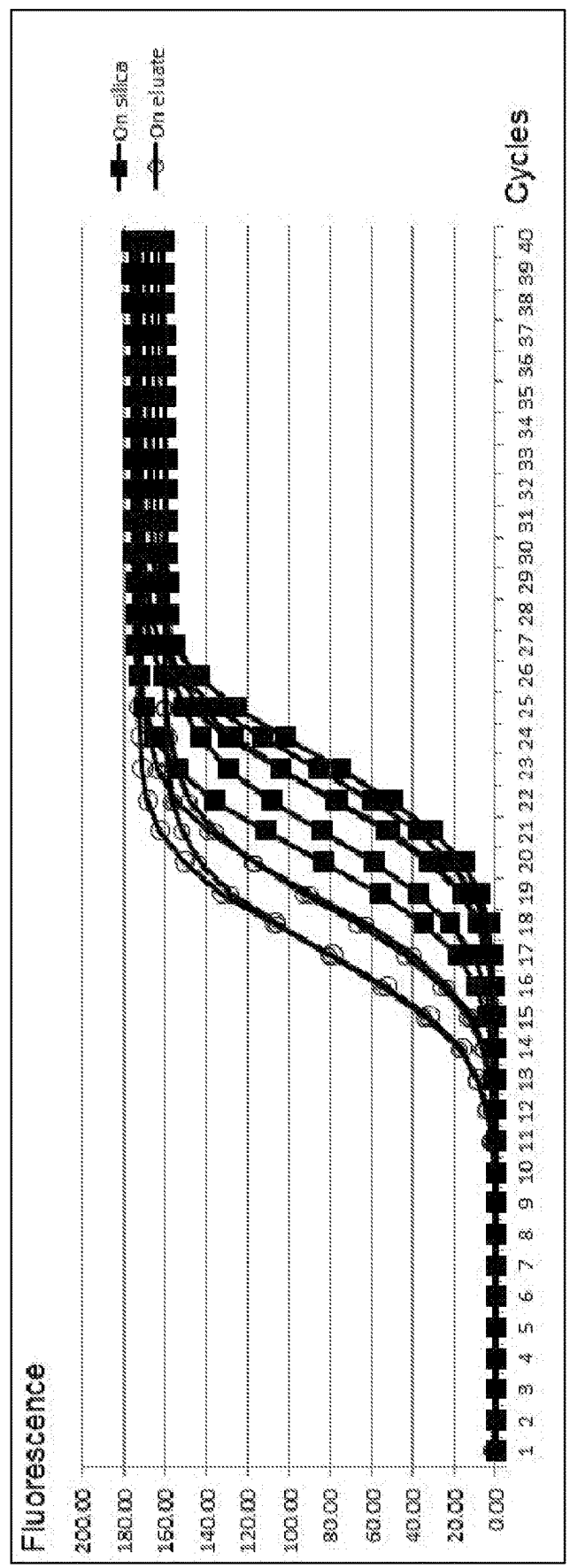
FIGS. 45A and 45B show fluorescence traces for amplification experiments in the presence of (-■-) and absence of (-○-) magnetic silica.
Figure 45B:
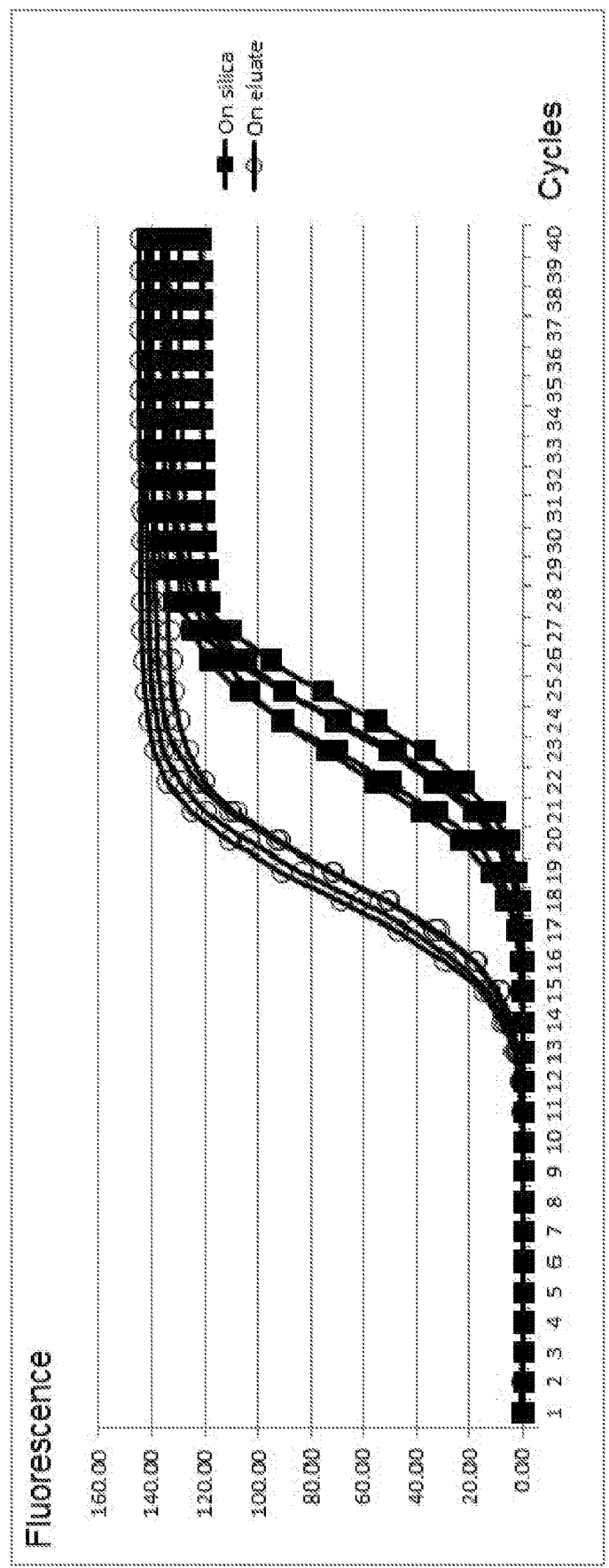

FIGS. 45A-45B show that amplification was successful in the presence of magnetic silica and in the eluted controls. As shown in Table 1, for *S. aureus* performing PCR in the presence of magnetic silica caused approximately a 4-cycle delay, and for coronavirus performing PCR in the presence of magnetic silica caused approximately a 5-cycle delay.

TABLE 1

|  | Eluted | On Magnetic silica |
| --- | --- | --- |
| *S. aureus* | 12.9 +/− 0.9 | 16.9 +/− 1.2 |
| Coronavirus | 13.8 +/− 0.4 | 18.8 +/− 0.8 |

These experiments show that it is possible to perform a molecular diagnostic process in just two containers, with one container for lysis and binding of targets to magnetic silica, and with a second container for washing steps and amplification directly on magnetic silica, without the need for a separate elution step and without the need for sequestering and separating the magnetic silica from the amplification reaction.

In a second experiment, lysis with Zr silicate beads and binding with magnetic silica in one container was compared to lysis and binding in separate containers. The aim of this experiment is to show the compatibility of performing the lysis and the binding in a same mixture.

*S. aureus* cells were grown overnight on a TSA plate to form colonies. A calibrated bacterial suspension (MF 0.5) was obtained by adding the colonies in a suspension medium, using a Densitometer (bioMerieux). Six lysing tubes were prepared by adding 600 mg of Zr silicate beads and 600 µl of Sample Buffer (SB1A). 100 µl of bacterial suspension was added to the tubes. Three of the six lysing tubes were supplemented with 1.5 mg of magnetic silica, while the remaining three tubes were not provided with any magnetic silica. Lysis was performed using a vortex at 3000 rpm for a duration of 5 minutes. For the lysing tubes containing zirconium and magnetic silica, after lysis the silica was transferred in wash buffer using a magnet. For the lysing tubes containing only zirconium beads, after lysis magnetic silica was added for the binding process. The magnetic silica was then transferred in wash buffer. After washing steps, the nucleic acids were eluted off of the beads and the eluates were separately subjected to PCR amplification.

Figure 46:
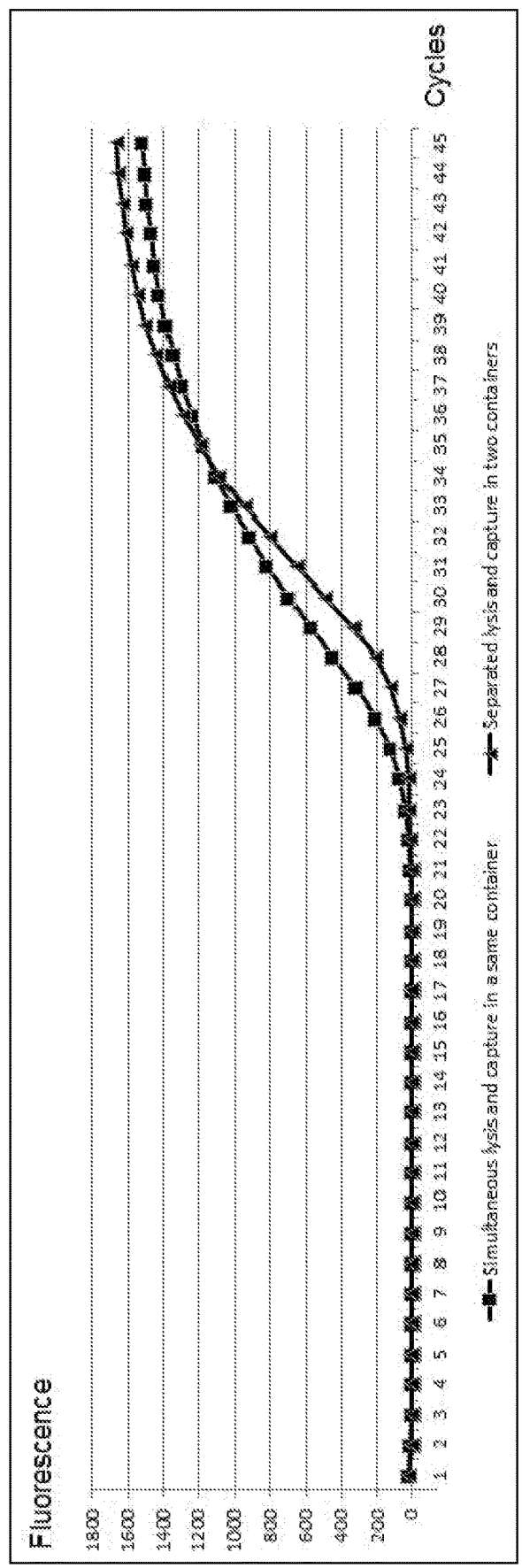
FIG. 46 shows fluorescence traces for amplification experiments with lysis and magnetic capture in the same container (-■-) and separated lysis and capture (-▲-).

FIG. 46 shows the average results for the PCR for lysis and binding in one container (-■-) and lysis and binding in separate containers (-▲-). These experiments show that it is possible to perform lysis in a container that contains zirconium beads for the lysis and magnetic silica for binding and capturing nucleic acids. Surprisingly and unexpectedly, a gain of 2 PCR cycles is observed when the lysis and the binding are performed in the same container.

In a third experiment, lysis in a FilmArray pouch in the presence of both Zr silicate beads and magnetic silica beads in one reaction blister was compared to a condition with no lysis particles and to a FilmArray control. In the control, lysis is performed in one FilmArray blister in the presence Zr silicate and the magnetic beads are added to the lysis blister after lysis. In the no lysis particles pouch, magnetic beads are added to the lysis blister after beating the lysis blister with a bead beater bar, but pouches were manufactured without lysis particles. In the experimental condition, pouches were manufactured with magnetic beads positioned in the lysis blister along with the lysis particles, rather than adding the magnetic beads to the lysis blister subsequent to lysis.

The sample included a mixture of genomic salmon sperm DNA along with *E. coli* bacteria. The salmon sperm DNA was analyzed on a fragment analyzer—in order to be seen on a fragment analyzer, the DNA needs to be present in a high quantity. *E. coli* DNA was analyzed using a benchtop PCR assay, neuC. In each case, the FilmArray protocol was allowed to run normally through lysis, capture, wash, and then stopped after elution. In each case, the eluate was removed from the pouch and divided into two downstream analyzers. One volume fraction was processed in the fragment analyzer (FIG. 47A) and another volume fraction was processed using benchtop PCR (FIG. 47B).

Figure 47B:
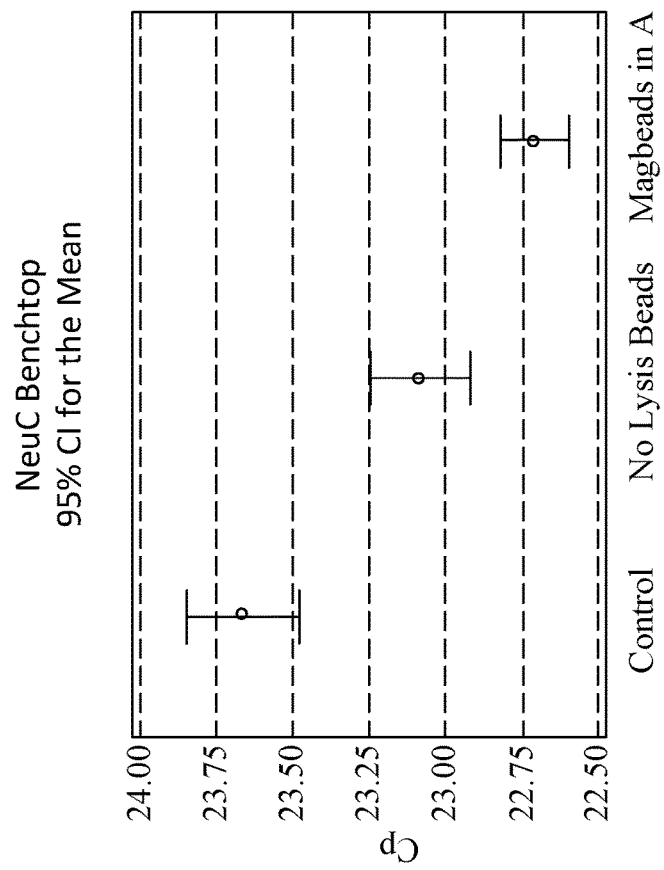
FIG. 47B amplification of DNA from an *E. coli* lysate with lysis particles and magnetic silica beads in separate containers, with magnetic silica beads and no lysis particles, and with lysis particles and magnetic silica beads in the same container.
Figure 47A:
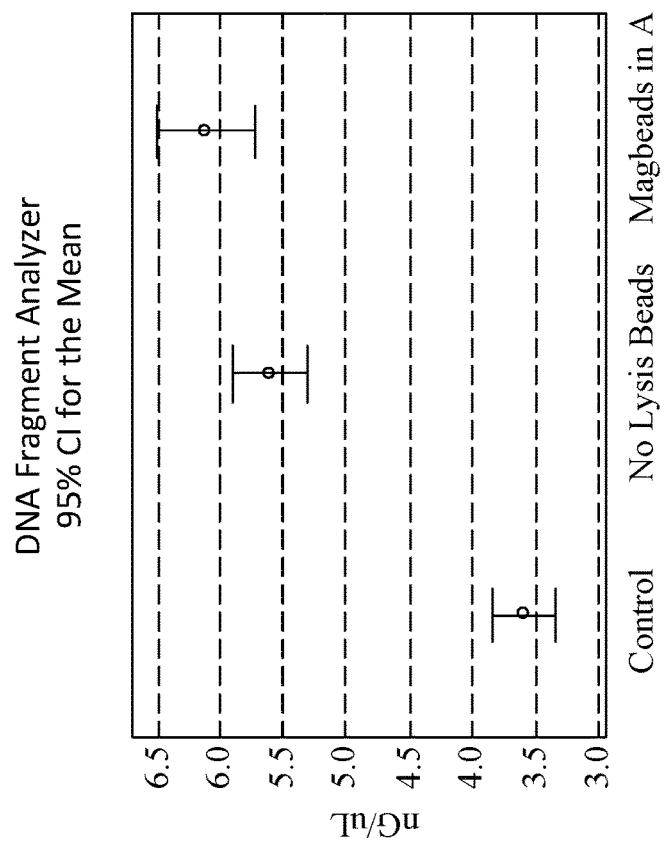
FIG. 47A shows the recovery of salmon sperm DNA with lysis particles and magnetic silica beads in separate containers, with magnetic silica beads and no lysis particles, and with lysis particles and magnetic silica beads in the same container.

In FIG. 47A the salmon sperm DNA captured in each case is reported as an effective concentration of nucleic acids in the solution in ng/µl. Higher values equal a higher amount of DNA in the solution. In the FilmArray control, an effective concentration of salmon sperm DNA of 3.6 ng/µl was observed. In the experimental condition with lysis and magnetic beads in the same container, an effective concentration of 6.2 ng/µl was observed. This represents a roughly 1.7 fold increase in efficiency for sample preparation and nucleic acid extraction. FIG. 47A shows that the experimental condition may even be better than the no lysis particles control. This is surprising given that the salmon sperm DNA does not need to be lysed in order to be captured by the magnetic silica beads.

FIG. 47B illustrates the Cp (i.e., the cycle where the assay was detected) for the three conditions. Ass illustrated in FIG. 46B, the control was the worst performer with a Cp of ~23.75, the experimental condition was the best performer with a Cp of ~22.75, and the no lysis particles condition was intermediate. A shift of 1 Cp usually indicates a doubling of DNA, so going from a control condition of 23.75 to a test condition of 22.75 indicates a 2-fold increase in sample preparation extraction. This indicates that it is be possible to have magnetic beads present in the lysis and still obtain good lysis and nucleic acid recovery. Surprisingly, these data also appear to show that Zr silicate beads bind nucleic acid, that having magnetic beads present in the lysis out competes Zr silicate for capture, and that, as a result, having magnetic beads present in the lysis is more efficient for nucleic acid capture, which may increase assay sensitivity and same PCR cycling time.

Example 9: Nucleic Acid Capture Beads in an Alternative Amplification Method

Figure 48:
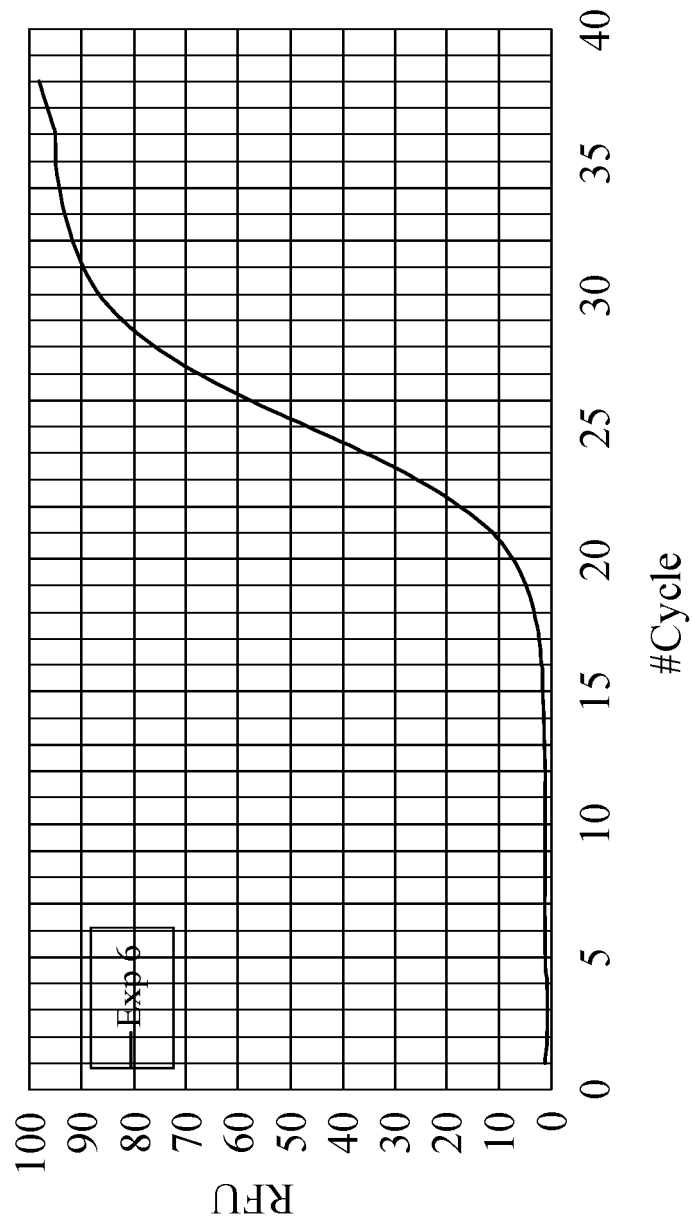
FIG. 48 shows a fluorescence trace for a PCR experiment in the presence of magnetic silica beads where the beads are not sequestered in the reaction chamber during amplification.
Figure 49:
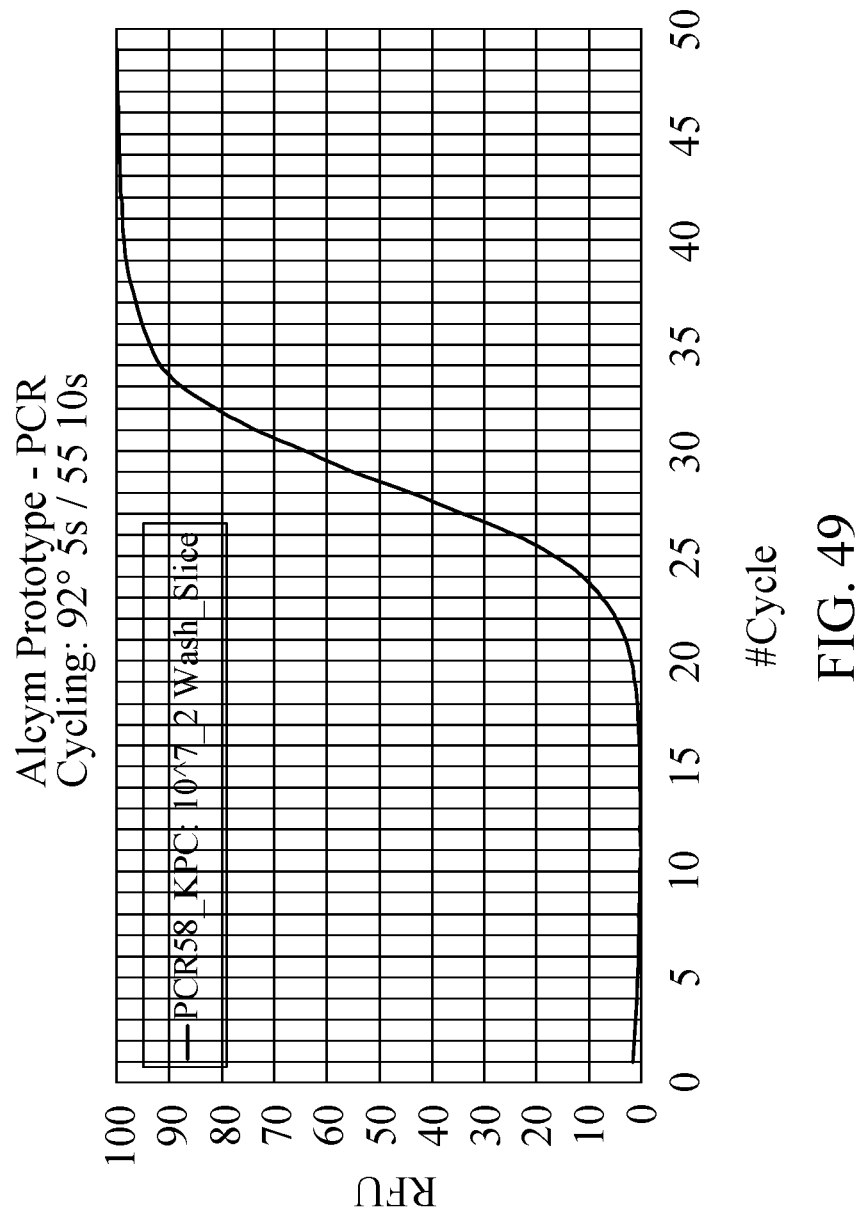
FIG. 49 shows a fluorescence trace for a PCR experiment in the presence of magnetic silica beads after lysis with lysis particles where the beads are not sequestered in the reaction chamber during amplification.
Figure 50:
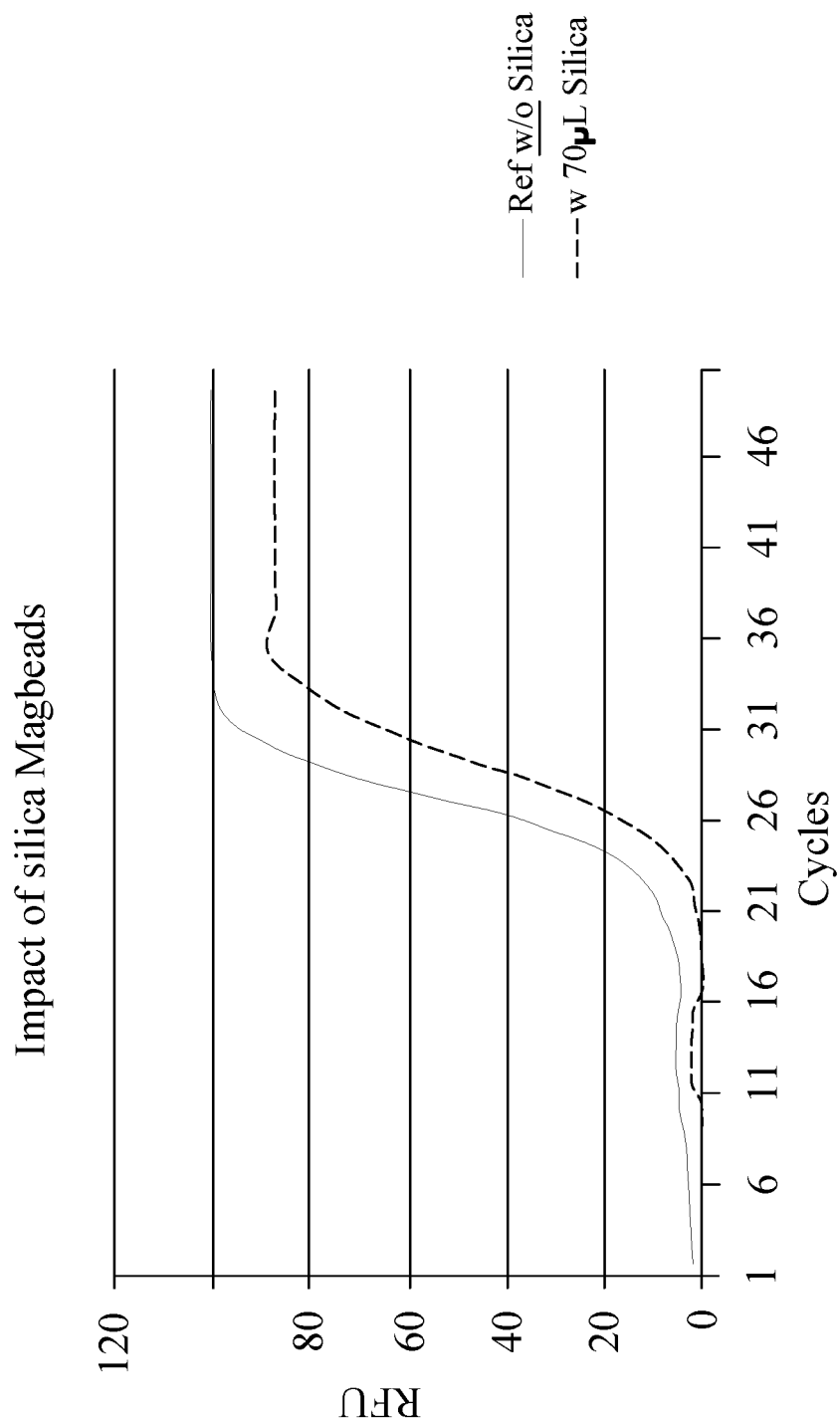
FIG. 50 shows fluorescence detection for PCR amplification in the presence of and the absence of magnetic silica beads.

Referring now to FIGS. 48-50, results are illustrated of a series of experiments in an instrument similar to the instrument described in U.S. Pat. No. 9,586,208, the entirety of which was already incorporated herein by reference. In one embodiment of U.S. Pat. No. 9,586,208, thermal cycling is accomplished by compressing the contents (e.g., 150-300 µl) of a fluid-filled blister back and forth between two heaters, wherein one heater is set at a high temperature for, for example, denaturation and the second is set at a lower temperature for, for example, annealing. Typical thermocyclers are usually composed of one heater that uses three temperatures and uses larger sample volumes.

Here, to obtain faster cycles, the system is designed to move and cycle a lower sample volume in two heating zones thanks to two immobilized heaters (respectively at 92° C. and 55-60° C.). Amplification of DNA targets in this example was done in 40 cycles of 5 seconds at 92° C. for denaturation and 10 seconds at 55° C. for annealing. Amplification product was detected in real-time with LC Green and fluorescence detection, as is known in the art. After PCR, specific amplification products were identified by fluorescence detection of DNA melting of the amplicons using temperature ramp over the course of 100 seconds.

Pure DNA targets of KPC (*Klebsiella Pneumoniae* Carbapenemase) equivalent to an input of $10^6$ geq were bound to 1.5 mg of magnetic silica beads. DNA targets bound to magnetic silica beads were then resuspended in 80 μL of TrisHCl pH8.5 and then mixed with a PCR mastermix for amplification. In amplification, the silica magnetic beads were either sequestered with a magnet, or the magnetic silica was allowed to mix freely during amplification. Here, the best results were achieved without sequestering the magnetic silica beads during amplification. The increase in fluorescence for amplification in this experiment is shown in FIG. 48. The Cp for this experiment is approximately 18-19 and the melt peak is specific to KPC (at 86-87° C.).

Referring to FIG. 49, the increase in fluorescence for another amplification experiment in the presence of magnetic silica beads is shown. In this experiment, KPC cells were lysed in the presence of lysis particles and magnetic silica beads. The example shown here corresponds to an input of ~500,000 CFU of KPC cells. The magnetic silica beads with the bound nucleic acid were transferred to a container for cycling as in the first example. Prior to amplification, several wash steps (1 to 3 depending on the protocol) were employed to remove residual lysis components (e.g., Guanidine) that could inhibit the PCR reaction. After washing, the magnetic silica beads were then resuspended in 80 μL of TrisHCl pH8.5 and then mixed with a PCR mastermix for amplification. The increase in fluorescence for amplification in this experiment is shown in FIG. 49. The Cp for this experiment is approximately 22-24. The Cp in this experiment was later than for the experiment corresponding to FIG. 48, but it is important to remember that the first experiment was done with DNA and did not require lysis, while this experiment was done with KPC cells and required lysis.

In a third experiment, it was shown that magnetic silica beads do not interfere with fluorescence detection. FIG. 50 compares relative fluorescence in no silica and in the presence of magnetic silica beads. No significant difference was seen. However, in the presence of larger quantities of silica (e.g., 3 mg), no fluorescence signal was measured (data not shown), presumably due to the silica beads blocking passage of light through the sample.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. A container for performing nucleic acid amplification on a sample in a closed system, the container comprising:
   a first layer and a second layer defining a multifunction chamber therebetween, the container provided with magnetic particles and reagents for sample preparation, nucleic acid recovery, and a first-stage nucleic acid amplification reaction, the multifunction chamber comprising a chamber for first-stage nucleic acid amplification, wherein the magnetic particles are provided in a chamber that is fluidly connected to the multifunction chamber or are provided in the multifunction chamber, and wherein the reagents are provided in chambers that are fluidly connected to the multifunction chamber; and
   a second-stage reaction zone disposed between the first layer and the second layer and fluidly connected to the multifunction chamber, the second-stage reaction zone comprising a plurality of second-stage reaction chambers different from the chamber for first-stage nucleic acid amplification, each second-stage reaction chamber comprising a pair of primers configured for further amplification of the sample, the second-stage reaction zone configured for contemporaneous thermal cycling of all of the plurality of second-stage reaction chambers,
   wherein the first layer and the second layer are flexible barrier films having a water vapor transmission rate (WVTR) in a range of about 0.05 $g/m^2/24$ hrs to about 2 $g/m^2/24$ hrs, and
   wherein the magnetic particles and the reagents are provided in one or more fluid-filled reagent blisters in fluid communication with the multifunction chamber, and wherein the fluid-filled reagent blisters and are filled at the time of manufacture of the container.

2. The container of claim 1, wherein the multifunction chamber is provided with cell lysis components and the magnetic particles.

3. The container of claim 2, wherein the cell lysis components comprise lysis particles.

4. The container of claim 1, wherein the container further comprises a sample lysis chamber in fluid communication with the multifunction chamber, wherein the sample lysis chamber is provided with cell lysis components and the magnetic particles, and the multifunction chamber is provided with magnetic bead wash components and first-stage nucleic acid amplification components.

5. The container of claim 1 wherein the magnetic particles are nucleic acid-binding magnetic particles.

6. The container of claim 1 further comprising a sample receiving chamber in fluid communication with the multifunction chamber.

7. The container of claim 6 wherein the sample receiving chamber comprises a sample collection swab.

8. The container of claim 7 wherein the sample collection swab comprises an elongate shaft, wherein the sample receiving chamber and the elongate shaft of the swab are fabricated from chemically compatible materials that can be at least partially fused with a heat seal.

9. The container of claim 1, further comprising an openable seal between the fluid-filled reagent blisters and the multifunction chamber.

10. The container of claim 9 wherein the openable seal is a burstable seal.

11. The container of claim 9 wherein the openable seal is a peelable, tacked together film seal.

\* \* \* \* \*